(12) United States Patent
Bramucci et al.

(10) Patent No.: US 7,105,296 B2
(45) Date of Patent: Sep. 12, 2006

(54) GENES ENCODING BAEYER-VILLIGER MONOOXYGENASES

(75) Inventors: Michael G. Bramucci, Folsom, PA (US); Patricia C. Brzostowicz, West Chester, PA (US); Kristy N Kostichka, Wilmington, DE (US); Vasantha Nagarajan, Wilmington, DE (US); Pierre E. Rouviere, Wilmington, DE (US); Stuart M. Thomas, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 281 days.

(21) Appl. No.: 10/230,026

(22) Filed: Aug. 28, 2002

(65) Prior Publication Data

US 2003/0124695 A1  Jul. 3, 2003

Related U.S. Application Data

(60) Provisional application No. 60/315,546, filed on Aug. 29, 2001.

(51) Int. Cl.
| | |
|---|---|
| *C12N 9/02* | (2006.01) |
| *C12N 1/20* | (2006.01) |
| *C12N 15/00* | (2006.01) |
| *C12Q 1/00* | (2006.01) |
| *C12Q 1/68* | (2006.01) |
| *C12P 21/04* | (2006.01) |
| *C07H 21/04* | (2006.01) |

(52) U.S. Cl. .............................. 435/6; 435/4; 435/189; 435/69.1; 435/71.1; 435/252.3; 435/320.1; 536/23.2; 536/23.7

(58) Field of Classification Search ................. 435/189, 435/440, 4, 6, 25, 7.4, 69.1, 71.1, 252.3, 435/320.1; 536/23.2, 23.1, 23.7
See application file for complete search history.

(56) References Cited

OTHER PUBLICATIONS

Sequence Search Alignment.*
Walsh et al.Chem, Int, Ed. Engl , vol. 27: pp. 333-343 Enzymic Baeyer- Villiger Oxidations by Flavin-Dependent Monooxygenases (1988).
J.Stewart,Cyclohexanone Monooxypenase:A use ful Reagent for Asymmetric Baeyer-Villiger Reactions Curr. Org. Chem. vol. 2: pp. 195-216 (1998).
Banerjee, Stereoselective Microbial Baeyer-Villiger Oxidations A. In Stereosel, Biocatal.; Patel, R.N., Ed.; Marcel Dekker: New York, Chapter 29, pp. 867-876 (2000).
Mihovilovic et al. Asymmetric Baeyer-Villiger Oxidation of 4-Momo-and 4,4-Disubstituted Cyclohexanones by Whole Cells of Engineered *Escherichia coli*J. Org. Chem, vol. 66(3): pp. 773-738 (2001).
Brzostowicz et al. Simultaneous I dentification of Two Cyclohexanone Oxidation Genes from an Environmental Brevibacterium Isolate Using mRNA Differential Display, J. Bact. vol. 182 (15): pp. 4241-4248 (2000).
Van Der Werf, J. Biochem., Purification and characterization of a Baeyer-Villiger mono-oxygenase from *Rhodococcus erythropolis* DCL14 involved in three different monocyclic monoterpene degradation pathways, vol. 347: pp. 693-701 (2000).

(Continued)

*Primary Examiner*—P. Achutamurthy
*Assistant Examiner*—Yong D. Pak

(57) ABSTRACT

Genes have been isolated from a variety of bacteria encoding Baeyer-Villiger monooxygenase activity. The genes and their products are useful for the conversion of ketones to the corresponding esters. A series of motifs, common to all genes, has been identified as diagnostic for genes encoding proteins of this activity.

3 Claims, 14 Drawing Sheets

OTHER PUBLICATIONS

Morii.S, et al. Steroid Monooxygenase of *Rhodococcus rhodochrous*:Sequencing of the Genomic DNA, and Hyperexpression, Purification, and Characterization of the Recombinant Enzyme J. Biochem vol. 126 (3) :pp. 624-631 (1999).

Amann,R.I. et al. Phylogenetic Identification and In Situ Detection of Individual Microbial Cells without Cultivation Microbiological Rev. vol. 59 (1): pp. 143-169 (1995).

Kane, M.D. et al., Monitoring the enrichment and Isolation of Sulfate-Reducing Bacteria by Using Oligonucleotide Hybridization Probe Designed from Environmentally Derived 16S rRNA Sequences, Appl. Environ. Microbiol. vol. 59: pp. 682-686 (1993).

Cheng, Q., et al.Genetic Analysis of a Gene Cluster for Cyclohexanol Oxidation in *Acinetobacter* sp. Strain SE 19 by In Vitro Transposition J. Bacteriol. vol. 182: pp. 4744-4715 (2000).

Chen, Y.C., et al. *Acinetobacter* Cyclohexanone Monooxygenase:Gene Cloning and Sequence Determination J. Bacteriol vol. 170 (2): pp. 781-789 (1988).

Seeger, K.J. et al., NCBI, AL109747. Direct Submission (Aug. 3, 1999) to the EMBL Data Library.

Redenbach, M., et al.A set of ordered cosmids and detailed genetic and physical map for the 8Mb *Streptomyces coelicior* A3(2) chromosome Mol. Microbiol. vol. 21 (1): pp. 77-96 (1996).

Nierman, W.C.,et al. Complete genome sequence of *Caulobacter crescentus* Proc. Natl. Acad. Sci. U.S.A. vol. 98 (7): pp. 4136-4141 (2001).

Freiberg, C.A. et al. Molecular basis of symbiosis between Rhizobium and legumes NATURE vol. 387: pp. 394-401 (1997).

Stover, C.K. et al. Complete genome sequence of *Pseudomonas aeruginosa* PA01, an opportunistic pathogen NATURE vol. 406 (6799): pp. 959-694 (2000).

Cole, S.T., et al. Deciphering the biology of *Mycobacterium tuberculosis* from the complete genome sequence NATURE vol. 393 (6685): pp. 537-544 (1998).

Miyamoto et al. Biochimica et al. Bacterial steroid momooxygenase catalyzing the Baeyer-Viliger oxidation of C21-ketosteroids from *Rhodococcus rhodochrous*: the isolation and characterization Biophysica Acta 1251:115-124 (1995).

* cited by examiner

Figure 6A

BVMO Family 1 consensus:

MTAQESLTVVDAVVIGAGPGGIYAVHKLREQGLTVVGPDAADGPGGTWYWNRYPGALSDTESHVYRFSPDEDLLQDWTWKE
TYPTQPEILEYLEDVVDRFDLRRDFRFGTEVTSATYLEDENLWEVTTDGGEVYRARFVVNAVGLLSAINFPNIPGLDTFEG
ETIHTAAWPEGVDLTGKRVGVIGTGSTGIQVITALAPEVEHLTVFVRTPQYSVPVGNRPVTAEQIDAIKADYDEIWAQVKR
SGVAPGFEESTVPAMSVSEEERNRVPEEAWEEGGGFRFMFGTFGDIATDEAANETAASFIRSKIREIVKDPETARKLTPTG
LFARRRLCDDGYYEVYNRPNVEAVDIKENPIREITAKGVVTEDGVLHELDVLVFATGFDAVDGNYRRIDIRGRGGLSLNDH
WDGQPTSYLGLSTAGFPNWFMVLGPNGPFTNLPPSIETQVEWISDTIAYAEENGIRAIEPTPEAEDEWTATCTDIANATLF
TKADSWIFGANVPGKKPSVLFYLGGLGNYRAVLADVAAAGYRGPALKSADAVTA (SEQ ID NO:47)

Signature Sequence Positions
BVMO Family 1

| Amino acid | Consensus position | Signature Position | Amino acid | Consensus position | Signature Position | Amino acid | Consensus position | Signature Position |
|---|---|---|---|---|---|---|---|---|
| D | 11 | P-1 | G | 178 | P-26 | P | 354 | P-51 |
| G | 16 | P-2 | V | 181 | P-27 | I | 355 | P-52 |
| G | 18 | P-3 | V | 183 | P-28 | D | 374 | P-53 |
| G | 21 | P-4 | G | 185 | P-29 | A | 379 | P-54 |
| G | 32 | P-5 | G | 187 | P-30 | T | 380 | P-55 |
| G | 45 | P-6 | G | 190 | P-31 | G | 381 | P-56 |
| G | 46 | P-7 | Q | 192 | P-32 | D | 383 | P-57 |
| W | 48 | P-8 | I | 194 | P-33 | G | 387 | P-58 |
| N | 51 | P-9 | A | 198 | P-34 | G | 399 | P-59 |
| Y | 53 | P-10 | L | 204 | P-35 | W | 406 | P-60 |
| P | 54 | P-11 | V | 206 | P-36 | G | 415 | P-61 |
| G | 55 | P-12 | F | 207 | P-37 | P | 422 | P-62 |
| D | 59 | P-13 | R | 209 | P-38 | N | 423 | P-63 |
| Y | 65 | P-14 | R | 265 | P-39 | P | 430 | P-64 |
| D | 101 | P-15 | G | 276 | P-40 | P | 433 | P-65 |
| L | 102 | P-16 | F | 286 | P-41 | N | 436 | P-66 |
| W | 124 | P-17 | F | 302 | P-42 | E | 464 | P-67 |
| G | 144 | P-18 | K | 306 | P-43 | W | 473 | P-68 |
| G | 156 | P-19 | D | 313 | P-44 | W | 492 | P-69 |
| F | 160 | P-20 | L | 320 | P-45 | G | 495 | P-70 |
| G | 162 | P-21 | P | 322 | P-46 | N | 497 | P-71 |
| H | 166 | P-22 | R | 329 | P-47 | P | 499 | P-72 |
| T | 167 | P-23 | Y | 336 | P-48 | G | 500 | P-73 |
| W | 170 | P-24 | N | 344 | P-49 | K | 501 | P-74 |
| P | 171 | P-25 | V | 345 | P-50 | | | |

BVMO Family 2 consensus:   Figure 6B

```
MVXIPXRHXEVVIIGAGFAGIGAAVELKRXGIDDFVLLERADDVGGTWRDNTYPGAACDVPSXLYSYSFAP
NPNWTRLFAXQPEIYDYLEDVAAXXGLXXHVRFGVEVTEARWDESAQLWRVXTASGELTAXFLVAATGPLS
KPKIPDLPGLESFBGXKFHSAXWNHDLDLRGERVAVVGTGASAVQFVPEIADKAXTLTVFQRTPQWVLPRP
DXTLPXAXRAVFSRVPGTQKWLRKRLYGIPEALGSGFVXPXWLLPKXXALARAHLRRQVRDPELEXRLTPD
YTPGCKRMLLSNDWYPALXKPNVSLVTSGVVEVTEXGVVDADGVEHEVDTIIFATGPHXTDXPXAMKIFGR
SGRSLADHWNGSAXAYLGTAVSGFPNLPXLLGPNTGLGHTSIVKILEAQAEYIASALXXMRREGLGALDVR
AEVQXXPNXAVQERLATTVWNAGGCSSWYXDPDGRNSTXWPWSTXXFRARTRRFDPSDYXPSSPTPETXXG
(SEQ ID NO:48)
```

Signature Sequence Positions
BVMO Family 2

| Amino acid | Consensus position | Signature Position | Amino acid | Consensus position | Signature Position | Amino acid | Consensus position | Signature Position |
|---|---|---|---|---|---|---|---|---|
| G | 15 | P-1 | F | 155 | P-27 | R | 291 | P-53 |
| G | 17 | P-2 | G | 157 | P-28 | L | 302 | P-54 |
| G | 20 | P-3 | F | 160 | P-29 | V | 307 | P-55 |
| E | 39 | P-4 | H | 161 | P-30 | G | 321 | P-56 |
| G | 45 | P-5 | W | 165 | P-31 | D | 333 | P-57 |
| G | 46 | P-6 | G | 173 | P-32 | T | 339 | P-58 |
| W | 48 | P-7 | G | 180 | P-33 | G | 340 | P-59 |
| N | 51 | P-8 | G | 182 | P-34 | F | 341 | P-60 |
| Y | 53 | P-9 | A | 183 | P-35 | G | 357 | P-61 |
| P | 54 | P-10 | S | 184 | P-36 | W | 364 | P-62 |
| G | 55 | P-11 | A | 185 | P-37 | G | 373 | P-63 |
| D | 59 | P-12 | Q | 187 | P-38 | F | 379 | P-64 |
| P | 61 | P-13 | P | 190 | P-39 | P | 380 | P-65 |
| L | 64 | P-14 | Q | 203 | P-40 | N | 381 | P-66 |
| Y | 65 | P-15 | R | 204 | P-41 | G | 387 | P-67 |
| S | 66 | P-16 | W | 208 | P-42 | P | 388 | P-68 |
| S | 68 | P-17 | P | 211 | P-43 | S | 396 | P-69 |
| W | 75 | P-18 | D | 214 | P-44 | E | 402 | P-70 |
| E | 84 | P-19 | P | 229 | P-45 | Q | 404 | P-71 |
| Y | 88 | P-20 | R | 236 | P-46 | Y | 407 | P-72 |
| W | 120 | P-21 | L | 268 | P-47 | V | 429 | P-73 |
| G | 139 | P-22 | Q | 271 | P-48 | V | 445 | P-74 |
| P | 144 | P-23 | D | 274 | P-49 | G | 460 | P-75 |
| P | 147 | P-24 | L | 277 | P-50 | R | 461 | P-76 |
| P | 150 | P-25 | P | 283 | P-51 | P | 467 | P-77 |
| G | 151 | P-26 | K | 290 | P-52 | | | |

Figure 6C

BVMO Family 3 consensus:

MSTEHLDVLIIGAGLSGIGAAXRLXREXGIXPAILEARDNVGGTWDLFNYPGIRSDSDHLTXGKGAFRPFPXAKXLADGPS
HELXXYVRDTAXEXGLRXHIXPGTKVVAAKXXAXSLWTVTVXXKGETEVXTYNVLXXANGYYSYDKGNIPDFPGEFXGXLV
HPQXYPEXLDYRGKKVVVIGSGASGXTLAPXMXXXAXHVTMLQRSGTYIALPSDAVVPXQLAGXRXXXXXLQXXQLRXPPW
XAKRLXLLLIRRQLGKNVXLXGPPTPSYXPWDQHLCVVPNGDLLKXLGSGDAXIXTDIDTFTGKGVXFASGREXDADVVVT
ATGLNXXXGGPFIXXDGLLVDLXXRXALFYKXXXXSDNLNFLGXVGYTNASWTLRADLAXLVACRLLXXMXXRSAXXXXXH
AXAEXXXLLASGYKXRXXGXMPXQGXKXXWXXXXNYXXDRXLXXXXXXXXXXXXPSKXXXAXXXX (SEQ ID NO 49)

Signature Sequence Positions
BVMO Family 1

| Amino acid | Consensus position | Signature Position | Amino acid | Consensus position | Signature Position |
|---|---|---|---|---|---|
| G | 12 | P-1 | G | 159 | P-22 |
| A | 13 | P-2 | H | 163 | P-23 |
| G | 14 | P-3 | K | 176 | P-24 |
| G | 17 | P-4 | V | 178 | P-25 |
| A | 21 | P-5 | V | 180 | P-26 |
| E | 36 | P-6 | G | 182 | P-27 |
| G | 42 | P-7 | G | 184 | P-28 |
| G | 43 | P-8 | A | 198 | P-29 |
| W | 45 | P-9 | R | 206 | P-30 |
| S | 57 | P-10 | P | 220 | P-31 |
| F | 67 | P-11 | P | 242 | P-32 |
| D | 78 | P-12 | P | 269 | P-33 |
| Y | 87 | P-13 | G | 293 | P-34 |
| V | 107 | P-14 | G | 314 | P-35 |
| W | 118 | P-15 | D | 320 | P-36 |
| V | 120 | P-16 | A | 325 | P-37 |
| T | 121 | P-17 | T | 326 | P-38 |
| G | 141 | P-18 | G | 327 | P-39 |
| P | 151 | P-19 | D | 361 | P-40 |
| G | 155 | P-20 | L | 415 | P-41 |
| F | 157 | P-21 | Y | 419 | P-42 |

Figure 7A

```
2005                    ----------MTDE-------FDVVIVGAGLAGMQMLHEVR-MVGLTAKV
1273                    ----MTDPDFSTAP-------LDVVVIGAGVAGMYAMHRLR-EQGLRVHG
Arthrobacter            ----MTAQNTFQT--------VDAVVIGAGPGGIYAVHKLHNEQGLTVVG
2082                    ----MTTQKALTT--------VDAIVIGAGFGGIYAVHKLANELGLTTVG
Rhodococcus-phi2-Mono   ----MTAQTIHT---------VDAVVIGAGPGGIYAVHKLHHELGLTTVG
Rhodococcus-phi1-Mono   ----MTAQISPTV--------VDAVVIGAGPGGIYAVHKLHNEQGLTVVG
Acidovorax              ----MSSSPSSAIK-------FDAIVVGAGPGGMYMLHKLRDQLGLKVKV
Brevibacterium-Mono1    ------MPITQQLD-------HDAIVIGAGFSGLAILHHLR-EIGLDTQI
2093                    ----MTTTESRTQTDKAGAVTLDALIIGAGVAGLYQLHMLR-EQGLNVRA
Brevibacterium-Mono2    NTSTMPAPTAAQAN-ADETEVLDALIVGGGFSGPVSVDRLR-EDGFKVKV
                            *.:::*.*..*       :. :       *: .

2005                    FEAGGGAGGTWYWNRYPGARCDVESLEYSYQFSEVLQQEWEWTRRYADQA
1273                    FEAGSGVGGTWYFNRYPGARCDVESFDYSYSFSEELQQDWDWSEKYAAQP
Arthrobacter            FDKADGPGGTWYWNRYPGALSDTESHVYRFSPDRGLLQDGTWKHTYITQP
2082                    FDKADGPGGTWYWNRYPGALSDTESHVYRFSFDRDLLQDGTWKHTYFTQP
Rhodococcus-phi2-Mono   FDKADGPGGTWYWNRYPGALSDTESHLYRFSFDRDLLQDGTWKNTYVTQP
Rhodococcus-phi1-Mono   FDKADGPGGTWYWNRYPGALSDTESHLYRFSFDRDLLQDGTWKTTYITQP
Acidovorax              FDTAGGIGGTWYWNRYPGALSDTHSHVYQYSFDEAMLQEWTWKNKYLTQP
Brevibacterium-Mono1    VEATDGIGGTWWINRYPGVRTDSEFHYYSFSPSKEVRDEWTWTQRYPDGE
2093                    YDAAEDVGGTWYWNRYPGARFDSEAYIYQYLFSEDLYKWWSWSQRFPAQP
Brevibacterium-Mono2    WDAAGGPGGIWWWNCYPGARTDSTGQIYQFQY-KDLWKDFDFKELYPDFN
                         :   ** *: ***.  *         * :::::   *: .  :

2005                    EIMRYISHVVETFDLARDIRFWTRVEAMTYEETTARWTVQTDSAGEVVAK
1273                    EILSYLDHVADRFDLRTGPTFDTRVLSAQPDEGTATWRVQTDGGHDVTSR
Arthrobacter            EILEYLEDVVDRFDLRRHFRFGTEVKSATYLEDEGLWEVTTGGGAVYRAK
2082                    EILEYLEDVVSRFDLRRHFHFGTAVESAVYLEDEQLWEVTFTDTGEIYRAT
Rhodococcus-phi2-Mono   EILEYLEDVVDRPDLRRHFRPGTEVTSAIYLDDENLWEVTTDGGDVYRAT
Rhodococcus-phi1-Mono   EILEYLESVVDRFDLRRHFRFGTEVTSAIYLEDENLWEVSTDKGEVYRAK
Acidovorax              EILAYLEYVADRLDLRPDIQLNTTVTSMHFNEVHNIWEVRTDRGCYYTAR
Brevibacterium-Mono1    EVCAYLNFIADRLDLRKDIQLNSRVNTARWNETEKYWDVIFEDGSSKRAR
2093                    EIERWMRYVADTLDLRRSIQFSTTITSAEFDEVAERWTIRTDRGEEISTR
Brevibacterium-Mono2    GVREYPEYVDSQLDLSRDVTFNTFAESCTWDDAAKEWTVRSSEGREQRAR
                         :  ::  :  .**   . : :  :.         *  .        :

2005                    FVIMATGCLSEPNVPYIPGVETPAGDVLHTGRWPQDFVDFTGKRVGVIGT
1273                    FVVCATGSLSTANVPNIAGRETFGGDVFHTGFWPHEGVDFTGKRVGVIGT
Arthrobacter            YVINAVGLLSAINFPNLPGIDTFEGETIHTAAWP-QGKSLAGRRVGVIGT
2082                    YVVNAVGLLSAINRPDLPGLETFEGETIHTAAWP-EGKDLTGRRVGVIGT
Rhodococcus-phi2-Mono   YVVNAVGLLSAINFPNLPGLDTFEGETIHTAAWP-EGKSLAGRRVGVIGT
Rhodococcus-phi1-Mono   YVVNAVGLLSAINFPDLPGLDTFEGETIHTAAWP-EGKNLAGKRVGVIGT
Acidovorax              FIVTALGLLSAINWPNIPGRESFQGEMYHTAAWP-KDVELRGKRVGVIGT
Brevibacterium-Mono1    FLISAMGALSQAIFPAIDGIDEFNGAKYHTAAWPADGVDFTGKKVGVIGV
2093                    FFITCCGMLSAPMEDLFPGQQDFRGQIFHTSRWPHGDVELTGKRVGVVGV
Brevibacterium-Mono2    AVIVATGFGAKFLYPNIEGLDSFEGECHHTARWPQGGLDMTGKRVVVMGT
                         .:  *  . .   :        *        **. **       *;:*.

2005                    GSSGVQAIPLIARQAAELVVFQRTPAYTLPAVDEPLDPELQAAIKADYRG
1273                    GSSGIQSIPLIAEQADHLYVFQRSAMYSVPAGNTPLDDKRRAEIKAGYAE
Arthrobacter            GSTGQQVITALAPEVEHLTVFVRTPQYSVPVGKRPVTQQIDEIKADYDN
2082                    GSTGQQVITALAPTVEHLTVFVRTPQYSVPVGKRAVTDEQIDAVKADYEN
Rhodococcus-phi2-Mono   GSTGQQVITALAPEVEHLTVFVRTPQYSVPVGNRPVTPEQIDAIKADYDR
Rhodococcus-phi1-Mono   GSTGQQVITALAPEVEHLTVFVRTPQYSVPVGNRPVTKEQIDAIKADYDG
Acidovorax              GSTGVQLITAIAPEVKHLTVFQRTPQYSVPTGNRPVSAQEIAEVKRNFSK
Brevibacterium-Mono1    GASGIQIIPELAKLAGELFVFQRTPNYVVESMNDKVDAEWMQYVRDNYDE
2093                    GATGIQVIQTIADEVDQLKVFVRTPQYALPMKNPQYDSDDVAAYKDRFEE
Brevibacterium-Mono2    GASGIQVIQEAAAVAEHLTVFQRTPNLALPMRQQRLSADDNDRYRENIED
                         *::*    *      *  .*  **  *:. .       *        :

2005                    FRARNNEVPTAGLSRFPTNPNSVFLFSTKERDAILEHNWNRGG--PLMLR
1273                    RRALSK--RSGGGSPFVSDPRSALEVSEAERNAAYBERWKLGG--VLFAK
Arthrobacter            IWAQVK--RSGVAFGFEESTVPAMSVTEEERRQVYEKAWEYGGGFRFMFE
```

Figure 7B

```
2005                         IWTQVK--RSSVAPGFEESTVPAMSVSABBRLRVYEEAWEQGGGFRFMPG
1273                         IWEQAK--NSAVAPGFEESTLPAMSVSEEERNRIFQEAWDHGGGFRFMPG
Arthrobacter                 IWDSVK--XSAVAPGFEESTLPAMSVSEEERNRIFQEAWDHGGGPRFMPG
2082                         VWQQVR--ESAVAPGFEESTVPAMSVSEAERQRVFQEAENQGNGFYYMPG
Rhodococcus-phi2-Mono        IPERAS--KHPPGVDMEYPTDSAVEVSEEERKRVFESKWEEGG-FHPANE
Rhodococcus-phi1-Mono        LRTTLP--HTFTGFEYDPEYVWADLAPE-QRREVLENIYETGS-LKLWLS
Acidovorax                   RPQIRD--NSFAGFDFYFIPQNAADTPEDERTAIYEKMWDEGG-FPLWLG
Brevibacterium-Mono1                   .     ;*   :  :. *.
2093
Brevibacterium-Mono2

2005                         AFGDLLVDSAANEVVAEFVRNKIRQIVTDPEVAAKLTP-T--HVIGCKRI
1273                         TFADQTSNIEANGTAAAFAERKIRSEVQDQAIADLLIPND--HPIGTKRI
Arthrobacter                 TFSDIATDEEANETAASFIRNKIVETIKDPETARKLTP----TGLFARRP
2082                         TPGDIATDEEANETAASFIRSKITAMIEDPETARKLTP----TGLFARRP
Rhodococcus-phi2-Mono        TFGDIATDEAANEAAASFIRSKIAEIIEDPETARKLMP----TGLFAKRP
Rhodococcus-phi1-Mono        TFGDIATDEAANEAAASFIRSKIAEIIEDPETARKLMP----TGLYAKRP
Acidovorax                   TPCDIATDPQAMEAAATFIRNRIAEIVKDPETARKLTP----TDVYARRP
Brevibacterium-Mono1         CFTDLGTSPEASELASEFIRSKIREVVKDPATADLLCPKS--YSFNGKRV
2093                         SPAEMFPDEQVSDEISEFVREKMRARLIDPELCDLLIPTD--YGFGTHRV
Brevibacterium-Mono2         NFQGLLTDEAANHTFYNFWRSKVHDRVKDPKTAEMLAPATPPHPFGVKRP
                              *    .  ..  *. *;   :  *   .  * *    .  :*

2005                         CLSDGYYETYNRVNVRLVDIKRHPIEEITPTTARTGE-DSHDLDMLVFAT
1273                         VTDTNYYQSYNRDNVSLVDLKSAPIEAIDEAGIKTAD-AHYELDALVFAT
Arthrobacter                 LCDDGYPQVFNRPNVEAVAIKENPIREVTAKGVVTEDGVLHELDVIVFAT
2082                         LCDDGYFQVFNRPNVEAVAIKENPIREITAKGVVTEDGVLHKLDVLVLAT
Rhodococcus-phi2-Mono        LCDAGYHQVFNRPNVEAVAIKENPIREVTAKGVVTEDGVLHELDVLVFAT
Rhodococcus-phi1-Mono        LCDNGYYEVYNRPNVEAVAIKENPIREVTAKGVVTEDGVLHELDVLVFAT
Acidovorax                   LCDSGYYRTYNRSNVSLVDVKATPISAMTPRGIRTADGVEHELDMLILAT
Brevibacterium-Mono1         PTGNGYYETFNRTNVHLLDARQTPITRISSKGIVHGD-TEYELDAIVFAT
2093                         PLETNYLEVYHRPNVTAIGVKNNPIARIVPQGIEL/TDGTPHELDVIILAT
Brevibacterium-Mono2         SLEQNYFDVYNQDNVDLIDSNATPITRVLPNGVETPD-GVVECDVLVLAT
                              .*  .   ::: **  :    **   :   .  * *  *  :::**

2005                         GYDAITGALSRIDIRGRAGLSLQEAWS-DGPRTYLGLGVSGFPNLFIMTG
1273                         GFDAMTGALDRIEIRGRNGETLRENWH-AGPRTYLGLGVHGFPNLPIVTG
Arthrobacter                 GPDAVDGNYRRMEISGRDGVNINDHWD-GQPTSYLGVSTAKFPNWFMVLG
2082                         GFDAVDGNYRRMTISGRGGLNINDHWD-GQPTSYLGIATANFPNWFMVLG
Rhodococcus-phi2-Mono        GPDAVDGNYRRIEIRGRDGLHINDHWD-GQPTSYLGVSTANFPNWFMVLG
Rhodococcus-phi1-Mono        GPDAVDGNYRRIEIRGRNGLHINDHWD-GQPTSYLGVTTANFPNWFMVLG
Acidovorax                   GYDAVDGNYRRIDLRGRGGQTINEHWN-DTPTSYVGVSTANFPNMPKILG
Brevibacterium-Mono1         GFDAMTGTLTNIDIVGRDGVILRDKWAQDGLRTNIGLTVNGFPNFLMSLG
2093                         GFDAGTGALTRIDIRGRGGRSLKEDWG-RDIRTTMGLKVHGYPNMLTTAV
Brevibacterium-Mono2         GFDNNSGGINAIDIKA-GGQLLRDKWA-TGVDTYMGLSTHGFPNLMPLYG
                             *;*         :  .  *  :.:  *       :    :  ;*:   :

2005                         PGSPSV-LTNVLVAIHQHATWIGECLKHMTDNDIRTMEATPEAEQNWGDH
1273                         PGSPSV-LSNMILAAEQHVDWIAGAINHLDSAGIDTFIEPSAEAVDNWLDE
Arthrobacter                 PNGP---FTNLPPSIETQVEWISDTVAYAEENGIRAIEPTPEAEAEWTET
2082                         PNGP---FTNLPPSIETQVEWISDTIGYVERTGVRAIEPTPEAEASAWTAT
Rhodococcus-phi2-Mono        PNGP---FTNLPPSIETQVEWISDTIGYAERNGVRAIEPTPEAEAEWTET
Rhodococcus-phi1-Mono        PNGP---FTNLPPSIETQVEWISDTVAYAERNEIRAIEPTPEAEEEWTQT
Acidovorax                   PNGP---FTNLPPSIEAQVEWITDLVAHMRQHGLATAEPTRDAEDAMGRT
Brevibacterium-Mono1         PQTP---YSNLVVPIQLGAQWMQRFLKFIQERGIEVFESSREAEEIWNAE
2093                         PLAPSAALCNMTTCLQQQTEWISEAIRYMQERDLTVIEPTKEAEDAWVAH
Brevibacterium-Mono2         PQSPSG-PCNGTDFGGAPGDMVADFLIWLKDNGISRFESTEEVEREWRAH
                              *   *          ;  :        *.: :,     *

2005                         VRDLAEQTLLSS----CGSWYLGANIPGXRQVFNPLVG-PPDYAKKCAEI
1273                         CSRRASATLFPS----ANSWYMGANIPGKPRIFMPFIGGPGVYSDICADV
Arthrobacter                 CTQIANMTVFTK----VDSWIFGANVPGKKPSVLFYLGGLGNYRGVLDDV
2082                         CTDIANMTVFTK----VDSWIFGANVPGKKPSVLFYLGGLGNYRAVLADV
Rhodococcus-phi2-Mono        CTAIANATLFTK----GDSWIFGANIPGKTPSVLFYLGGLRNYRAVLAEV
Rhodococcus-phi1-Mono        CTDIANATLFTR----GDSWIFGANVPGKKPSVLFYLGGLGNYRNVLAGV
Acidovorax                   CAEIAEQTLFGQ----VESWIFGANSPGKKHTLMFYLAGLGNYRKQLADV
Brevibacterium-Mono1         TIRGAESTVMSIEGPKAGAWFIGGNIPGKSREYQVYMGGGQVYQDWCREA
2093                         HDETAAVNLISK----TDSWYVGSNVPGKPRRVLSYTGGVGAYREKAQEI
Brevibacterium-Mono2         VDDIFVNSLFPK----AKSWYWGANVPGKPAQMLNYSEASPHI------
                               .:*      :*  *.* ***
```

```
2005                    ASAGYPGFAFQYDP--VPVNQS----  [SEQ ID NO:34]
1273                    AAAGYRGFELN-----SAVHA-----  [SEQ ID NO:26]
Arthrobacter            TANGYRGFELKS-E--AAVAA-----  [SEQ ID NO:12]
2082                    TEGGYQGFALKT-A--DTVDA-----  [SEQ ID NO:44]
Rhodococcus-phi2-Mono   ATDGYRGFDVKS-A--ENVTV-----  [SEQ ID NO:10]
Rhodococcus-phi1-Mono   VADSYRGFELKS-A--VPVTAZ----  [SEQ ID NO:8]
Acidovorax              ANAQYQGFAFQP-L------------  [SEQ ID NO:18]
Brevibacterium-Mono1    EESDYATFLNADSIDGEKVRESAGMK  [SEQ ID NO:14]
2093                    ADAGYKGFNLR---------------  [SEQ ID NO:46]
Brevibacterium-Mono2    --------------------------  [SEQ ID NO:16]
```

Figure 8A

```
1870    ----VNNES-------------DHFEVVIIGGGISGIGAAIHLQRLG-IDNFALLEKADS
2022    ----VKLP-------------EHVETLIVGAGFAGMGLAARMLRDNRTADVVLIERGAD
1985    ---MVDIDPTSGPSAGDEETRTRRTRVVVIGAGFGGIGTAVRLKQSG-IDDFVVLERAAE
1294    ------MSSR----------VNDGHIAIIGTGFSGLCMAIELKKKG-IDDFVLYERADD
2035    MAEIVNGPQ----IKPATAKCDERLHAIVIGAGIAGMLASVELSRAG--IPHVILEKNDD
                   .  ::* *:.*:  : .: :.   .*:* .

1870    LGGTWRANTYPGCACDVPSGLYSYSFAANPDWTRLFAEQPEIREVIENTAGTHGVDKHVR
2022    IGGTWRDNTYPGCACDVPTALYSYSFAPSADWSHTFARQPEIYDYLKKVAADTGIGDRVI
1985    PGGTWQVNTYPGAQCDIPSILYSFSFAPNPNWTRLYPLQPEIYDYLRDCVHRFGLAGHPH
1294    VGGTWRDNTYPGAACDVPSVLYSYSPAQNPNWTRIFPPWSELLDYLRSVAAQYDLLPHIR
2035    VGGSNWENRYPGAGVDTPSHLYSISSFP-RNWSTHPGKRDEVQGYLEDFAEANDIRRNVR
        **:*  * ***.  * *: *** **           :*:  :    *;  *:..  .:  ..

1870    FGVEMLSARWDASQSLWKITTS----SGE-LTARFVIAAAGPWNEPLTPAIPGLEAFEGE
2022    LNCELEAAVWDEDAALWRVRTS----LGS-LTVKALVAATGALSTPKIPDFPGLDQFSGT
1985    CNQDVTEASWDEQAQIWRVHTA----ETV-WEAQFLVAATGPFSAPATPDLPGLESFRGQ
1294    FGVEVSEMRFDEDRLRWNIQFA----SGESVTAAVVVNGSGGLSNPYIPQLPGLESFEGA
2035    PRHEVTRAEFEESKQSWRVSVQRPGEASETLEAPILISAVGLLNRPKIPHLPGIETFRGR
         ::     ::  .  *.:        . :: . * . * *  ;**;: * *

1870    VPHSSQWNHDYD----LTGKLVAVVGTGASAVQFVPRIVSQVSALHLYQRTAQWVLPKPD
2022    TPHSATWNHEKE----LRGERVAVIGTGASAVQFVPBIADPAAHVTVFQRTPAWVIPRMD
1985    MFHTADNNHDHD----LRGERIAVVGTGASAVQIIPRLQPLADTLTVPQRTPTWILPHPD
1294    AFHSAKWRHDLD----MSGRRVAVIGSGASAIQFVPEIAPHTETLHVFQRSPNWVMPRGD
2035    LFHSAEWPSELDDPESLRGKRVGIVGTGASAMQIGPAIADRVGSLTIFQRSPQNIAPNDD
         **;:  *   : :      : *. :.::*:****:*;  *   .   : ::*::. *: *. *

1870    --HYVPRIERSVMRFVPGAQKALRSIEYGIM--EALGLGFRNP-WILRIVQKLGSAQ---
2022    --RTLPAAQKAVYSRIPATQKVVRGAVYGFR--ELLGAAMSHATWVLPAFEAAARLH---
1985    --QPMTGWPSALFERVPLTQRLARKGLDLLQ--EALVPGFVYKPSLLKGLAALGRAH---
1294    --AALSPATRERFSRRPYRQRMLRWRTYWAF--EKLASAFLGNRKLVEQYRSQALAN---
2035    YFTTIDDGVHWLMDNIPGYREMYRARLSWIFNDKVYSSLQVDPDWPEPSASINATNHGHR
                :       *  :.  *           :       .  :

1870    ------LRLQVRD-PKLRKALTPDYTLGCKRLLMSNSYYPALGKPNVSVHANAVEQIRGN
2022    ------LRRQVKD-PELRRKL/TPDFTIGCKRMLLSNDWLRTLDRADVSLVDSGLVSVTEG
1985    ------LRRQVRD-PELRAKLLPHYAFGCKRPTFSNTYYPALASPNVEVVTDGIVEVQER
1294    ------LQQQVPD-SDLRQKVTPDYDPGCKRRLISDDWYPALQRENVHLNTSGVSEIRPH
2035    KPYERYLRDQLGDRTDLIEASLPDYPPFGKRMLLDNGWFTNLRKPDVTLVPHGVDALTPS
              *;   *  ..*      *.;  **  :: :   *   : :*: .   . :

1870    TVIGADGVEAEVDAIIFGTGFHILDMPIASKVFDGEGRSLDDHWQGSPQ-AYFGSAVSGF
2022    GVVDGHGVEHKVDTIIFATGPTPTEPPVAHLITGKRGETLAAHWNGSPN-AYKGTAVSGF
1985    GVLTADGAFREVDTIVNGTGFRMGDNPSPDTIRGQDGRSLAQTWNGSAE-AFLGTTISGF
1294    SIIDSEGAEHEVDTLIPATGFPQATSFLAPHKVFGREGVELSDSWREGAA-TKLGLASAAF
2035    GLVDTNGVEHQLDVIVMATGFHSVRVLYPMDIVGRSGRSTGEIWGEHDARAYLGITVPDF
          :: .*.  ::*.:::.*** ::  . *         *    : *:. *

1870    PNAFILLGPSLGTGHTSAFHIL-EAQLNYVAQAIGHARRHGWQTIDVREEVQAAFNSQVQ
2022    PNLFLMYGPNTNLGHSSIVYML-ESQAEYVNDALNTMKRERLDALDVNESVQVIIYNKGIQ
1985    PNFFMILGPNS-VVYTSQVVTI-EAQVEYIVSCILQNDERGIGSIDVRADVQREFVRATD
1294    PNLHFLNGPNTGLGHNSIIFMI-EAQARYIASAVQYMRRKSITALELDRTVQTGSYAATQ
2035    PNFFVMTGPNTGLGHGGSFITILECQVRYIMDALKLMQSENLGAMECRAEVNDRYNEAVD
        **  ::  **.       :    :  . : *.* .*: ..:   :::  *:        :

1870    EALGTTVYNAGGCESYFFDVNGRNSFNWPWSSGAMRRRLRDFDPYAYNHTSNPESDNTPP
2022    HELQHTVWNKGGCSSWYIDPEGRNSVQWPTFTFKFRSLLEHFDRENYSAR-KIESVQA--
1985    RRLATSVWNAGGCSSYYLVDGGRNYTPYPGFNRSFRARTKRADLAHYAQVQPVSSAALT-
1294    ERMRRTVWASGGCDSWYQSADGRIDTLWPASTIEYWLRTRLFRKSDPHALTTGKG-----
2035    RQHAQMVWTHPAMENWYRNPDGRVVSVLPWRINDYWAHTYRVDPSDFRTEPARSESVPTP
           *;  , ..::   **  *            :          :        .
```

```
1870   EPTPSEPTPSEPTPSEPTTSPEPEYT  (SEQ ID NO:30)
2022   --------------------------  (SEQ ID NO:38)
1985   --TARETVRSR---------------  (SEQ ID NO:24)
1294   --------------------------  (SEQ ID NO:42)
2035   --TARG--------------------  (SEQ ID NO:36)
```

Figure 9

```
1861    -MSTEHLDVLIVGAGLSGIGAAYRLQTELPGKSYAILEARANSGGTWDLFKY--PGIRSD
1976    --MTQHVDVLIIGAGLSGIGAACHLIREQTGSTYAILERRENIGGTWDLFKY--PGIRSD
1413    --MSTEGKYALIGAGPSGLAGARNLDR--AGIAFDGFESHDDVGGLWDIDNP--HSTVYE
2034    MSPSPLPSVCIIGAGPTGITTAKRMKE--FGIPFDCYEASDEVGGNWYYKNPNGMSACYQ
         :   . ::***.:*:  * .:     * ..:   *   : ** *    :   .  :

1861    SDMFTLGYP---FRPWTDAKAIADGDS---ILRYVRDTARENGIDKKIRYNRKVTAASWS
1976    SDMLTFGPG---FRPWIGTKVLADGAS---IRDYVEETAKEYGVTDHINFGRKVVAMDFD
1413    SAHLISSKGTTAFAEFPMADSVADYPSHIELAEYFRDYADTHDLRRHFAFG--TTVIDVL
2034    SLHIDTSKWRLAFEDFPVSADLPDFPHHSELFQYFKDYVEHFGLRESIIFN-TSVVAAER
        * :      *     * :  :.*     : *..:.  .:     :  : .    ..

1861    SATSTWTVTVTTGD--EDETLTCNFLYLCSGYYSYDGGYTPDFPGRESFAGEVVHPQFWP
1976    RTAAQWSVTVLVEATGETETWTANVLVGACGYYNYDKGYRPAFPGEDDFRGQIVHPQHWP
1413    PVDSLWQVTTRSRS-GETSVARYRGVIIANGTLSKPN--IPTFRG--DFTGTLMHTSEYR
2034    DANGLWTVTRSDGE-----VRTYDVLMVCNGHHWDPN--IPDYPG--EFDGVLMHSHSYN
         . . * **          .      :   .   *    * : *  .** **  ::*.  :

1861    ---EELDYSDKKVVVIGSGATAVTLVPTMSRDASHVTMLQRSPTYILALPSSDKLSDTIR
1976    ---EDLDYTGKKVVVIGSGATAITLIPSMAPTAGHVTMLQRSPTWIQALPSEDPVAKGLK
1413    ---SAEIFRGKRVLVIGAGNSG----CDIAVDAVH----------QAECVDLSVRRGYY
2034    DPFDPIDMRGKKVVVVGMGNSG----LDIASELGQR---------YLADKLIVSARRGVW
              .*:*:*:*:*  *  :.       ::      :                *

1861    -AVLPNQLAHSIARWKSVVVNLSFYQLCRRSPARAKRMLNLAISRQLPKDIPLDP---HF
1976    LARVPDQIAYKIGRARNIALQRASFQLSRTNPKLAKKLFLAQIRLQLGKNVDLR----HF
1413    --FVPKYLF---GR-PSDTLN----QGKPLPPWIKQRVDTLLLKQFTGDPVRFG----FP
2034    --VLPKYLG---GV-PGDKLI------T--PPWMPRGLRLFLSRRFLGKNLGTMEGYGLP
          :*. :          . . :        *            : :              . :

1861    TPSYDPWDQRLCVVPDGDLFKALRSGKASIETDHIDTFTETGILLASGRELEADIIVTAT
1976    TPSYNPWDQRLCVVPNGDLFKVLKSGKADIVTDRIATFTEKGIVTESGREIEADVIVTAT
1413    APDYKIYES-HPVV-NSLILHHIGHGDVHVRAD-VDRFEGKTVRFVDGSSADYDLVLCAT
2034    KPDHRPFEA-HPSA-SGEFLGRAGSGDITFKPA-ITKLDGKQVHFADGTAEDVDVVVCAT
         *.: ::     ... ::      *.   . .    :   .      .*   : *::: **

1861    GLKMEACGGMSIEVDGELVTLGDRYAYKGMMISDVPNFAMCVGYTNASWTLRADLTSMYV
1976    GLNVQILGGATMSIDGEPVKLNETVAYKSVLYSDIPNFLMILGYTNASWTLKADLAASYL
1413    GYHLDYPFIAREDLDWSGAAPDLFLNVASRRH-DNLFVLGMVEASGLGWQGR-YQQAELV
2034    GYNISFPFFDDPNLLPDKDNRFPLFKRMMKPGIDNLFFMGLAQPMPTLVNFA-EQQSKLV
        * ::.          .: .                 *          .        : :

1861    CRLLTEMDKRDYSKCVPHAT-EEMDQRPILD--LASGYVMRAVEQFPKQGSKSPWNMRQN
1976    CRVLKIMRDRSYTTFEVHAEPEDFAEESLMGGALTSGYIQRGDGEMPRQGARGAWKVVNN
1413    AKLITARTEAPAAAREFSAA-----AAGPPPD--LSGGYK------YLKLG------RMA
2034    AAYLTGKYQLPSANEMQEIT----KADEAYF--LAPYYK--S-PRHTIQLEFDPYVRNMN
         . :.   .    :                    *:   *

1861    YILDR-LHSTFGSINDHMTFSKAPARHSTPVPSKS- [SEQ ID NO:32]
1976    YYRDRKLMHDAEIEDGVLQFSKVDIAVVPDSKVASA [SEQ ID NO:40]
1413    YYVNK----D-------------------------- [SEQ ID NO:22]
2034    KEIAKGTKRAAASGNKLPVAARAAAHELEKADRA-  [SEQ ID NO:28]
```

GENES ENCODING BAEYER-VILLIGER MONOOXYGENASES

This application claims the benefit of U.S. Provisional Application No. 60/315,546, filed Aug. 29, 2001.

FIELD OF THE INVENTION

The invention relates to the field of molecular biology and microbiology. More specifically, genes have been isolated from a variety of bacteria encoding Baeyer-Villiger monooxygenase activity.

BACKGROUND OF THE INVENTION

In 1899, Baeyer and Villiger reported on a reaction of cyclic ketones with peroxymonosulfuric acid to produce lactones (*Chem Ber* 32:3625–3633 (1899)). Since then, the Baeyer-Villiger (BV) reaction has been broadly used in organic synthesis. BV reactions are one of only a few methods available for cleaving specific carbon-carbon bonds under mild conditions, thereby converting ketones into esters (Walsh and Chen, *Angew. Chem. Int. Ed. Engl* 27:333–343 (1988)).

In the last several decades, the importance of minimizing environmental impact in industrial processes has catalyzed a trend whereby alternative methods are replacing established chemical techniques. In the arena of Baeyer-Villiger (BV) oxidations, considerable interest has focused on discovery of enantioselective versions of the Baeyer-Villiger oxidation that are not based on peracids. Enzymes, which are often enantioselective, are valued alternatives as renewable, biodegradable resources.

Many microbial Baeyer-Villiger monooxygenases enzymes (BVMOs), which convert ketones to esters or the corresponding lactones (cyclic esters) (Stewart, *Curr. Org. Chem.* 2:195–216 (1998), have been identified from both bacterial and fungal sources. In general, microbial BV reactions are carried out by monooxygenases (EC 1.14.13.x) which use $O_2$ and either NADH or NADPH as a co-reductant. One of the oxygen atoms is incorporated into the lactone product between the carbonyl carbon and the flanking carbon while the other is used to oxidize the reduced NADPH producing $H_2O$ (Banerjee, A. In *Stereosel, Biocatal.*; Patel, R. N., Ed.; Marcel Dekker: New York, 2000; Chapter 29, pp 867–876). All known BVMOs have a flavin coenzyme which acts in the oxidation reaction; the predominant coenzyme form is flavin adenine dinucleotide cofactor (FAD).

The natural physiological role of most characterized BVMOs is degradation of compounds to permit utilization of smaller hydrocarbons and/or alcohols as sources of carbon and energy. As a result of this, BVMOs display remarkably broad substrate acceptance, high enantioselectivies, and great stereoselctivity and regioselectivity (Mihovilovic et al. *J. Org. Chem.* 66:733–738 (2001). Suitable substrates for the enzymes can be broadly classified as cyclic ketones, ketoterpenes, and steroids. However, few enzymes have been subjected to extensive biochemical characterization. Key studies in relation to each broad ketone substrate class are summarized below.

1. Cyclic ketones: Activity of cyclohexanone monooxygenase upon cyclic ketone substrates in *Acinetobacter* sp. NCIB 9871 has been studied extensively (reviewed in Stewart, *Curr. Org. Chem.* 2:195–216 (1998), Table 2; Walsh and Chen, *Angew. Chem. Int. Ed. Engl* 27:333–343 (1988), Tables 4–5). Specificity has also been biochemically analyzed in *Brevibacterium* sp. HCU (Brzostowicz et al., *J. Bact.* 182(15):4241–4248 (2000)).

2. Ketoterpenes: A monocyclic monoterpene ketone monooxygenase has been characterized from *Rhodococcus erythropolis* DCL14 (Van der Werf, *J. Biochem.* 347:693–701 (2000)). In addition to broad substrate specificity against ketoterpenes, the enzyme also has activity against substituted cyclohexanones.

3. Steroids: The steroid monooxygenase of *Rhodococcus rhodochrous* (Morii et al. *J. Biochem* 126:624–631 (1999)) is well characterized, both biochemically and by sequence data.

The genes and gene products listed above are useful for specific Baeyer-Villiger reactions targeted toward cyclic ketone, ketoterpene, or steroid compounds, however the enzymes are limited in their ability to predict other newly discovered proteins which would have similar activity.

The problem to be solved, therefore is to provide a suite of bacterial flavoprotein Baeyer-Villiger monooxygenase enzymes that can efficiently perform oxygenation reactions on cyclic ketones and ketoterpenes compounds. Identity of a suite of enzymes with this broad substrate acceptance would facilitate commercial applications of these enzymes and reduce efforts with respect to optimization of multiple enzymes for multiple reactions. Maximum efficiency is especially relevant today, when many enzymes are genetically engineered such that the enzyme is recombinantly expressed in a desirable host organism. Additionally, a collection of BVMO's with diverse amino acid sequences could be used to create a general predictive model based on amino acid sequence conservation of other BVMO enzymes. Finally, a broad class of BVMO's could also be used as basis for the in vitro evolution of novel enzymes.

Applicants have solved the stated problem by isolating several novel organisms with BVMO activity, identifying and characterizing BMVO genes, expressing these genes in microbial hosts, and demonstrating activity of the genes against a wide range of ketone substrates, including cyclic ketones and ketoterpenes. Several signature sequences have been identified, based on amino acid sequence alignments, which are characteristic of specific BVMO families and have diagnostic utility.

SUMMARY OF THE INVENTION

The invention provides an isolated nucleic acid fragment isolated from Rhodococcus selected from the group consisting of:

(a) an isolated nucleic acid fragment encoding a Baeyer-Villiger monooxygenase polypeptide having an amino acid sequence selected from the group consisting of SEQ ID NOs:8, 10, 22, 24, 26, 28, 30, 32, 34, 36, 38, 40, 42, 44, and 46.

(b) an isolated nucleic acid molecule encoding a Baeyer-Villiger monooxygenase polypeptide that hybridizes with (a) under the following hybridization conditions: 0.1×SSC, 0.1% SDS, 65° C. and washed with 2×SSC, 0.1% SDS followed by 0.1×SSC, 0.1% SDS; or an isolated nucleic acid fragment that is complementary to (a) or (b).

Similarly the invention provides an isolated nucleic acid fragment isolated from *Arthrobacter* selected from the group consisting of:

(a) an isolated nucleic acid fragment encoding a Baeyer-Villiger monooxygenase polypeptide having an amino acid sequence as set forth in SEQ ID NO:12;

(b) an isolated nucleic acid molecule encoding a Baeyer-Villiger monooxygenase polypeptide that hybridizes with (a) under the following hybridization conditions: 0.1×SSC, 0.1% SDS, 65° C. and washed with 2×SSC, 0.1% SDS followed by 0.1×SSC, 0.1% SDS; or an isolated nucleic acid fragment that is complementary to (a), or (b).

Additionally the invention provides an isolated nucleic acid fragment isolated from Acidovorax selected from the group consisting of:

(a) an isolated nucleic acid fragment encoding a Baeyer-Villiger monooxygenase polypeptide having an amino acid sequence as set forth in SEQ ID NO:18

(b) an isolated nucleic acid molecule encoding a Baeyer-Villiger monooxygenase polypeptide that hybridizes with (a) under the following hybridization conditions: 0.1×SSC, 0.1% SDS, 65° C. and washed with 2×SSC, 0.1% SDS followed by 0.1×SSC, 0.1% SDS; or an isolated nucleic acid fragment that is complementary to (a), or (b).

In additional embodiments the invention provides polypeptides encoded by the present sequences as well as genetic chimera of the present sequences and transformed hosts expressing the same.

In a preferred embodiment the invention provides a method for the identification of a polypeptide having monooxygenase activity comprising:

(a) obtaining the amino acid sequence of a polypeptide suspected of having monooxygenase activity; and (b) aligning the amino acid sequence of step (a) with the amino acid sequence of a Baeyer-Villiger monooxygenase consensus sequence selected from the group consisting of SEQ ID NO:47, SEQ ID NO:48 and SEQ ID NO:49, wherein where at least 80% of the amino acid residues at positions p1–p74 of SEQ ID NO:47, or at least 80% of the amino acid residues at p1–p76 of SEQ ID NO:48 or at least 80% of the amino acid residues of p1–p41 of SEQ ID NO:49 are completely conserved, the polypeptide of (a) is identified as having monooxygenase activity.

In an alternate embodiment the invention provides a method for identifying a gene encoding a Baeyer-Villiger monooxygenase polypeptide comprising:

(a) probing a genomic library with a nucleic acid fragment encoding a polypeptide wherein where at least 80% of the amino acid residues at positions p1–p74 of SEQ ID NO:47, or at least 80% of the amino acid residues at p1–p76 of SEQ ID NO:48 or at least 80% of the amino acid residues of p1–p41 of SEQ ID NO:49 are completely conserved;

(b) identifying a DNA clone that hybridizes with a nucleic acid fragment of step (a);

(c) sequencing the genomic fragment that comprises the clone identified in step (b), wherein the sequenced genomic fragment encodes a Baeyer-Villiger monooxygenase polypeptide.

In a preferred embodiment the invention provides a method for the biotransformation of a ketone substrate to the corresponding ester, comprising: contacting a transformed host cell under suitable growth conditions with an effective amount of ketone substrate whereby the corresponding ester is produced, said transformed host cell comprising a nucleic acid fragment encoding an isolated nucleic acid fragment of any of the present nucleic acid sequences; under the control of suitable regulatory sequences.

In an alternate embodiment the invention provides a method for the in vitro transformation of a ketone substrate to the corresponding ester, comprising: contacting a ketone substrate under suitable reaction conditions with an effective amount of a Baeyer-Villiger monooxygenase enzyme, the enzyme having an amino acid seqeunce selected from the group consisting of SEQ ID NOs:8, 10, 22, 24, 26, 28, 30, 32, 34, 36, 38, 40, 42, 44, and 46.

Additionally the invention provides a mutated microbial gene encoding a protein having an altered biological activity produced by a method comprising the steps of:

(i) digesting a mixture of nucleotide sequences with restriction endonucleases wherein said mixture comprises:
  a) a native microbial gene selected from the group consisting of SEQ ID NOs:7, 9, 11, 13, 15, 17, 19, 21, 23, 25, 27, 29, 31, 33, 35, 37, 39, 41, 43, and 45;
  b) a first population of nucleotide fragments which will hybridize to said native microbial sequence;
  c) a second population of nucleotide fragments which will not hybridize to said native microbial sequence;
  wherein a mixture of restriction fragments are produced;
(ii) denaturing said mixture of restriction fragments;
(iii) incubating the denatured said mixture of restriction fragments of step (ii) with a polymerase;
(iv) repeating steps (ii) and (iii) wherein a mutated microbial gene is produced encoding a protein having an altered biological activity. Additionally the invention provides unique strains of Acidovorax sp. comprising the 16s rDNA sequence as set forth in SEQ ID NO:5, Arthrobacter sp. comprising the 16s rDNA sequence as set forth in SEQ ID NO:1, and Rhodococcus sp. comprising the 16s rDNA sequence as set forth in SEQ ID NO:6.

In another embodiment the invention provides an Acidovorax sp. comprising the 16s rDNA sequence as set forth in SEQ ID NO:5. Additionally the invention provides an Arthrobacter sp. comprising the 16s rDNA sequence as set forth in SEQ ID NO:1. Similarly the invention provides a Rhodococcus sp. comprising the 16s rDNA sequence as set forth in SEQ ID NO:6.

Additionally the invention provides an isolated nucleic acid useful for the identification of a BV monooxygenase selected from the group consisting of SEQ ID 70–113.

BRIEF DESCRIPTION OF THE DRAWINGS AND SEQUENCE DESCRIPTIONS

FIGS. 1, 2, 3, 4, and 5 show chnB monooxygenase activity of Brevibacterium sp. HCU, Acinetobacter SE19, Rhodococcus sp. phi1, Rhodococcus sp. phi2, Arthrobacter sp. BP2 and Acidovorax sp. CHX genes over-expressed in E. coli assayed against various ketone substrates.

FIG. 6 illustrates the signature sequences of the three BVMO groups based on the consensus sequences derived from the alignments of FIG. 7, FIG. 8 and FIG. 9.

FIG. 7 shows a Clustal W alignment of a family of Baeyer-Villiger monoxygenases (Family 1) and the associated signature sequence.

FIG. 8 shows a Clustal W alignment of a family of Baeyer-Villiger monoxygenases (Family 2) and the associated signature sequence.

FIG. 9 shows a Clustal W alignment of a family of BC monoxygenases (Family 3) and the associated signature sequence.

Figure 1:
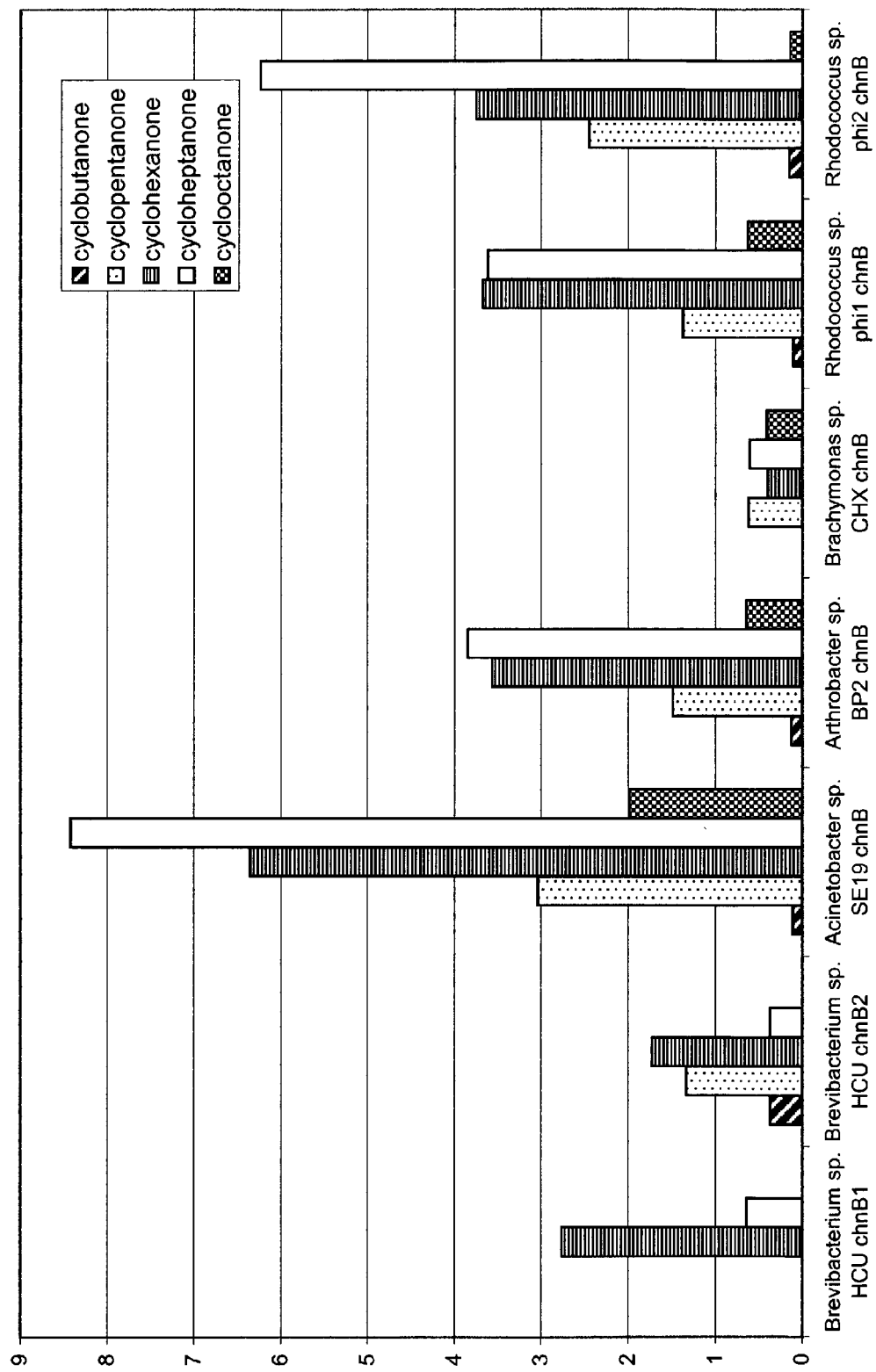

The invention can be more fully understood from the following detailed description and the accompanying sequence descriptions which form a part of this application.

The following sequences conform with 37 C.F.R. 1.821–1.825 ("Requirements for Patent Applications Containing Nucleotide Sequences and/or Amino Acid Sequence Disclosures—the Sequence Rules") and consistent with World Intellectual Property Organization (WIPO) Standard ST.25 (1998) and the sequence listing requirements of the EPO and PCT (Rules 5.2 and 49.5 (a-bis), and Section 208 and Annex C of the Administrative Instructions). The symbols and format used for nucleotide and amino acid sequence data comply with the rules set forth in 37 C.F.R. §1.822.

SEQ ID NOs:1–49 are full length genes or proteins as identified in Table 1.

TABLE 1

Summary of Gene and Protein SEQ ID Numbers

| Gene Name | Organism | Gene SEQ ID No | Protein SEQ ID No |
|---|---|---|---|
| 16s rDNA sequence | *Arthrobacter* sp. BP2 | 1 | — |
| 16s rDNA sequence | *Rhodococcus* sp. phi1 | 2 | — |
| 16s rDNA sequence | *Rhodococcus* sp. phi2 | 3 | — |
| 16s rDNA sequence | *Brevibacterium* sp. HCU | 4 | — |
| 16s rDNA sequence | *Acidovorax* sp. CHX | 5 | — |
| 16s rDNA sequence | *Rhodococcus erythropolis* AN12 | 6 | — |
| chnB Monooxygenase phi1 | *Rhodococcus* sp. phi1 | 7 | 8 |
| chnB Monooxygenase phi2 | *Rhodococcus* sp. phi2 | 9 | 10 |
| chnB Monooxygenase BP2 | *Arthrobacter* sp. BP2 | 11 | 12 |
| chnB1 Monooxygenase HCU #1 | *Brevibacterium* sp. HCU | 13 | 14 |
| chnB2 Monooxygenase HCU #2 | *Brevibacterium* sp. HCU | 15 | 16 |
| chnB Monooxygenase CHX | *Acidovorax* sp. CHX | 17 | 18 |
| chnB Monooxygenase SE19 | *Acinetobacter* sp. SE19 | 19 | 20 |
| ORF 8 chnB Monooxygenase (1413) | *Rhodococcus erythropolis* AN12 | 21 | 22 |
| ORF 9 chnB Monooxygenase (1985) | *Rhodococcus erythropolis* AN12 | 23 | 24 |
| ORF 10 chnB Monooxygenase (1273) | *Rhodococcus erythropolis* AN12 | 25 | 26 |
| ORF 11 chnB Monooxygenase (2034) | *Rhodococcus erythropolis* AN12 | 27 | 28 |
| ORF 12 chnB Monooxygenase (1870) | *Rhodococcus erythropolis* AN12 | 29 | 30 |
| ORF 13 chnB Monooxygenase (1861) | *Rhodococcus erythropolis* AN12 | 31 | 32 |
| ORF 14 chnB Monooxygenase (2005) | *Rhodococcus erythropolis* AN12 | 33 | 34 |
| ORF 15 chnB Monooxygenase (2035) | *Rhodococcus erythropolis* AN12 | 35 | 36 |
| ORF 16 chnB Monooxygenase (2022) | *Rhodococcus erythropolis* AN12 | 37 | 38 |
| ORF 17 chnB Monooxygenase (1976) | *Rhodococcus erythropolis* AN12 | 39 | 40 |
| ORF 18 chnB Monooxygenase (1294) | *Rhodococcus erythropolis* AN12 | 41 | 42 |
| ORF 19 chnB Monooxygenase (2082) | *Rhodococcus erythropolis* AN12 | 43 | 44 |
| ORF 20 chnB Monooxygenase (2093) | *Rhodococcus erythropolis* AN12 | 45 | 46 |
| Signature Sequence #1 | Consensus Sequence | — | 47 |
| Signature Sequence #2 | Consensus Sequence | — | 48 |
| Signature Sequence #3 | Consensus Sequence | — | 49 |

SEQ ID NOs:50–62 are primers used for 16s rDNA sequencing.

SEQ ID NO:63 describes a primer used for RT-PCR and out-PCR.

SEQ ID NOs:64 and 65 are primers used for sequencing of inserts within pCR2.1

SEQ ID NOs:66 and 67 are primers used to amplify monooxygenase genes from *Acinetobacter* sp. SE19.

SEQ ID NOs:68–107 are primers used for amplification of full length Baeyer-Villiger monooxygenases.

SEQ ID NOs:108–113 are primers used to screen cosmid libraries.

DETAILED DESCRIPTION OF THE INVENTION

The invention provides nucleic acid and amino acid sequences defining a group of Baeyer-Villiger monooxygenase enzymes. These enzymes have been found to have the ability to use a wide variety of ketone substrates that include two general classes of compounds, cyclic ketones and ketoterpenes. These enzymes are characterized by function as well as a series of diagnostic signature sequences. The enzymes may be expressed recombinantly for the conversion of ketone substrates to the corresponding lactones or esters.

In this disclosure, a number of terms and abbreviations are used. The following definitions are provided.

"Open reading frame" is abbreviated ORF.

"Polymerase chain reaction" is abbreviated PCR.

"Gas Chromatography Mass spectrometry" is abbreviated GC-MS.

"Baeyer-Villiger" is abbreviated BV.

"Baeyer-Villiger monooxygenase" is abbreviated BVMO.

The term "Baeyer-Villiger monooxygenase", refers to a bacterial enzyme that has the ability to oxidize a ketone substrate to the corresponding lactone or ester.

The term "ketone substrate" includes a substrate for a Baeyer-Villiger monooxygenase that comprises a class of compounds which include cyclic ketones and ketoterpenes. Ketone substrates of the invention are defined by the general formula:

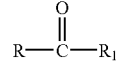

wherein R and $R_1$ are independently selected from substituted or unsubstituted phenyl, substituted or unsubstituted alkyl, substituted or unsubstituted alkenyl, or substituted or unsubstituted alkylidene.

The term "alkyl" will mean a univalent group derived from alkanes by removal of a hydrogen atom from any carbon atom: $C_nH_{2n+1}$—. The groups derived by removal of a hydrogen atom from a terminal carbon atom of unbranched alkanes form a subclass of normal alkyl (n-alkyl) groups: $H[CH_2]_n$—. The groups $RCH_2$—, $R_2CH$— (R not equal to H), and $R_3C$— (R not equal to H) are primary, secondary and tertiary alkyl groups respectively.

The term "alkenyl" will mean an acyclic branched or unbranched hydrocarbon having one carbon-carbon double bond and the general formula $C_nH_{2n}$. Acyclic branched or unbranched hydrocarbons having more than one double bond are alkadienes, alkatrienes, etc.

The term "alkylidene" will mean the divalent groups formed from alkanes by removal of two hydrogen atoms from the same carbon atom, the free valiances of which are part of a double bond (e.g. $(CH_3)_2C$, also known as propan-2-ylidene).

As used herein, an "isolated nucleic acid molecule" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

A nucleic acid molecule is "hybridizable" to another nucleic acid molecule, such as a cDNA, genomic DNA, or RNA, when a single stranded form of the nucleic acid molecule can anneal to the other nucleic acid molecule under the appropriate conditions of temperature and solution ionic strength. Hybridization and washing conditions are well known and exemplified in Sambrook, J., Fritsch, E. F. and Maniatis, T. *Molecular Cloning: A Laboratory Manual*, Second Edition, Cold Spring Harbor Laboratory Press, Cold Spring Harbor (1989), particularly Chapter 11 and Table 11.1 therein (entirely incorporated herein by reference). The conditions of temperature and ionic strength determine the "stringency" of the hybridization. Stringency conditions can be adjusted to screen for moderately similar fragments, such as homologous sequences from distantly related organisms, to highly similar fragments, such as genes that duplicate functional enzymes from closely related organisms. Typical stringent hybridization conditions are for example, hybridization at 0.1×SSC, 0.1% SDS, 65° C. with a wash with 2×SSC, 0.1% SDS followed by 0.1×SSC, 0.1% SDS. Generally post-hybridization washes determine stringency conditions. One set of preferred conditions uses a series of washes starting with 6×SSC, 0.5% SDS at room temperature for 15 min, then repeated with 2×SSC, 0.5% SDS at 45° C. for 30 min, and then repeated twice with 0.2×SSC, 0.5% SDS at 50° C. for 30 min. A more preferred set of stringent conditions uses higher temperatures in which the washes are identical to those above except for the temperature of the final two 30 min washes in 0.2×SSC, 0.5% SDS was increased to 60° C. Another preferred set of highly stringent conditions uses two final washes in 0.1×SSC, 0.1% SDS at 65° C. Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of Tm for hybrids of nucleic acids having those sequences. The relative stability (corresponding to higher Tm) of nucleic acid hybridizations decreases in the following order: RNA: RNA, DNA:RNA, DNA:DNA. For hybrids of greater than 100 nucleotides in length, equations for calculating Tm have been derived (see Sambrook et al., supra, 9.50–9.51). For hybridizations with shorter nucleic acids, i.e., oligonucleotides, the position of mismatches becomes more important, and the length of the oligonucleotide determines its specificity (see Sambrook et al., supra, 11.7–11.8). In one embodiment the length for a hybridizable nucleic acid is at least about 10 nucleotides. Preferable a minimum length for a hybridizable nucleic acid is at least about 15 nucleotides; more preferably at least about 20 nucleotides; and most preferably the length is at least 30 nucleotides. Furthermore, the skilled artisan will recognize that the temperature and wash solution salt concentration may be adjusted as necessary according to factors such as length of the probe.

The term "complementary" is used to describe the relationship between nucleotide bases that are capable to hybridizing to one another. For example, with respect to DNA, adenosine is complementary to thymine and cytosine is complementary to guanine. Accordingly, the instant invention also includes isolated nucleic acid fragments that are complementary to the complete sequences as reported in the accompanying Sequence Listing as well as those substantially similar nucleic acid sequences.

The term "percent identity", as known in the art, is a relationship between two or more polypeptide sequences or two or more polynucleotide sequences, as determined by comparing the sequences. In the art, "identity" also means the degree of sequence relatedness between polypeptide or polynucleotide sequences, as the case may be, as determined by the match between strings of such sequences. "Identity" and "similarity" can be readily calculated by known methods, including but not limited to those described in: *Computational Molecular Biology* (Lesk, A. M., ed.) Oxford University Press, New York (1988); *Biocomputing: Informatics and Genome Projects* (Smith, D. W., ed.) Academic Press, New York (1993); *Computer Analysis of Sequence Data, Part I* (Griffin, A. M., and Griffin, H. G., eds.) Humana Press, New Jersey (1994); *Sequence Analysis in Molecular Biology* (von Heinje, G., ed.) Academic Press (1987); and *Sequence Analysis Primer* (Gribskov, M. and Devereux, J., eds.) Stockton Press, New York (1991). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR Inc., Madison, Wis.). Multiple alignment of the sequences was performed using the Clustal method of alignment (Higgins and Sharp (1989) *CABIOS*. 5:151–153) with the default parameters (GAP PENALTY=10, GAP LENGTH PENALTY=10). Default parameters for pairwise alignments using the Clustal method were KTUPLE 1, GAP PENALTY=3, WINDOW=5 and DIAGONALS SAVED=5.

Suitable nucleic acid fragments (isolated polynucleotides of the present invention) encode polypeptides that are at least about 70% identical, preferably at least about 80% identical to the amino acid sequences reported herein. Preferred nucleic acid fragments encode amino acid sequences that are about 85% identical to the amino acid sequences reported herein. More preferred nucleic acid fragments encode amino acid sequences that are at least about 90% identical to the amino acid sequences reported herein. Most preferred are nucleic acid fragments that encode amino acid sequences that are at least about 95% identical to the amino acid sequences reported herein. Suitable nucleic acid fragments not only have the above homologies but typically encode a polypeptide having at least 50 amino acids, preferably at least 100 amino acids, more preferably at least 150 amino acids, still more preferably at least 200 amino acids, and most preferably at least 250 amino acids.

"Codon degeneracy" refers to the nature in the genetic code permitting variation of the nucleotide sequence without effecting the amino acid sequence of an encoded polypeptide. Accordingly, the instant invention relates to any nucleic acid fragment that encodes all or a substantial portion of the amino acid sequence encoding the instant microbial polypeptides as set forth in SEQ ID NOs:8, 10, 12, 14, 16, 18, 20, 22, 24, 26, 28, 30, 32, 34, 36, 38, 40, 42, 44, and 46. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structures.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined, DNA fragments of different lengths may have identical promoter activity.

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 9928508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Transformation" refers to the transfer of a nucleic acid fragment into the genome of a host organism, resulting in genetically stable inheritance. Host organisms containing the transformed nucleic acid fragments are referred to as "transgenic" or "recombinant" or "transformed" organisms.

The terms "plasmid", "vector" and "cassette" refer to an extra chromosomal element often carrying genes which are not part of the central metabolism of the cell, and usually in the form of circular double-stranded DNA molecules. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403–410 (1990), and DNASTAR (DNASTAR, Inc. 1228 S. Park St. Madison, Wis. 53715 USA), and the FASTA program incorporating the Smith-Waterman algorithm (W. R. Pearson, *Comput. Methods Genome Res.*, [Proc. Int. Symp.] (1994), Meeting Date 1992, 111–20. Editor(s): Suhai, Sandor. Publisher: Plenum, New York, N.Y.). Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

The term "signature sequence" means a set of amino acids conserved at specific positions along an aligned sequence of evolutionarily related proteins. While amino acids at other positions can vary between homologous proteins, amino acids which are highly conserved at specific positions indicate amino acids which are essential in the structure, the stability, or the activity of a protein. Because they are identified by their high degree of conservation in aligned sequences of a family of protein homologues, they can be used as identifiers, or "signatures", to determine if a protein with a newly determined sequence belongs to a previously identified protein family. Signature sequences of the present invention are specifically described FIG. 6 showing the signature sequence comprised of p1–p74 of SEQ ID NO:47, p1–p76 of SEQ ID NO:48 and p1–p41 of SEQ ID NO:49.

Standard recombinant DNA and molecular cloning techniques used here are well known in the art and are described by Sambrook, J., Fritsch, E. F. and Maniatis, T., *Molecular Cloning: A Laboratory Manual*, Second Edition, Cold Spring Harbor Laboratory Press, Cold Spring Harbor, N.Y. (1989) (hereinafter "Maniatis"); and by Silhavy, T. J., Bennan, M. L. and Enquist, L. W., *Experiments with Gene Fusions*, Cold Spring Harbor Laboratory Cold Press Spring Harbor, N.Y. (1984); and by Ausubel, F. M. et al., *Current Protocols in Molecular Biology*, published by Greene Publishing Assoc. and Wiley-Interscience (1987).

Isolation of Microorganisms Having Baeyer-Villiger Monooxygenase Activity

Microorganisms having Baeyer-Villiger monooxygenase activity may be isolated from a variety of sources. Suitable sources include industrial waste streams, soil from contaminated industrial sites and waste stream treatment facilities. The Baeyer-Villiger monooxygenase containing microorganisms of the instant invention were isolated from activated sludge from waste water treatment plants.

Samples suspected of containing a microorganism having Baeyer-Villiger monooxygenase activity may be enriched by incubation in a suitable growth medium in combination with at least one ketone substrate. Suitable ketone substrates for use in the instant invention include cyclic ketones and ketoterpenes having the general formula:

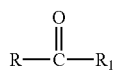

wherein R and $R_1$ are independently selected from substituted or unsubstituted phenyl, substituted or unsubstituted alkyl, or substituted or unsubstituted alkenyl or substituted or unsubstituted alkylidene. These compounds may be synthetic or natural secondary metabolites Particularly useful ketone substrates include, but are not limited to Norcamphor, Cyclobutanone, Cyclopentanone, 2-methyl-cyclopentanone, Cyclohexanone, 2-methyl-cyclohexanone, Cyclohex-2-ene-1-one, 1,2-cyclohexanedione, 1,3-cyclohexanedione, 1,4-cyclohexanedione, Cycloheptanone, Cyclooctanone, Cyclodecanone, Cycloundecanone, Cyclododecanone, Cyclotridecanone, Cyclopenta-decanone, 2-tridecanone, dihexyl ketone, 2-phenyl-cyclohexanone, Oxindole, Levoglucosenone, dimethyl sulfoxide, dimethy-2-piperidone, Phenylboronic acid, and beta-ionone. Growth medium and techniques needed in the enrichment and screening of microorganisms are well known in the art and examples may be found in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)); or by Thomas D. Brock in *Biotechnology: A Textbook of Industrial Microbiology*, Second Edition, Sinauer Associates, Inc., Sunderland, Mass. (1989).

Characterization of the Baeyer-Villiger Monooxygenase Containing Microorganisms:

The sequence of the small subunit ribosomal RNA or DNA (16S rDNA) is frequently used for taxonomic identification of novel bacterial. Currently, more than 7,000 bacterial 16S rDNA sequences are now available. Highly conserved regions of the 16S rDNA provide priming sites for broad-range polymerase chain reaction (PCR) (or RT-PCR) and obviate the need for specific information about a targeted microorganism before this procedure. This permits identification of a previously uncharacterized bacterium by broad range bacterial 16S rDNA amplification, sequencing, and phylogenetic analysis.

This invention describes the isolation and identification of 7 different bacteria based on their taxonomic identification following amplification of the 16S rDNA using primers corresponding to conserved regions of the 16S rDNA molecule (Amann, R. I. et al. *Microbiol. Rev.* 59(1):143–69 (1995); Kane, M. D. et al. *Appl. Environ. Microbiol.* 59:682–686 (1993)), followed by sequencing and BLAST analysis (Basic Local Alignment Search Tool; Altschul, S. F., et al., *J. Mol. Biol.* 215:403–410 (1993); see also www.ncbi.nlm.nih.gov/BLAST/). Bacterial strains were identified as highly homologous to bacteria of the genera *Brevibacterium, Arthrobacter, Acinetobacter, Acidovorax,* and *Rhodococcus*.

Comparison of the 16S rRNA nucleotide base sequence from strain AN12 to public databases reveals that the most similar known sequences (98% homologous) are the 16S rRNA gene sequences of bacteria belonging to the genus *Rhodococcus*.

Comparison of the 16S rRNA nucleotide base sequence from strain CHX to public databases reveals that the most similar known sequences (97% homologous) are the 16S rRNA gene sequences of bacteria of the genus *Acidovorax*.

Comparison of the 16S rRNA nucleotide base sequence from strain BP2 to public databases reveals that the most similar known sequences (99% homologous) are the 16S rRNA gene sequences of bacteria of the genus *Arthrobacter*.

Comparison of the 16S rRNA nucleotide base sequence from strain SE19 to public databases reveals that the most similar known sequences (99% homologous) are the 16S rRNA gene sequences of bacteria of the genus *Acinetobacter*.

Comparison of the 16S rRNA nucleotide base sequence from strains phi1 and phi2 to public databases reveals that the most similar known sequences (99% homologous) are the 16S rRNA gene sequences of bacteria belonging to the genus *Rhodococcus*.

Identification of Baeyer-Villiger Monooxygenase Homologs

The present invention provides examples of Baeyer-Villiger monooxygenase genes and gene products having the ability to convert suitable ketone substrates comprising cyclic ketones and ketoterpenes to the corresponding lactone or ester. For example, genes encoding BVMO's have been isolated from *Arthrobacter* (SEQ ID NO:11), *Brevibacterium* (SEQ ID NOs:13 and 15), *Acidovorax* (SEQ ID NO:17), *Acinetobacter* (SEQ ID NO:19), and *Rhodococcus* (SEQ ID NOs:7, 9, 21, 23, 25, 27, 29, 31, 33, 35, 37, 39, 41, 43, and 45).

Comparison of the *Arthrobacter* sp. BP2 chnB nucleotide base and deduced amino acid sequences to public databases reveals that the most similar known sequences range from a distant as about 57% identical to the amino acid sequence of reported herein over length of 532 amino acids using a Smith-Waterman alignment algorithm (W. R. Pearson, supra). Preferred amino acid fragments are at least about 70%–80% and more preferred amino acid fragments are at least about 80%–90% identical to the sequences herein. Most preferred are nucleic acid fragments that are at least 95% identical to the amino acid fragments reported herein. Similarly, preferred chnB encoding nucleic acid sequences corresponding to the instant ORF's are those encoding active proteins and which are at least 80% identical to the nucleic acid sequences reported herein. More preferred chnB nucleic acid fragments are at least 90% identical to the sequences herein. Most preferred are chnB nucleic acid fragments that are at least 95% identical to the nucleic acid fragments reported herein.

Comparison of the *Acidovorax* sp. CHX chnB nucleotide base and deduced amino acid sequences to public databases reveals that the most similar known sequences range from a distant as about 57% identical to the amino acid sequence of reported herein over length of 538 amino acids using a Smith-Waterman alignment algorithm (W. R. Pearson, supra). Preferred amino acid fragments are at least about 70%–80% and more preferred amino acid fragments are at least about 80%–90% identical to the sequences herein. Most preferred are nucleic acid fragments that are at least 95% identical to the amino acid fragments reported herein. Similarly, preferred chnB encoding nucleic acid sequences corresponding to the instant ORF's are those encoding active proteins and which are at least 80% identical to the nucleic acid sequences reported herein. More preferred chnB nucleic acid fragments are at least 90% identical to the sequences herein. Most preferred are chnB nucleic acid fragments that are at least 95% identical to the nucleic acid fragments reported herein.

Comparison of the *Rhodococcus* sp. phi1 chnB nucleotide base and deduced amino acid sequences to public databases reveals that the most similar known sequences range from a distant as about 55% identical to the amino acid sequence of reported herein over length of 542 amino acids using a Smith-Waterman alignment algorithm (W. R. Pearson, supra). Preferred amino acid fragments are at least about 70%–80% and more preferred amino acid fragments are at least about 80%–90% identical to the sequences herein. Most preferred are nucleic acid fragments that are at least 95% identical to the amino acid fragments reported herein. Similarly, preferred chnB encoding nucleic acid sequences corresponding to the instant ORF's are those encoding active proteins and which are at least 80% identical to the nucleic acid sequences reported herein. More preferred chnB nucleic acid fragments are at least 90% identical to the sequences herein. Most preferred are chnB nucleic acid fragments that are at least 95% identical to the nucleic acid fragments reported herein.

Comparison of the *Rhodococcus* sp. phi2 chnB nucleotide base and deduced amino acid sequences to public databases reveals that the most similar known sequences range from a distant as about 53% identical to the amino acid sequence of reported herein over length of 541 amino acids using a Smith-Waterman alignment algorithm (W. R. Pearson, supra). Preferred amino acid fragments are at least about 70%–80% and more preferred amino acid fragments are at least about 80%–90% identical to the sequences herein. Most preferred are nucleic acid fragments that are at least 95% identical to the amino acid fragments reported herein. Similarly, preferred chnB encoding nucleic acid sequences corresponding to the instant ORF's are those encoding active proteins and which are at least 80% identical to the nucleic acid sequences reported herein. More preferred chnB nucleic acid fragments are at least 90% identical to the sequences herein. Most preferred are chnB nucleic acid fragments that are at least 95% identical to the nucleic acid fragments reported herein.

Comparison of the *Rhodococcus erythropolis* AN12 ORF8 chnB nucleotide base and deduced amino acid sequences to public databases reveals that the most similar known sequences range from a distant as about 37% identical to the amino acid sequence of reported herein over length of 439 amino acids using a Smith-Waterman alignment algorithm (W. R. Pearson, supra). Preferred amino acid fragments are at least about 70%–80% and more preferred amino acid fragments are at least about 80%–90% identical to the sequences herein. Most preferred are nucleic acid fragments that are at least 95% identical to the amino acid fragments reported herein. Similarly, preferred chnB encoding nucleic acid sequences corresponding to the instant ORF's are those encoding active proteins and which are at least 80% identical to the nucleic acid sequences reported herein. More preferred chnB nucleic acid fragments are at least 90% identical to the sequences herein. Most preferred are chnB nucleic acid fragments that are at least 95% identical to the nucleic acid fragments reported herein.

Comparison of the *Rhodococcus erythropolis* AN1 ORF9 chnB nucleotide base and deduced amino acid sequences to public databases reveals that the most similar known sequences range from a distant as about 44% identical to the amino acid sequence of reported herein over length of 518 amino acids using a Smith-Waterman alignment algorithm (W. R. Pearson, supra). Preferred amino acid fragments are at least about 70%–80% and more preferred amino acid fragments are at least about 80%–90% identical to the sequences herein. Most preferred are nucleic acid fragments that are at least 95% identical to the amino acid fragments reported herein. Similarly, preferred chnB encoding nucleic acid sequences corresponding to the instant ORF's are those encoding active proteins and which are at least 80% identical to the nucleic acid sequences reported herein. More preferred chnB nucleic acid fragments are at least 90% identical to the sequences herein. Most preferred are chnB nucleic acid fragments that are at least 95% identical to the nucleic acid fragments reported herein.

Comparison of the *Rhodococcus erythropolis* AN1 ORF10 chnB nucleotide base and deduced amino acid sequences to public databases reveals that the most similar known sequences range from a distant as about 64% identical to the amino acid sequence of reported herein over length of 541 amino acids using a Smith-Waterman alignment algorithm (W. R. Pearson, supra). Preferred amino acid fragments are at least about 70%–80% and more preferred amino acid fragments are at least about 80%–90% identical to the sequences herein. Most preferred are nucleic acid fragments that are at least 95% identical to the amino acid fragments reported herein. Similarly, preferred chnB encoding nucleic acid sequences corresponding to the instant ORF's are those encoding active proteins and which are at least 80% identical to the nucleic acid sequences reported herein. More preferred chnB nucleic acid fragments are at least 90% identical to the sequences herein. Most preferred are chnB nucleic acid fragments that are at least 95% identical to the nucleic acid fragments reported herein.

Comparison of the *Rhodococcus erythropolis* AN1 ORF11 chnB nucleotide base and deduced amino acid sequences to public databases reveals that the most similar known sequences range from a distant as about 65% identical to the amino acid sequence of reported herein over length of 462 amino acids using a Smith-Waterman alignment algorithm (W. R. Pearson, supra). Preferred amino acid fragments are at least about 70%–80% and more preferred amino acid fragments are at least about 80%–90% identical to the sequences herein. Most preferred are nucleic acid fragments that are at least 95% identical to the amino acid fragments reported herein. Similarly, preferred chnB encoding nucleic acid sequences corresponding to the instant ORF's are those encoding active proteins and which are at least 80% identical to the nucleic acid sequences reported herein. More preferred chnB nucleic acid fragments are at least 90% identical to the sequences herein. Most preferred are chnB nucleic acid fragments that are at least 95% identical to the nucleic acid fragments reported herein.

Comparison of the *Rhodococcus erythropolis* AN1 ORF12 chnB nucleotide base and deduced amino acid sequences to public databases reveals that the most similar known sequences range from a distant as about 45% identical to the amino acid sequence of reported herein over length of 523 amino acids using a Smith-Waterman alignment algorithm (W. R. Pearson, supra). Preferred amino acid fragments are at least about 70%–80% and more preferred amino acid fragments are at least about 80%–90% identical to the sequences herein. Most preferred are nucleic acid fragments that are at least 95% identical to the amino acid fragments reported herein. Similarly, preferred chnB encoding nucleic acid sequences corresponding to the instant ORF's are those encoding active proteins and which are at least 80% identical to the nucleic acid sequences reported herein. More preferred chnB nucleic acid fragments are at least 90% identical to the sequences herein. Most preferred are chnB nucleic acid fragments that are at least 95% identical to the nucleic acid fragments reported herein.

Comparison of the *Rhodococcus erythropolis* AN1 ORF13 chnB nucleotide base and deduced amino acid sequences to public databases reveals that the most similar known sequences range from a distant as about 55% identical to the amino acid sequence of reported herein over length of 493 amino acids using a Smith-Waterman alignment algorithm (W. R. Pearson, supra). Preferred amino acid fragments are at least about 70%–80% and more preferred amino acid fragments are at least about 80%–90% identical to the sequences herein. Most preferred are nucleic acid fragments that are at least 95% identical to the amino acid fragments reported herein. Similarly, preferred chnB encoding nucleic acid sequences corresponding to the instant ORF's are those encoding active proteins and which are at least 80% identical to the nucleic acid sequences reported herein. More preferred chnB nucleic acid fragments are at least 90% identical to the sequences herein. Most preferred are chnB nucleic acid fragments that are at least 95% identical to the nucleic acid fragments reported herein.

Comparison of the *Rhodococcus erythropolis* AN1 ORF14 chnB nucleotide base and deduced amino acid sequences to public databases reveals that the most similar known sequences range from a distant as about 51% identical to the amino acid sequence of reported herein over length of 539 amino acids using a Smith-Waterman alignment algorithm (W. R. Pearson, supra). Preferred amino acid fragments are at least about 70%–80% and more preferred amino acid fragments are at least about 80%–90% identical to the sequences herein. Most preferred are nucleic acid fragments that are at least 95% identical to the amino acid fragments reported herein. Similarly, preferred chnB encoding nucleic acid sequences corresponding to the instant ORF's are those encoding active proteins and which are at least 80% identical to the nucleic acid sequences reported herein. More preferred chnB nucleic acid fragments are at least 90% identical to the sequences herein. Most preferred are chnB nucleic acid fragments that are at least 95% identical to the nucleic acid fragments reported herein.

Comparison of the *Rhodococcus erythropolis* AN1 ORF15 chnB nucleotide base and deduced amino acid sequences to public databases reveals that the most similar known sequences range from a distant as about 39% identical to the amino acid sequence of reported herein over length of 649 amino acids using a Smith-Waterman alignment algorithm (W. R. Pearson, supra). Preferred amino acid fragments are at least about 70%–80% and more preferred amino acid fragments are at least about 80%–90% identical to the sequences herein. Most preferred are nucleic acid fragments that are at least 95% identical to the amino acid fragments reported herein. Similarly, preferred chnB encoding nucleic acid sequences corresponding to the instant ORF's are those encoding active proteins and which are at least 80% identical to the nucleic acid sequences reported herein. More preferred chnB nucleic acid fragments are at least 90% identical to the sequences herein. Most preferred are chnB nucleic acid fragments that are at least 95% identical to the nucleic acid fragments reported herein.

Comparison of the *Rhodococcus erythropolis* AN1 ORF16 chnB nucleotide base and deduced amino acid sequences to public databases reveals that the most similar known sequences range from a distant as about 43% identical to the amino acid sequence of reported herein over length of 494 amino acids using a Smith-Waterman alignment algorithm (W. R. Pearson, supra). Preferred amino acid fragments are at least about 70%–80% and more preferred amino acid fragments are at least about 80%–90% identical to the sequences herein. Most preferred are nucleic acid fragments that are at least 95% identical to the amino acid fragments reported herein. Similarly, preferred chnB encoding nucleic acid sequences corresponding to the instant ORF's are those encoding active proteins and which are at least 80% identical to the nucleic acid sequences reported herein. More preferred chnB nucleic acid fragments are at least 90% identical to the sequences herein. Most preferred are chnB nucleic acid fragments that are at least 95% identical to the nucleic acid fragments reported herein.

Comparison of the *Rhodococcus erythropolis* AN1 ORF17 chnB nucleotide base and deduced amino acid sequences to public databases reveals that the most similar known sequences range from a distant as about 53% identical to the amino acid sequence of reported herein over length of 499 amino acids using a Smith-Waterman alignment algorithm (W. R. Pearson, supra). Preferred amino acid fragments are at least about 70%–80% and more preferred amino acid fragments are at least about 80%–90% identical to the sequences herein. Most preferred are nucleic acid fragments that are at least 95% identical to the amino acid fragments reported herein. Similarly, preferred chnB encoding nucleic acid sequences corresponding to the instant ORF's are those encoding active proteins and which are at least 80% identical to the nucleic acid sequences reported herein. More preferred chnB nucleic acid fragments are at least 90% identical to the sequences herein. Most preferred are chnB nucleic acid fragments that are at least 95% identical to the nucleic acid fragments reported herein.

Comparison of the *Rhodococcus erythropolis* AN1 ORF18 chnB nucleotide base and deduced amino acid sequences to public databases reveals that the most similar known sequences range from a distant as about 44% identical to the amino acid sequence of reported herein over length of 493 amino acids using a Smith-Waterman alignment algorithm (W. R. Pearson, supra). Preferred amino acid fragments are at least about 70%–80% and more preferred amino acid fragments are at least about 80%–90% identical to the sequences herein. Most preferred are nucleic acid fragments that are at least 95% identical to the amino acid fragments reported herein. Similarly, preferred chnB encoding nucleic acid sequences corresponding to the instant ORF's are those encoding active proteins and which are at least 80% identical to the nucleic acid sequences reported herein. More preferred chnB nucleic acid fragments are at least 90% identical to the sequences herein. Most preferred are chnB nucleic acid fragments that are at least 95% identical to the nucleic acid fragments reported herein.

Comparison of the *Rhodococcus erythropolis* AN1 ORF19 chnB nucleotide base and deduced amino acid sequences to public databases reveals that the most similar known sequences range from a distant as about 54% identical to the amino acid sequence of reported herein over length of 541 amino acids using a Smith-Waterman alignment algorithm (W. R. Pearson, supra). Preferred amino acid fragments are at least about 70%–80% and more preferred amino acid fragments are at least about 80%–90% identical to the sequences herein. Most preferred are nucleic acid fragments that are at least 95% identical to the amino acid fragments reported herein. Similarly, preferred chnB encoding nucleic acid sequences corresponding to the instant ORF's are those encoding active proteins and which are at least 80% identical to the nucleic acid sequences reported herein. More preferred chnB nucleic acid fragments are at least 90% identical to the sequences herein. Most preferred are chnB nucleic acid fragments that are at least 95% identical to the nucleic acid fragments reported herein.

Comparison of the *Rhodococcus erythropolis* AN1 ORF20 chnB nucleotide base and deduced amino acid sequences to public databases reveals that the most similar known sequences range from a distant as about 42% identical to the amino acid sequence of reported herein over length of 545 amino acids using a Smith-Waterman alignment algorithm (W. R. Pearson, supra). Preferred amino acid fragments are at least about 70%–80% and more preferred amino acid fragments are at least about 80%–90% identical to the sequences herein. Most preferred are nucleic acid fragments that are at least 95% identical to the amino acid fragments reported herein. Similarly, preferred chnB encoding nucleic acid sequences corresponding to the instant ORF's are those encoding active proteins and which are at least 80% identical to the nucleic acid sequences reported herein. More preferred chnB nucleic acid fragments are at least 90% identical to the sequences herein. Most preferred are chnB nucleic acid fragments that are at least 95% identical to the nucleic acid fragments reported herein.

In addition to the identification of the above mentioned sequences and the biochemical characterization of the activity of the gene product, Applicants have made the discovery that many of these monooxygenase proteins share diagnostic signature sequences which may be used for the identification of other proteins having similar activity. For example, the present monooxygenases may be grouped into three general families based on sequence alignment. One group, referred to herein BV Family 1, is comprised of the monooxygenase sequences shown in FIG. 7 and generating the consensus sequence as set forth in SEQ ID NO:47. As will be seen in FIG. 7, there are a group of completely conserved amino acids in 74 positions across all of the sequences of FIG. 7. These positions are further delineated in FIG. 6, and indicated as p1–p74.

Similarly, BV Family 2 is comprised of the monooxygenase sequences shown on FIG. 8, and generating the consensus sequence as set forth in SEQ ID NO:48. The signature seqeunce of BV Family 2 monooxygenases is shown in FIG. 6 having the positions p1–p76. BV Family 3 monooxygenases are shown in FIG. 9, generating the consensus sequence as set for the in SEQ ID NO:49, having the signature sequence as shown in FIG. 6 of positions p1–p41.

Although there is variation among the sequences of the various families, all of the individual members of these families have been shown to possess monooxygenase activity. Thus, it is contemplated that where a polypeptide possesses the signature sequences as defined in FIGS. 6–9 that it will have monooxygenase activity. It is thus within the scope of the present invention to provide a method for identifying a gene encoding a Baeyer-Villiger monooxygenase polypeptide comprising:

(a) probing a genomic library with a nucleic acid fragment encoding a polypeptide wherein where at least 80% of the amino acid residues at positions p1–p74 of SEQ ID NO:47, or at least 80% of the amino acid residues at p1–p76 of SEQ ID NO:48 or at least 80% of the amino acid residues of p1–p41 of SEQ ID NO:49 are completely conserved;

(b) identifying a DNA clone that hybridizes with a nucleic acid fragment of step (a);

(c) sequencing the genomic fragment that comprises the clone identified in step (b), wherein the sequenced genomic fragment encodes a Baeyer-Villiger monooxygenase polypeptide.

In a preferred embodiment the invention provides the above method wherein where at least 100% of the amino acid residues at positions p1–p74 of SEQ ID NO:47, or at least 100% of the amino acid residues at p1–p76 of SEQ ID NO:48 or at least 100% of the amino acid residues of p1–p41 of SEQ ID NO:49 are completely conserved.

It will be appreciated that other Baeyer-Villiger monooxygenase genes having similar substrate specificity may be identified and isolated on the basis of sequence dependent protocols or according to alignment against the signature sequences disclosed herein.

Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g polymerase chain reaction (PCR), Mullis et al., U.S. Pat. No. 4,683,202), ligase chain reaction (LCR), Tabor, S. et al., *Proc. Acad. Sci. USA* 82: 1074, (1985)) or strand displacement amplification (SDA, Walker, et al., *Proc. Natl. Acad. Sci. U.S.A.*, 89: 392, (1992)).

For example, genes encoding similar proteins or polypeptides to the present Baeyer-Villiger monooxygenases could be isolated directly by using all or a portion of the nucleic acid fragments set forth in SEQ ID NOs:7, 9, 11, 13, 15, 17, 19, 21, 23, 25, 27, 29, 31, 33, 35, 37, 39, 41, 43, and 45 or as DNA hybridization probes to screen libraries from any desired bacteria using methodology well known to those skilled in the art. Specific oligonucleotide probes based upon the instant nucleic acid sequences can be designed and synthesized by methods known in the art (Maniatis, supra). Moreover, the entire sequences can be used directly to synthesize DNA probes by methods known to the skilled artisan such as random primers DNA labeling, nick translation, or end-labeling techniques, or RNA probes using available in vitro transcription systems. In addition, specific primers can be designed and used to amplify a part of or full-length of the instant sequences. The resulting amplification products can be labeled directly during amplification reactions or labeled after amplification reactions, and used as probes to isolate full length DNA fragments under conditions of appropriate stringency.

Typically, in PCR-type primer directed amplification techniques, the primers have different sequences and are not complementary to each other. Depending on the desired test conditions, the sequences of the primers should be designed to provide for both efficient and faithful replication of the target nucleic acid. Methods of PCR primer design are common and well known in the art. (Thein and Wallace, "The use of oligonucleotide as specific hybridization probes in the Diagnosis of Genetic Disorders", in *Human Genetic Diseases: A Practical Approach*, K. E. Davis Ed., (1986) pp. 33–50 IRL Press, Herndon, Va.; Rychlik, W. (1993) In White, B. A. (ed.), *Methods in Molecular Biology*, Vol. 15, pages 31–39, PCR Protocols: Current Methods and Applications. Humania Press, Inc., Totowa, N.J.)

Generally PCR primers may be used to amplify longer nucleic acid fragments encoding homologous genes from DNA or RNA. However, the polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding microbial genes. Alternatively, the second primer sequence may be based upon sequences derived from the cloning vector. For example, the skilled artisan can follow the RACE protocol (Frohman et al., *PNAS USA* 85:8998 (1988)) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., *PNAS USA* 86:5673 (1989); Loh et al., *Science* 243:217 (1989)).

Accordingly the invention provides a method for identifying a nucleic acid molecule encoding a Baeyer-Villiger monooxygenase comprising: (a) synthesizing at least one oligonucleotide primer corresponding to a portion of the sequence selected from the group consisting of SEQ ID NOs:7, 9, 11, 13, 15, 17, 19, 21, 23, 25, 27, 29, 31, 33, 35, 37, 39, 41, 43, and 45 and (b) amplifying an insert present in a cloning vector using the oligonucleotide primer of step (a); wherein the amplified insert encodes a Baeyer-Villiger monooxygenase Alternatively the instant sequences may be employed as hybridization reagents for the identification of homologs. The basic components of a nucleic acid hybridization test include a probe, a sample suspected of containing the gene or gene fragment of interest, and a specific hybridization method. Probes of the present invention are typically single stranded nucleic acid sequences which are complementary to the nucleic acid sequences to be detected. Probes are "hybridizable" to the nucleic acid sequence to be detected. The probe length can vary from 5 bases to tens of thousands of bases, and will depend upon the specific test to be done. Typically a probe length of about 15 bases to about 30 bases is suitable. Only part of the probe molecule need be complementary to the nucleic acid sequence to be detected. In addition, the complementarity between the probe and the target sequence need not be perfect. Hybridization does occur between imperfectly complementary molecules with the result that a certain fraction of the bases in the hybridized region are not paired with the proper complementary base.

Hybridization methods are well defined. Typically the probe and sample must be mixed under conditions which will permit nucleic acid hybridization. This involves contacting the probe and sample in the presence of an inorganic or organic salt under the proper concentration and temperature conditions. The probe and sample nucleic acids must be in contact for a long enough time that any possible hybridization between the probe and sample nucleic acid may occur. The concentration of probe or target in the mixture will determine the time necessary for hybridization to occur. The higher the probe or target concentration the shorter the hybridization incubation time needed. Optionally a chaotropic agent may be added. The chaotropic agent stabilizes nucleic acids by inhibiting nuclease activity. Furthermore, the chaotropic agent allows sensitive and stringent hybridization of short oligonucleotide probes at room temperature [Van Ness and Chen (1991) *Nucl. Acids Res.* 19:5143–5151]. Suitable chaotropic agents include guanidinium chloride, guanidinium thiocyanate, sodium thiocyanate, lithium tetrachloroacetate, sodium perchlorate, rubidium tetrachloroacetate, potassium iodide, and cesium trifluoroacetate, among others. Typically, the chaotropic agent will be present at a final concentration of about 3M. If desired, one can add formamide to the hybridization mixture, typically 30–50% (v/v).

Various hybridization solutions can be employed. Typically, these comprise from about 20 to 60% volume, preferably 30%, of a polar organic solvent. A common hybridization solution employs about 30–50% v/v formamide, about 0.15 to 1 M sodium chloride, about 0.05 to 0.1 M buffers, such as sodium citrate, Tris-HCl, PIPES or HEPES (pH range about 6–9), about 0.05 to 0.2% detergent, such as sodium dodecylsulfate, or between 0.5–20 mM EDTA, FICOLL (Pharmacia Inc.) (about 300–500 kilodaltons), polyvinylpyrrolidone (about 250–500 kdal), and serum albumin. Also included in the typical hybridization solution will be unlabeled carrier nucleic acids from about 0.1 to 5 mg/mL, fragmented nucleic DNA, e.g., calf thymus or salmon sperm DNA, or yeast RNA, and optionally from about 0.5 to 2% wt/vol glycine. Other additives may also be included, such as volume exclusion agents which include a variety of polar water-soluble or swellable agents, such as polyethylene glycol, anionic polymers such as polyacrylate or polymethylacrylate, and anionic saccharidic polymers, such as dextran sulfate.

Thus, the invention provides a method for identifying a nucleic acid molecule encoding a Baeyer-Villiger monooxygenase comprising:(a) probing a genomic library with a portion of a nucleic acid molecule selected from the group consisting of SEQ ID NOs:7, 9, 11, 13, 15, 17, 19, 21, 23, 25, 27, 29, 31, 33, 35, 37, 39, 41, 43, and 45;(b) identifying a DNA clone that hybridizes under conditions of 0.1×SSC, 0.1% SDS, 65° C. and washed with 2×SSC, 0.1% SDS followed by 0.1×SSC, 0.1% SDS with the nucleic acid molecule of (a); and (c) sequencing the genomic fragment that comprises the clone identified in step (b), wherein the sequenced genomic fragment encodes Baeyer-Villiger monooxygenase.

Recombinant Expression-Microbial

The genes and gene products of the present BVMO sequences may be introduced into microbial host cells. Preferred host cells for expression of the instant genes and nucleic acid molecules are microbial hosts that can be found broadly within the fungal or bacterial families and which grow over a wide range of temperature, pH values, and solvent tolerances. Because of transcription, translation and the protein biosynthetic apparatus is the same irrespective of the cellular feedstock, functional genes are expressed irrespective of carbon feedstock used to generate cellular biomass. Large scale microbial growth and functional gene expression may utilize a wide range of simple or complex carbohydrates, organic acids and alcohols, saturated hydrocarbons such as methane or carbon dioxide in the case of photosynthetic or chemoautotrophic hosts. However, the functional genes may be regulated, repressed or depressed by specific growth conditions, which may include the form and amount of nitrogen, phosphorous, sulfur, oxygen, carbon or any trace micronutrient including small inorganic ions. In addition, the regulation of functional genes may be achieved by the presence or absence of specific regulatory molecules that are added to the culture and are not typically considered nutrient or energy sources. Growth rate may also be an important regulatory factor in gene expression. Examples of suitable host strains include but are not limited to fungal or yeast species such as *Aspergillus, Trichoderma, Saccharomyces, Pichia, Candida, Hansenula,* or bacterial species such as member of the proteobacteria and actinomycetes as well as the specific genera *Rhodococcus, Acinetobacter, Arthrobacter, Mycobacteria, Nocardia, Brevibacterium, Acidovorax, Bacillus, Streptomyces, Escherichia, Salmonella, Pseudomonas, Aspergillus, Saccharomyces, Pichia, Candida, Cornyebacterium,* and *Hansenula*.

Particularly suitable in the present invention as hosts for monooxygenase are the members of the Proteobacteria and Actinomycetes. The Proteobacteria form a physiologically diverse group of microorganisms and represent five subdivisions ($\alpha$, $\beta$, $\gamma$, $\epsilon$, $\delta$) (Madigan et al., *Brock Biology of Microorganisms*, 8th edition, Prentice Hall, UpperSaddle River, N.J. (1997)). All five subdivisions of the Proteobacteria contain microorganisms that use organic compounds as sources of carbon and energy. Members of the Proteobacteria suitable in the present invention include, but are not limited to *Burkholderia, Alcaligenes, Pseudomonas, Sphingomonas, Pandoraea, Delftia* and *Comamonas*.

Microbial expression systems and expression vectors containing regulatory sequences that direct high level expression of foreign proteins are well known to those skilled in the art. Any of these could be used to construct chimeric genes for production of the any of the gene products of the instant sequences. These chimeric genes could then be introduced into appropriate microorganisms via transformation to provide high level expression of the enzymes.

Vectors or cassettes useful for the transformation of suitable host cells are well known in the art. Typically the vector or cassette contains sequences directing transcription and translation of the relevant gene, a selectable marker, and sequences allowing autonomous replication or chromosomal integration. Suitable vectors comprise a region 5' of the gene which harbors transcriptional initiation controls and a region 3' of the DNA fragment which controls transcriptional termination. It is most preferred when both control regions are derived from genes homologous to the transformed host cell, although it is to be understood that such control regions need not be derived from the genes native to the specific species chosen as a production host.

Initiation control regions or promoters, which are useful to drive expression of the instant ORF's in the desired host cell are numerous and familiar to those skilled in the art. Virtually any promoter capable of driving these genes is suitable for the present invention including but not limited to CYC1, HIS3, GAL1, GAL10, ADH1, PGK, PHO5, GAPDH, ADC1, TRP1, URA3, LEU2, ENO, TPI (useful for expression in *Saccharomyces*); AOX1 (useful for expression in *Pichia*); and lac, ara, tet, trp, $IP_L$, $IP_R$, T7, tac, and trc (useful for expression in *Escherichia coli*) as well as the amy, apr, npr promoters and various phage promoters useful for expression in *Bacillus*.

Termination control regions may also be derived from various genes native to the preferred hosts. Optionally, a termination site may be unnecessary, however, it is most preferred if included.

Recombinant Expression—Plants

The sequences encoding the BVMO's of the present invention may be used to create transgenic plants having the ability to express the microbial proteins. Preferred plant hosts will be any variety that will support a high production level of the instant proteins.

Suitable green plants will included but are not limited to of soybean, rapeseed (*Brassica napus, B. campestris*), sunflower (*Helianthus annus*), cotton (*Gossypium hirsutum*), corn, tobacco (*Nicotiana tabacum*), alfalfa (*Medicago sativa*), wheat (*Triticum* sp), barley (*Hordeum vulgare*), oats (*Avena sativa, L*), sorghum (*Sorghum bicolor*), rice (*Oryza sativa*), Arabidopsis, cruciferous vegetables (broccoli, cauliflower, cabbage, parsnips, etc.), melons, carrots, celery, parsley, tomatoes, potatoes, strawberries, peanuts, grapes, grass seed crops, sugar beets, sugar cane, beans, peas, rye, flax, hardwood trees, softwood trees, and forage grasses. Algal species include but not limited to commercially significant hosts such as *Spirulina* and *Dunalliela*. Overexpression of the proteins of the instant invention may be accomplished by first constructing chimeric genes in which the coding region are operably linked to promoters capable of directing expression of a gene in the desired tissues at the desired stage of development. For reasons of convenience, the chimeric genes may comprise promoter sequences and translation leader sequences derived from the same genes. 3' Non-coding sequences encoding transcription termination signals must also be provided. The instant chimeric genes may also comprise one or more introns in order to facilitate gene expression.

Any combination of any promoter and any terminator capable of inducing expression of a coding region may be used in the chimeric genetic sequence. Some suitable examples of promoters and terminators include those from nopaline synthase (nos), octopine synthase (ocs) and cauliflower mosaic virus (CaMV) genes. One type of efficient plant promoter that may be used is a high level plant promoter. Such promoters, in operable linkage with the genetic sequences or the present invention should be capable of promoting expression of the present gene product. High level plant promoters that may be used in this invention include the promoter of the small subunit (ss) of the ribulose-1,5-bisphosphate carboxylase from example from soybean (Berry-Lowe et al., *J. Molecular and App. Gen.*, 1:483–498 1982)), and the promoter of the chlorophyll a/b binding protein. These two promoters are known to be light-induced in plant cells (See, for example, *Genetic Engineering of Plants, an Agricultural Perspective*, A. Cashmore, Plenum, N.Y. (1983), pages 29–38; Coruzzi, G. et al., *The Journal of Biological Chemistry*, 258:1399 (1983), and Dunsmuir, P. et al., *Journal of Molecular and Applied Genetics*, 2:285 (1983)).

Plasmid vectors comprising the instant chimeric genes can then be constructed. The choice of plasmid vector depends upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., *EMBO J.* 4:2411–2418 (1985); De Almeida et al., *Mol. Gen. Genetics* 218:78–86 (1989)), and thus that multiple events must be screened in order to obtain lines displaying the desired expression level and pattern. Such screening may be accomplished by Southern analysis of DNA blots (Southern, *J. Mol. Biol.* 98:503, (1975)). Northern analysis of mRNA expression (Kroczek, *J. Chromatogr. Biomed. Appl.*, 618 (1–2):133–145 (1993)), Western analysis of protein expression, or phenotypic analysis.

For some applications it will be useful to direct the instant proteins to different cellular compartments. It is thus envisioned that the chimeric genes described above may be further supplemented by altering the coding sequences to encode enzymes with appropriate intracellular targeting sequences such as transit sequences (Keegstra, K., *Cell* 56:247–253 (1989)), signal sequences or sequences encoding endoplasmic reticulum localization (Chrispeels, J. J., *Ann. Rev. Plant Phys. Plant Mol. Biol.* 42:21–53 (1991)), or nuclear localization signals (Raikhel, N. *Plant Phys.* 100: 1627–1632 (1992)) added and/or with targeting sequences that are already present removed. While the references cited give examples of each of these, the list is not exhaustive and more targeting signals of utility may be discovered in the future that are useful in the invention.

Process for the Production of Lactones and Esters from Ketone Substrates

Once the appropriate nucleic acid sequence has been expressed in a recombinant organism, the organism may be contacted with a suitable ketone substrate for the production of the corresponding ester. The Baeyer-Villiger monooxygenases of the instant invention will act on a variety of ketone substrates comprising cyclic ketones and ketoterpenes to produce the corresponding lactone or ester. Suitable ketone substrates for the conversion to esters are defined by the general formula:

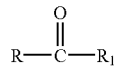

wherein R and $R_1$ are independently selected from substituted or unsubstituted phenyl, substituted or unsubstituted alkyl, or substituted or unsubstituted alkenyl or substituted or unsubstituted alkylidene. Particularly useful ketone substrates include, but are not limited to Norcamphor, Cyclobutanone, Cyclopentanone, 2-methyl-cyclopentanone, Cyclohexanone, 2-methyl-cyclohexanone, Cyclohex-2-ene-1-one, 1,2-cyclohexanedione, 1,3-cyclohexanedione, 1,4-cyclohexanedione, Cycloheptanone, Cyclooctanone, Cyclodecanone, Cycloundecanone, Cyclododecanone, Cyclotridecanone, Cyclopenta-decanone, 2-tridecanone, dihexyl ketone, 2-phenyl-cyclohexanone, Oxindole, Levoglucosenone, dimethyl sulfoxide, dimethy-2-piperidone, Phenylboronic acid, and beta-ionone.

Alternatively it is contemplated that the enzymes of the invention may be used in vitro for the transformation of ketone substrates to the corresponding esters. The monooxygenase enzymes may be produced recombinantly or isolated from native sources, purified and reacted with the appropriate substrate under suitable conditions of pH and temperature.

Where large scale commercial production of lactones or esters is desired, a variety of culture methodologies may be applied. For example, large scale production from a recombinant microbial host may be produced by both batch or continuous culture methodologies.

A classical batch culturing method is a closed system where the composition of the media is set at the beginning of the culture and not subject to artificial alterations during the culturing process. Thus, at the beginning of the culturing process the media is inoculated with the desired organism or organisms and growth or metabolic activity is permitted to occur adding nothing to the system. Typically, however, a "batch" culture is batch with respect to the addition of carbon source and attempts are often made at controlling factors such as pH and oxygen concentration. In batch systems the metabolite and biomass compositions of the system change constantly up to the time the culture is terminated. Within batch cultures cells moderate through a static lag phase to a high growth log phase and finally to a stationary phase where growth rate is diminished or halted. If untreated, cells in the stationary phase will eventually die. Cells in log phase are often responsible for the bulk of production of end product or intermediate in some systems. Stationary or post-exponential phase production can be obtained in other systems.

A variation on the standard batch system is the Fed-Batch system. Fed-Batch culture processes are also suitable in the present invention and comprise a typical batch system with the exception that the substrate is added in increments as the culture progresses. Fed-Batch systems are useful when catabolite repression is apt to inhibit the metabolism of the cells and where it is desirable to have limited amounts of substrate in the media. Measurement of the actual substrate concentration in Fed-Batch systems is difficult and is therefore estimated on the basis of the changes of measurable factors such as pH, dissolved oxygen and the partial pressure of waste gases such as $CO_2$. Batch and Fed-Batch culturing methods are common and well known in the art and examples may be found in Thomas D. Brock in Biotechnology: *A Textbook of Industrial Microbiology*, Second Edition (1989) Sinauer Associates, Inc., Sunderland, Mass., or Deshpande, Mukund V., *Appl. Biochem. Biotechnol.*, 36, 227, (1992), herein incorporated by reference.

Commercial production of lactones and esters of the present invention may also be accomplished with a continuous culture. Continuous cultures are an open system where a defined culture media is added continuously to a bioreactor and an equal amount of conditioned media is removed simultaneously for processing. Continuous cultures generally maintain the cells at a constant high liquid phase density where cells are primarily in log phase growth. Alternatively continuous culture may be practiced with immobilized cells where carbon and nutrients are continuously added, and valuable products, by-products or waste products are continuously removed from the cell mass. Cell immobilization may be performed using a wide range of solid supports composed of natural and/or synthetic materials.

Continuous or semi-continuous culture allows for the modulation of one factor or any number of factors that affect cell growth or end product concentration. For example, one method will maintain a limiting nutrient such as the carbon source or nitrogen level at a fixed rate and allow all other parameters to moderate. In other systems a number of factors affecting growth can be altered continuously while the cell concentration, measured by media turbidity, is kept constant. Continuous systems strive to maintain steady state growth conditions and thus the cell loss due to media being drawn off must be balanced against the cell growth rate in the culture. Methods of modulating nutrients and growth factors for continuous culture processes as well as techniques for maximizing the rate of product formation are well known in the art of industrial microbiology and a variety of methods are detailed by Brock, supra.

Baeyer-Villiger Monooxygenases Having Enhanced Activity

It is contemplated that the present BVMO sequences may be used to produce gene products having enhanced or altered activity. Various methods are known for mutating a native gene sequence to produce a gene product with altered or enhanced activity including but not limited to error prone PCR (Melnikov et al., *Nucleic Acids Research*, (Feb. 15, 1999) Vol. 27, No. 4, pp. 1056–1062); site directed mutagenesis (Coombs et al., *Proteins* (1998), 259–311, 1 plate. Editor(s): Angeletti, Ruth Hogue. Publisher: Academic, San Diego, Calif.) and "gene shuffling" (U.S. Pat. Nos. 5,605,793; 5,811,238; 5,830,721; and 5,837,458, incorporated herein by reference).

The method of gene shuffling is particularly attractive due to its facile implementation, and high rate of mutagenesis and ease of screening. The process of gene shuffling involves the restriction endonuclease cleavage of a gene of interest into fragments of specific size in the presence of additional populations of DNA regions of both similarity to or difference to the gene of interest. This pool of fragments will then be denatured and reannealed to create a mutated gene. The mutated gene is then screened for altered activity.

The BVMO sequences of the present invention may be mutated and screened for altered or enhanced activity by this method. The sequences should be double stranded and can be of various lengths ranging form 50 bp to 10 kb. The sequences may be randomly digested into fragments ranging from about 10 bp to 1000 bp, using restriction endonucleases well known in the art (Maniatis supra). In addition to the instant microbial sequences, populations of fragments that are hybridizable to all or portions of the microbial sequence may be added. Similarly, a population of fragments which are not hybridizable to the instant sequence may also be added. Typically these additional fragment populations are added in about a 10 to 20 fold excess by weight as compared to the total nucleic acid. Generally if this process is followed the number of different specific nucleic acid fragments in the mixture will be about 100 to about 1000. The mixed population of random nucleic acid fragments are denatured to form single-stranded nucleic acid fragments and then reannealed. Only those single-stranded nucleic acid fragments having regions of homology with other single-stranded nucleic acid fragments will reanneal. The random nucleic acid fragments may be denatured by heating. One skilled in the art could determine the conditions necessary to completely denature the double stranded nucleic acid. Preferably the temperature is from 80° C. to 100° C. The nucleic acid fragments may be reannealed by cooling. Preferably the temperature is from 20° C. to 75° C. Renaturation can be accelerated by the addition of polyethylene glycol ("PEG") or salt. A suitable salt concentration may range from 0 mM to 200 mM. The annealed nucleic acid fragments are then incubated in the presence of a nucleic acid polymerase and dNTP's (i.e. dATP, dCTP, dGTP and dTTP). The nucleic acid polymerase may be the Klenow fragment, the Taq polymerase or any other DNA polymerase known in the art. The polymerase may be added to the random nucleic acid fragments prior to annealing, simultaneously with annealing or after annealing. The cycle of denaturation, renaturation and incubation in the presence of polymerase is repeated for a desired number of times. Preferably the cycle is repeated from 2 to 50 times, more preferably the sequence is repeated from 10 to 40 times. The resulting nucleic acid is a larger double-stranded polynucleotide ranging from about 50 bp to about 100 kb and may be screened for expression and altered activity by standard cloning and expression protocol. (Manatis supra).

Furthermore, a hybrid protein can be assembled by fusion of functional domains using the gene shuffling (exon shuffling) method (Nixon et al, PNAS, 94:1069–1073 (1997)). The functional domain of the instant gene can be combined with the functional domain of other genes to create novel enzymes with desired catalytic function. A hybrid enzyme may be constructed using PCR overlap extension method and cloned into the various expression vectors using the techniques well known to those skilled in art.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual;* Cold Spring Harbor Laboratory Press: Cold Spring Harbor, (1989) (Maniatis) and by T. J. Silhavy, M. L. Bennan, and L. W. Enquist, Experiments with Gene Fusions, Cold Spring Harbor Laboratory, Cold Spring Harbor, N.Y. (1984) and by Ausubel, F.

M. et al., Current Protocols in Molecular Biology, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, Eds., American Society for Microbiology, Washington, D.C. (1994)) or by Thomas D. Brock in *Biotechnology: A Textbook of Industrial Microbiology*, Second Ed., Sinauer Associates, Inc.: Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Bacterial Strains and Plasmids: *Rhodococcus erythropolis* AN12, *Brevibacterium* sp. HCU, *Arthrobacter* sp. BP2, *Rhodococcus* sp. phi1, *Rhodococcus* sp. phi2, *Acidovorax* sp. CHX, and *Acinetobacter* sp. SE19 were isolated from enrichment of activated sludge obtained from industrial wastewater treatment facilities. Max Efficiency competent cells of *E. coli* DH5α and DH10B were purchased from GIBCO/BRL (Gaithersburg, Md.). Expression plasmid pQE30 were purchased from Qiagen (Valencia, Calif.), while cloning vector pCR2.1 and expression vector pTrc/His2-Topo were purchased from Invitrogen (San Diego, Calif.).

Taxonomic identification of *Rhodococcus erythropolis* AN12, *Brevibacterium* sp. HCU, *Arthrobacter* sp. BP2, *Rhodococcus* sp. phi1, *Rhodococcus* sp. phi2, *Acidovorax* sp. CHX, and *Acinetobacter* sp. SE19 was performed by PCR amplification of 16S rDNA from chromosomal DNA using primers corresponding to conserved regions of the 16S rDNA molecule (Table 2). The following temperature program was used: 95° C. (5 min) for 1 cycle followed by 25 cycles of: 95° C. (1 min), 55° C. (1 min), 72° C. (1 min), followed by a final extension at 72° C. (8 min). Following DNA sequencing (according to the method shown below), the 16S rDNA gene sequence of each isolate was used as the query sequence for a BLAST search (Altschul, et al., *Nucleic Acids Res.* 25:3389–3402 (1997)) against GenBank for similar sequences.

TABLE 2

Primers to Conserved Regions of 16s rDNA

| SEQ ID NO | Primer Sequence (5'–3') | Reference |
|---|---|---|
| 50 | GAGTTTGATCCTGGCTCAG | (HK12) Amann, R. I. et al. Microbiol. Rev. 59(1): 143–69 (1995) |
| 51 | CAGG(A/C)GCCGCGGTAAT(A/T)C | Amann, R. I. et al. Microbiol. Rev. 59(1): 143–69 (1995) |
| 52 | GCTGCCTCCCGTAGGAGT | (HK21) Amann, R. I. et al. Microbiol. Rev. 59(1): 143–69 (1995) |
| 53 | CTACCAGGGTAACTAATCC | Amann, R. I. et al. Microbiol. Rev. 59(1): 143–69 (1995) |
| 54 | ACGGGCGGTGTGTAC | Amann, R. I. et al. Microbiol. Rev. 59(1): 143–69 (1995) |
| 55 | CACGAGCTGACGACAGCCAT | Amann, R. I. et al. Microbiol. Rev. 59(1): 143–69 (1995) |
| 56 | TACCTTGTTACGACTT | (HK13) Amann, R. I. et al. Microbiol. Rev. 59(1): 143–69 (1995) |
| 57 | G(A/T)ATTACCGCGGC(G/T)GCTG | Amann, R. I. et al. Microbiol. Rev. 59(1): 143–69 (1995) |
| 58 | GGATTAGATACCCTGGTAG | Amann, R. I. et al. Microbiol. Rev. 59(1): 143–69 (1995) |
| 59 | ATGGCTGTCGTCAGCTCGTG | Amann, R. I. et al. Microbiol. Rev. 59(1): 143–69 (1995) |
| 60 | GCCCCCG(C/T)CAATTCCT | (HK15) Kane, M. D. et al. Appl. Environ. Microbiol. 59: 682–686 (1993) |
| 61 | GTGCCAGCAG(C/T)(A/C)GCGGT | (HK14) Kane, M. D. et al. Appl. Environ. Microbiol. 59: 682–686 (1993) |
| 62 | GCCAGCAGCCGCGGTA | (JCR15) Kane, M. D. et al. Appl. Environ. Microbiol. 59: 682–686 (1993) |

Note:
Parenthetical information in bold is the original name for the primer, according to the reference provided.

Sequencing

Sequence was generated on an ABI Automatic sequencer using dye terminator technology (U.S. Pat. No. 5,366,860; EP 272007) using a combination of vector and insert-specific primers. Sequence editing was performed using either Sequencher (Gene Codes Corp., Ann Arbor, Mich.) or the Wisconsin GCG program (Wisconsin Package Version 9.0, Genetics Computer Group (GCG), Madison, Wis.) and the CONSED package (version 7.0). All sequences represent coverage at least two times in both directions.

Manipulations of genetic sequences were accomplished using the suite of programs available from the Genetics Computer Group Inc. (Wisconsin Package Version 9.0, Genetics Computer Group (GCG), Madison, Wis.). Where the GCG program "Pileup" was used, the gap creation default value of 12 and the gap extension default value of 4 were used. Where the GCG "Gap" or "Bestfit" programs were used, the default gap creation penalty of 50 and the default gap extension penalty of 3 were used. In any case where GCG program parameters were not prompted for, in these or any other GCG program, default values were used.

The meaning of abbreviations is as follows: "sec" means second(s), "min" means minute(s), "h" means hour(s), "d" means day(s), "µL" means microliter, "mL" means milliliters, "L" means liters, "µM" means micromolar, "mM" means millimolar, "M" means molar, "mmol" means millimole(s), "µmole" mean micromole", "g" means gram, "µg" means microgram, "ng" means nanogram, "U" means units, "mU" means milliunits, "ppm" means parts per million, "psi" means pounds per square inch, and "kB" means kilobase.

Example 1

Monooxygenase Gene Discovery in a Mixed Microbial Population

This Example describes the isolation of the cyclohexanone degrading organisms *Arthrobacter* sp. BP2, *Rhodococcus* sp. phi1, and *Rhodococcus* sp. phi2 by enrichment of a mixed microbial community. Differential display techniques applied to cultures containing the mixed microbial population permitted discovery of monooxygenase genes.

Enrichment for Cyclohexanone Degraders

A mixed microbial community was obtained from a wastewater bioreactor and maintained on minimal medium (50 mM KHPO$_4$ (pH 7.0), 10 mM (NH$_4$)SO$_4$, 2 mM MgCl$_2$, 0.7 mM CaCl$_2$, 50 µM MnCl$_2$, 1 µM FeCl$_3$, 1 µM ZnCl$_3$, 1.72 µM CuSO$_4$, 2.53 µM CoCl$_2$, 2.42 µM Na$_2$MoO$_2$, and 0.0001% FeSO$_4$) with trace amounts of yeast extract casamino acids and peptone (YECAAP) at 0.1% concentration with 0.1% cyclohexanol and cyclohexanone added as carbon sources. Increased culture growth in the presence of cyclohexanone indicated a microbial population with members that could convert cyclohexanone.

Isolation of Strains

Seven individual strains were isolated from the community by spreading culture on R2A Agar (Becton Dickinson and Company, Cockeysville, Md.) at 30° C. Strains were streaked to purity on the same medium. Among these seven strains, the strain identified as *Arthrobacter* species BP2 formed large colonies of a light yellow color. One *Rhodococcus* strain, identified as species phi1, formed small colonies that were orange in color. The other *Rhodococcus* strain, designated species phi2, formed small colonies that were red in color.

Individuals strains were identified by comparing 16s rDNA sequences to known 16S rRNA sequences in the GenBank sequence database. The 16S rRNA gene sequence from strain BP2 (SEQ ID NO:1) was at least 99% homologous to the 16S rRNA gene sequences of bacteria belonging to the genus *Arthrobacter*. The 16S rRNA gene sequences from strains phi1 and phi2 were each at least 99% homologous to the 16S rRNA gene sequences of bacteria belonging to the genus of gram positive bacteria, *Rhodococcus*. The complete 16s DNA sequence of *Rhodococcus* sp. phi1 is shown as SEQ ID NO:2, while that of *Rhodococcus* sp. phi2 is listed as SEQ ID NO:3.

Induction of Cyclohexanone Oxidation Genes

For induction of cyclohexanone oxidation genes within members of this community, 1 ml of inoculum from a waste water bioreactor was suspended in 25 ml minimal medium with 0.1% YECAAP and incubated overnight at 30° C. with agitation. The next day 10 ml of the overnight culture was resuspended in a total volume of 50 ml minimal medium with 0.1% YECAAP. The optical density of the culture was 0.29 absorbance units at 600 nm. After equilibration at 30° C. for 30 min, the culture was split into two separate 25 ml volumes. To one of these cultures, 25 µl (0.1%) cyclohexanone (Sigma-Aldrich, St. Louis, Mo.) was added. Both cultures were incubated for an additional 3 hrs. At this time, cultures were moved onto ice, harvested by centrifugation at 4° C., washed with two volumes of minimal salts medium and diluted to an optical density of 1.0 absorbance unit (600 nm). Approximately 6 ml of culture was placed in a water jacketed respirometry cell equipped with an oxygen electrode (Yellow Springs Instruments Co., Yellow Springs, Ohio) at 30° C. to confirm cyclohexanone enzymes were induced. After establishing the baseline respiration for each cell suspension, cyclohexanone was added to a final concentration of 0.1% and the rate of $O_2$ consumption was further monitored. For the control culture, 2 mM potassium acetate was added 200 sec after the cyclohexanone.

Isolation of Total Community RNA

After the 3 hr induction period with cyclohexanone described above, the control and induced sample (2 mL each) were harvested at 1400 rpm in a 4° C. centrifuge and resuspended in 900 µl Buffer RLT (Qiagen, Valencia, Calif.). A 300 µl volume of zirconia beads (Biospec Products, Bartlesville, Okla.) was added and cells were disrupted using a bead beater (Biospec Products) at 2400 beats per min for 3 min. Each of these samples was split into six aliquots for nucleic acid isolation using the RNeasy Mini Kit (Qiagen, Valencia, Calif.) and each was eluted with 100 RNase-free dH$_2$O supplied with the kit. DNA was degraded in the samples using 10 mM MgCl$_2$, 60 mM KCl and 2 U RNase-free DNase I (Ambion, Austin, Tex.) at 37° C. for 4 hr. Following testing for total DNA degradation by PCR using one of the arbitrary oligonucleotides used for RT-PCR, RNA was purified using the RNeasy Mini Kit and eluted in 100 µl RNase-free dH$_2$O as described previously.

Generation of RAPDs from Arbitrarily Reverse-transcribed Total RNA

A set of 244 primers with the sequence CGGAGCA-GATCGAVVVV (SEQ ID NO:63); where VVVV represent all the combinations of the three bases A, G and C) was used in separate RT-PCR reactions as with RNA from either the control or induced cells. The SuperScript™ One-Step™ RT-PCR System (Life Technologies Gibco BRL, Rockville, Md.) reaction mixture was used with 2–5 ng of total RNA in a 25 µl total reaction volume. The PCR was conducted using the following temperature program:

1 cycle: 4° C. (2 min), 5 min ramp to 37° C. (1 hr), followed by 95° C. incubation (3 min);

1 cycle: 94° C. (1 min), 40° C. (5 min), and 72° C. (5 min);

40 cycles: 94° C. (1 min), 60° C. (1 min), and 72° C. (1 min);

1 cycle: 70° C. (5 min) and 4° C. hold until separated by electorphoresis.

Products of these PCR amplifications (essentially RAPD fragments) were separated by electrophoresis at 1 V/cm on polyacrylamide gels (Amersham Pharmacia Biotech, Piscataway, N.J.). Products resulting from the control mRNA (no cyclohexanone induction) and induced mRNA fragments were visualized by silver staining using an automated gel stainer (Amersham Pharmacia Biotech, Piscataway, N.J.).

Reamplification of Differentially Expressed DNA Fragments

A 25 µl volume of a sodium cyanide elution buffer (10 mg/ml NaCN, 20 mM Tris-HCl (pH 8.0), 50 mM KCl and 0.05% NP40) was incubated with an excised gel band of a differentially display fragment at 95° C. for 20 min. Reamplification of this DNA fragment was achieved in a PCR reaction using 5 µl of the elution mixture in a 25 µl reaction using the primer from which the fragment was originally generated. The temperature program for reamplification was: 94° C. (5 min); 20 cycles of 94° C. (1 min), 55° C. (1 min), and 72° C. (1 min); followed by 72° C. (7 min). The reamplification products were directly cloned into the pCR2.1-TOPO vector (Invitrogen, Carlsbad, Calif.) and were sequenced using an ABI model 377 with ABI BigDye terminator sequencing chemistry (Perseptive Biosystems, Framinham, Mass.). Eight clones were submitted for sequencing from each reamplified band. The nucleotide sequence of the cloned fragments was compared against the non-redundant GenBank database using the BlastX program (NCBI).

Sequencing of Cyclohexanone Oxidation Pathway Genes

Oligonucleotides were designed to amplify by PCR individual differentially expressed fragments. Following DNA isolation from individual strains, these oligonucleotide primers were used to determine which strain contained DNA encoding the individual differentially expressed fragments. Cosmids were screened by PCR using primers designed against differentially displayed fragments with homology to known cyclohexanone degradation genes. Each recombinant *E. coli* cell culture carrying a cosmid clone (1.0 µl) was used as the template in a 25 ul PCR reaction mixture. The primer pair A102FI (SEQ ID NO:108) and CONR (SEQ ID NO:109) was used to screen the *Arthrobacter* sp. BP2 library, primer pair A228FI (SEQ ID NO:110) and A228R1 (SEQ ID NO:111) was used to screen the *Rhodococcus* sp. phi2 library, and the primer pair of A2FI (SEQ ID NO:112) and A34R1 (SEQ ID NO:113) was used to screen the *Rhodococcus* sp. phi1 library. Cosmids from recombinant *E. coli* which produced the correct product size in PCR reactions were isolated, digested partially with Sau3AI and 10–15 kB fragments from this partial digest were sub-cloned into the blue/white screening vector pSU19 (Bartolome, B. et al. *Gene*. 102(1): 75–8 (Jun. 15, 1991); Martinez, E. et al. *Gene*. 68(1): 159–62 (Aug. 15, 1988)). These sub-clones were isolated using Qiagen Turbo96 Miniprep kits and re-screened by PCR as previously described. Sub-clones carrying the correct sequence fragment were transposed with pGPS1.1 using the GPS-1 Genome Priming System kit (New England Biolabs, Inc., Beverly, Mass.). A number of these transposed plasmids were sequenced from each end of the transposon to obtain kilobase long DNA fragments. Sequence assembly was performed with the Sequencher program (Gene Codes Corp., Ann Arbor Mich.).

Example 2

Isolation of *Brevibacterium* sp. HCU Monooxygenase Genes Involved in the Oxidation of Cyclohexanone This Example describes the isolation of the cyclohexanol and cyclohexanone degrader *Brevibacterium* sp. HCU. Discovery of BV monooxygenase genes from the organism was accomplished using differential display methods.

Strain Isolation

Selection for a halotolerant bacterium degrading cyclohexanol and cyclohexanone was performed on agar plates of a halophilic minimal medium (Per liter: 15 g Agar, 100 g NaCl, 10 g MgSO$_4$, 2 g KCl, 1 g NH$_4$Cl, 50 mg KH$_2$PO$_4$, 2 mg FeSO$_4$, 8 g, Tris-HCl (pH 7)) containing traces of yeast extract and casaminoacids (0.005% each) and incubated under vapors of cyclohexanone at 30° C. The inoculum was a resuspension of sludge from industrial wastewater treatment plant. After two weeks, beige colonies were observed and streaked to purity on fresh agar plates grown under the same conditions.

The complete 16s DNA sequence of the isolated *Brevibacterium* sp. HCU was found to be unique and is shown as SEQ ID NO:4. Comparison to other 16S rRNA sequences in the GenBank sequence database found the 16S rRNA gene sequence from strain HCU was at least 99% homologous to the 16S rRNA gene sequences of bacteria belonging to the genus *Brevibacterium*.

Induction of the Cyclohexanone Degradation Pathway

Induciblity of the cyclohexanone pathway was tested by respirometry in low salt medium. One colony of *Brevibacterium* sp. HCU was inoculated in 300 ml of S12 mineral medium (50 mM KHPO$_4$ buffer (pH 7.0), 10 mM (NH4)$_2$SO$_4$, 2 mM MgCl$_2$, 0.7 mM CaCl$_2$, 50 uM MnCl$_2$, 1 µM FeCl$_3$, 1 µM ZnCl$_3$, 1.72 µM CuSO$_4$, 2.53 µM CoCl$_2$, 2.42 µM Na$_2$MoO$_2$, and 0.0001% FeSO$_4$) containing 0.005% yeast extract. The culture was then split into two flasks which received respectively 10 mM acetate and 10 mM cyclohexanone. Each flask was incubated for 6 hrs at 30° C. to allow for the induction of the cyclohexanone degradation genes. The cultures were then chilled on iced, harvested by centrifugation and washed three times with ice-cold S12 medium lacking traces of yeast extract. Cells were finally resuspended to an optical density of 2.0 at 600 nm and kept on ice until assayed.

Half a ml of each culture was placed in a water jacketed respirometry cell equipped with an oxygen electrode (Yellow Spring Instruments Co., Yellow spring, Ohio) and containing 5 ml of air saturated S12 medium at 30° C. After establishing the baseline respiration for each of the cell suspensions, acetate or cyclohexanone was added to a final concentration of 0.02% and the rate of O$_2$ consumption was further monitored.

Identification of Cyclohexanone Oxidation Genes

Identification of genes involved in the oxidation of cyclohexanone made use of the fact that this oxidation pathway is inducible. The mRNA populations of a control culture and a cyclohexanone-induced culture were compared using a technique based on the random amplification of DNA fragments by reverse transcription followed by PCR.

Isolation of Total Cellular RNA

The cyclohexanone oxidation pathway was induced by addition of 0.1% cyclohexanone into one of two "split" 10 ml cultures of *Brevibacterium* sp. HCU grown in S12 medium. Each culture was chilled rapidly in an ice-water bath and transferred to a 15 ml tube. Cells were collected by centrifugation for 2 min at 12,000×g in a rotor chilled to −4° C. The supernatants were discarded, the pellets resuspended in 0.7 ml of ice-cold solution of 1% SDS and 100 mM sodium acetate at pH 5 and transferred to a 2 ml tube containing 0.7 ml of aqueous phenol pH 5 and 0.3 ml of 0.5 mm zirconia beads (Biospec Products, Bartlesville, Okla.). The tubes were placed in a bead beater (Biospec) and disrupted at 2,400 beats per min for two min.

Following the disruption of the cells, the liquid phases of the tubes were transferred to new microfuge tubes and the phases separated by centrifugation for 3 min at 15,000×g. The aqueous phase containing total RNA was extracted twice more with phenol at pH 5 and twice with a mixture of phenol/chloroform/isoamyl alcohol pH 7.5 until a precipitate was no longer visible at the phenol/water interface. Nucleic acids were then recovered from the aqueous phase by ethanol precipitation with three volumes of ethanol and the pellet resuspended in 0.5 ml of diethyl pyrocarbonate (DEPC) treated water. DNA was digested by 6 units of RNAse-free DNAse (Boehringer Mannheim, Indianapolis, Ind.) for 1 hr at 37° C. The total RNA solution was then extracted twice with phenol/chloroform/isoamyl alcohol pH 7.5, recovered by ethanol precipitation and resuspended in 1 ml of DEPC treated water to an approximate concentration of 0.5 mg per ml.

Generation of RAPDs Patterns from Arbitrarily Reverse-Transcribed Total RNA

Arbitrarily amplified DNA fragments were generated from the total RNA of control and induced cells by following the protocol described by Wong K. K. et al. (*Proc Natl Acad Sci USA.* 91:639 (1994)). A series of parallel reverse transcription (RT)/PCR amplification experiments were performed using a RT-PCR oligonucleotide set. This set consisted of 81 primers, each designed with the sequence CGGAGCAGATCGAVVVV (SEQ ID NO:63) where VVVV represent all the combinations of the three bases A, G and C at the last four positions of the 3'-end.

The series of parallel RT-PCR amplification experiments were performed on the total RNA from the control and induced cells, each using a single RT-PCR oligonucleotide. Briefly, 50 µl reverse transcription (RT) reactions were performed on 20–100 ng of total RNA using 100 U Moloney Murine Leukemia Virus (MMLV) reverse transcriptase (Promega, Madison, Wis.) with 0.5 mM of each dNTP and 1 mM for each oligonucleotide primer. Reactions were prepared on ice and incubated at 37° C. for 1 hr.

Five µl from each RT reaction were then used as template in a 50 µl PCR reaction containing the same primer used for the RT reaction (0.25 µM), dNTPs (0.2 mM each), magnesium acetate (4 mM) and 2.5 U of the Taq DNA polymerase Stoffel fragment (Perkin Elmer, Foster City, Calif.). The following temperature program was used: 94° C. (5 min), 40° C. (5 min), 72° C. (5 min) for 1 cycle followed by 40 cycles of 94° C. (1 min), 60° C. (1 min), 72° C. (5 min).

RAPD fragments were separated by electrophoresis on acrylamide gels (15 cm×15 cm×1.5 mm, 6% acrylamide, 29:1 acryl:bisacrylamide, 100 mM Tris, 90 mM borate, 1 mM EDTA pH 8.3). Five 11 from each PCR reaction were analyzed with the reactions from the control and the induced RNA for each primer running side by side. Electrophoresis was performed at 1 V/cm. DNA fragments were visualized by silver staining using the Plus One® DNA silver staining kit in the Hoefer automated gel stainer (Amersham Pharmacia Biotech, Piscataway, N.J.).

Reamplification of the Differentially Expressed DNA

Stained gels were rinsed extensively for one hr with distilled water. Bands generated from the RNA of cyclohexanone induced cells but absent in the reaction from the RNA of control cells were excised from the gel and placed in a tube containing 50 µl of 10 mM KCl and 10 mM Tris-HCl (pH 8.3) and heated to 95° C. for 1 hr to allow some of the DNA to diffuse out of the gel. Serial dilutions of the eluate over a 200 fold range were used as template for a new PCR reaction using the Taq polymerase. The primer used for each reamplification (0.25 µM) was the one that had generated the pattern.

Each reamplified fragment was cloned into the blue/white cloning vector pCR2.1 (Invitrogen, San Diego, Calif.) and sequenced using the universal forward and reverse primers (M13 Reverse Primer (SEQ ID NO:64) and M13 (−20) Forward Primer (SEQ ID NO:65).

Extension of Monooxygenase Fragments by Out-PCR.

Kilobase-long DNA fragments extending the sequences fragments identified by differential display were generated by "Out-PCR", a PCR technique using an arbitrary primer in addition to a sequence specific primer. The first step of this PCR-based gene walking technique consisted of randomly copying the chromosomal DNA using a primer of arbitrary sequence in a single round of amplification under low stringency conditions. The primers used for Out-PCR were chosen from a primer set used for mRNA differential display and their sequences were CGGAGCAGATCGAVVVV (SEQ ID NO:63) where VVVV was A, G or C. Ten Out-PCR reactions were performed, each using one primer of arbitrary sequence. The reactions (50 µl) included a 1× concentration of the rTth XL buffer provided by the manufacturer (Perkin-Elmer, Foster City, Calif.), 1.2 mM magnesium acetate, 0.2 mM of each dNTP, 10–100 ng genomic DNA, 0.4 mM of one arbitrary primer and 1 unit of rTth XL polymerase (Perkin-Elmer). A five min annealing (45° C.) and 15 min extension cycle (72° C.) lead to the copying of the genomic DNA at arbitrary sites and the incorporation of a primer of arbitrary but known sequence at the 3' end.

After these initial low stringency annealing and replication steps, each reaction was split into two tubes. One tube received a specific primer (0.4 mM) designed against the end of the sequence to be extended and directed outward, while the second tube received water and was used as a control. Thirty additional PCR cycles were performed under higher stringency conditions with denaturization at 94° C. (1 min), annealing at 60° C. (0.5 min) and extension at 72° C. (10 min). The long extension time was designed to allow for the synthesis of long DNA fragments by the long range rTth XL DNA polymerase. The products of each pair of reactions were analyzed in adjacent lanes on an agarose gel.

Bands present in the sample having received the specific primer but not in the control sample were excised from the agarose gel, melted in 0.5 ml $H_2O$ and used as the template in a new set of PCR reactions. A 1× concentration of rTth XL buffer, 1.2 mM magnesium acetate, 0.2 mM of each dNTP, 0.4 mM of primers, 1/1000 dilution of the melted slice and 1 unit of rTth XL polymerase were used for these reactions. The PCR was performed at 94° C. (1 min), 60° C. (0.5 min), and 72° C. (15 min) per cycle for 20 cycles. For each of these reamplification reactions, two control reactions, lacking either the arbitrary primer or the specific primer, were included in order to confirm that the reamplification of the band of interest required both the specific and arbitrary primer. DNA fragments that required both the specific and arbitrary primer for amplification were sequenced. For sequencing, the long fragments obtained by Out-PCR were partially digested with MboI and cloned into pCR2.1 (Invitrogen, Carlsbad, Calif.). Sequences for these partial fragments were obtained using primers designed against the vector sequence.

Example 3

Isolation of a *Acidovorax* sp. CHX Monooxygenase Gene Involved in Degradation of Cyclohexane This Example describes the isolation of the cyclohexane degrader *Acidovorax* sp. CHX. Discovery of a BVMO gene was accomplished using differential display methods.

Strain Isolation

An enrichment for bacteria growing on cyclohexane as a sole carbon source was started by adding 5 ml of an industrial wastewater sludge to 20 ml of mineral medium (50 mM KHPO$_4$ (pH 7.0), 10 mM (NH$_4$)SO$_4$, 2 mM MgCl$_2$, 0.7 mM CaCl$_2$, 50 µM MnCl$_2$, 1 µM FeCl$_3$, 1 µM ZnCl$_3$, 1.72 µM CuSO$_4$, 2.53 µM CoCl$_2$, 2.42 µM Na$_2$MoO$_2$, and 0.0001% FeSO$_4$) in a 125 ml Erlenmeyer flask sealed with a Teflon lined screw cap. A test tube containing 1 ml of a mixture of mineral oil and cyclohexane (8/1 v/v) was fitted in the flask to provide a low vapor pressure of cyclohexane (approximately 30% of the vapor pressure of pure cyclohexane). The enrichment was incubated at 30° C. for a week. Periodically, 1 to 10 dilutions of the enrichment were performed in the same mineral medium supplemented with 0.005% of yeast extract under low cyclohexane vapors. After several transfers, white flocks could be seen in the enrichments under cyclohexane vapors. If cyclohexane was omitted, the flocks did not grow.

After several transfers, the flocks could be grown with 4 µl of liquid cyclohexanone added directly to 10 ml of medium. To isolate colonies, flocks were washed in medium and disrupted by thorough shaking in a bead beater. The cells released from the disrupted flocks were streaked onto R2A medium agar plates and incubated under cyclohexane vapors. Pinpoint colonies were picked under a dissecting microscope and inoculated in 10 ml of mineral medium supplemented with 0.01% yeast extract and 4 µl of cyclohexane. The flocks were grown, disrupted and streaked again until a pure culture was obtained.

Taxonomic identification of this isolate was performed by PCR amplification of 16S rDNA, as described in the General Methods. The 16S rRNA gene sequence from strain CHX was at least 98% homologous to the 16S rRNA gene sequence of an uncultured bacterium (Seq. Accession number AF143840) and 95% homologous to the 16s rRNA gene sequences of the genus *Acidovorax termperans* (Accession number AF078766). The complete 16s DNA sequence of the isolated *Acidovorax* sp. CHX is shown as SEQ ID NO:5.

Induction of Cyclohexane Degradation Genes

For induction of cyclohexane degradation genes, colonies of *Acidovorax* sp. CHX were scraped from an R2A agar plate and inoculated into 25 ml R2A broth. This culture was incubated overnight at 30° C. The next day 25 ml of fresh R2A broth was added and growth was continued for 15 min. The culture was split into two separate flasks, each of which received 25 ml. To one of these flasks, 5 µl of pure cyclohexane was added to induce expression of cyclohexane degradation genes. The other flask was kept as a control. Differential display was used to identify the *Acidovorax* sp. CHX monooxygenase gene. Identification of cyclohexane induced gene sequences and sequencing cyclohexanone oxidation genes from strains was performed in a similar manner as described in Example 1.

Example 4

Isolation of a *Acinetobacter* sp. SE19 Monooxygenase Gene Involved in Degradation of Cyclohexanol This Example describes the isolation of the cyclohexanol degrader *Acinetobacter* sp. SE19. Discovery of a BV monooxygenase gene was accomplished by screening of cosmid libraries, followed by sequencing of shot-gun libraries.

Isolation of Strain

An enrichment for bacteria that grow on cyclohexanol was isolated from a cyclopentanol enrichment culture. The enrichment culture was established by inoculating 1 mL of activated sludge into 20 mL of S12 medium (10 mM ammonium sulfate, 50 mM potassium phosphate buffer (pH 7.0), 2 mM MgCl$_2$, 0.7 mM CaCl$_2$, 50 uM MnCl$_2$, 1 uM FeCl$_3$, 1 uM ZnCl$_3$, 1.72 uM CuSO$_4$, 2.53 uM CoCl$_2$, 2.42 uM Na$_2$MoO$_2$, and 0.0001% FeSO$_4$) in a sealed 125 mL screw-cap Erlenmeyer flask. The enrichment culture was supplemented with 100 ppm cyclopentanol added directly to the culture medium and was incubated at 35° C. with reciprocal shaking. The enrichment culture was maintained by adding 100 ppm cyclopentanol every 2–3 days. The culture was diluted every 2–10 days by replacing 10 mL of the culture with the same volume of S12 medium. After 15 days of incubation, serial dilutions of the enrichment culture were spread onto LB plates. Single colonies were screened for the ability to grow on S12 liquid with cyclohexanol as the sole carbon and energy source. The cultures were grown at 35° C. in sealed tubes. One of the isolates, strain SE19 was selected for further characterization.

The 16s rRNA genes of SE19 isolates were amplified by PCR according to the procedures of the General Methods. Result from all isolates showed that strain SE19 has close homology to *Acinetobacter haemolyticus* and *Acinetobacter junii*, (99% nucleotide identity to each).

Construction of *Acinetobacter* Cosmid Libraries

*Acinetobacter* sp. SE19 was grown in 25 ml LB medium for 6 h at 37° C. with aeration. Bacterial cells were centrifuged at 6,000 rpm for 10 min in a Sorvall RC5C centrifuge at 4° C. Supernatant was decanted and the cell pellet was frozen at –80° C. Chromosomal DNA was prepared as outlined below with special care taken to avoid shearing of DNA. The cell pellet was gently resuspended in 5 ml of 50 mM Tris-10 mM EDTA (pH 8) and lysozyme was added to a final concentration of 2 mg/ml. The suspension was incubated at 37° C. for 1 h. Sodium dodecyl sulfate was then added to a final concentration of 1% and proteinase K was added at 100 µg/ml. The suspension was incubated at 55° C. for 2 h. The suspension became clear and the clear lysate was extracted with equal volume of phenol:chloroform:isoamyl alcohol (25:24:1). After centrifuging at 12,000 rpm for 20 min, the aqueous phase was carefully removed and transferred to a new tube. Two volumes of ethanol were added and the DNA was gently spooled with a sealed glass pasteur pipet. The DNA was dipped into a tube containing 70% ethanol. After air drying, the DNA was resuspended in 400 µl of TE (10 mM Tris-1 mM EDTA, pH 8) with RNaseA (100 µg/ml) and stored at 4° C. The concentration and purity of DNA was determined spectrophotometrically by OD$_{260}$/OD$_{280}$. A diluted aliquot of DNA was run on a 0.5% agarose gel to determine the intact nature of DNA.

Chromosomal DNA was partially digested with Sau3AI (GIBRO/BRL, Gaithersburg, Md.) as outlined by the instruction manual for the SuperCos 1 Cosmid Vector Kit. DNA (10 µg) was digested with 0.5 unit of Sau3AI at room temperature in 100 µl of reaction volume. Aliquots of 20 µl were withdrawn at various time points of the digestion: e.g., 0, 3, 6, 9, 12 min. DNA loading buffer was added and samples were analyzed on a 0.5% agarose gel to determine the extent of digestion. A decrease in size of chromosomal DNA corresponded to an increase in the length of time for Sau3AI digestion. The preparative reaction was performed using 50 µg of DNA digested with 1 unit of Sau3AI for 3 min at room temperature. The digestion was terminated by addition of 8 mM of EDTA. The DNA was extracted once with phenol:chloroform:isoamyl alcohol and once with chloroform. The aqueous phase was adjusted to 0.3 M NaOAc and ethanol precipitated. The partially digested DNA was dephosphorylated with calf intestinal alkaline phosphatase and ligated to SuperCos 1 vector, which had been treated according to the instructions in the SuperCos 1 Cosmid Vector Kit. The ligated DNA was packaged into lamda phage using Gigapack III XL packaging extract, as recommended by Stratagene (manufacturer's instructions were followed). The packaged *Acinetobacter* genomic DNA library contained a phage titer of $5.6 \times 10^4$ colony forming units per µg of DNA as determined by transfecting *E. coli* XL1-Blue MR. Cosmid DNA was isolated from six randomly chosen *E. coli* transformants and found to contain large inserts of DNA (25–40 kb).

Identification and Characterization of Cosmid Clones Containing a Cyclohexanone Monooxygenase Gene The cosmid library of Acinetobacter sp. SE19 was screened based on the homology of the cyclohexanone monooxygenase gene. Two primers, monoL: GAGTCT-GAGCATATGTCACAAAAAATGGATTTTG (SEQ ID NO:66) and monoR: GAGTCTGAGGGATCCTTAGGCAT-TGGCAGGTTGCTTGAT (SEQ ID NO:67) were designed based on the published sequence of cyclohexanone monooxygenase gene of *Acinetobacter* sp. NCIB 9871. The cosmid library was screened by PCR using monoL and monoR primers. Five positive clones (5B12, 5F5, 8F6, 14B3 and 14D7) were identified among about 1000 clones screened. They all contain inserts of 35–40 kb that show homology to the cyclohexanone monooxygenase gene amplified by monoL and monoR primers. Southern hybridization using this gene fragment as a probe indicated that the cosmid clone 5B12 has about 20 kb region upstream of the monooxygenase gene and cosmid clone 8F6 has about 30 kb downstream of the monooxygenase gene. Cosmid clone 14B3 contains rearranged *Acinetobacter* DNA adjacent to the monooxygenase gene.

Construction of Shot-gun Sequencing Libraries

Shot gun libraries of 5B12 and 8F6 were constructed. Cosmid DNA was sheared in a nebulizer (Inhalation Plastics Inc., Chicago, Ill.) at 20 psi for 45 sec and the 1–3 kb portion was gel purified. Purified DNA was treated with T4 DNA polymerase and T4 polynucleotide kinase following manufacturer's (GIBCO/BRL) instructions. Polished inserts were ligated into pUC18 vectors using Ready-To-Go pUC18SmaI/BAP+Ligase (GIBCO/BRL). The ligated DNA was transformed into *E. coli* DH5α cells and plated on LB with ampicillin and X-gal. A majority of the transformants were white and those containing inserts were sequenced with the universal and reverse primers of pUC18 by standard sequencing methods.

Shot gun library inserts were sequenced with pUC18 universal and reverse primers. Sequences of 200–300 clones from each library were assembled using Sequencher 3.0 program. A contig of 17419 bp containing the cyclohexanone monooxygenase gene was formed.

Example 5

Isolation and Sequencing of *Rhodococcus erythropolis* AN12

This Example describes isolation of *Rhodococcus erythropolis* AN12 strain from wastestream sludge. A shotgun sequencing strategy approach permitted sequencing of the entire microbial genome.

Isolation of *Rhodococcus erythropolis* AN12

Strain AN12 of *Rhodococcus erythropolis* was isolated on the basis of ability to grow on aniline as the sole source of carbon and energy. Bacteria that grow on aniline were isolated from an enrichment culture. The enrichment culture was established by inoculating 1 ml of activated sludge into 10 ml of S12 medium (10 mM ammonium sulfate, 50 mM potassium phosphate buffer (pH 7.0), 2 mM $MgCl_2$, 0.7 mM $CaCl_2$, 50 µM $MnCl_2$, 1 µM $FeCl_3$, 1 µM $ZnCl_3$, 1.72 µM $CuSO_4$, 2.53 µM $CoCl_2$, 2.42 µM $Na_2MoO_2$, and 0.0001% $FeSO_4$) in a 125 ml screw cap Erlenmeyer flask. The activated sludge was obtained from a DuPont wastewater treatment facility. The enrichment culture was supplemented with 100 ppm aniline added directly to the culture medium and was incubated at 25° C. with reciprocal shaking. The enrichment culture was maintained by adding 100 ppm of aniline every 2–3 days. The culture was diluted every 14 days by replacing 9.9 ml of the culture with the same volume of S12 medium. Bacteria that utilize aniline as a sole source of carbon and energy were isolated by spreading samples of the enrichment culture onto S12 agar. Aniline was placed on the interior of each petri dish lid. The petri dishes were sealed with parafilm and incubated upside down at room temperature (25° C.). Representative bacterial colonies were then tested for the ability to use aniline as a sole source of carbon and energy. Colonies were transferred from the original S12 agar plates used for initial isolation to new S12 agar plates and supplied with aniline on the interior of each petri dish lid. The petri dishes were sealed with parafilm and incubated upside down at room temperature (25° C.).

A 16S rRNA gene of strain AN12 was sequenced (SEQ ID NO:6) as described in the General Methods and compared to other 16S rRNA sequences in the GenBank sequence database. The 16S rRNA gene sequence from strain AN12 was at least 98% homologous to the 16S rRNA gene sequences of high G+C Gram positive bacteria belonging to the genus *Rhodococcus*.

Preparation of Genomic DNA for Sequencing and Sequence Generation

Genomic DNA and library construction were prepared according to published protocols (Fraser et al. *Science* 270(5235): 397–403 (1995)). A cell pellet was resuspended in a solution containing 100 mM Na-EDTA (pH 8.0), 10 mM Tris-HCl (pH 8.0), 400 mM NaCl, and 50 mM $MgCl_2$.

Genomic DNA preparation After resuspension, the cells were gently lysed in 10% SDS, and incubated for 30 minutes at 55° C. After incubation at room temperature, proteinase K (Boehringer Mannheim, Indianapolis, Ind.) was added to 100 µg/ml and incubated at 37° C. until the suspension was clear. DNA was extracted twice with Tris-equilibrated phenol and twice with chloroform. DNA was precipitated in 70% ethanol and resuspended in a solution containing 10 mM Tris-HCl and 1 mM Na-EDTA (TE buffer) pH 7.5. The DNA solution was treated with a mix of RNAases, then extracted twice with Tris-equilibrated phenol and twice with chloroform. This was followed by precipitation in ethanol and resuspension in TE buffer.

Library construction 200 to 500 µg of chromosomal DNA was resuspended in a solution of 300 mM sodium acetate, 10 mM Tris-HCl, 1 mM Na-EDTA, and 30% glycerol, and sheared at 12 psi for 60 sec in an Aeromist Downdraft Nebulizer chamber (IBI Medical products, Chicago, Ill.). The DNA was precipitated, resuspended and treated with Bal31 nuclease (New England Biolabs, Beverly, Mass.). After size fractionation, a fraction (2.0 kb, or 5.0 kb) was excised, cleaned and a two-step ligation procedure was used to produce a high titer library with greater than 99% single inserts.

Sequencing A shotgun sequencing strategy approach was adopted for the sequencing of the whole microbial genome (Fleischmann, R. et al. Whole-Genome Random sequencing and assembly of *Haemophilus influenzae* Rd. *Science* 269 (5223): 496–512 (1995)).

Example 6

Identification and Characterization of Bacterial Genes

Genes encoding each monooxygenase were identified by conducting BLAST (Basic Local Alignment Search Tool; Altschul, S. F., et al., (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the SWISS-PROT protein sequence database, EMBL, and DDBJ databases). The sequences obtained in Examples 1, 2, 3, 4, and 5 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX BLOSUM62 algorithm with a gap exisitense cost of 11 per residue gap cost of 2, filtered, gap alignment (Gish, W. and States, D. J. *Nature Genetics* 3:266–272 (1993)) provided by the NCBI.

All comparisons were done using either the BLASTNnr or BLASTXnr algorithm. The results of the BLAST comparisons are given in Table 3 which summarize the sequence to which each sequence has the most similarity. Table 3 displays data based on the BLASTXnr algorithm with values reported in expect values. The Expect value estimates the statistical significance of the match, specifying the number of matches, with a given score, that are expected in a search of a database of this size absolutely by chance.

TABLE 3

| ORF Name | Gene Name and Organism of Isolation | Similarity Identified | SEQ ID base | SEQ ID Peptide | % Identity[a] | % Similarity[b] | E-value[c] | Citation |
|---|---|---|---|---|---|---|---|---|
| 1 | chnB *Rhodococcus* sp. phi 1 | >gb|AAG10021.1|AF282240_5 (AF282240) cyclohexanone monooxygenase [*Acinetobacter* sp. SE19] | 7 | 8 | 55 | 71 | e−174 | Cheng, Q., et al. J. Bacteriol. 182: 4744–4751 (2000) |
| 2 | chnB *Rhodococcus* sp. phi 2 | >gb|AAG10021.1|AF282240_5 (AF282240) cyclohexanone monooxygenase [*Acinetobacter* sp. SE19] | 9 | 10 | 53 | 67 | e−163 | Cheng, Q., et al. J. Bacteriol. 182: 4744–4751 (2000) |
| 3 | chnB *Arthrobacter* sp. BP2 | >gb|AAG10021.1|AF282240_5 (AF282240) cyclohexanone monooxygenase [*Acinetobacter* sp. SE19] | 11 | 12 | 57 | 72 | e−106 | Cheng, Q., et al. J. Bacteriol. 182: 4744–4751 (2000) |
| 4 | chnB1 *Brevibacterium* sp. HCU | >pir||JC7158 steroid monooxygenase (EC 1.14.99.-) - *Rhodococcus rhodochrous* dbj|BAA24454.1| (AB010439) steroid monooxygenase [*Rhodococcus rhodochrous*] | 13 | 14 | 44 | 59 | e−122 | Morii, S., et al. J. Biochem. 126 (3): 624–631 (1999) |
| 5 | chnB2 *Brevibacterium* sp. HCU | >pir||JC7158 steroid monooxygenase (EC 1.14.99.-) - *Rhodococcus rhodochrous* dbj|BAA24454.1| (AB010439) steroid monooxygenase [*Rhodococcus rhodochrous*] | 15 | 16 | 38 | 53 | 2e−94 | Morii, S., et al. J. Biochem. 126 (3): 624–631 (1999) |
| 6 | chnB *Acidovorax* sp.CHX | >gb|AAG10021.1|AF282240_5 (AF282240) cyclohexanone monooxygenase [*Acinetobacter* sp. SE19] | 17 | 18 | 57 | 73 | 0.0 | Cheng, Q., et al. J. Bacteriol. 182: 4744–4751 (2000) |
| 7 | chnB *Acinetobacter* sp. SE19 | >dbj|BAA86293.1| (AB006902) cyclohexanone 1,2-monooxygenase [*Acinetobacter* sp.]dbj|BAB61738.1| (AB026668) cyclohexanone 1,2-monooxygenase [*Acinetobacter* sp. NCIMB9871] | 19 | 20 | 99 | 99 | 0.0 | Chen, Y. C., et al. J. Bacteriol. 170 (2): 781–789 (1988) |
| 8 | ORF 8 chnB *Rhodococcus erythropolis* AN12 | >pir||T37052 probable flavin-containing monooxygenase - *Streptomyces coelicolor* emb|CAB52349.1|(AL109747) putative flavin-containing monooxygenase [*Streptomyces coelicolor* A3(2)] | 21 | 22 | 37 | 50 | 6e−58 | Seeger, K. J., et al. Direct Submission (??-AUG-1999) to the EMBL Data Library |
| 9 | ORF 9 chnB *Rhodococcus erythropolis* AN12 | >emb|CAB59668.1|(AL132674) monooxygenase. [*Streptomyces coelicolor* A3(2)] | 23 | 24 | 44 | 61 | e−118 | Redenbach, M., et al. Mol. Microbiol. 21 (1): 77–96 (1996) |

TABLE 3-continued

| ORF Name | Gene Name and Organism of Isolation | Similarity Identified | SEQ ID base | SEQ ID Peptide | % Identity[a] | % Similarity[b] | E-value[c] | Citation |
|---|---|---|---|---|---|---|---|---|
| 10 | ORF 10 chnB Rhodococcus erythropolis AN12 | >pir\|JC7158 steroid monooxygenase (EC 1.14.99.-) - Rhodococcus rhodochrous dbj\|BAA24454.1\|(AB010439) steroid monooxygenase [Rhodococcus rhodochrous] | 25 | 26 | 64 | 76 | 0.0 | Morii, S., et al. J. Biochem. 126 (3), 624–631 (1999) |
| 11 | ORF 11 chnB Rhodococcus erythropolis AN12 | >gb\|AAK22759.1\|(AE005753) monooxygenase, flavin-binding family [Caulobacter crescentus] | 27 | 28 | 65 | 74 | e-176 | Nierman, W. C., et al. Proc. Natl. Acad. Sci. U.S.A. 98 (7): 4136–4141 (2001) |
| 12 | ORF 12 chnB Rhodococcus erythropolis AN12 | >emb\|CAB59668.1\|(AL132674) monooxygenase. [Streptomyces coelicolor A3(2)] | 29 | 30 | 45 | 63 | e-124 | Redenbach, M., et al. Mol. Microbiol. 21 (1): 77–96 (1996) |
| 13 | ORF 13 chnB Rhodococcus erythropolis AN12 | >gb\|AAK24539.1\|(AE005925) monooxygenase, flavin-binding family [Caulobacter crescentus] | 31 | 32 | 55 | 68 | e-159 | Nierman, W. C., et al. Proc. Natl. Acad. Sci. U.S.A. 98 (7): 4136–4141 (2001) |
| 14 | ORF 14 chnB Rhodococcus erythropolis AN12 | >pir\|JC7158 steroid monooxygenase (EC 1.14.99.-) - Rhodococcus rhodochrous dbj\|BAA24454.1\|(AB010439) steroid monooxygenase [Rhodococcus rhodochrous] | 33 | 34 | 51 | 65 | e-154 | Morii, S., et al. J. Biochem. 126 (3), 624–631 (1999) |
| 15 | ORF 15 chnB Rhodococcus erythropolis AN12 | >sp\|P55487\|Y4ID_RHISN PROBABLE MONOOXYGENASE Y4ID gb\|AAB91699.1\|(AE000078) Y4iD [Rhizobium sp. NGR234] | 35 | 36 | 39 | 58 | e-145 | Freiberg, C. A., et al. Nature 387: 394–401 (1997). |
| 16 | ORF 16 chnB Rhodococcus erythropolis AN12 | >pir\|A83453 probable flavin-containing monooxygenase PA1538 [imported] - Psuedomonas aeruginosa (strain PAO1) gb\|AAG04927.1\|AE004582_5 (AE004582) probable flavin-containing monooxygenase [Psuedomonas aeruginosa] | 37 | 38 | 43 | 59 | e-119 | Stover, C. K., et al. Nature 406 (6799): 959–964 (2000) |
| 17 | ORF 17 chnB Rhodococcus erythropolis AN12 | >pir\|G70852 hypothetical protein Rv3083 - Mycobacterium tuberculosis (strain H37RV) emb\|CAA16141.1\| (AL021309) hypothetical protein Rv3083 [Mycobacterium tuberculosis] gb\|AAK47504.1\| (AE007134) monooxygenase, flavin-binding family [Mycobacterium tuberculosis CDC1551] | 39 | 40 | 53 | 70 | e-150 | Cole, S. T., et al. Nature 393 (6685): 537–544 (1998) |
| 18 | ORF 18 chnB Rhodococcus erythropolis AN12 | >pir\|A83453 probable flavin-containing monooxygenase PA1538 [imported] - Psuedomonas aeruginosa (strain PAO1) gb\|AAG04927.1\|AE004582_5 (AE004582) probable flavin-containing monooxygenase [Psuedomonas aeruginosa] | 41 | 42 | 44 | 60 | e-117 | Stover, C. K., et al. Nature 406 (6799): 959–964 (2000) |
| 19 | ORF 19 chnB Rhodococcus erythropolis AN12 | >gb\|AAG10021.1\|AF282240_5 (AF282240) cyclohexanone monooxygenase [Acinetobacter sp. SE19] | 43 | 44 | 54 | 69 | e-168 | Cheng, Q., et al. J. Bacteriol. 182 (17): 4744–4751 (2000) |
| 20 | ORF 20 chnB Rhodococcus erythropolis AN12 | >pir\|JC7158 steroid monooxygenase (EC 1.14.99.-) - Rhodococcus rhodochrous dbj\|BAA24454.1\| (AB010439) steroid monooxygenase [Rhodococcus rhodochrous] | 45 | 46 | 42 | 60 | e-123 | Morii, S., et al. J. Biochem. 126 (3): 624–631 (1999) |

[a]% Identity is defined as percentage of amino acids that are identical between the two proteins.
[b]% Similarity is defined as percentage of amino acids that are identical or conserved between the two proteins.
[c]Expect value. The Expect value estimates the statistical significance of the match, specifying the number of matches, with a given score, that are expected in a search of a database of this size absolutely by chance.

Example 7

Cloning and Expression of Monooxygenase Genes into Escherichia coli

This example illustrates the expression in *E. coli* of isolated full length BVMO genes from *Brevibacterium* sp. HCU, *Acinetobacter* SE19, *Rhodococcus* sp. phi1, *Rhodococcus* sp. phi2, *Arthrobacter* sp. BP2 and *Acidovorax* sp. CHX.

Full length BVMO's were PCR amplified, using chromosomal DNA as the template and the primers shown below in Table 4.

TABLE 4

Primers Used for Amplification of Full-Length BV Monooxygenases

| Monooxygenase | Forward Primer | Reverse Primer |
|---|---|---|
| *Brevibacterium* sp. HCU chnB1 | atgccaattacacaacaacttgacc (SEQ ID NO: 68) | ctatttcataccgccgattcac (SEQ ID NO: 69) |
| *Brevibacterium* sp. HCU chnB2 | atgacgtcaaccatgcctgcac (SEQ ID NO: 70) | cacttaagtcgcattcagccc (SEQ ID NO: 71) |
| *Acinetobacter* sp. SE19 chnB | atggattttgatgctatcgtg (SEQ ID NO: 72) | ggcattggcaggttgcttg (SEQ ID NO: 73) |
| *Arthrobacter* sp. BP2 chnB | atgactgcacagaacactttcc (SEQ ID NO: 74) | tcaaagccgcggtatccg (SEQ ID NO: 75) |
| *Rhodococcus* sp. phi1 chnB | atgactgcacagatctcacccac (SEQ ID NO: 76) | tcaggcggtcaccgggacagcg (SEQ ID NO: 77) |
| *Rhodococcus* sp. phi2 chnB | atgaccgcacagaccatccacac (SEQ ID NO: 78) | tcagaccgtgaccatctcgg (SEQ ID NO: 79) |
| *Acidovorax* sp. CHX chnB | atgtcttcctcgccaagcagc (SEQ ID NO: 80) | cagtggttggaacgcaaagcc (SEQ ID NO: 81) |

Following amplification, the chnB gene fragments were cloned into pTrcHis-TOPO TA vectors with either an N-terminal tail or C-terminal tail, as provided by the vector sequence (N-terminal tail for *Brevibacterium* sp. HCU, *Rhodococcus* sp. phi1, *Rhodococcus* sp. phi2, and *Arthrobacter* sp. BP2 monooxygenases; C-terminal tail for Acinetobacter sp. SE19 and *Acidovorax* sp. CHX monooxygenases). These vectors were transformed into *E. coli*, with transformants grown in Luria-Bertani broth supplemented with ampicillin (100 ug/ml) and riboflavin (0.1 ug/ml) at 30° C. until the absorbance at 600 nm (A600) reached 0.5. When the A600 was reached, the temperature was shifted to 16° C.

The encoded monooxygenase sequences were expressed upon addition of IPTG to the culture media, 30 min after the temperature shift to 16° C. The cultures were grown further overnight (14 hrs) and harvested by centrifugation in a cold centrifuge. The cells were treated with lysozyme (100 mg/ml) for 30 min on ice and sonicated. Following sonication, cell extracts were centrifuged and the supernatant was equilibrated with Ni-NTA resin (Qiagen, Valencia, Calif.) for 1 hr at 4° C. Protein bound resin was washed successively with increasing concentrations of imidazole buffer until the protein of interest was released from the resin. The purified protein was concentrated and the buffer exchanged to remove the imidazole. The protein concentration was adjusted to 1 ug/ml.

Example 8

Assays of chnB Monooxygenase Activities of Brevibacterium sp. HCU, Acinetobacter SE19, Rhodococcus sp. phi1, Rhodococcus sp. phi2, Arthrobacter sp. BP2 and Acidovorax sp. CHX.

The chnB monooxygenase activity of each over-expressed enzyme from Example 7 was assayed against various ketone substrates: cyclobutanone, cyclopentanone, 2-methylcyclopentanone, cyclohexanone, 2-methylcyclohexanone, cyclohex-2-ene-1-one, 1,2-cyclohexanedione, 1,3-cyclohexanedione, 1,4-cyclohexanedione, cycloheptanone, cyclooctanone, cyclodecanone, cycloundodecanone, cyclododecanone, cyclotridecanone, cyclopentadecanone, 2-tridecanone, 2-phenylcyclohexanone, diheyl ketone, norcamphor, beta-ionone, oxindole, levoglucosenone, dimethyl sulfoxide, dimethyl-2-piperidone, and phenylboronic acid. Compounds were selected on the basis of previous observations by van der Werf (*J. Biochem.* 347:693–701 (2000)) and Miyamoto et al. (*Biochimica* et *Biophysica Acta* 1251: 115–124 (1995)) and by searches for the ketone substructure.

All compounds were obtained from Sigma-Aldrich with only two exceptions. Levoglucosenone was obtained from Toronto Research Chemicals, Inc. and dimethyl-2-piperidone was prepared according to U.S. Pat. No. 6,077,955. For enzyme assays all compounds were dissolved to a concentration of 0.1 M in methanol, with the exceptions of norcamphor (dissolved in ethyl acetate), cyclododecanone, cycltridecanone and cyclopentadecanone (dissolved in propanol), and levoglucosenone (dissolved with acetone).

The monooxygenase activity of each over-expressed enzyme was assayed spectrophotometrically at 340 nm by monitoring the oxidation of NADPH. Assays were performed in individual quartz cuvettes, with a pathlength of 1 cm. The following components were added to the cuvette for the enzyme assays: 380 ul of 33.3 mM MES-HEPES-sodium acetate buffer (pH 7.5), 5 µl of 0.1 M substrate (1.25 mM final concentration), 10 µl of 1 µg/pl enzyme solution (10 ng total, 0.025 ng/µl) and 5 ul NADPH (1.2 M, 15 mM final concentration ). An Ultrospec 4000 (Pharmacia Biotech, Cambridge, England) was used to read the absorbance of the samples over a two to ten minute time period and the SWIFT (Pharmacia Biotech) program was used to calculate the slope of the reduction in absorbance over time. For the *Brevibacterium* sp. HCU chnB2, the rates were multiplied by a factor of 3.25 to adjust for decrease in activity due to storage as suggested by the literature (*J. Bacteriol.* 2000. 182: p. 4241–4248). Monooxygenase activity of each over-expressed enzyme is shown in Table 5, with respect to each ketone substrate. The specific activity values listed are given in umol/min/mg. The notation "ND" refers to "No Activity Detected".

Figure 2:
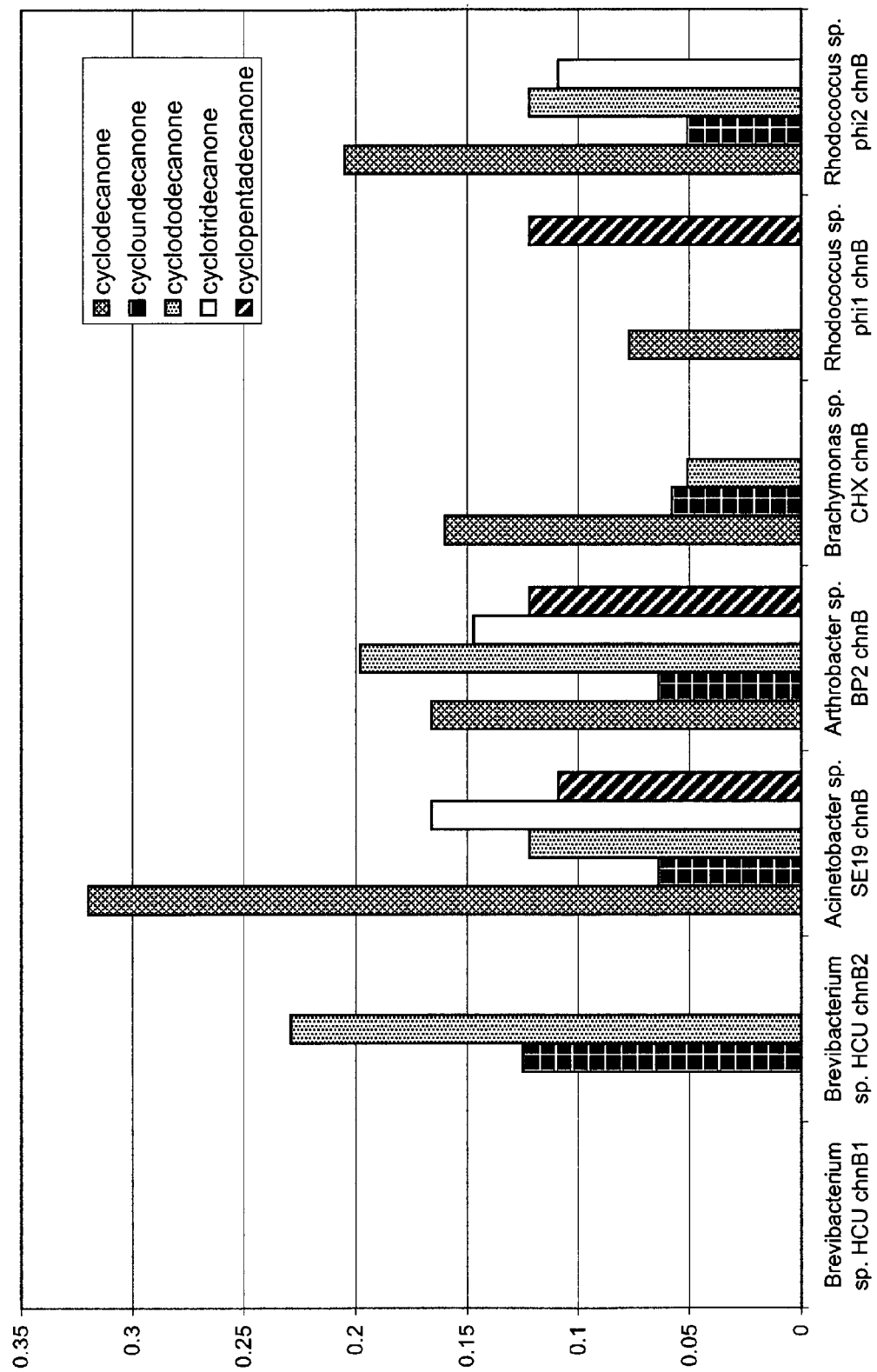
Figure 3:
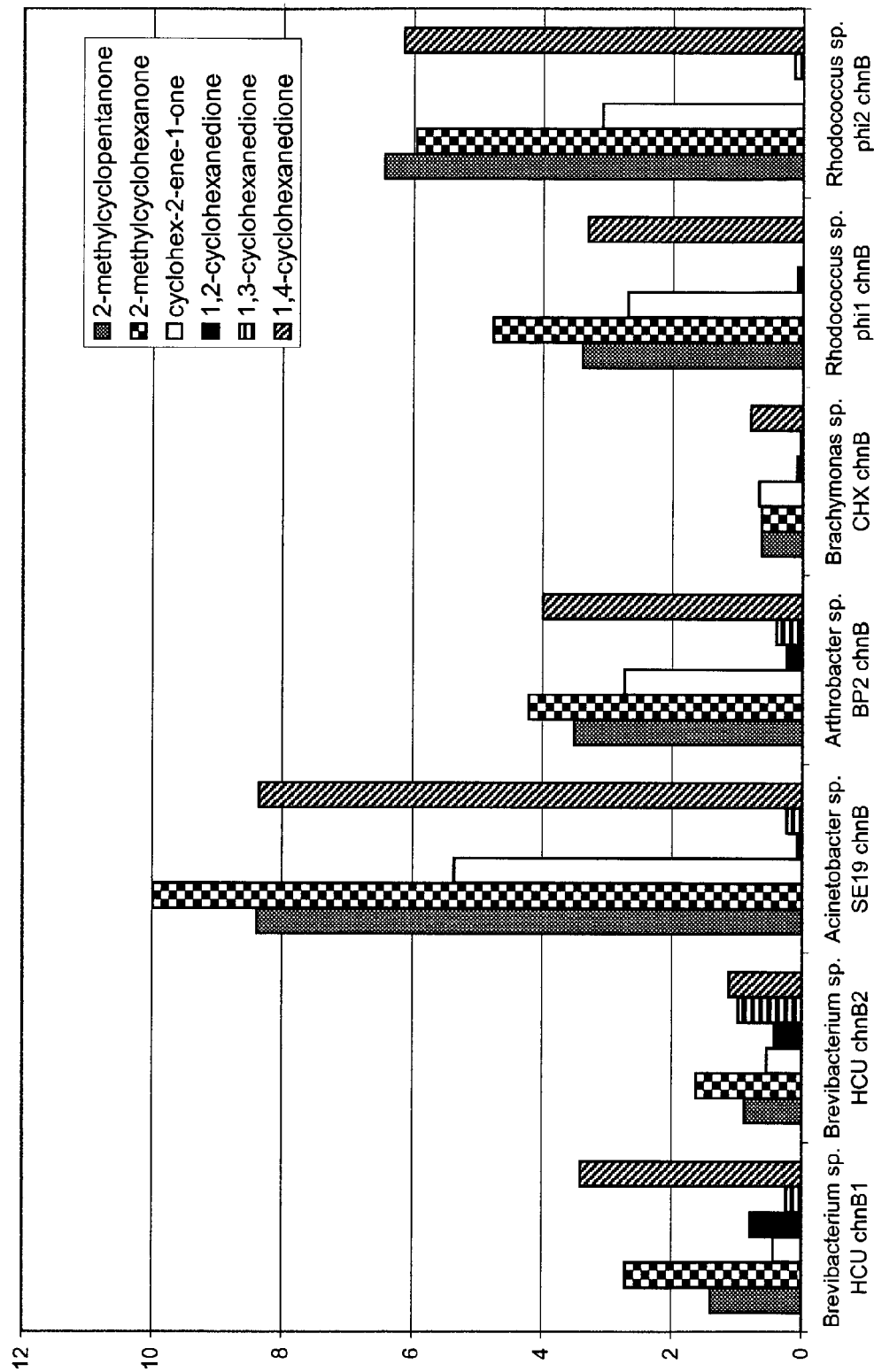
Figure 4:
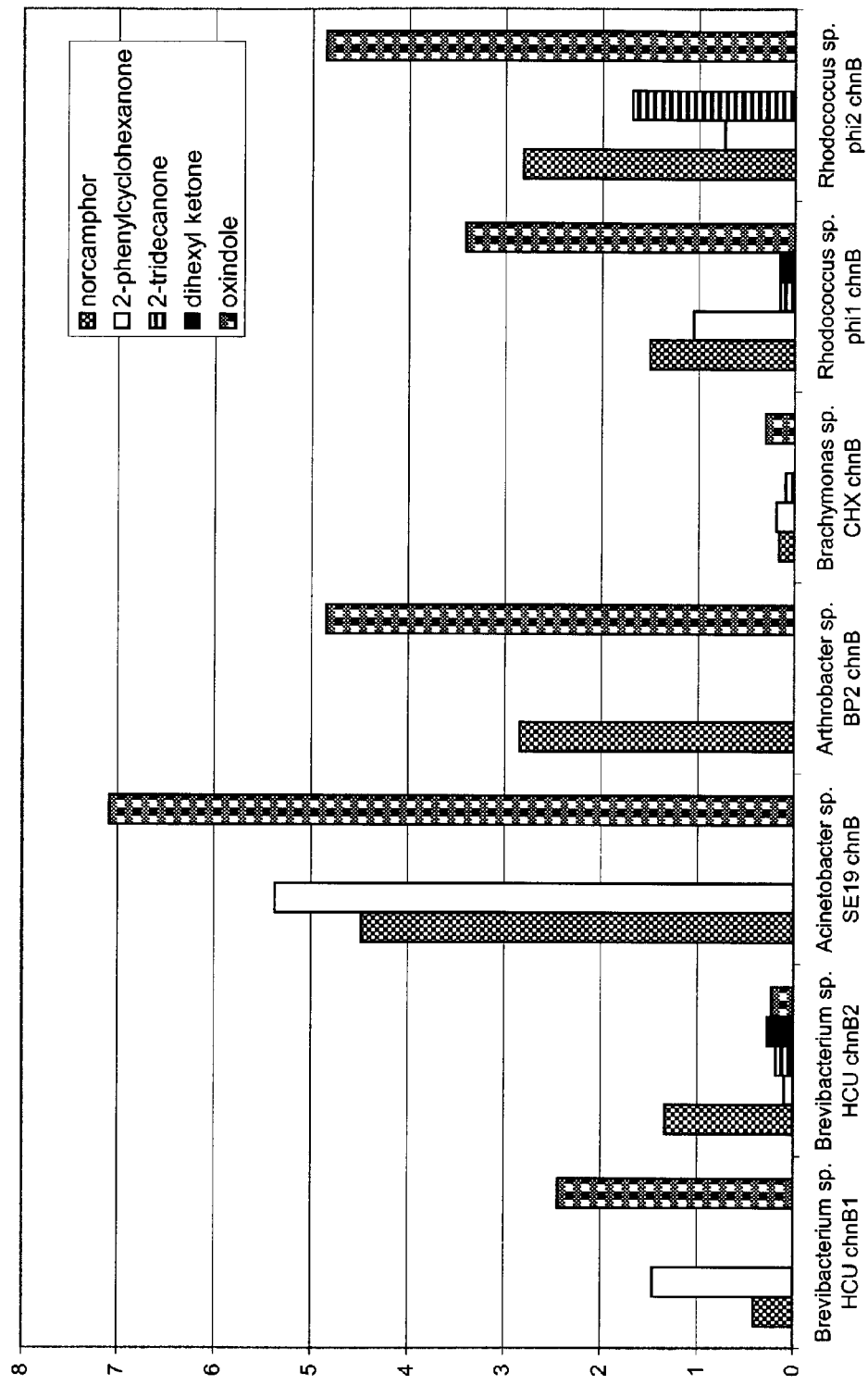
Figure 5:
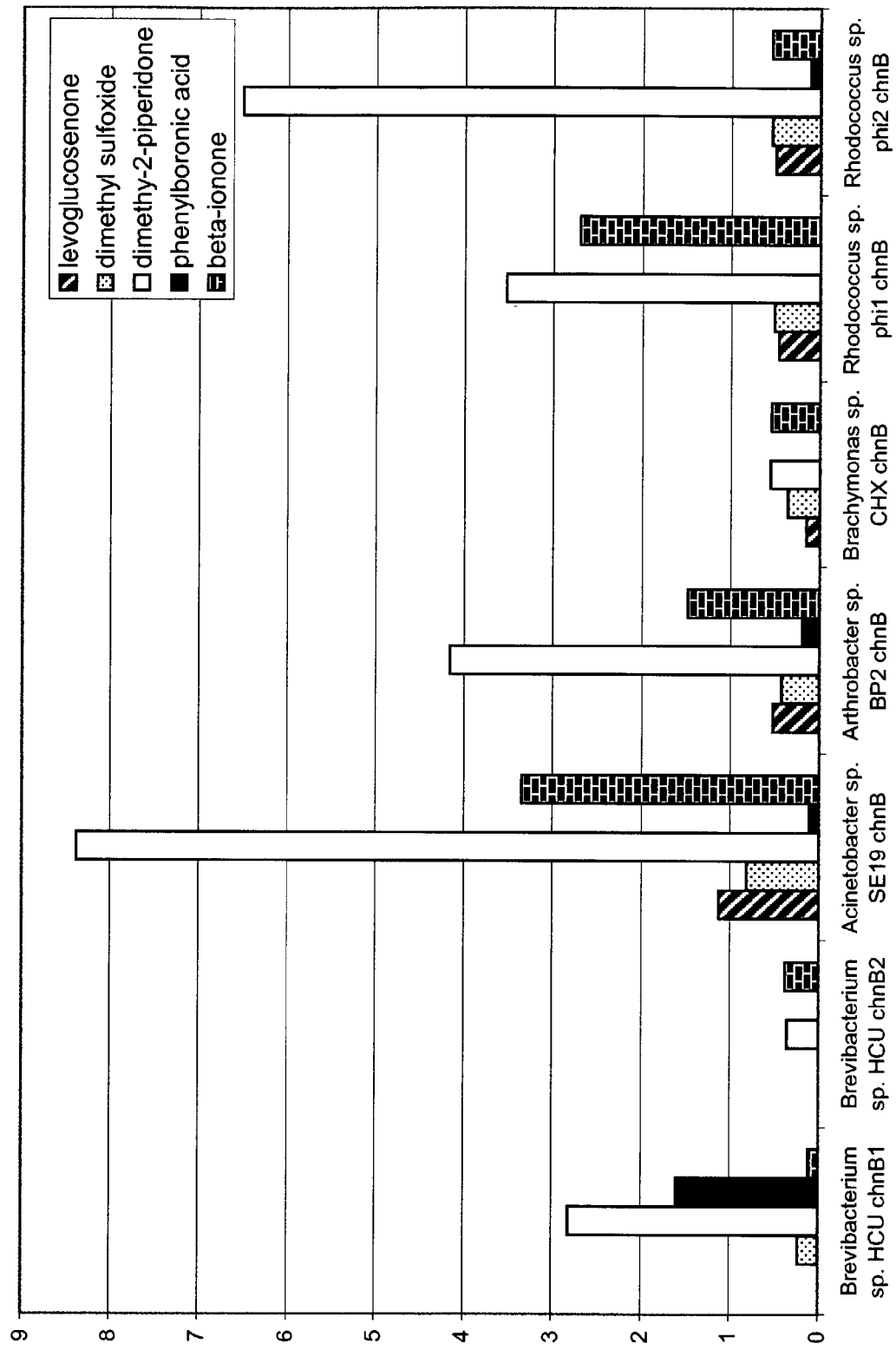

Graphical representation of the data shown in Table 5 is also provided in FIGS. 1, 2, 3, 4, and 5.

TABLE 5

Specific Activity of Monooxygenase Enzymes Against Various Ketone Substrates

| Compound | sp. HCU chnB1 | sp. HCU chnB2 | sp. SE19 chnB | sp. BP2 chnB | sp. CHX chnB | sp. phi1 chnB | sp. phi2 chnB |
|---|---|---|---|---|---|---|---|
| Norcamphor | 0.410 | 1.331 | 4.474 | 2.842 | 0.166 | 1.504 | 2.816 |
| Cyclobutanone | ND | 0.374 | 0.109 | 0.128 | ND | 0.102 | 0.154 |
| Cyclopentanone | ND | 1.331 | 3.034 | 1.491 | 0.621 | 1.370 | 2.451 |
| 2-methyl-cyclopentanone | 1.395 | 0.874 | 8.378 | 3.514 | 0.627 | 3.392 | 6.445 |
| Cyclohexanone | 2.765 | 1.726 | 6.349 | 3.565 | 0.397 | 3.680 | 3.750 |
| 2-methyl-cyclohexanone | 2.714 | 1.622 | 9.990 | 4.205 | 0.627 | 4.774 | 5.952 |
| Cyclohex-2-ene-1-one | 0.435 | 0.541 | 5.357 | 2.739 | 0.666 | 2.694 | 3.091 |
| 1,2-cyclohexanedione | 0.787 | 0.416 | 0.077 | 0.237 | 0.096 | 0.083 | ND |

TABLE 5-continued

Specific Activity of Monooxygenase Enzymes Against Various Ketone Substrates

| Compound | sp. HCU chnB1 | sp. HCU chnB2 | sp. SE19 chnB | sp. BP2 chnB | sp. CHX chnB | sp. phi1 chnB | sp. phi2 chnB |
|---|---|---|---|---|---|---|---|
| 1,3-cyclohexanedione | 0.237 | 0.978 | 0.237 | 0.397 | 0.032 | ND | 0.141 |
| 1,4-cyclohexanedione | 3.405 | 1.123 | 8.346 | 3.994 | 0.794 | 3.302 | 6.150 |
| Cycloheptanone | 0.646 | 0.374 | 8.422 | 3.846 | 0.608 | 3.622 | 6.234 |
| Cyclooctanone | ND | ND | 1.984 | 0.646 | 0.410 | 0.627 | 0.141 |
| Cyclodecanone | ND | ND | 0.320 | 0.166 | 0.160 | 0.077 | 0.205 |
| Cycloundecanone | ND | 0.125 | 0.064 | 0.064 | 0.058 | ND | 0.051 |
| Cyclododecanone | ND | 0.229 | 0.122 | 0.198 | 0.051 | ND | 0.122 |
| Cyclotridecanone | ND | ND | 0.166 | 0.147 | ND | ND | 0.109 |
| Cyclopentadecanone | ND | ND | 0.109 | 0.122 | ND | 0.122 | ND |
| 2-tridecanone | ND | 0.187 | ND | ND | 0.096 | 0.160 | 1.690 |
| dihexyl ketone | ND | 0.270 | ND | ND | ND | 0.160 | ND |
| 2-phenyl-cyclohexanone | 1.459 | 0.104 | 5.370 | ND | 0.192 | 1.050 | 0.730 |
| Oxindole | 2.438 | 0.229 | 7.091 | 4.845 | 0.307 | 3.411 | 4.858 |
| Levoglucosenone | ND | ND | 1.126 | 0.525 | 0.147 | 0.461 | 0.506 |
| dimethyl sulfoxide | 0.230 | ND | 0.819 | 0.422 | 0.358 | 0.518 | 0.544 |
| dimethy-2-piperidone | 2.822 | 0.354 | 8.384 | 4.154 | 0.557 | 3.539 | 6.509 |
| Phenylboronic acid | 1.606 | ND | 0.102 | 0.192 | ND | ND | 0.109 |
| beta-ionone | 0.109 | 0.374 | 3.347 | 1.485 | 0.544 | 2.707 | 0.544 |

Example 9

Cloning of *Rhodococcus erythropolis* AN12 Monooxygenase Genes into *Escherichia coli*

This example illustrates the construction of a suite of recombinant *E. coli*, each containing a full length BVMOs from *Rhodococcus erythropolis* AN12.

Full length BV monooxygenases were PCR amplified, using chromosomal DNA as the template and the primers shown below in Table 6.

TABLE 6

Primers Used for Amplification of Full-Length BV *Rhodococcus erythropolis* AN12 Monooxygenases

| chnB Monooxygenase | Forward Primer | Reverse Primer |
|---|---|---|
| ORF 8 | atg agc aca gag ggc aag tac gc (SEQ ID NO: 82) | [tca] gtc ctt gtt cac gta gta ggc c (SEQ ID NO: 83) |
| ORF 9 | atg gtc gac atc gac cca acc tc (SEQ ID NO: 84) | tta tcg gct cct cac ggt ttc tcg (SEQ ID NO: 85) |
| ORF 10 | atg acc gat cct gac ttc tcc acc (SEQ ID NO: 86) | tca tgc gtg cac cgc act gtt cag (SEQ ID NO: 87) |
| ORF 11 | atg agc ccc tcc ccc ttg ccg ag (SEQ ID NO: 88) | tca tgc gcg atc cgc ctt ctc gag (SEQ ID NO: 89) |
| ORF 12 | gtg aac aac gaa tct gac cac ttc (SEQ ID NO: 90) | tca tgc ggt gta ctc cgg ttc cg (SEQ ID NO: 91) |
| ORF 13 | atg agc acc gaa cac ctc gat g (SEQ ID NO: 92) | tca act ctt gct cgg tac cgg cg (SEQ ID NO: 93) |
| ORF 14 | atg aca gac gaa ttc gac gta gtg at (SEQ ID NO: 94) | tca gct ctg gtt cac agg gac gg (SEQ ID NO: 95) |
| ORF 15 | atg gcg gag ata gtc aat ggt cc (SEQ ID NO: 96) | tca ccc tcg cgc ggt cgg agt c (SEQ ID NO: 97) |
| ORF 16 | gtg aag ctt ccc gaa cat gtc gaa ac (SEQ ID NO: 98) | tca tgc ctg gac gct ttc gat ctt g (SEQ ID NO: 99) |
| ORF 17 | atg aca cag cat gtc gac gta ctg a (SEQ ID NO: 100) | cta tgc gct ggc gac ctt gct atc (SEQ ID NO: 101) |
| ORF 18 | atg tca tca cgg gtc aac gac ggc c (SEQ ID NO: 102) | tca tcc ttt gcc tgt cgt cag tgc (SEQ ID NO: 103) |
| ORF 19 | atg act aca caa aag gcc ctg acc (SEQ ID NO: 104) | tca ggc gtc gac ggt gtc ggc c (SEQ ID NO: 105) |
| ORF 20 | atg aca act acc gaa tcc aga act c (SEQ ID NO: 106) | tca gcg cag att gaa gcc ctt gta tc (SEQ ID NO: 107) |

Following amplification, the gene fragments were cloned into pTrcHis-TOPO TA vectors with either an N-terminal tail or C-terminal tail, as provided by the vector sequence. These vectors were transformed into *E. coli*, with transformants grown in Luria-Bertani broth supplemented with ampicillin (100 ug/ml).

Example 10

Assays of chnB Monooxygenase Activities of *Rhodococcus erythropolis* AN12

The chnB monooxygenase activity of each expressed enzyme from Example 9 was tested for activity according to its ability to convert cyclohexanone to caprolactone.

Conversion of Cyclohexanone to Caprolactone.

Clones containing the full length monooxygenase genes were transferred from LB agar plate to 5 mL of M63 minimal media (GIBCO) containing 10 mM glycerol, 50 ug/mL ampicillin, 0.1 mM IPTG, and 500 mg/L cyclohexanone. In addition to the clones containing full length monooxygenases, a plasmid without an insert and a "no cell" control were also assayed. The encoded monooxygenase sequences were expressed upon addition of IPTG to the culture media. The cultures were incubated overnight at room temperature (24° C.). Samples (1.25 mL) for analysis were taken immediately after inoculation and after overnight incubation; cells were removed by centrifugation (4° C., 13,000 rpm).

GC-MS Detection of Caprolactone

Caprolactone formed by the action of the cloned monooxygenase was extracted from the aqueous phase with ethylacetate (1.0 ml aqueous/0.5 mL ethylacetate). Caprolactone was detected by gas chromotagraphy mass spectrometry (GC-MS) analysis, using an Agilent 6890 Gas chromatograph system.

The analysis of the ethylacetate phase was performed by injecting 1 uL of the ethyl acetate phase into the GC. The inlet temperature was 115° C. and the column temperature profile was 50° C. for 4 min and ramped to 250° C. at 20° C./min, for a total run time of 14 min. The compounds were separated with an Hewlet Packard HP-5MS (5% phenyl Methyl Siloxane) column (30 m length, 250 um diameter, and 0.25 um film thickness). The mass spectrometer was run in Electron Ionization mode. The background mass spectra was subtracted from the spectra at the retention time of caprolactone (9.857 min). Presence of caprolactone was confirmed by comparison of the test reactions to an authentic standard obtained from Aldrich Chemical Company (St. Louis, Mo.).

Results of these assays are shown below in Table 7, in terms of the presence or absence of detectable caprolactone formation according to the activity of each expressed BV monooxygenase enzyme.

TABLE 7

Ability of Monooxygenase Enzymes to Convert Cyclohexanone to Caprolactone

| | Formation of Caprolactone | | |
|---|---|---|---|
| | Detected | Not Detected | Not Assayed |
| chnB Monooxygenases | ORF 8 ORF 9 ORF 11 | ORF 15 No cell control Plasmid control | ORF 10 ORF 13 ORF 14 |

TABLE 7-continued

Ability of Monooxygenase Enzymes to Convert Cyclohexanone to Caprolactone

| | Formation of Caprolactone | | |
|---|---|---|---|
| | Detected | Not Detected | Not Assayed |
| | ORF 12 ORF 16 ORF 17 ORF 18 ORF 19 | | ORF 20 |

Example 11

Identification of Signature Sequences Between Families of BV Monooxygenases

Sequence analysis of the 20 genes encoding Baeyer-Villiger monooxygenases identified in the previous examples allows definition of three different BV signature sequence families based on amino acid similarities. Each family possesses several member genes for which biochemical validation of the enzyme as a functional BV enzyme capable of the oxidation of cyclohexanone was demonstrated (Examples, supra). Sequence alignment of the homologues for each family was performed by Clustal W alignment (Higgins and Sharp (1989) *CABIOS.* 5:151–153). This allows the identification of a set of amino acids that are conserved at specific positions in the alignment created from all the sequences available.

The results of these Clustal W alignments are shown in FIGS. 7, 8, and 9 for BV Family 1, BV family 2, and BV Family 3. In all cases, an "*" indicates a conserved signature amino acid position. The conserved amino acid signature sequence for each Family is shown in FIG. 6, along with the signature sequence P-# positions. This conserved amino acid/position set becomes a signature for each family. Any new protein with a sequence that can be aligned with those of the existing members of the family and which includes at the specific positions a at least 80% of the signature sequence amino acids can be considered a member of the specific family.

BV Family 1

This family comprises the chnB monooxygenase sequences of *Arthrobacter* sp. BP2 (SEQ ID NO:12), *Rhodococcus* sp. phi1 (SEQ ID NO:8), *Rhodococcus* sp. phi2 (SEQ ID NO:10), *Acidovorax* sp. CHX (SEQ ID NO:14), *Brevibacterium* sp. HCU (SEQ ID NOs:16 and 18), and *Rhodococcus erythropolis* AN12 ORF10, ORF14, ORF19, and ORF20 (SEQ ID NOs:26, 34, 44 and 46). Within a length of 540 amino acids, a total of 74 positions are conserved (100%).This signature sequence of Family 1 BV monooxygenases is shown beneath each alignment of proteins (FIG. 7) and is listed as SEQ ID NO:47. The ability to identify the signature sequence within this family of proteins was made possible by: 1) the number of sequences of BV monooxygenases; and 2) the characterization of their activity as BV-monooxygenases.

Based on the limited number (4 total) of BV monooxygenase sequences in the public domain, for which biochemical data is also available, 3 of these sequences align with the signature sequence discovered for Family 1. These sequences are:

(1) *Acinetobacter* sp. NCIMB9871 chnB (NCBI Accession Number AB026668, based on Chen, Y. C. et al. (*J Bacteriol.* 170(2):781–789 (1988)). Key biochemical characterization of this protein was performed by Donogue et al. (*Eur J Biochem.* 16;63(1):175–92 (1976)), Trudgill et al, (*Methods Enzymol.* 188:70–77 (1990)), and Iwaki et al. (*Appl Environ Microbiol.* 65(11):5158–62 (1999)). This enzyme shares 72 of the 74 conserved amino acids in the signature sequence of Family 1 BV monooxygenases.

(2) *Rhodococcus erythropolis* limB (NCBI Accession Number AJ272366, based on the work of Barbirato et al. (*FEBS Lett.* 438 (3): 293–296 (1998)) and van der Werf et al. (*Biol. Chem.* 274 (37): 26296–26304 (1999)). Key biochemical characterization of this protein was performed by van der Werf, M, J. et al. (*Microbiology* 146 (Pt 5):1129–41 (2000); *Biochem J.* 1 ;347 Pt 3:693–701 (2000); and *Appl Environ Microbiol.* 65(5):2092–102 (1999)). This enzyme is known as a carvone monooxygenase (3) *Rhodococcus rhodochrous* smo (NCBI Accession Number AB010439). This enzyme was sequenced and characterized by Morii, S. et al. (*J. Biochem.* 126 (3), 624–631 (1999)). This enzyme is known as a steroid monooxygenase. It shares 74 of the 74 conserved amino acids in the signature sequence of Family 1 BV monooxygenases.

The enzymes described in the public domain having the highest sequence similarity to Group 1 have been characterized as dimethylaniline hydroxylases.

BV Family 2

This family comprises the chnB monooxygenase sequences of *Rhodococcus erythropolis* AN12 ORF9, ORF12, ORF15, ORF 16, and ORF18 (SEQ ID NOs:24, 30, 36, 38, and 42). Within a length of 497 amino acids, a total of 76 positions are conserved (100%). This signature sequence for Family 2 BV monooxygenases is shown beneath each alignment of proteins (FIG. 8) and is listed as SEQ ID NO:48. The ability to identify the signature sequence within this family of proteins was made possible by: 1) the number of sequences of BV monooxygenases; and 2) the characterization of their activity as BV-monooxygenases.

Based on the limited number (4 total) of BV monooxygenase sequences in the public domain, for which biochemical data is also available, only 1 of these sequences align with the signature sequence discovered for Family 2. This sequence is *Pseudomonas putida* JD1 Key biochemical characterization of this protein was performed by Tanner A., et al. (*J Bacteriol.* 182(23):6565–6569 (2000)). This enzyme is known as an acetophenone monooxygenase. It shares 69 of the 76 conserved amino acids in the signature sequence of Family 2 BV monooxygenases.

BV Family 3

This family comprises the chnB monooxygenase sequences of *Rhodococcus erythropolis* AN12 ORF8, ORF 11, ORF 13, and ORF17 (SEQ ID NOs:22, 28, 32, and 40). Within a length of 471 amino acids, a total of 41 positions are conserved (100%). This signature sequence for Family 3 BV monooxygenases is shown beneath each alignment of proteins (FIG. 9) and is listed as SEQ ID NO:49. The ability to identify the signature sequence within this family of proteins was made possible by: 1) the number of sequences of BV monooxygenases; and 2) the characterization of their activity as BV-monooxygenases.

There are no sequences in the public domain with demonstrated BV activity that belong to this group. The dimethylaniline N-oxidase shares only 30 amino acids out of 41 conserved amino acids discovered in the signature sequence, which represents less than 80% of the conserved positions.

What is claimed is:

1. A method of obtaining a nucleic acid fragment encoding a polypeptide having Baeyer-Villiger monooxygenase activity comprising:
   (a) probing a genomic library with an isolated nucleic acid fragment encoding the amino acid sequence of SEQ ID NO:47;
   (b) identifying a DNA clone that hybridizes with the nucleic acid fragment of step (a) under the stringent conditions of hybridization at 0.1×SSC, 0.1% SDS, 65° C. with a wash with 2×SSC, 0.1% SDS followed by 0.1×SSC, 0.1% SDS; and
   (c) sequencing the genomic fragment that comprises the clone identified in step (b);
   wherein the sequenced genomic fragment encodes a polypeptide having Baeyer-Villiger monooxygenase activity.

2. A method of obtaining a nucleic acid fragment encoding a Baeyer-Villiger monooxygenase polypeptide comprising:
   (a) synthesizing at least one oligonucleotide primer selected from SEQ ID NOs: 68–81; and
   (b) amplifying a polynucleotide comprising the isolated nucleic acid sequence encoding the amino acid sequence of SEQ ID NO:47, said polynucleotide present in a cloning vector, using the oligonucleotide primer of step (a);
   wherein the amplified polynucleotide encodes a polypeptide having Baeyer-Villiger monooxygenase activity.

3. A method for identifying a gene encoding a polypeptide having Baeyer-Villiger monooxygenase activity comprising:
   (a) probing a genomic library with a nucleic acid fragment encoding a polypeptide having the amino acid sequence of SEQ ID NO:47;
   (b) identifying a DNA clone that hybridizes with the nucleic acid fragment of step (a) under stringent conditions of hybridization at 0.1×SSC, 0.1% SDS, 65° C. with a wash step with 2×SSC, 0.1% SDS followed by 0.1×SSC, 0.1% SDS, 65° C.; and
   (c) sequencing the genomic fragment that comprises the clone identified in step (b);
   wherein the sequenced genomic fragment encodes a polypeptide having Baeyer-Villiger monooxygenase activity.

* * * * *

SEQUENCE LISTING

<160> NUMBER OF SEQ ID NOS: 113

<210> SEQ ID NO 1
<211> LENGTH: 791
<212> TYPE: DNA
<213> ORGANISM: Arthrobacter sp. BP2

<400> SEQUENCE: 1

```
accaccttcg acggctcccc cccacaaggg ttaggccacc ggcttcgggt gttaccaact        60
ttcgtgactt gacgggcggt gtgtacaagg cccgggaacg tattcaccgc agcgttgctg       120
atctgcgatt actagcgact ccgacttcat ggggtcgagt tgcagacccc aatccgaact       180
gagaccggct ttttgggatt agctccacct cacagtatcg caaccctttg taccggccat       240
tgtagcatgc gtgaagccca agacataagg ggcatgatga tttgacgtcg tccccacctt       300
cctccgagtt gaccccggca gtctcctatg agtccccggc cgaaccgctg gcaacataga       360
acgagggttg cgctcgttgc gggacttaac ccaacatctc acgacacgag ctgacgacaa       420
ccatgcacca cctgtaaacc ggccgcaagc ggggcacctg tttccaggtc tttccggtcc       480
atgtcaagcc ttggtaaggt tcttcgcgtt gcatcgaatt aatccgcatg ctccgccgct       540
tgtgcgggcc cccgtcaatt cctttgagtt ttagccttgc ggccgtactc cccaggcggg       600
gcacttaatg cgttagctac ggcgcggaaa acgtggaatg tcccccacac ctagtgccca       660
acgtttacgg catggactac cagggtatct aatcctgttc gctccccatg ctttcgctcc       720
```

-continued

```
tcagcgtcag ttacagccca gagacctgcc tttgccatcg gtgttcctct tgatatctgc      780
gcatttcacc g                                                            791
```

```
<210> SEQ ID NO 2
<211> LENGTH: 1303
<212> TYPE: DNA
<213> ORGANISM: Rhodococcus sp. phi1

<400> SEQUENCE: 2
gtgcttaaca catgcaagtc gaacgatgaa gcccagcttg ctgggtggat tagtggcgaa       60
cgggtgagta acacgtgggt gatctgccct gcactctggg ataagcctgg gaaactgggt      120
ctaataccgg atatgacctc gggatgcatg tcctggggtg aaagttttt cggtgcagga      180 tgagcccgcg gcctatcagc ttgttggtgg ggtaatggcc taccaaggcg acgacgggta      240
gccggcctga gagggcgacc ggccacactg ggactgagac acgcccaga ctcctacggg      300 aggcagcagt ggggaatatt gcacaatggg cgcaagcctg atgcagcgac gccgcgtgag      360
ggatgacggc cttcgggttg taaacctctt tcacccatga cgaagcgcaa gtgacggtag      420
tgggagaaga agcaccggcc aactacgtgc cagcagccgc ggtaatacgt aggtgcgagc      480
gttgtccgga attactgggc gtaaagagct cgtaggcgt ttgtcgcgtc gtctgtgaaa      540
tcccgcagct caactgcggg cttgcaggcg atacgggcag actcgagtac tgcaggggag      600
actggaattc ctggtgtagc ggtgaaatgc gcagatatca ggaggaacac cggtggcgaa      660
ggcgggtctc tgggcagtaa ctgacgctga ggagcgaaag cgtgggtagc gaacaggatt      720 agatacctg gtagtccacg ccgtaaacgg tgggcgctag gtgtgggttt ccttccacgg      780
gatccgtgcc gtagccaacg cattaagcgc cccgcctggg gagtacgcc gcaaggctaa      840 aactcaaagg aattgacggg ggcccgcaca agcggcggag catgtggatt aattcgatgc      900
aacgcgaaga accttacctg ggtttgacat gtaccgacg actgcagaga tgtggtttcc      960
cttgtggccg gtagacaggt ggtgcatggc tgtcgtcagc tcgtgtcgtg agatgttggg     1020
ttaagtcccg caacgagcgc aaccttgtc ctgtgttgcc agcacgtgat ggtgggact     1080 cgcaggagac tgccggggtc aactcggagg aaggtgggga cgacgtcaag tcatcatgcc     1140
ccttatgtcc agggcttcac acatgctaca atggtcggta cagagggctg cgataccgtg     1200
aggtggagcg aatcccttaa agccggtctc agttcggatc ggggtctgca actcgacccc     1260
gtgaagtcgg agtcgctagt aatcgcagat cagcaacgct gcg                      1303
```

```
<210> SEQ ID NO 3
<211> LENGTH: 1296
<212> TYPE: DNA
<213> ORGANISM: Rhodococcus sp. phi2

<400> SEQUENCE: 3
gcttaacaca tgcaagtcga acgatgaagc cagcttgct gggtggatta gtggcgaacg       60
ggtgagtaac acgtgggtga tctgccctgc acttcgggat aagcctggga actgggtct      120 aataccggat aggacctcgg gatgcatgtt ccggggtgga aaggttttcc ggtgcaggat     180
gggcccgcgg cctatcagct tgttggtggg gtaacggccc accaaggcga cgacgggtag     240
ccggcctgag agggcgaccg gccacactgg gactgagaca cggcccagac tcctacggga     300
ggcagcagtg gggaatattg cacaatgggc gcaagcctga tgcagcgacg ccgcgtgagg     360
gatgacggcc ttcgggttgt aaacctcttt cagtaccgac gaagcgcaag tgacggtagg     420
```

| | |
|---|---|
| tacagaagaa gcaccggcca actacgtgcc agcaagccgc ggtaatacgt aaggtgcgaa | 480 |
| gcgttgtccg gaattactgg gcgtaaagag ctcgtaggcg gtttgtcgcg tcgtctgtga | 540 |
| aaacccgcag ctcaactgcg ggcttgcagg cgatacgggc agacttgagt actgcagggg | 600 |
| agactggaat tcctggtgta gcggtgaaat gcgcagatat caggaggaac accggtggcg | 660 |
| aaggcgggtc tctgggcagt aactgacgct gaggagcgaa agcgtgggta gcaacagga | 720 |
| ttagataccc tggtagtcca cgccgtaaac ggtgggcgct aggtgtgggt ttccttccac | 780 |
| gggatccgtg ccgtagctaa cgcattaagc gccccgcctg ggagtacgg ccgcaaggct | 840 |
| aaaactcaaa ggaattgacg ggggcccgca caagcggcgg agcatgtgga ttaattcgat | 900 |
| gcaacgcgaa gaaccttacc tgggtttgac ataccggga ccgccccaga gatgggttt | 960 |
| cccttgtggt cggtgtacag gtggtgcatg gctgtcgtca gctcgtgtcg tgagatgttg | 1020 |
| ggttaagtcc cgcaacgagc gcaacccttg tcctgtgttg ccagcacgta atggtgggga | 1080 |
| ctcgcaggag actgccgggg tcaactcgga ggaaggtggg gacgacgtca agtcatcatg | 1140 |
| cccctttatgt ccagggcttc acacatgcta caatggccgg tacagagggc tgcgataccg | 1200 |
| cgaggtggag cgaatccctt aaagccggtc tcagttcgga tcggggtctg caactcgacc | 1260 |
| ccgtgaagtc ggagtcgcta gtaatcgcag atcagc | 1296 |

<210> SEQ ID NO 4
<211> LENGTH: 1388
<212> TYPE: DNA
<213> ORGANISM: Brevibacterium sp. HCU

<400> SEQUENCE: 4

| | |
|---|---|
| cgcccttgag tttgatcctg gctcaggacg aacgctggct gcgtgcttaa cacatgcaag | 60 |
| tcgaacgctg aagccgacag cttgctgttg gtggatgagt ggcgaacggg tgagtaacac | 120 |
| gtgagtaacc tgcccctgat ttcgggataa gcctgggaaa ctgggtctaa taccggatac | 180 |
| gaccacctga cgcatgttgg gtggtggaaa gttttcgat cggggatggg ctcgcggcct | 240 |
| atcagcttgt tggtggggta atggcctacc aaggcgacga cgggtagccg gcctgagagg | 300 |
| gcgaccggcc acactgggac tgagacacgg cccagactcc tacgggaggc agcagtgggg | 360 |
| aatattgcac aatgggggaa accctgatgc agcgacgcag cgtgcgggat gacggccttc | 420 |
| gggttgtaaa ccgctttcag cagggaagaa gcgaaagtga cggtacctgc agaagaagta | 480 |
| ccggctaact acgtgccagc agccgcggta atacgtaggg tacgagcgtt gtccggaatt | 540 |
| attgggcgta aagagctcgt aggtggttgg tcacgtctgc tgtggaaacg caacgcttaa | 600 |
| cgttgcgcgt gcagtgggta cgggctgact agagtgcagt aggggagtct ggaattcctg | 660 |
| gtgtagcggt gaaatgcgca gatatcagga ggaacaccgg tggcgaaggc gggactctgg | 720 |
| gctgtaactg acactgagga gcgaaagcat ggggagcgaa caggattaga taccctggta | 780 |
| gtccatgccg taaacgttgg gcactaggtg tgggggacat ccacgttct ccgcgccgta | 840 |
| gctaacgcat taagtgcccc gcctggggag tacggtcgca aggctaaaac tcaaaggaat | 900 |
| tgacggggc ccgcacaagc ggcggagcat gcggattaat tcgatgcaac gcgaagaacc | 960 |
| ttaccaaggc ttgacataca ctggaccgtt ctggaaacag ttcttctctt tggagctggt | 1020 |
| gtacaggtgg tgcatggttg tcgtcagctc gtgtcgtgag atgttgggtt aagtcccgca | 1080 |
| acgagcgcaa ccctcgttct atgttgccag cacgtgatgg tgggaactca taggagactg | 1140 |
| ccggggtcaa ctcggaggaa ggtggggatg acgtcaaatc atcatgccct ttatgtcttg | 1200 |
| ggcttcacgc atgctacaat ggctggtaca gagagaggcg aacccgtgag ggtgagcgaa | 1260 |

-continued

| | |
|---|---|
| tcccttaaag ccagtctcag ttcggatcgt agtctgcaat tcgactacgt gaagtcggag | 1320 |
| tcgctagtaa tcgcagatca gcaacgctgc ggtgaatacg ttcccgggcc ttgtacacac | 1380 |
| cgcccgta | 1388 |

<210> SEQ ID NO 5
<211> LENGTH: 895
<212> TYPE: DNA
<213> ORGANISM: Brachymonas sp. CHX

<400> SEQUENCE: 5

| | |
|---|---|
| taggctaact acttctggca gaacccgctc ccatggtgtg acgggcggtg tgtacaagac | 60 |
| ccgggaacgt attcaccgcg acatgctgat ccgcgattac tagcgattcc gacttcacgc | 120 |
| agtcgagttg cagactgcga tccggactac gaccggcttt gtgggattgg ctcccccctcg | 180 |
| cgggttggct accctctgta ccggccattg tatgacgtgt gtagcccac ctataagggc | 240 |
| catgaggact tgacgtcatc cccaccttcc tccggtttgt caccggcagt cccattagag | 300 |
| tgcccttcg tagcaactaa tgcaagggt tgcgctcgtt gcgggactta acccaacatc | 360 |
| tcacgacacg agctgacgac agccatgcag cacctgtgtg caggttctct ttcgagcact | 420 |
| cccaaatctc ttcaggattc ctgccatgtc aaaggtgggt aaggttttc gcgttgcatc | 480 |
| gaattaaacc acatcatcca ccgcttgtgc gggtccccgt caattccttt gagtttcaac | 540 |
| cttgcggccg tactcccag gcggtcaact tcacgcgttg gcttcgttac tgagtcagct | 600 |
| aagacccaac aaccagttga catcgtttag ggcgtggact accagggtat ctaatcctgt | 660 |
| ttgctcccca cgctttcgtg catgagcgtc agtgcaggcc cagggattg ccttcgccat | 720 |
| cggtgttcct ccgcatatct acgcatttca ctgctacacg cggaattcca tccccctctg | 780 |
| ccgcactcca gctttgcagt cacaaaggca gttcccaggt tgagcccggg gatttcacct | 840 |
| ctgtcttaca aaaccgcctg cgcacgcttt acgcccagta attccgatga acgct | 895 |

<210> SEQ ID NO 6
<211> LENGTH: 1439
<212> TYPE: DNA
<213> ORGANISM: Rhodococcus erythropolis AN12
<220> FEATURE:
<221> NAME/KEY: misc_feature
<222> LOCATION: (1417)..(1417)
<223> OTHER INFORMATION: N = G or A or T or C

<400> SEQUENCE: 6

| | |
|---|---|
| aaaacgctgg gcgggcgttg cttaacacat gcaattcgag cggtaaggcc tttcggggta | 60 |
| cacaagcggc gaacgggtga gtaacacgtg ggtgatctgc cctgcacttc gggataagcc | 120 |
| tgggaaactg ggtctaatac cggatatgac ctcaggtcgc atgacttggg gtggaaaaat | 180 |
| ttatcggtgc aggatgggcc cgcggcctat cagcttgttg gtgggtaat ggcctaccaa | 240 |
| ggcgacaacg ggtacccgac ctgaaagggt gaccggccac actgggactg aaacacggcc | 300 |
| caaactccta cgggaggcag cagtggggaa tattgcacaa tgggcgaaag cctgatgcac | 360 |
| cgaccccgcg tgagggatga cggccttcgg gttgtaaacc tctttcagca gggacaaacg | 420 |
| caagtgacgg tacctgcaga agaagccccg gctaactacg tgccagcagc cgcggtatta | 480 |
| cttagggtgc aagcgttgtc cggaattact gggcgtaaag agttcgtacg cggtttgtcg | 540 |
| cgtcgtttgt gaaaccagc agctcaactg ctggcttgca ggcgatacgg gcagacttga | 600 |
| gtactgcagg ggagactgga attcctggtg tagcggtgaa atgcgcagat atcaggagga | 660 |

-continued

| | |
|---|---|
| acaccggtgg cgaaggcggg tctctgggca ctaactgacg ctgaggaacg aaagcgtggg | 720 |
| tagcgaacag gattacatac cctggtagtc cacgccgtaa acggtgggcg ctaggtgtgg | 780 |
| gttccttcca cggaatccgt gccgtagcta acgcattaag cgccccgcct ggggagtacg | 840 |
| gccgcaaggc taaaactcaa aggaattgac gggggcccgc acaatcggcg aacatgtgg | 900 |
| attaattcga tgcaacgcga agaaccttac tgggtttgac atataccgga aagctgcaga | 960 |
| gatgtggccc cctttgtggt cggtatacag gtggtgcatg gctgtcgtca gctcgtgtcg | 1020 |
| tgagatgttg ggttaagtcc cgcaacgagc gcaaccccta tcttatgttg ccagcacgtt | 1080 |
| atggtgggga ctcgtaagag actgccgggg tcaactcgga ggaaggtggg gacgacgtca | 1140 |
| agtcatcatg ccccttatgt ccagggcttc acacatgcta caatggccag tacagagggc | 1200 |
| tgcgagaccg tgaggtggag cgaatccctt aaagctggtc tcagttcgga tcggggtctg | 1260 |
| caactcgacc ccgtgaagtc ggagtcgcta gtaatcgcag atcagcaacg ctgcggtgaa | 1320 |
| tacgttcccg ggccttgtac acaccgcccg tcacgtcatg aaagtcggta acacccgaag | 1380 |
| ccggtggctt aaccccttgt gcgaggagcc gtcgaangtg ggatcggcga ttgggcgcc | 1439 |

```
<210> SEQ ID NO 7
<211> LENGTH: 1626
<212> TYPE: DNA
<213> ORGANISM: Rhodococcus sp. phi1

<400> SEQUENCE: 7
```

| | |
|---|---|
| atgactgcac agatctcacc cacagttgtc gacgccgttg tcatcggcgc cggattcggc | 60 |
| ggcatctacg ccgtgcacaa gctgcacaac gaacagggcc tgaccgtggt cggtttcgac | 120 |
| aaggcggacg gccccggcgg tacctggtac tggaaccgct accgggagc gctctccgac | 180 |
| accgagagtc atctctaccg cttctcgttc gaccgcgacc tgctgcagga cggcacgtgg | 240 |
| aagaccacgt acatcaccca gcccgagatc ctcgagtatc tcgagagcgt cgtcgaccgg | 300 |
| ttcgacctgc gtcgtcactt ccggttcggc accgaggtca cctcggcgat ctacctcgag | 360 |
| gacgagaacc tgtgggaggt ctccaccgac aagggtgagg tctaccgggc caagtacgtc | 420 |
| gtcaacgccg tgggcctgct ctccgccatc aacttccccg acctccccgg cctcgacacc | 480 |
| ttcgagggcg agaccatcca caccgccgcc tggcccgagg caagaaccct cgccggcaag | 540 |
| cgtgtcggtg tcatcggtac cggatcgacc gggcagcagg tcatcaccgc cctcgcgccg | 600 |
| gaggtcgagc acctcaccgt cttcgtccgc accccgcagt actccgtgcc ggtcggcaac | 660 |
| cgtcccgtga cgaaggaaca gatcgacgcg atcaaggccg actacgacgg tatctgggac | 720 |
| agcgtcaaga gtccgcggt ggccttcggg ttcgaggagt ccaccctgcc tgccatgtcc | 780 |
| gtctcggaag aggagcgcaa ccgcatcttc caggagcgcg gggaccacgg cggcggcttc | 840 |
| cgcttcatgt tcggcacctt cggcgacatc gccaccgacg aggccgccaa cgaagctgcg | 900 |
| gcatcgttca tccgctccaa gatcgccgag atcatcgagg atccggaaac ggcccgcaag | 960 |
| ctgatgccga ccggtctgta cgccaagcgt ccgctgtgcg acaacggcta ctacgaggtg | 1020 |
| tacaaccgcc cgaacgtcga ggccgtcgcg atcaaggaga ccccatccg tgaggtcacc | 1080 |
| gccaagggcg tcgtgaccga ggacggtgtc ctccacgaac tcgacgtgct cgtcttcgcc | 1140 |
| accggcttcg acgccgtcga cggcaactac cgccggatcg agatccgcgg ccggaacggc | 1200 |
| ctgcacatca acgaccactg ggacggccag ccgacgagct acctcggcgt caccaccgcg | 1260 |
| aacttcccca ctggttcat ggtgctcggt cccaacggcc cgttcacaaa cctgccgccg | 1320 |
| agcatcgaaa cgcaggtcga gtggatcagc gacaccgtcg cctacgccga gcgcaacgag | 1380 |

```
atccgtgcga tcgaacccac cccggaggcc gaggaggagt ggacgcagac ctgcaccgac    1440
atcgcgaacg ccacgctgtt cacccgcggt gactcctgga tcttcggcgc gaatgttccg    1500
ggcaagaagc cgagcgtcct gttctacctg ggcggactgg gcaactaccg caacgtcctc    1560
gcgggtgtcg tcgccgacag ctaccgaggt ttcgagttga agtccgctgt cccggtgacc    1620
gcctga                                                               1626
```

<210> SEQ ID NO 8
<211> LENGTH: 542
<212> TYPE: PRT
<213> ORGANISM: Rhodococcus sp. phi1

<400> SEQUENCE: 8

```
Met Thr Ala Gln Ile Ser Pro Thr Val Val Asp Ala Val Val Ile Gly
1               5                   10                  15

Ala Gly Phe Gly Gly Ile Tyr Ala Val His Lys Leu His Asn Glu Gln
            20                  25                  30

Gly Leu Thr Val Val Gly Phe Asp Lys Ala Asp Gly Pro Gly Gly Thr
        35                  40                  45

Trp Tyr Trp Asn Arg Tyr Pro Gly Ala Leu Ser Asp Thr Glu Ser His
    50                  55                  60

Leu Tyr Arg Phe Ser Phe Asp Arg Asp Leu Leu Gln Asp Gly Thr Trp
65                  70                  75                  80

Lys Thr Thr Tyr Ile Thr Gln Pro Glu Ile Leu Glu Tyr Leu Glu Ser
                85                  90                  95

Val Val Asp Arg Phe Asp Leu Arg Arg His Phe Arg Phe Gly Thr Glu
            100                 105                 110

Val Thr Ser Ala Ile Tyr Leu Glu Asp Glu Asn Leu Trp Glu Val Ser
        115                 120                 125

Thr Asp Lys Gly Glu Val Tyr Arg Ala Lys Tyr Val Val Asn Ala Val
    130                 135                 140

Gly Leu Leu Ser Ala Ile Asn Phe Pro Asp Leu Pro Gly Leu Asp Thr
145                 150                 155                 160

Phe Glu Gly Glu Thr Ile His Thr Ala Ala Trp Pro Glu Gly Lys Asn
                165                 170                 175

Leu Ala Gly Lys Arg Val Gly Val Ile Gly Thr Gly Ser Thr Gly Gln
            180                 185                 190

Gln Val Ile Thr Ala Leu Ala Pro Glu Val Glu His Leu Thr Val Phe
        195                 200                 205

Val Arg Thr Pro Gln Tyr Ser Val Pro Val Gly Asn Arg Pro Val Thr
    210                 215                 220

Lys Glu Gln Ile Asp Ala Ile Lys Ala Asp Tyr Asp Gly Ile Trp Asp
225                 230                 235                 240

Ser Val Lys Lys Ser Ala Val Ala Phe Gly Phe Glu Glu Ser Thr Leu
                245                 250                 255

Pro Ala Met Ser Val Ser Glu Glu Arg Asn Arg Ile Phe Gln Glu
            260                 265                 270

Ala Trp Asp His Gly Gly Gly Phe Arg Phe Met Phe Gly Thr Phe Gly
        275                 280                 285

Asp Ile Ala Thr Asp Glu Ala Ala Asn Glu Ala Ala Ser Phe Ile
    290                 295                 300

Arg Ser Lys Ile Ala Glu Ile Ile Glu Asp Pro Glu Thr Ala Arg Lys
305                 310                 315                 320
```

-continued

```
Leu Met Pro Thr Gly Leu Tyr Ala Lys Arg Pro Leu Cys Asp Asn Gly
            325                 330                 335
Tyr Tyr Glu Val Tyr Asn Arg Pro Asn Val Glu Ala Val Ala Ile Lys
                340                 345                 350
Glu Asn Pro Ile Arg Glu Val Thr Ala Lys Gly Val Val Thr Glu Asp
            355                 360                 365
Gly Val Leu His Glu Leu Asp Val Leu Val Phe Ala Thr Gly Phe Asp
        370                 375                 380
Ala Val Asp Gly Asn Tyr Arg Arg Ile Glu Ile Arg Gly Arg Asn Gly
385                 390                 395                 400
Leu His Ile Asn Asp His Trp Asp Gly Gln Pro Thr Ser Tyr Leu Gly
                405                 410                 415
Val Thr Thr Ala Asn Phe Pro Asn Trp Phe Met Val Leu Gly Pro Asn
            420                 425                 430
Gly Pro Phe Thr Asn Leu Pro Pro Ser Ile Glu Thr Gln Val Glu Trp
        435                 440                 445
Ile Ser Asp Thr Val Ala Tyr Ala Glu Arg Asn Glu Ile Arg Ala Ile
            450                 455                 460
Glu Pro Thr Pro Glu Ala Glu Glu Glu Trp Thr Gln Thr Cys Thr Asp
465                 470                 475                 480
Ile Ala Asn Ala Thr Leu Phe Thr Arg Gly Asp Ser Trp Ile Phe Gly
                485                 490                 495
Ala Asn Val Pro Gly Lys Lys Pro Ser Val Leu Phe Tyr Leu Gly Gly
            500                 505                 510
Leu Gly Asn Tyr Arg Asn Val Leu Ala Gly Val Val Ala Asp Ser Tyr
        515                 520                 525
Arg Gly Phe Glu Leu Lys Ser Ala Val Pro Val Thr Ala Glx
530                 535                 540
```

<210> SEQ ID NO 9
<211> LENGTH: 1623
<212> TYPE: DNA
<213> ORGANISM: Rhodococcus sp. phi2

<400> SEQUENCE: 9

```
atgaccgcac agaccatcca caccgtcgac gccgtcgtca tcggcgccgg attcggcggc    60
atctacgccg tccacaagct gcaccacgaa ctcggcctga ccaccgtcgg attcgacaag   120
gcagacggcc ccggcggcac ctggtactgg aaccgctacc cggcgcccct ctccgacacg   180
gagagccacc tctaccgctt ctccttcgac gcgacctgc tgcaggacgg cacctggaag   240
aacacgtacg tcacccagcc cgagatcctg gagtatctcg aggacgtcgt cgaccgcttc   300
gacctgcgcc gccacttccg gttcggcacc gaggtcacct cggcgatcta tctcgacgac   360
gagaacctct gggaggtcac caccgacggc ggcgacgtct atcgggcgac ctacgtcgtc   420
aacgccgtcg gctgctctc cgccatcaac ttcccgaacc tgcccggcct ggacacgttc   480
gagggcgaga ccatccacac cgccgcctgg ccggagggca agagcctcgc cgggcgccgc   540
gtcggcgtca tcggtaccgg ttccaccggc cagcaggtca tcacggcgct ggcgccggag   600
gtcgagcacc tcaccgtctt cgtccggacc ccgcagtact ccgtaccggt cggcaaccgt   660
cccgtgaccc cggagcagat cgacgcgatc aaggccgact acgaccgaat ctgggagcag   720
gccaagaact ccgcggtggc cttcggcttc gaggagtcca ccctgccggc catgtccgtc   780
tcggaggagg agcgcaaccg gatcttccag gaggcctggg accacggcgg cggattccgt   840
ttcatgttcg gcaccttcgg tgacatcgcc accgacgagg ccgccaacga agccgccgcg   900
```

-continued

```
tcgttcatcc gctccaagat cgccgagatc atcgaggatc cggagaccgc ccgcaagctg      960
atgccgaccg gtctgttcgc caagcgcccg ctgtgcgacg ccggctacca ccaggtcttc     1020
aaccggccga acgtggaagc ggttgccatc aaggagaacc ccatccgcga ggtcaccgcg     1080
aagggcgtgg tgaccgagga cggcgtcctg cacgagttgg acgtgctcgt cttcgccacc     1140
ggcttcgacg ccgtggacgg caactaccgg cgcatcgaga tccgcggccg ggacggcctg     1200
cacatcaacg accactggga cggccagccg accagctacc tgggcgtctc cacggcgaac     1260
ttccccaact ggttcatggt gctgggcccc aacggtccgt tcacgaacct gcccccgagc     1320
atcgagaccc aggtcgagtg gatcagcgac acgatcgggg acgccgagcg caacggtgtg     1380
cgggccatcg agcccacgcc ggaggccgag gccgaatgga ccgagacctg caccgcgatc     1440
gcgaacgcca cgctgttcac caagggcgat tcgtggatct tcggcgcgaa catcccgggc     1500
aagacgccga cgtactgtt ctacctgggc ggcctgcgca actaccgtgc cgtcctcgcc      1560
gaggtcgcga ccgacggata ccggggcttc gacgtgaagt ccgccgagat ggtcacggtc     1620
tga                                                                   1623
```

<210> SEQ ID NO 10
<211> LENGTH: 541
<212> TYPE: PRT
<213> ORGANISM: Rhodococcus sp. phi2

<400> SEQUENCE: 10

```
Met Thr Ala Gln Thr Ile His Thr Val Asp Ala Val Ile Gly Ala
 1               5                  10                  15

Gly Phe Gly Gly Ile Tyr Ala Val His Lys Leu His His Glu Leu Gly
                20                  25                  30

Leu Thr Thr Val Gly Phe Asp Lys Ala Asp Gly Pro Gly Gly Thr Trp
            35                  40                  45

Tyr Trp Asn Arg Tyr Pro Gly Ala Leu Ser Asp Thr Glu Ser His Leu
        50                  55                  60

Tyr Arg Phe Ser Phe Asp Arg Asp Leu Leu Gln Asp Gly Thr Trp Lys
65                  70                  75                  80

Asn Thr Tyr Val Thr Gln Pro Glu Ile Leu Glu Tyr Leu Glu Asp Val
                85                  90                  95

Val Asp Arg Phe Asp Leu Arg Arg His Phe Arg Phe Gly Thr Glu Val
               100                 105                 110

Thr Ser Ala Ile Tyr Leu Asp Asp Glu Asn Leu Trp Glu Val Thr Thr
           115                 120                 125

Asp Gly Gly Asp Val Tyr Arg Ala Thr Tyr Val Val Asn Ala Val Gly
       130                 135                 140

Leu Leu Ser Ala Ile Asn Phe Pro Asn Leu Pro Gly Leu Asp Thr Phe
145                 150                 155                 160

Glu Gly Glu Thr Ile His Thr Ala Ala Trp Pro Glu Gly Lys Ser Leu
               165                 170                 175

Ala Gly Arg Arg Val Gly Val Ile Gly Thr Gly Ser Thr Gly Gln Gln
           180                 185                 190

Val Ile Thr Ala Leu Ala Pro Glu Val Glu His Leu Thr Val Phe Val
       195                 200                 205

Arg Thr Pro Gln Tyr Ser Val Pro Val Gly Asn Arg Pro Val Thr Pro
   210                 215                 220

Glu Gln Ile Asp Ala Ile Lys Ala Asp Tyr Asp Arg Ile Trp Glu Gln
225                 230                 235                 240
```

```
Ala Lys Asn Ser Ala Val Ala Phe Gly Phe Glu Glu Ser Thr Leu Pro
            245                 250                 255

Ala Met Ser Val Ser Glu Glu Arg Asn Arg Ile Phe Gln Glu Ala
        260                 265                 270

Trp Asp His Gly Gly Phe Arg Phe Met Phe Gly Thr Phe Gly Asp
    275                 280                 285

Ile Ala Thr Asp Glu Ala Ala Asn Glu Ala Ala Ser Phe Ile Arg
    290                 295                 300

Ser Lys Ile Ala Glu Ile Ile Glu Asp Pro Glu Thr Ala Arg Lys Leu
305                 310                 315                 320

Met Pro Thr Gly Leu Phe Ala Lys Arg Pro Leu Cys Asp Ala Gly Tyr
                325                 330                 335

His Gln Val Phe Asn Arg Pro Asn Val Glu Ala Val Ala Ile Lys Glu
                340                 345                 350

Asn Pro Ile Arg Glu Val Thr Ala Lys Gly Val Val Thr Glu Asp Gly
                355                 360                 365

Val Leu His Glu Leu Asp Val Leu Val Phe Ala Thr Gly Phe Asp Ala
370                 375                 380

Val Asp Gly Asn Tyr Arg Arg Ile Glu Ile Arg Gly Arg Asp Gly Leu
385                 390                 395                 400

His Ile Asn Asp His Trp Asp Gly Gln Pro Thr Ser Tyr Leu Gly Val
                405                 410                 415

Ser Thr Ala Asn Phe Pro Asn Trp Phe Met Val Leu Gly Pro Asn Gly
                420                 425                 430

Pro Phe Thr Asn Leu Pro Pro Ser Ile Glu Thr Gln Val Glu Trp Ile
                435                 440                 445

Ser Asp Thr Ile Gly Tyr Ala Glu Arg Asn Gly Val Arg Ala Ile Glu
                450                 455                 460

Pro Thr Pro Glu Ala Glu Ala Glu Trp Thr Glu Thr Cys Thr Ala Ile
465                 470                 475                 480

Ala Asn Ala Thr Leu Phe Thr Lys Gly Asp Ser Trp Ile Phe Gly Ala
                485                 490                 495

Asn Ile Pro Gly Lys Thr Pro Ser Val Leu Phe Tyr Leu Gly Gly Leu
                500                 505                 510

Arg Asn Tyr Arg Ala Val Leu Ala Glu Val Ala Thr Asp Gly Tyr Arg
                515                 520                 525

Gly Phe Asp Val Lys Ser Ala Glu Met Val Thr Val Glx
                530                 535                 540

<210> SEQ ID NO 11
<211> LENGTH: 1596
<212> TYPE: DNA
<213> ORGANISM: Arthrobacter sp. BP2

<400> SEQUENCE: 11
atgactgcac agaacacttt ccagaccgtt gacgccgtcg tcatcggcgc cggcttcggc      60
ggcatctacg ccgtccacaa gcttcacaac gagcagggtc tgaccgttgt cggcttcgac     120
aaggccgacg gtcccggcgg cacctggtac tggaaccgct acccgggcgc tctctctgac     180
accgagagcc acgtctaccg cttctctttc gataagggcc tcctgcagga cggcaccctg     240
aagcacacct acatcaccca gcccgagatc ctcgagtacc ttgaggacgt cgttgaccgc     300
tttgacctgc ggcgccactt ccgctttggt accgaggtca agtccgccac ctacctcgaa     360
gacgagggcc tgtgggaagt gaccaccggc ggcggcgcgg tgtaccgggc taagtacgtc     420
```

```
atcaacgccg tggggctgct gtcagccatc aacttcccga acctgcccgg gatcgacacc    480
tttgagggcg agaccatcca caccgccgcc tggccgcagg gcaagtccct cgccggtcgc    540
cgcgtgggtg tgatcggcac cggttccacc ggccagcagg tcatcacggc gctggcaccg    600
gaagttgaac acctgaccgt cttcgtcagg accccgcagt actccgtccc ggtgggcaag    660
cgccccgtga ccacccagca gattgacgag atcaaggccg actacgacaa catctgggca    720
caggtcaagc gttccggcgt agccttcggc ttcgaggaaa gcaccgtgcc ggccatgagc    780
gtcaccgaag aagaacgccg ccaggtctac gagaaggcct gggaatacgg cggcggcttc    840
cgcttcatgt tcgaaacctt cagcgacatc gccaccgacg aggaggccaa cgagactgcg    900
gcatccttca tccggaacaa gatcgtcgag accatcaagg atccggagac ggcacggaaa    960
ctgacgccga cgggcttgtt cgcccgtcgc ccgctctgcg acgacggctt acttccaggt   1020
gttcaaccgg cccaacgtcg aggctgtcgc tatcaaggaa aaccccattc gggaagtcac   1080
ggccaagggt gtggtgacgg aggacggcgt gctgcacgag ctggacgtca tcgtcttcgc   1140
gaccggtttc gacgccgtgg acggcaatta ccgccgcatg gagatcagcg gcgcgacgg    1200 cgtgaacatc aacgaccact gggacgggca gcccaccagc tacctgggcg tttccacagc   1260
gaagttcccc aactggttca tggtgctggg acccaacggc ccgttcacga acctgccgcc   1320
gagcatcgag acgcaggtcg aatggatcag cgacacggtg gcctacgcgg aggaaaacgg   1380
aatccgggcg atcgagccga ccccggaggc cgaagccgag tggaccgaga cgtgcacaca   1440
gatcgcgaac atgacggtgt tcaccaaggt cgattcatgg atcttcggcg cgaacgttcc   1500
gggcaagaag cccagcgtgc tgttctatct gggcggcctg ggcaactacc gcggcgtcct   1560
ggacgatgtc accgacaacg gataccgcgg ctttga                             1596
```

<210> SEQ ID NO 12
<211> LENGTH: 532
<212> TYPE: PRT
<213> ORGANISM: Arthrobacter sp. BP2

<400> SEQUENCE: 12

```
Met Thr Ala Gln Asn Thr Phe Gln Thr Val Asp Ala Val Val Ile Gly
1               5                   10                  15

Ala Gly Phe Gly Gly Ile Tyr Ala Val His Lys Leu His Asn Glu Gln
            20                  25                  30

Gly Leu Thr Val Val Gly Phe Asp Lys Ala Asp Gly Pro Gly Gly Thr
        35                  40                  45

Trp Tyr Trp Asn Arg Tyr Pro Gly Ala Leu Ser Asp Thr Glu Ser His
    50                  55                  60

Val Tyr Arg Phe Ser Phe Asp Lys Gly Leu Leu Gln Asp Gly Thr Trp
65                  70                  75                  80

Lys His Thr Tyr Ile Thr Gln Pro Glu Ile Leu Glu Tyr Leu Glu Asp
                85                  90                  95

Val Val Asp Arg Phe Asp Leu Arg Arg His Phe Arg Phe Gly Thr Glu
            100                 105                 110

Val Lys Ser Ala Thr Tyr Leu Glu Asp Glu Gly Leu Trp Glu Val Thr
        115                 120                 125

Thr Gly Gly Gly Ala Val Tyr Arg Ala Lys Tyr Val Ile Asn Ala Val
    130                 135                 140

Gly Leu Leu Ser Ala Ile Asn Phe Pro Asn Leu Pro Gly Ile Asp Thr
145                 150                 155                 160
```

-continued

```
Phe Glu Gly Glu Thr Ile His Thr Ala Ala Trp Pro Gln Lys Ser
                165                 170                 175

Leu Ala Gly Arg Arg Val Gly Val Ile Gly Thr Gly Ser Thr Gly Gln
            180                 185                 190

Gln Val Ile Thr Ala Leu Ala Pro Glu Val Glu His Leu Thr Val Phe
        195                 200                 205

Val Arg Thr Pro Gln Tyr Ser Val Pro Val Gly Lys Arg Pro Val Thr
210                 215                 220

Thr Gln Gln Ile Asp Glu Ile Lys Ala Asp Tyr Asp Asn Ile Trp Ala
225                 230                 235                 240

Gln Val Lys Arg Ser Gly Val Ala Phe Gly Phe Glu Glu Ser Thr Val
                245                 250                 255

Pro Ala Met Ser Val Thr Glu Glu Arg Arg Gln Val Tyr Glu Lys
            260                 265                 270

Ala Trp Glu Tyr Gly Gly Phe Arg Phe Met Phe Glu Thr Phe Ser
        275                 280                 285

Asp Ile Ala Thr Asp Glu Glu Ala Asn Glu Thr Ala Ala Ser Phe Ile
290                 295                 300

Arg Asn Lys Ile Val Glu Thr Ile Lys Asp Pro Glu Thr Ala Arg Lys
305                 310                 315                 320

Leu Thr Pro Thr Gly Leu Phe Ala Arg Arg Pro Leu Cys Asp Asp Gly
                325                 330                 335

Leu Leu Pro Gly Val Gln Pro Ala Gln Arg Gly Cys Arg Tyr Gln
            340                 345                 350

Gly Lys Pro His Ser Gly Ser His Gly Gln Gly Cys Gly Asp Gly Gly
        355                 360                 365

Arg Arg Ala Ala Arg Ala Gly Arg His Arg Leu Arg Asp Arg Phe Arg
370                 375                 380

Arg Arg Gly Arg Gln Leu Pro Pro His Gly Asp Gln Arg Ala Arg Arg
385                 390                 395                 400

Arg Glu His Gln Arg Pro Leu Gly Arg Ala Ala His Gln Leu Pro Gly
                405                 410                 415

Arg Phe His Ser Glu Val Pro Gln Leu Val His Gly Ala Gly Thr Gln
            420                 425                 430

Arg Pro Val His Glu Pro Ala Glu His Arg Asp Ala Gly Arg Met
        435                 440                 445

Asp Gln Arg His Gly Gly Leu Arg Gly Lys Arg Asn Pro Gly Asp
450                 455                 460

Arg Ala Asp Pro Gly Gly Arg Ser Arg Val Asp Arg Asp Val His Thr
465                 470                 475                 480

Asp Arg Glu His Asp Gly Val His Gln Gly Arg Phe Met Asp Leu Arg
                485                 490                 495

Arg Glu Arg Ser Gly Gln Glu Ala Gln Arg Ala Val Leu Ser Gly Arg
            500                 505                 510

Pro Gly Gln Leu Pro Arg Arg Pro Gly Arg Cys His Arg Gln Arg Ile
        515                 520                 525

Pro Arg Leu Glx
    530
```

<210> SEQ ID NO 13
<211> LENGTH: 1662
<212> TYPE: DNA
<213> ORGANISM: Brevibacterium sp. HCU
<220> FEATURE:
<221> NAME/KEY: CDS

<222> LOCATION: (1)..(1662)
<223> OTHER INFORMATION:

<400> SEQUENCE: 13

| atg | cca | att | aca | caa | caa | ctt | gac | cac | gac | gct | atc | gtc | atc | ggc | gcc | 48 |
|---|---|---|---|---|---|---|---|---|---|---|---|---|---|---|---|---|
| Met | Pro | Ile | Thr | Gln | Gln | Leu | Asp | His | Asp | Ala | Ile | Val | Ile | Gly | Ala | |
| 1 | | | | 5 | | | | | 10 | | | | | 15 | | |

| ggc | ttc | tcc | gga | cta | gcc | att | ctg | cac | cac | ctg | cgt | gaa | atc | ggc | cta | 96 |
|---|---|---|---|---|---|---|---|---|---|---|---|---|---|---|---|---|
| Gly | Phe | Ser | Gly | Leu | Ala | Ile | Leu | His | His | Leu | Arg | Glu | Ile | Gly | Leu | |
| | | | 20 | | | | | 25 | | | | | 30 | | | |

| gac | act | caa | atc | gtc | gaa | gca | acc | gac | ggc | att | gga | gga | act | tgg | tgg | 144 |
|---|---|---|---|---|---|---|---|---|---|---|---|---|---|---|---|---|
| Asp | Thr | Gln | Ile | Val | Glu | Ala | Thr | Asp | Gly | Ile | Gly | Gly | Thr | Trp | Trp | |
| | | 35 | | | | | 40 | | | | | 45 | | | | |

| atc | aac | cgc | tac | ccg | ggg | gtg | cgg | acc | gac | agc | gag | ttc | cac | tac | tac | 192 |
|---|---|---|---|---|---|---|---|---|---|---|---|---|---|---|---|---|
| Ile | Asn | Arg | Tyr | Pro | Gly | Val | Arg | Thr | Asp | Ser | Glu | Phe | His | Tyr | Tyr | |
| 50 | | | | | 55 | | | | | 60 | | | | | | |

| tct | ttc | agc | ttc | agc | aag | gaa | gtt | cgt | gac | gag | tgg | aca | tgg | act | caa | 240 |
|---|---|---|---|---|---|---|---|---|---|---|---|---|---|---|---|---|
| Ser | Phe | Ser | Phe | Ser | Lys | Glu | Val | Arg | Asp | Glu | Trp | Thr | Trp | Thr | Gln | |
| 65 | | | | 70 | | | | | 75 | | | | | 80 | | |

| cgc | tac | cca | gac | ggt | gaa | gaa | gtt | tgc | gcc | tat | ctc | aat | ttc | att | gct | 288 |
|---|---|---|---|---|---|---|---|---|---|---|---|---|---|---|---|---|
| Arg | Tyr | Pro | Asp | Gly | Glu | Glu | Val | Cys | Ala | Tyr | Leu | Asn | Phe | Ile | Ala | |
| | | | | 85 | | | | | 90 | | | | | 95 | | |

| gat | cga | ctt | gat | ctt | cgg | aag | gac | att | cag | ctc | aac | tca | cga | gtg | aat | 336 |
|---|---|---|---|---|---|---|---|---|---|---|---|---|---|---|---|---|
| Asp | Arg | Leu | Asp | Leu | Arg | Lys | Asp | Ile | Gln | Leu | Asn | Ser | Arg | Val | Asn | |
| | | | 100 | | | | | 105 | | | | | 110 | | | |

| act | gcc | cgt | tgg | aat | gag | acg | gaa | aag | tac | tgg | gac | gtc | att | ttc | gaa | 384 |
|---|---|---|---|---|---|---|---|---|---|---|---|---|---|---|---|---|
| Thr | Ala | Arg | Trp | Asn | Glu | Thr | Glu | Lys | Tyr | Trp | Asp | Val | Ile | Phe | Glu | |
| | | 115 | | | | | 120 | | | | | 125 | | | | |

| gac | ggg | tcc | tcg | aaa | cgc | gct | cgc | ttc | ctc | atc | agc | gca | atg | ggt | gca | 432 |
|---|---|---|---|---|---|---|---|---|---|---|---|---|---|---|---|---|
| Asp | Gly | Ser | Ser | Lys | Arg | Ala | Arg | Phe | Leu | Ile | Ser | Ala | Met | Gly | Ala | |
| | 130 | | | | | 135 | | | | | 140 | | | | | |

| ctt | agc | cag | gcg | att | ttc | ccg | gcc | atc | gac | gga | atc | gac | gaa | ttc | aac | 480 |
|---|---|---|---|---|---|---|---|---|---|---|---|---|---|---|---|---|
| Leu | Ser | Gln | Ala | Ile | Phe | Pro | Ala | Ile | Asp | Gly | Ile | Asp | Glu | Phe | Asn | |
| 145 | | | | 150 | | | | | 155 | | | | | 160 | | |

| ggc | gcg | aaa | tat | cac | act | gcg | gct | tgg | cca | gct | gat | ggc | gta | gat | ttc | 528 |
|---|---|---|---|---|---|---|---|---|---|---|---|---|---|---|---|---|
| Gly | Ala | Lys | Tyr | His | Thr | Ala | Ala | Trp | Pro | Ala | Asp | Gly | Val | Asp | Phe | |
| | | | | 165 | | | | | 170 | | | | | 175 | | |

| acg | ggc | aag | aag | gtt | gga | gtc | att | ggg | gtt | ggg | gcc | tcg | gga | att | caa | 576 |
|---|---|---|---|---|---|---|---|---|---|---|---|---|---|---|---|---|
| Thr | Gly | Lys | Lys | Val | Gly | Val | Ile | Gly | Val | Gly | Ala | Ser | Gly | Ile | Gln | |
| | | | 180 | | | | | 185 | | | | | 190 | | | |

| atc | att | ccc | gag | ctc | gcc | aag | ttg | gct | ggc | gaa | cta | ttc | gta | ttc | cag | 624 |
|---|---|---|---|---|---|---|---|---|---|---|---|---|---|---|---|---|
| Ile | Ile | Pro | Glu | Leu | Ala | Lys | Leu | Ala | Gly | Glu | Leu | Phe | Val | Phe | Gln | |
| | | 195 | | | | | 200 | | | | | 205 | | | | |

| cga | act | ccg | aac | tat | gtg | gtt | gag | agc | aac | aac | gac | aaa | gtt | gac | gcc | 672 |
|---|---|---|---|---|---|---|---|---|---|---|---|---|---|---|---|---|
| Arg | Thr | Pro | Asn | Tyr | Val | Val | Glu | Ser | Asn | Asn | Asp | Lys | Val | Asp | Ala | |
| | 210 | | | | | 215 | | | | | 220 | | | | | |

| gag | tgg | atg | cag | tac | gtt | cgc | gac | aac | tat | gac | gaa | att | ttc | gaa | cgc | 720 |
|---|---|---|---|---|---|---|---|---|---|---|---|---|---|---|---|---|
| Glu | Trp | Met | Gln | Tyr | Val | Arg | Asp | Asn | Tyr | Asp | Glu | Ile | Phe | Glu | Arg | |
| 225 | | | | 230 | | | | | 235 | | | | | 240 | | |

| gca | tcc | aag | cac | ccg | ttc | ggg | gtc | gat | atg | gag | tat | ccg | acg | gat | tcc | 768 |
|---|---|---|---|---|---|---|---|---|---|---|---|---|---|---|---|---|
| Ala | Ser | Lys | His | Pro | Phe | Gly | Val | Asp | Met | Glu | Tyr | Pro | Thr | Asp | Ser | |
| | | | | 245 | | | | | 250 | | | | | 255 | | |

| gcc | gtc | gag | gtt | tca | gaa | gaa | gaa | cgt | aag | cga | gtc | ttt | gaa | agc | aaa | 816 |
|---|---|---|---|---|---|---|---|---|---|---|---|---|---|---|---|---|
| Ala | Val | Glu | Val | Ser | Glu | Glu | Glu | Arg | Lys | Arg | Val | Phe | Glu | Ser | Lys | |
| | | | 260 | | | | | 265 | | | | | 270 | | | |

| tgg | gag | gag | gga | ggc | ttc | cat | ttt | gca | aac | gag | tgt | ttc | acg | gac | ctg | 864 |
|---|---|---|---|---|---|---|---|---|---|---|---|---|---|---|---|---|
| Trp | Glu | Glu | Gly | Gly | Phe | His | Phe | Ala | Asn | Glu | Cys | Phe | Thr | Asp | Leu | |
| | | 275 | | | | | 280 | | | | | 285 | | | | |

| ggt | acc | agt | cct | gag | gcc | agc | gag | ctg | gcg | tca | gag | ttc | ata | cgt | tcg | 912 |
|---|---|---|---|---|---|---|---|---|---|---|---|---|---|---|---|---|
| Gly | Thr | Ser | Pro | Glu | Ala | Ser | Glu | Leu | Ala | Ser | Glu | Phe | Ile | Arg | Ser | |

```
                290                 295                 300
aag att cgg gag gtc gtt aag gac ccc gct acg gca gat ctc ctt tgt     960
Lys Ile Arg Glu Val Val Lys Asp Pro Ala Thr Ala Asp Leu Leu Cys
305                 310                 315                 320 ccc aag tcg tac tcg ttc aac ggt aag cga gtg ccg acc ggc cac ggc    1008
Pro Lys Ser Tyr Ser Phe Asn Gly Lys Arg Val Pro Thr Gly His Gly
                325                 330                 335 tac tac gag acg ttc aat cgc acg aat gtg cac ctt ttg gat gcc agg    1056
Tyr Tyr Glu Thr Phe Asn Arg Thr Asn Val His Leu Leu Asp Ala Arg
            340                 345                 350 ggc act cca att act cgg atc agc agc aaa ggt atc gtt cac gga gac    1104
Gly Thr Pro Ile Thr Arg Ile Ser Ser Lys Gly Ile Val His Gly Asp
        355                 360                 365 acc gaa tac gaa cta gat gca atc gtg ttc gca acc ggc ttc gac gcg    1152
Thr Glu Tyr Glu Leu Asp Ala Ile Val Phe Ala Thr Gly Phe Asp Ala
    370                 375                 380 atg aca ggt acg ctc acc aac att gac atc gtc ggc cgc gac gga gtc    1200
Met Thr Gly Thr Leu Thr Asn Ile Asp Ile Val Gly Arg Asp Gly Val
385                 390                 395                 400 atc ctc cgc gac aag tgg gcc cag gat ggg ctt agg aca aac att ggt    1248
Ile Leu Arg Asp Lys Trp Ala Gln Asp Gly Leu Arg Thr Asn Ile Gly
                405                 410                 415 ctt act gta aac ggc ttc ccg aac ttc ctg atg tct ctt gga cct cag    1296
Leu Thr Val Asn Gly Phe Pro Asn Phe Leu Met Ser Leu Gly Pro Gln
            420                 425                 430 acc ccg tac tcc aac ctt gtt gtt cct att cag ttg gga gcc caa tgg    1344
Thr Pro Tyr Ser Asn Leu Val Val Pro Ile Gln Leu Gly Ala Gln Trp
        435                 440                 445 atg cag cga ttc ctt aag ttc att cag gaa cgc ggc att gaa gtg ttc    1392
Met Gln Arg Phe Leu Lys Phe Ile Gln Glu Arg Gly Ile Glu Val Phe
    450                 455                 460 gag tcg tcg aga gaa gct gaa gaa atc tgg aat gcc gaa acc att cgc    1440
Glu Ser Ser Arg Glu Ala Glu Glu Ile Trp Asn Ala Glu Thr Ile Arg
465                 470                 475                 480 ggc gct gaa tct acg gtc atg tcc atc gaa gga ccc aaa gcc ggc gca    1488
Gly Ala Glu Ser Thr Val Met Ser Ile Glu Gly Pro Lys Ala Gly Ala
                485                 490                 495 tgg ttc atc ggc ggc aac att ccc ggt aaa tca cgt gag tac cag gtg    1536
Trp Phe Ile Gly Gly Asn Ile Pro Gly Lys Ser Arg Glu Tyr Gln Val
            500                 505                 510 tat atg ggc ggc ggt cag gtc tac cag gac tgg tgc cgc gag gcg gaa    1584
Tyr Met Gly Gly Gly Gln Val Tyr Gln Asp Trp Cys Arg Glu Ala Glu
        515                 520                 525 gaa tcc gac tac gcc act ttt ctg aat gct gac tcc att gac ggc gaa    1632
Glu Ser Asp Tyr Ala Thr Phe Leu Asn Ala Asp Ser Ile Asp Gly Glu
    530                 535                 540 aag gtt cgt gaa tcg gcg ggt atg aaa tag                            1662
Lys Val Arg Glu Ser Ala Gly Met Lys
545                 550

<210> SEQ ID NO 14
<211> LENGTH: 553
<212> TYPE: PRT
<213> ORGANISM: Brevibacterium sp. HCU

<400> SEQUENCE: 14

Met Pro Ile Thr Gln Gln Leu Asp His Asp Ala Ile Val Ile Gly Ala
1               5                   10                  15

Gly Phe Ser Gly Leu Ala Ile Leu His His Leu Arg Glu Ile Gly Leu
            20                  25                  30
```

```
Asp Thr Gln Ile Val Glu Ala Thr Asp Gly Ile Gly Gly Thr Trp Trp
        35                  40                  45

Ile Asn Arg Tyr Pro Gly Val Arg Thr Asp Ser Glu Phe His Tyr Tyr
    50                  55                  60

Ser Phe Ser Phe Ser Lys Glu Val Arg Asp Glu Trp Thr Trp Thr Gln
65                  70                  75                  80

Arg Tyr Pro Asp Gly Glu Val Cys Ala Tyr Leu Asn Phe Ile Ala
                85                  90                  95

Asp Arg Leu Asp Leu Arg Lys Asp Ile Gln Leu Asn Ser Arg Val Asn
            100                 105                 110

Thr Ala Arg Trp Asn Glu Thr Glu Lys Tyr Trp Asp Val Ile Phe Glu
        115                 120                 125

Asp Gly Ser Ser Lys Arg Ala Arg Phe Leu Ile Ser Ala Met Gly Ala
    130                 135                 140

Leu Ser Gln Ala Ile Phe Pro Ala Ile Asp Gly Ile Asp Glu Phe Asn
145                 150                 155                 160

Gly Ala Lys Tyr His Thr Ala Ala Trp Pro Ala Asp Gly Val Asp Phe
                165                 170                 175

Thr Gly Lys Lys Val Gly Val Ile Gly Val Gly Ala Ser Gly Ile Gln
            180                 185                 190

Ile Ile Pro Glu Leu Ala Lys Leu Ala Gly Glu Leu Phe Val Phe Gln
        195                 200                 205

Arg Thr Pro Asn Tyr Val Val Glu Ser Asn Asn Asp Lys Val Asp Ala
    210                 215                 220

Glu Trp Met Gln Tyr Val Arg Asp Asn Tyr Asp Glu Ile Phe Glu Arg
225                 230                 235                 240

Ala Ser Lys His Pro Phe Gly Val Asp Met Glu Tyr Pro Thr Asp Ser
                245                 250                 255

Ala Val Glu Val Ser Glu Glu Arg Lys Arg Val Phe Glu Ser Lys
            260                 265                 270

Trp Glu Glu Gly Gly Phe His Phe Ala Asn Glu Cys Phe Thr Asp Leu
        275                 280                 285

Gly Thr Ser Pro Glu Ala Ser Glu Leu Ala Ser Glu Phe Ile Arg Ser
    290                 295                 300

Lys Ile Arg Glu Val Val Lys Asp Pro Ala Thr Ala Asp Leu Leu Cys
305                 310                 315                 320

Pro Lys Ser Tyr Ser Phe Asn Gly Lys Arg Val Pro Thr Gly His Gly
                325                 330                 335

Tyr Tyr Glu Thr Phe Asn Arg Thr Asn Val His Leu Leu Asp Ala Arg
            340                 345                 350

Gly Thr Pro Ile Thr Arg Ile Ser Ser Lys Gly Ile Val His Gly Asp
        355                 360                 365

Thr Glu Tyr Glu Leu Asp Ala Ile Val Phe Ala Thr Gly Phe Asp Ala
    370                 375                 380

Met Thr Gly Thr Leu Thr Asn Ile Asp Ile Val Gly Arg Asp Gly Val
385                 390                 395                 400

Ile Leu Arg Asp Lys Trp Ala Gln Asp Gly Leu Arg Thr Asn Ile Gly
                405                 410                 415

Leu Thr Val Asn Gly Phe Pro Asn Phe Leu Met Ser Leu Gly Pro Gln
            420                 425                 430

Thr Pro Tyr Ser Asn Leu Val Val Pro Ile Gln Leu Gly Ala Gln Trp
        435                 440                 445
```

-continued

```
Met Gln Arg Phe Leu Lys Phe Ile Gln Glu Arg Gly Ile Glu Val Phe
    450                 455                 460
Glu Ser Ser Arg Glu Ala Glu Ile Trp Asn Ala Glu Thr Ile Arg
465                 470                 475                 480
Gly Ala Glu Ser Thr Val Met Ser Ile Glu Gly Pro Lys Ala Gly Ala
                485                 490                 495
Trp Phe Ile Gly Gly Asn Ile Pro Gly Lys Ser Arg Glu Tyr Gln Val
                500                 505                 510
Tyr Met Gly Gly Gln Val Tyr Gln Asp Trp Cys Arg Glu Ala Glu
            515                 520                 525
Glu Ser Asp Tyr Ala Thr Phe Leu Asn Ala Asp Ser Ile Asp Gly Glu
    530                 535                 540
Lys Val Arg Glu Ser Ala Gly Met Lys
545                 550
```

<210> SEQ ID NO 15
<211> LENGTH: 1590
<212> TYPE: DNA
<213> ORGANISM: Brevibacterium sp. HCU
<220> FEATURE:
<221> NAME/KEY: CDS
<222> LOCATION: (1)..(1590)
<223> OTHER INFORMATION:

<400> SEQUENCE: 15

```
atg acg tca acc atg cct gca ccg aca gca gca cag gcg aac gca gac       48
Met Thr Ser Thr Met Pro Ala Pro Thr Ala Ala Gln Ala Asn Ala Asp
1               5                   10                  15 gag acc gag gtc ctc gac gca ctc atc gtg ggt ggc gga ttc tcg ggg       96
Glu Thr Glu Val Leu Asp Ala Leu Ile Val Gly Gly Gly Phe Ser Gly
                20                  25                  30 cct gta tct gtc gac cgc ctg cgt gaa gac ggg ttc aag gtc aag gtc     144
Pro Val Ser Val Asp Arg Leu Arg Glu Asp Gly Phe Lys Val Lys Val
            35                  40                  45 tgg gac gcc gcc ggc gga ttc ggc ggc atc tgg tgg tgg aac tgc tac     192
Trp Asp Ala Ala Gly Gly Phe Gly Gly Ile Trp Trp Trp Asn Cys Tyr
    50                  55                  60 ccg ggt gct cgt acg gac agc acc gga cag atc tat cag ttc cag tac     240
Pro Gly Ala Arg Thr Asp Ser Thr Gly Gln Ile Tyr Gln Phe Gln Tyr
65                  70                  75                  80 aag gac ctg tgg aag gac ttc gac ttc aag gag ctc tac ccc gac ttc     288
Lys Asp Leu Trp Lys Asp Phe Asp Phe Lys Glu Leu Tyr Pro Asp Phe
                85                  90                  95 aac ggg gtt cgg gag tac ttc gag tac gtc gac tcg cag ctc gac ctg     336
Asn Gly Val Arg Glu Tyr Phe Glu Tyr Val Asp Ser Gln Leu Asp Leu
            100                 105                 110 tcc cgc gac gtc aca ttc aac acc ttt gcg gag tcc tgc aca tgg gac     384
Ser Arg Asp Val Thr Phe Asn Thr Phe Ala Glu Ser Cys Thr Trp Asp
    115                 120                 125 gac gct gcc aag gag tgg acg gtg cga tcg tcg gaa gga cgt gag cag     432
Asp Ala Ala Lys Glu Trp Thr Val Arg Ser Ser Glu Gly Arg Glu Gln
130                 135                 140 cgg gcc cgt gcg gtc atc gtc gcc acc ggc ttc ggt gcg aag ccc ctc     480
Arg Ala Arg Ala Val Ile Val Ala Thr Gly Phe Gly Ala Lys Pro Leu
145                 150                 155                 160 tac ccg aac atc gag ggc ctc gac agc ttc gaa ggc gag tgc cat cac     528
Tyr Pro Asn Ile Glu Gly Leu Asp Ser Phe Glu Gly Glu Cys His His
                165                 170                 175 acc gca cgc tgg ccg cag ggt ggc ctc gac atg acg ggc aag cga gtc     576
Thr Ala Arg Trp Pro Gln Gly Gly Leu Asp Met Thr Gly Lys Arg Val
            180                 185                 190
```

-continued

```
              180                 185                 190
gtc gtc atg ggc acc ggt gct tcc ggc atc cag gtc att caa gaa gcc      624
Val Val Met Gly Thr Gly Ala Ser Gly Ile Gln Val Ile Gln Glu Ala
        195                 200                 205 gcg gcg gtt gcc gaa cac ctc acc gtc ttc cag cgc acc ccg aac ctt      672
Ala Ala Val Ala Glu His Leu Thr Val Phe Gln Arg Thr Pro Asn Leu
210                 215                 220 gcc ctg ccg atg cgg cag cag cgg ctg tcg gcc gat gac aac gat cgc      720
Ala Leu Pro Met Arg Gln Gln Arg Leu Ser Ala Asp Asp Asn Asp Arg
225                 230                 235                 240 tac cga gag aac atc gaa gat cgt ttc caa atc cgt gac aat tcg ttt      768
Tyr Arg Glu Asn Ile Glu Asp Arg Phe Gln Ile Arg Asp Asn Ser Phe
                245                 250                 255 gcc gga ttc gac ttc tac ttc atc ccg cag aac gcc gcg gac acc ccc      816
Ala Gly Phe Asp Phe Tyr Phe Ile Pro Gln Asn Ala Ala Asp Thr Pro
            260                 265                 270 gag gac gag cgg acc gcg atc tac gaa aag atg tgg gac gaa ggc gga      864
Glu Asp Glu Arg Thr Ala Ile Tyr Glu Lys Met Trp Asp Glu Gly Gly
        275                 280                 285 ttc cca ctg tgg ctc gga aac ttc cag gga ctc ctc acc gat gag gca      912
Phe Pro Leu Trp Leu Gly Asn Phe Gln Gly Leu Leu Thr Asp Glu Ala
290                 295                 300 gcc aac cac acc ttc tac aac ttc tgg cgt tcg aag gtg cac gat cgt      960
Ala Asn His Thr Phe Tyr Asn Phe Trp Arg Ser Lys Val His Asp Arg
305                 310                 315                 320 gtg aag gat ccc aag acc gcc gag atg ctc gca ccg gcg acc cca ccg     1008
Val Lys Asp Pro Lys Thr Ala Glu Met Leu Ala Pro Ala Thr Pro Pro
                325                 330                 335 cac ccg ttc ggc gtc aag cgt ccc tcg ctc gaa cag aac tac ttc gac     1056
His Pro Phe Gly Val Lys Arg Pro Ser Leu Glu Gln Asn Tyr Phe Asp
            340                 345                 350 gta tac aac cag gac aat gtc gat ctc atc gac tcg aat gcc acc ccg     1104
Val Tyr Asn Gln Asp Asn Val Asp Leu Ile Asp Ser Asn Ala Thr Pro
        355                 360                 365 atc acc cgg gtc ctt ccg aac ggg gtc gaa acc ccg gac gga gtc gtc     1152
Ile Thr Arg Val Leu Pro Asn Gly Val Glu Thr Pro Asp Gly Val Val
370                 375                 380 gaa tgc gat gtc ctc gtg ctg gcc acc ggc ttc gac aac aac agc ggc     1200
Glu Cys Asp Val Leu Val Leu Ala Thr Gly Phe Asp Asn Asn Ser Gly
385                 390                 395                 400 ggc atc aac gcc atc gat atc aaa gcc ggc ggg cag ctg ctc cgt gac     1248
Gly Ile Asn Ala Ile Asp Ile Lys Ala Gly Gly Gln Leu Leu Arg Asp
                405                 410                 415 aag tgg gcg acc ggc gtg gac acc tac atg ggg ctg tcg acg cac gga     1296
Lys Trp Ala Thr Gly Val Asp Thr Tyr Met Gly Leu Ser Thr His Gly
            420                 425                 430 ttc ccc aat ctc atg ttc ctc tac ggc ccg cag agc cct tcg ggc ttc     1344
Phe Pro Asn Leu Met Phe Leu Tyr Gly Pro Gln Ser Pro Ser Gly Phe
        435                 440                 445 tgc aat ggg acc gac ttc ggc gga gcg cca ggc gat atg gtc gcc gac     1392
Cys Asn Gly Thr Asp Phe Gly Gly Ala Pro Gly Asp Met Val Ala Asp
450                 455                 460 ttc ctc atc tgg ctc aag gac aac ggc atc tcg cgg ttc gaa tcc acc     1440
Phe Leu Ile Trp Leu Lys Asp Asn Gly Ile Ser Arg Phe Glu Ser Thr
465                 470                 475                 480 gaa gag gtc gag cgg gaa tgg cgc gcc cat gtc gac gac atc ttc gtc     1488
Glu Glu Val Glu Arg Glu Trp Arg Ala His Val Asp Asp Ile Phe Val
                485                 490                 495 aac tcg ctg ttc ccc aag gcg aag tcc tgg tac tgg ggc gcc aac gtc     1536
```

-continued

```
Asn Ser Leu Phe Pro Lys Ala Lys Ser Trp Tyr Trp Gly Ala Asn Val
            500                 505                 510 ccc ggc aag ccg gcg cag atg ctc aac tat tcg gag gcg tcc ccg cat    1584
Pro Gly Lys Pro Ala Gln Met Leu Asn Tyr Ser Glu Ala Ser Pro His
        515                 520                 525 atc tag                                                             1590
Ile
```

<210> SEQ ID NO 16
<211> LENGTH: 529
<212> TYPE: PRT
<213> ORGANISM: Brevibacterium sp. HCU

<400> SEQUENCE: 16

```
Met Thr Ser Thr Met Pro Ala Pro Thr Ala Ala Gln Ala Asn Ala Asp
1               5                   10                  15

Glu Thr Glu Val Leu Asp Ala Leu Ile Val Gly Gly Gly Phe Ser Gly
                20                  25                  30

Pro Val Ser Val Asp Arg Leu Arg Glu Asp Gly Phe Lys Val Lys Val
            35                  40                  45

Trp Asp Ala Ala Gly Gly Phe Gly Gly Ile Trp Trp Asn Cys Tyr
    50                  55                  60

Pro Gly Ala Arg Thr Asp Ser Thr Gly Gln Ile Tyr Gln Phe Gln Tyr
65                  70                  75                  80

Lys Asp Leu Trp Lys Asp Phe Asp Phe Lys Glu Leu Tyr Pro Asp Phe
                85                  90                  95

Asn Gly Val Arg Glu Tyr Phe Glu Tyr Val Asp Ser Gln Leu Asp Leu
            100                 105                 110

Ser Arg Asp Val Thr Phe Asn Thr Phe Ala Glu Ser Cys Thr Trp Asp
        115                 120                 125

Asp Ala Ala Lys Glu Trp Thr Val Arg Ser Ser Glu Gly Arg Glu Gln
    130                 135                 140

Arg Ala Arg Ala Val Ile Val Ala Thr Gly Phe Gly Ala Lys Pro Leu
145                 150                 155                 160

Tyr Pro Asn Ile Glu Gly Leu Asp Ser Phe Glu Gly Glu Cys His His
                165                 170                 175

Thr Ala Arg Trp Pro Gln Gly Gly Leu Asp Met Thr Gly Lys Arg Val
            180                 185                 190

Val Val Met Gly Thr Gly Ala Ser Gly Ile Gln Val Ile Gln Glu Ala
        195                 200                 205

Ala Ala Val Ala Glu His Leu Thr Val Phe Gln Arg Thr Pro Asn Leu
    210                 215                 220

Ala Leu Pro Met Arg Gln Gln Arg Leu Ser Ala Asp Asp Asn Asp Arg
225                 230                 235                 240

Tyr Arg Glu Asn Ile Glu Asp Arg Phe Gln Ile Arg Asp Asn Ser Phe
                245                 250                 255

Ala Gly Phe Asp Phe Tyr Phe Ile Pro Gln Asn Ala Ala Asp Thr Pro
            260                 265                 270

Glu Asp Glu Arg Thr Ala Ile Tyr Glu Lys Met Trp Asp Glu Gly Gly
        275                 280                 285

Phe Pro Leu Trp Leu Gly Asn Phe Gln Gly Leu Leu Thr Asp Glu Ala
    290                 295                 300

Ala Asn His Thr Phe Tyr Asn Phe Trp Arg Ser Lys Val His Asp Arg
305                 310                 315                 320

Val Lys Asp Pro Lys Thr Ala Glu Met Leu Ala Pro Ala Thr Pro Pro
```

```
                   325                 330                 335
His Pro Phe Gly Val Lys Arg Pro Ser Leu Glu Gln Asn Tyr Phe Asp
            340                 345                 350

Val Tyr Asn Gln Asp Asn Val Asp Leu Ile Asp Ser Asn Ala Thr Pro
            355                 360                 365

Ile Thr Arg Val Leu Pro Asn Gly Val Glu Thr Pro Asp Gly Val Val
        370                 375                 380

Glu Cys Asp Val Leu Val Leu Ala Thr Gly Phe Asp Asn Asn Ser Gly
385                 390                 395                 400

Gly Ile Asn Ala Ile Asp Ile Lys Ala Gly Gly Gln Leu Leu Arg Asp
                405                 410                 415

Lys Trp Ala Thr Gly Val Asp Thr Tyr Met Gly Leu Ser Thr His Gly
            420                 425                 430

Phe Pro Asn Leu Met Phe Leu Tyr Gly Pro Gln Ser Pro Ser Gly Phe
        435                 440                 445

Cys Asn Gly Thr Asp Phe Gly Gly Ala Pro Gly Asp Met Val Ala Asp
        450                 455                 460

Phe Leu Ile Trp Leu Lys Asp Asn Gly Ile Ser Arg Phe Glu Ser Thr
465                 470                 475                 480

Glu Glu Val Glu Arg Glu Trp Arg Ala His Val Asp Asp Ile Phe Val
                485                 490                 495

Asn Ser Leu Phe Pro Lys Ala Lys Ser Trp Tyr Trp Gly Ala Asn Val
            500                 505                 510

Pro Gly Lys Pro Ala Gln Met Leu Asn Tyr Ser Glu Ala Ser Pro His
        515                 520                 525

Ile

<210> SEQ ID NO 17
<211> LENGTH: 1614
<212> TYPE: DNA
<213> ORGANISM: Brachymonas sp. CHX

<400> SEQUENCE: 17
atgtcttcct cgccaagcag cgccattcat ttcgatgcca tcgttgtggg cgccggattt      60
ggcggcatgt atatgctgca caaactgcgc gaccagctcg gactcaaggt caaggttttc     120
gacacagccg gcggcatcgg cggcacctgg tattggaatc gctatcctgg agccttgtcc     180
gacacgcaca gtcatgtcta tcagtattct ttcgacgaag cgatgctcca agaatggaca     240
tggaagaaca aatacctcac gcagccagaa atactggctt atctggagta tgtagcagac     300
cggctcgatc tgcgcccgga cattcagttg aacacgaccg tgacatcgat gcatttcaat     360
gaagtccaca acatctggga agtgcgcacg gaccggggcg ggtactacac cgcgcgcttt     420
atcgtgacgg cactgggttt gttatccgcg atcaactggc ccaacattcc gggccgcgaa     480
agcttccaag gcgagatgta tcacacagcc gcctggccaa agatgtcga actgcgcggc     540 aaacgcgtcg gcgtgatcgg caccggctcg acgggtgtgc agctgattac cgccatcgct     600
ccagaggtca acacctgac ggtcttccag cgtacaccgc aatacagcgt gccgacggga     660
aatcgtcctg tctccgcgca agaaatcgca gaagtcaagc gaaacttcag caaggtatgg     720
caacaagtac gtgaatccgc cgtcgcattc ggcttcgagg aaagcacagt gcccgcgatg     780
agcgtctccg aagccgaacg ccagcgcgtc tttcaggaag cctggaacca aggcaacggc     840
ttttactaca tgttcggcac attttgcgac atcgccaccg acccgcaggc caacgaagcc     900
gcagccacct tcatacgcaa caaaatcgcc gagatcgtca agacccggga accgcccgc      960
```

-continued

```
aagctcacgc ctacggatgt ttacgcccga cgcccgcttt gcgacagtgg ctactatcgc    1020
acctacaacc gcagcaacgt ctcactggtg gatgtgaagg cgacaccaat cagtgcgatg    1080
acgccccggg gcattcgcac cgccgacggt gtcgagcacg agttggatat gttgatcctt    1140
gccactggct atgacgccgt cgatggcaat taccgccgca tcgacctgcg cggccgtggc    1200
ggccaaacca tcaatgagca ctggaacgac actcctacca gttatgtagg ggtcagcacc    1260
gccaacttcc ccaacatgtt catgatcctg gcccgaatg cccattcac gaacctgccg      1320 ccgtcgatcg aagcacaggt cgaatggatc accgacctgg ttgcccacat gcgccagcac    1380
gggctcgcga cggccgaacc aacgcgcgat gctgaagatg cctggggccg cacctgcgcg    1440
gaaatcgccg agcagacgct ttttggccag gttaatcat ggatcttcgg tgccaacagc     1500
cccgggaaga acatactttt gatgttctat ctggccggcc tggggaacta ccgcaagcag    1560
ctcgccgacg tagcgaacgc gcaataccaa ggctttgcgt tccaaccact gtaa           1614
```

<210> SEQ ID NO 18
<211> LENGTH: 538
<212> TYPE: PRT
<213> ORGANISM: Brachymonas sp. CHX

<400> SEQUENCE: 18

```
Met Ser Ser Ser Pro Ser Ala Ile His Phe Asp Ala Ile Val Val
1               5                   10                  15

Gly Ala Gly Phe Gly Gly Met Tyr Met Leu His Lys Leu Arg Asp Gln
            20                  25                  30

Leu Gly Leu Lys Val Lys Val Phe Asp Thr Ala Gly Gly Ile Gly Gly
        35                  40                  45

Thr Trp Tyr Trp Asn Arg Tyr Pro Gly Ala Leu Ser Asp Thr His Ser
    50                  55                  60

His Val Tyr Gln Tyr Ser Phe Asp Glu Ala Met Leu Gln Glu Trp Thr
65                  70                  75                  80

Trp Lys Asn Lys Tyr Leu Thr Gln Pro Glu Ile Leu Ala Tyr Leu Glu
                85                  90                  95

Tyr Val Ala Asp Arg Leu Asp Leu Arg Pro Asp Ile Gln Leu Asn Thr
            100                 105                 110

Thr Val Thr Ser Met His Phe Asn Glu Val His Asn Ile Trp Glu Val
        115                 120                 125

Arg Thr Asp Arg Gly Gly Tyr Tyr Thr Ala Arg Phe Ile Val Thr Ala
    130                 135                 140

Leu Gly Leu Leu Ser Ala Ile Asn Trp Pro Asn Ile Pro Gly Arg Glu
145                 150                 155                 160

Ser Phe Gln Gly Glu Met Tyr His Thr Ala Ala Trp Pro Lys Asp Val
                165                 170                 175

Glu Leu Arg Gly Lys Arg Val Gly Val Ile Gly Thr Gly Ser Thr Gly
            180                 185                 190

Val Gln Leu Ile Thr Ala Ile Ala Pro Glu Val Lys His Leu Thr Val
        195                 200                 205

Phe Gln Arg Thr Pro Gln Tyr Ser Val Pro Thr Gly Asn Arg Pro Val
    210                 215                 220

Ser Ala Gln Glu Ile Ala Glu Val Lys Arg Asn Phe Ser Lys Val Trp
225                 230                 235                 240

Gln Gln Val Arg Glu Ser Ala Val Ala Phe Gly Phe Glu Glu Ser Thr
                245                 250                 255
```

-continued

```
Val Pro Ala Met Ser Val Ser Glu Ala Glu Arg Gln Arg Val Phe Gln
            260                 265                 270

Glu Ala Trp Asn Gln Gly Asn Gly Phe Tyr Tyr Met Phe Gly Thr Phe
        275                 280                 285

Cys Asp Ile Ala Thr Asp Pro Gln Ala Asn Glu Ala Ala Thr Phe
290                 295                 300

Ile Arg Asn Lys Ile Ala Glu Ile Val Lys Asp Pro Glu Thr Ala Arg
305                 310                 315                 320

Lys Leu Thr Pro Thr Asp Val Tyr Ala Arg Arg Pro Leu Cys Asp Ser
                325                 330                 335

Gly Tyr Tyr Arg Thr Tyr Asn Arg Ser Asn Val Ser Leu Val Asp Val
                340                 345                 350

Lys Ala Thr Pro Ile Ser Ala Met Thr Pro Arg Gly Ile Arg Thr Ala
                355                 360                 365

Asp Gly Val Glu His Glu Leu Asp Met Leu Ile Leu Ala Thr Gly Tyr
370                 375                 380

Asp Ala Val Asp Gly Asn Tyr Arg Arg Ile Asp Leu Arg Gly Arg Gly
385                 390                 395                 400

Gly Gln Thr Ile Asn Glu His Trp Asn Asp Thr Pro Thr Ser Tyr Val
                405                 410                 415

Gly Val Ser Thr Ala Asn Phe Pro Asn Met Phe Met Ile Leu Gly Pro
                420                 425                 430

Asn Gly Pro Phe Thr Asn Leu Pro Pro Ser Ile Glu Ala Gln Val Glu
                435                 440                 445

Trp Ile Thr Asp Leu Val Ala His Met Arg Gln His Gly Leu Ala Thr
        450                 455                 460

Ala Glu Pro Thr Arg Asp Ala Glu Asp Ala Trp Gly Arg Thr Cys Ala
465                 470                 475                 480

Glu Ile Ala Glu Gln Thr Leu Phe Gly Gln Val Glu Ser Trp Ile Phe
                485                 490                 495

Gly Ala Asn Ser Pro Gly Lys Lys His Thr Leu Met Phe Tyr Leu Ala
                500                 505                 510

Gly Leu Gly Asn Tyr Arg Lys Gln Leu Ala Asp Val Ala Asn Ala Gln
                515                 520                 525

Tyr Gln Gly Phe Ala Phe Gln Pro Leu Glx
    530                 535

<210> SEQ ID NO 19
<211> LENGTH: 1644
<212> TYPE: DNA
<213> ORGANISM: Acinetobacter sp. SE19
<220> FEATURE:
<221> NAME/KEY: CDS
<222> LOCATION: (1)..(1644)
<223> OTHER INFORMATION:

<400> SEQUENCE: 19 atg gag att atc atg tca caa aaa atg gat ttt gat gct atc gtg att      48
Met Glu Ile Ile Met Ser Gln Lys Met Asp Phe Asp Ala Ile Val Ile
1               5                   10                  15 ggt ggt ggt ttt ggc gga ctt tat gca gtc aaa aaa tta aga gac gag      96
Gly Gly Gly Phe Gly Gly Leu Tyr Ala Val Lys Lys Leu Arg Asp Glu
                20                  25                  30 ctc gaa ctt aag gtt cag gct ttt gat aaa gcc acg gat gtc gca ggt     144
Leu Glu Leu Lys Val Gln Ala Phe Asp Lys Ala Thr Asp Val Ala Gly
            35                  40                  45 act tgg tac tgg aac cgt tac cca ggt gca ttg tcg gat aca gaa acc     192
```

| | | | | | | | | | | | | | | | |
|---|---|---|---|---|---|---|---|---|---|---|---|---|---|---|---|
| Thr | Trp | Tyr | Trp | Asn | Arg | Tyr | Pro | Gly | Ala | Leu | Ser | Asp | Thr | Glu | Thr |
| | 50 | | | | 55 | | | | 60 | | | | | | |

| cac | ctc | tac | tgc | tat | tct | tgg | gat | aaa | gaa | tta | cta | caa | tcg | cta | gaa | 240 |
|---|---|---|---|---|---|---|---|---|---|---|---|---|---|---|---|---|
| His | Leu | Tyr | Cys | Tyr | Ser | Trp | Asp | Lys | Glu | Leu | Leu | Gln | Ser | Leu | Glu | |
| 65 | | | | 70 | | | | 75 | | | | | 80 | | | |

| atc | aag | aaa | aaa | tat | gtg | caa | ggc | cct | gat | gta | cgc | aag | tat | tta | cag | 288 |
|---|---|---|---|---|---|---|---|---|---|---|---|---|---|---|---|---|
| Ile | Lys | Lys | Lys | Tyr | Val | Gln | Gly | Pro | Asp | Val | Arg | Lys | Tyr | Leu | Gln | |
| | | | | 85 | | | | 90 | | | | 95 | | | | |

| caa | gtg | gct | gaa | aag | cat | gat | tta | aag | aag | agc | tat | caa | ttc | aat | acc | 336 |
|---|---|---|---|---|---|---|---|---|---|---|---|---|---|---|---|---|
| Gln | Val | Ala | Glu | Lys | His | Asp | Leu | Lys | Lys | Ser | Tyr | Gln | Phe | Asn | Thr | |
| | | | 100 | | | | 105 | | | | 110 | | | | | |

| gcg | gtt | caa | tcg | gct | cat | tac | aac | gaa | gca | gat | gcc | ttg | tgg | gaa | gtc | 384 |
|---|---|---|---|---|---|---|---|---|---|---|---|---|---|---|---|---|
| Ala | Val | Gln | Ser | Ala | His | Tyr | Asn | Glu | Ala | Asp | Ala | Leu | Trp | Glu | Val | |
| | | 115 | | | | 120 | | | | 125 | | | | | | |

| acc | act | gaa | tat | ggt | gat | aag | tac | acg | gcg | cgt | ttc | ctc | atc | act | gct | 432 |
|---|---|---|---|---|---|---|---|---|---|---|---|---|---|---|---|---|
| Thr | Thr | Glu | Tyr | Gly | Asp | Lys | Tyr | Thr | Ala | Arg | Phe | Leu | Ile | Thr | Ala | |
| 130 | | | | 135 | | | | 140 | | | | | | | | |

| tta | ggc | tta | ttg | tct | gcg | cct | aac | ttg | cca | aac | atc | aaa | ggc | att | aat | 480 |
|---|---|---|---|---|---|---|---|---|---|---|---|---|---|---|---|---|
| Leu | Gly | Leu | Leu | Ser | Ala | Pro | Asn | Leu | Pro | Asn | Ile | Lys | Gly | Ile | Asn | |
| 145 | | | | 150 | | | | 155 | | | | 160 | | | | |

| cag | ttt | aaa | ggt | gag | ctg | cat | cat | acc | agc | cgc | tgg | cca | gat | gac | gta | 528 |
|---|---|---|---|---|---|---|---|---|---|---|---|---|---|---|---|---|
| Gln | Phe | Lys | Gly | Glu | Leu | His | His | Thr | Ser | Arg | Trp | Pro | Asp | Asp | Val | |
| | | | 165 | | | | 170 | | | | 175 | | | | | |

| agt | ttt | gaa | ggt | aaa | cgt | gtc | ggc | gtg | att | ggt | acg | ggt | tcc | acc | ggt | 576 |
|---|---|---|---|---|---|---|---|---|---|---|---|---|---|---|---|---|
| Ser | Phe | Glu | Gly | Lys | Arg | Val | Gly | Val | Ile | Gly | Thr | Gly | Ser | Thr | Gly | |
| | | 180 | | | | 185 | | | | 190 | | | | | | |

| gtt | cag | gtt | att | acg | gct | gtg | gca | cct | ctg | gct | aaa | cac | ctc | act | gtc | 624 |
|---|---|---|---|---|---|---|---|---|---|---|---|---|---|---|---|---|
| Val | Gln | Val | Ile | Thr | Ala | Val | Ala | Pro | Leu | Ala | Lys | His | Leu | Thr | Val | |
| | 195 | | | | 200 | | | | 205 | | | | | | | |

| ttc | cag | cgt | tct | gca | caa | tac | agc | gtt | cca | att | ggc | aat | gat | cca | ctg | 672 |
|---|---|---|---|---|---|---|---|---|---|---|---|---|---|---|---|---|
| Phe | Gln | Arg | Ser | Ala | Gln | Tyr | Ser | Val | Pro | Ile | Gly | Asn | Asp | Pro | Leu | |
| 210 | | | | 215 | | | | 220 | | | | | | | | |

| tct | gaa | gaa | gat | gtt | aaa | aag | atc | aaa | gac | aat | tat | gac | aaa | att | tgg | 720 |
|---|---|---|---|---|---|---|---|---|---|---|---|---|---|---|---|---|
| Ser | Glu | Glu | Asp | Val | Lys | Lys | Ile | Lys | Asp | Asn | Tyr | Asp | Lys | Ile | Trp | |
| 225 | | | | 230 | | | | 235 | | | | 240 | | | | |

| gat | ggt | gta | tgg | aat | tca | gcc | ctt | gcc | ttt | ggc | ctg | aat | gaa | agc | aca | 768 |
|---|---|---|---|---|---|---|---|---|---|---|---|---|---|---|---|---|
| Asp | Gly | Val | Trp | Asn | Ser | Ala | Leu | Ala | Phe | Gly | Leu | Asn | Glu | Ser | Thr | |
| | | | 245 | | | | 250 | | | | 255 | | | | | |

| gtg | cca | gca | atg | agc | gta | tca | gct | gaa | gaa | cgc | aag | gca | gtt | ttt | gaa | 816 |
|---|---|---|---|---|---|---|---|---|---|---|---|---|---|---|---|---|
| Val | Pro | Ala | Met | Ser | Val | Ser | Ala | Glu | Glu | Arg | Lys | Ala | Val | Phe | Glu | |
| | | 260 | | | | 265 | | | | 270 | | | | | | |

| aag | gca | tgg | caa | aca | ggt | ggc | ggt | ttc | cgt | ttc | atg | ttt | gaa | act | ttc | 864 |
|---|---|---|---|---|---|---|---|---|---|---|---|---|---|---|---|---|
| Lys | Ala | Trp | Gln | Thr | Gly | Gly | Gly | Phe | Arg | Phe | Met | Phe | Glu | Thr | Phe | |
| | 275 | | | | 280 | | | | 285 | | | | | | | |

| ggt | gat | att | gcc | acc | aat | atg | gaa | gcc | aat | atc | gaa | gcg | caa | aat | ttc | 912 |
|---|---|---|---|---|---|---|---|---|---|---|---|---|---|---|---|---|
| Gly | Asp | Ile | Ala | Thr | Asn | Met | Glu | Ala | Asn | Ile | Glu | Ala | Gln | Asn | Phe | |
| 290 | | | | 295 | | | | 300 | | | | | | | | |

| att | aag | ggt | aaa | att | gct | gaa | atc | gtc | aaa | gat | cca | gcc | att | gca | cag | 960 |
|---|---|---|---|---|---|---|---|---|---|---|---|---|---|---|---|---|
| Ile | Lys | Gly | Lys | Ile | Ala | Glu | Ile | Val | Lys | Asp | Pro | Ala | Ile | Ala | Gln | |
| 305 | | | | 310 | | | | 315 | | | | 320 | | | | |

| aag | ctt | atg | cca | cag | gat | ttg | tat | gca | aaa | cgt | ccg | ttg | tgt | gac | agt | 1008 |
|---|---|---|---|---|---|---|---|---|---|---|---|---|---|---|---|---|
| Lys | Leu | Met | Pro | Gln | Asp | Leu | Tyr | Ala | Lys | Arg | Pro | Leu | Cys | Asp | Ser | |
| | | | 325 | | | | 330 | | | | 335 | | | | | |

| ggt | tac | tac | aac | acc | ttt | aac | cgt | gac | aat | gtc | cgt | tta | gaa | gat | gtg | 1056 |
|---|---|---|---|---|---|---|---|---|---|---|---|---|---|---|---|---|
| Gly | Tyr | Tyr | Asn | Thr | Phe | Asn | Arg | Asp | Asn | Val | Arg | Leu | Glu | Asp | Val | |
| | | 340 | | | | 345 | | | | 350 | | | | | | |

| aaa | gcc | aat | ccg | att | gtt | gaa | att | acc | gaa | aac | ggt | gtg | aaa | ctc | gaa | 1104 |
|---|---|---|---|---|---|---|---|---|---|---|---|---|---|---|---|---|
| Lys | Ala | Asn | Pro | Ile | Val | Glu | Ile | Thr | Glu | Asn | Gly | Val | Lys | Leu | Glu | |
| | 355 | | | | 360 | | | | 365 | | | | | | | |

```
aat ggc gat ttc gtt gaa tta gac atg ctg ata tgt gcc aca ggt ttt      1152
Asn Gly Asp Phe Val Glu Leu Asp Met Leu Ile Cys Ala Thr Gly Phe
370                 375                 380 gat gcc gtc gat ggc aac tat gtg cgc atg gac att caa ggt aaa aac      1200
Asp Ala Val Asp Gly Asn Tyr Val Arg Met Asp Ile Gln Gly Lys Asn
385                 390                 395                 400 ggc ttg gcc atg aaa gac tac tgg aaa gaa ggt ccg tcg agc tat atg      1248
Gly Leu Ala Met Lys Asp Tyr Trp Lys Glu Gly Pro Ser Ser Tyr Met
            405                 410                 415 ggt gtc acc gta aat aac tat cca aac atg ttc atg gtg ctt gga ccg      1296
Gly Val Thr Val Asn Asn Tyr Pro Asn Met Phe Met Val Leu Gly Pro
        420                 425                 430 aat ggc ccg ttt acc aac ctg ccg cca tca att gaa tca cag gtg gaa      1344
Asn Gly Pro Phe Thr Asn Leu Pro Pro Ser Ile Glu Ser Gln Val Glu
    435                 440                 445 tgg atc agt gat acc att caa tac acg gtt gaa aac aat gtt gaa tcc      1392
Trp Ile Ser Asp Thr Ile Gln Tyr Thr Val Glu Asn Asn Val Glu Ser
450                 455                 460 att gaa gcg aca aaa gaa gcg gaa gaa caa tgg act caa act tgc gcc      1440
Ile Glu Ala Thr Lys Glu Ala Glu Glu Gln Trp Thr Gln Thr Cys Ala
465                 470                 475                 480 aat att gcg gaa atg acc tta ttc cct aaa gcg caa tcc tgg att ttt      1488
Asn Ile Ala Glu Met Thr Leu Phe Pro Lys Ala Gln Ser Trp Ile Phe
            485                 490                 495 ggt gcg aat atc ccg ggc aag aaa aac acg gtt tac ttc tat ctc ggt      1536
Gly Ala Asn Ile Pro Gly Lys Lys Asn Thr Val Tyr Phe Tyr Leu Gly
        500                 505                 510 ggt tta aaa gaa tat cgc agt gcg cta gcc aac tgc aaa aac cat gcc      1584
Gly Leu Lys Glu Tyr Arg Ser Ala Leu Ala Asn Cys Lys Asn His Ala
    515                 520                 525 tat gaa ggt ttt gat att caa tta caa cgt tca gat atc aag caa cct      1632
Tyr Glu Gly Phe Asp Ile Gln Leu Gln Arg Ser Asp Ile Lys Gln Pro
530                 535                 540 gcc aat gcc taa                                                      1644
Ala Asn Ala
545

<210> SEQ ID NO 20
<211> LENGTH: 547
<212> TYPE: PRT
<213> ORGANISM: Acinetobacter sp. SE19

<400> SEQUENCE: 20

Met Glu Ile Ile Met Ser Gln Lys Met Asp Phe Asp Ala Ile Val Ile
1               5                   10                  15

Gly Gly Gly Phe Gly Gly Leu Tyr Ala Val Lys Lys Leu Arg Asp Glu
            20                  25                  30

Leu Glu Leu Lys Val Gln Ala Phe Asp Lys Ala Thr Asp Val Ala Gly
        35                  40                  45

Thr Trp Tyr Trp Asn Arg Tyr Pro Gly Ala Leu Ser Asp Thr Glu Thr
    50                  55                  60

His Leu Tyr Cys Tyr Ser Trp Asp Lys Glu Leu Leu Gln Ser Leu Glu
65                  70                  75                  80

Ile Lys Lys Lys Tyr Val Gln Gly Pro Asp Val Arg Lys Tyr Leu Gln
                85                  90                  95

Gln Val Ala Glu Lys His Asp Leu Lys Lys Ser Tyr Gln Phe Asn Thr
            100                 105                 110

Ala Val Gln Ser Ala His Tyr Asn Glu Ala Asp Ala Leu Trp Glu Val
        115                 120                 125
```

```
Thr Thr Glu Tyr Gly Asp Lys Tyr Thr Ala Arg Phe Leu Ile Thr Ala
    130                 135                 140

Leu Gly Leu Leu Ser Ala Pro Asn Leu Pro Asn Ile Lys Gly Ile Asn
145                 150                 155                 160

Gln Phe Lys Gly Glu Leu His His Thr Ser Arg Trp Pro Asp Asp Val
                165                 170                 175

Ser Phe Glu Gly Lys Arg Val Gly Val Ile Gly Thr Gly Ser Thr Gly
            180                 185                 190

Val Gln Val Ile Thr Ala Val Ala Pro Leu Ala Lys His Leu Thr Val
        195                 200                 205

Phe Gln Arg Ser Ala Gln Tyr Ser Val Pro Ile Gly Asn Asp Pro Leu
    210                 215                 220

Ser Glu Glu Asp Val Lys Ile Lys Asp Asn Tyr Asp Lys Ile Trp
225                 230                 235                 240

Asp Gly Val Trp Asn Ser Ala Leu Ala Phe Gly Leu Asn Glu Ser Thr
                245                 250                 255

Val Pro Ala Met Ser Val Ser Ala Glu Glu Arg Lys Ala Val Phe Glu
            260                 265                 270

Lys Ala Trp Gln Thr Gly Gly Phe Arg Phe Met Phe Glu Thr Phe
        275                 280                 285

Gly Asp Ile Ala Thr Asn Met Glu Ala Asn Ile Glu Ala Gln Asn Phe
    290                 295                 300

Ile Lys Gly Lys Ile Ala Glu Ile Val Lys Asp Pro Ala Ile Ala Gln
305                 310                 315                 320

Lys Leu Met Pro Gln Asp Leu Tyr Ala Lys Arg Pro Leu Cys Asp Ser
                325                 330                 335

Gly Tyr Tyr Asn Thr Phe Asn Arg Asp Asn Val Arg Leu Glu Asp Val
            340                 345                 350

Lys Ala Asn Pro Ile Val Glu Ile Thr Glu Asn Gly Val Lys Leu Glu
        355                 360                 365

Asn Gly Asp Phe Val Glu Leu Asp Met Leu Ile Cys Ala Thr Gly Phe
    370                 375                 380

Asp Ala Val Asp Gly Asn Tyr Val Arg Met Asp Ile Gln Gly Lys Asn
385                 390                 395                 400

Gly Leu Ala Met Lys Asp Tyr Trp Lys Glu Gly Pro Ser Ser Tyr Met
                405                 410                 415

Gly Val Thr Val Asn Asn Tyr Pro Asn Met Phe Met Val Leu Gly Pro
            420                 425                 430

Asn Gly Pro Phe Thr Asn Leu Pro Pro Ser Ile Glu Ser Gln Val Glu
        435                 440                 445

Trp Ile Ser Asp Thr Ile Gln Tyr Thr Val Glu Asn Asn Val Glu Ser
    450                 455                 460

Ile Glu Ala Thr Lys Glu Ala Glu Glu Gln Trp Thr Gln Thr Cys Ala
465                 470                 475                 480

Asn Ile Ala Glu Met Thr Leu Phe Pro Lys Ala Gln Ser Trp Ile Phe
                485                 490                 495

Gly Ala Asn Ile Pro Gly Lys Lys Asn Thr Val Tyr Phe Tyr Leu Gly
            500                 505                 510

Gly Leu Lys Glu Tyr Arg Ser Ala Leu Ala Asn Cys Lys Asn His Ala
        515                 520                 525

Tyr Glu Gly Phe Asp Ile Gln Leu Gln Arg Ser Asp Ile Lys Gln Pro
    530                 535                 540
```

-continued

Ala Asn Ala
545

<210> SEQ ID NO 21
<211> LENGTH: 1320
<212> TYPE: DNA
<213> ORGANISM: Rhodococcus erythropolis AN12

<400> SEQUENCE: 21

| | | | | | |
|---|---|---|---|---|---|
| atgagcacag | agggcaagta | cgcgctgatc | ggagcgggtc | cgtctggatt | ggccggcgcg | 60 |
| cgaaacctcg | atcgagccgg | catagcgttc | gacggcttcg | agagccacga | cgacgtcggt | 120 |
| gggctctggg | acatcgacaa | cccgcacagc | accgtctacg | agtcggcgca | cctcatttcg | 180 |
| tcgaagggca | ccaccgcatt | cgcggagttc | ccgatggcgg | attcggttgc | cgactacccg | 240 |
| agccacatcg | aacttgccga | gtatttccgc | gactacgccg | atacccacga | tcttcgcagg | 300 |
| cactttgcct | tcggcactac | cgtcatcgac | gttttgccgg | tcgattcgct | gtggcaggtc | 360 |
| accacgcgta | gtcgcagcgg | tgagacttca | gtcgcgcggt | atcgaggcgt | gatcatcgcg | 420 |
| aacggaacgc | tgtcgaagcc | gaacataccg | acgttccggg | gcgacttcac | cggcacgttg | 480 |
| atgcacacga | gcgagtaccg | cagtgccgag | atcttccgcg | aaagagagt | gctggtcatc | 540 |
| ggagcgggca | acagtggatg | cgacatcgcc | gtcgatgccg | tccaccaggc | cgagtgcgtc | 600 |
| gatttgagcg | ttcggcgagg | ctactacttc | gtccccaagt | atctgttcgg | gcgaccctcg | 660 |
| gacacgttga | atcagggaaa | gccgttgccg | ccgtggatca | acaacgcgt | cgacaccttg | 720 |
| ttactcaagc | agttcacggg | agatccggtg | cggttcggat | ttccggcacc | ggactacaag | 780 |
| atctacgaat | cgcatccggt | cgtgaactcg | ttgatcctgc | accacatcgg | gcacggtgac | 840 |
| gtgcacgtgc | gcgccgacgt | cgaccggttc | gaggggaaga | cggtgcggtt | tgtcgacgga | 900 |
| tcgtctgccg | actacgacct | cgttctctgc | gccacggggt | atcacctcga | ctatcccttc | 960 |
| atcgcgcgcg | aggacctgga | ctggtcgggt | gctgccccgg | acctgttcct | caacgtcgcg | 1020 |
| agtcgccgcc | acgacaatct | ctttgttctc | ggcatggtcg | aagcatccgg | tctcgggtgg | 1080 |
| cagggtcgtt | accagcaggc | cgagttggtg | gccaaattga | tcaccgcacg | caccgaagcc | 1140 |
| cccgccgcgg | cgcgcgaatt | ctcggcagcg | gcggccggcc | ctcctcccga | tctgtccggg | 1200 |
| ggatacaagt | acctgaagct | gggacgaatg | gcctactacg | tgaacaagga | cgcctaccga | 1260 |
| tcggcgatca | gacggcacat | cggactgctc | gatgccgctc | tgacgaaggg | aggtcagtga | 1320 |

<210> SEQ ID NO 22
<211> LENGTH: 439
<212> TYPE: PRT
<213> ORGANISM: Rhodococcus erythropolis AN12

<400> SEQUENCE: 22

Met Ser Thr Glu Gly Lys Tyr Ala Leu Ile Gly Ala Gly Pro Ser Gly
1               5                   10                  15

Leu Ala Gly Ala Arg Asn Leu Asp Arg Ala Gly Ile Ala Phe Asp Gly
            20                  25                  30

Phe Glu Ser His Asp Asp Val Gly Gly Leu Trp Asp Ile Asp Asn Pro
        35                  40                  45

His Ser Thr Val Tyr Glu Ser Ala His Leu Ile Ser Ser Lys Gly Thr
    50                  55                  60

Thr Ala Phe Ala Glu Phe Pro Met Ala Asp Ser Val Ala Asp Tyr Pro
65                  70                  75                  80

Ser His Ile Glu Leu Ala Glu Tyr Phe Arg Asp Tyr Ala Asp Thr His

```
                    85                  90                  95
Asp Leu Arg Arg His Phe Ala Phe Gly Thr Thr Val Ile Asp Val Leu
            100                 105                 110
Pro Val Asp Ser Leu Trp Gln Val Thr Thr Arg Ser Arg Ser Gly Glu
            115                 120                 125
Thr Ser Val Ala Arg Tyr Arg Gly Val Ile Ile Ala Asn Gly Thr Leu
130                 135                 140
Ser Lys Pro Asn Ile Pro Thr Phe Arg Gly Asp Phe Thr Gly Thr Leu
145                 150                 155                 160
Met His Thr Ser Glu Tyr Arg Ser Ala Glu Ile Phe Arg Gly Lys Arg
                165                 170                 175
Val Leu Val Ile Gly Ala Gly Asn Ser Gly Cys Asp Ile Ala Val Asp
            180                 185                 190
Ala Val His Gln Ala Glu Cys Val Asp Leu Ser Val Arg Arg Gly Tyr
            195                 200                 205
Tyr Phe Val Pro Lys Tyr Leu Phe Gly Arg Pro Ser Asp Thr Leu Asn
            210                 215                 220
Gln Gly Lys Pro Leu Pro Pro Trp Ile Lys Gln Arg Val Asp Thr Leu
225                 230                 235                 240
Leu Leu Lys Gln Phe Thr Gly Asp Pro Val Arg Phe Gly Phe Pro Ala
                245                 250                 255
Pro Asp Tyr Lys Ile Tyr Glu Ser His Pro Val Val Asn Ser Leu Ile
            260                 265                 270
Leu His His Ile Gly His Gly Asp Val His Val Arg Ala Asp Val Asp
            275                 280                 285
Arg Phe Glu Gly Lys Thr Val Arg Phe Val Asp Gly Ser Ser Ala Asp
290                 295                 300
Tyr Asp Leu Val Leu Cys Ala Thr Gly Tyr His Leu Asp Tyr Pro Phe
305                 310                 315                 320
Ile Ala Arg Glu Asp Leu Asp Trp Ser Gly Ala Ala Pro Asp Leu Phe
                325                 330                 335
Leu Asn Val Ala Ser Arg Arg His Asp Asn Leu Phe Val Leu Gly Met
            340                 345                 350
Val Glu Ala Ser Gly Leu Gly Trp Gln Gly Arg Tyr Gln Gln Ala Glu
            355                 360                 365
Leu Val Ala Lys Leu Ile Thr Ala Arg Thr Glu Ala Pro Ala Ala Ala
            370                 375                 380
Arg Glu Phe Ser Ala Ala Ala Gly Pro Pro Asp Leu Ser Gly
385                 390                 395                 400
Gly Tyr Lys Tyr Leu Lys Leu Gly Arg Met Ala Tyr Tyr Val Asn Lys
                405                 410                 415
Asp Ala Tyr Arg Ser Ala Ile Arg Arg His Ile Gly Leu Leu Asp Ala
            420                 425                 430
Ala Leu Thr Lys Gly Gly Gln
            435
```

<210> SEQ ID NO 23
<211> LENGTH: 1557
<212> TYPE: DNA
<213> ORGANISM: Rhodococcus erythropolis AN12

<400> SEQUENCE: 23

```
atggtcgaca tcgacccaac ctcggggcca tcggccggtg acgaggaaac tcgaactcgc      60
cgaacacgag tcgtcgtcat cggagccggt ttcggcggca tcggaacggc tgtccgcttg     120
```

```
aagcagtccg ggatcgacga cttcgtcgtt ctggaacgtg ccgcggagcc cggggggacc      180
tggcaggtca atacctaccc cggtgcacag tgcgacatcc cgtcgattct gtactcgttc      240
tcgtttgcgc ccaatccgaa ctggacgcgg ctgtatcccc tgcagcccga gatctacgac      300
tatctccggg attgcgtcca tcgcttcgga ctggccggtc atttccactg caaccaggac      360
gtgacagaag cttcgtggga cgagcaagcc cagatctggc gggtacacac tgcggaaacc      420
gtctgggagg cacagttcct ggtcgcggcc accggcccgt tcagtgcccc cgccacaccc      480
gaccttcccg ggctcgaatc gtttcgtggt cagatgttcc acaccgcgga ctggaaccac      540
gaccacgacc ttcgcggtga gcggatagcc gtggtcggca ccggcgcctc tgcggtgcag      600
atcatcccca gactgcaacc gctcgcggac acgttgaccg tgttccagcg acaccgacg       660 tggatcctgc cgcatccgga tcagccgatg accggctggc caagcgctct cttcgagcgg      720
gtgccgctca cccaacgact ggcacgcaag ggactcgacc tgcttcaaga agccctggta      780
cccggattcg tgtacaagcc gtcactgctc aaagggctgg ccgcactcgg ccgagcacac      840
cttcgccggc aggtgcggga cccggagctt cgcgcaaagc tgctccccca ctacgcattc      900
ggatgcaagc gtccgacgtt ctcgaacacc tactatcccg cgctggcgtc acccaatgtg      960
gaggtggtga cggacggaat cgtcgaggtg caggagcgcg gagttctcac cgcggacggc     1020
gccttccggg aagtcgacac catagtcatg gaaccggct ttcggatggg agacaacccg      1080
tcgttcgaca ccatccgagg ccaggacggc cgcagcctcg cacagacgtg gaacggcagt     1140
gccgaggcct tcctcggcac cactatcagc ggttttccga acttcttcat gatcctcggc     1200
cccaattccg tggtctacac ctcacaggtc gtcacgatcg aagcccaggt cgagtacatc     1260
gtgagctgca ttcttcaaat ggacgagcgc ggcatcggca gcatcgacgt ccgcgcagac     1320
gtgcaacgcg agttcgtacg cgcgacagac cgccgactcg ccaccagcgt gtggaacgcc     1380
ggcgggtgca gtagttacta cctcgtcgac ggcggtcgca actacacctt ctatcccgga     1440
ttcaaccgat cattccgggc caggaccaaa cgagccgacc tcgctcacta cgcgcaggta     1500
caacccgtct cgtccgcagc actcaccact gctcgagaaa ccgtgaggag ccgataa        1557
```

<210> SEQ ID NO 24
<211> LENGTH: 518
<212> TYPE: PRT
<213> ORGANISM: Rhodococcus erythropolis AN12

<400> SEQUENCE: 24

```
Met Val Asp Ile Asp Pro Thr Ser Gly Pro Ser Ala Gly Asp Glu Glu
1               5                   10                  15

Thr Arg Thr Arg Arg Thr Arg Val Val Val Ile Gly Ala Gly Phe Gly
                20                  25                  30

Gly Ile Gly Thr Ala Val Arg Leu Lys Gln Ser Gly Ile Asp Asp Phe
            35                  40                  45

Val Val Leu Glu Arg Ala Ala Glu Pro Gly Gly Thr Trp Gln Val Asn
        50                  55                  60

Thr Tyr Pro Gly Ala Gln Cys Asp Ile Pro Ser Ile Leu Tyr Ser Phe
65                  70                  75                  80

Ser Phe Ala Pro Asn Pro Asn Trp Thr Arg Leu Tyr Pro Leu Gln Pro
                85                  90                  95

Glu Ile Tyr Asp Tyr Leu Arg Asp Cys Val His Arg Phe Gly Leu Ala
            100                 105                 110

Gly His Phe His Cys Asn Gln Asp Val Thr Glu Ala Ser Trp Asp Glu
```

```
            115                 120                 125
Gln Ala Gln Ile Trp Arg Val His Thr Ala Glu Thr Val Trp Glu Ala
    130                 135                 140
Gln Phe Leu Val Ala Ala Thr Gly Pro Phe Ser Ala Pro Ala Thr Pro
145                 150                 155                 160
Asp Leu Pro Gly Leu Glu Ser Phe Arg Gly Gln Met Phe His Thr Ala
                165                 170                 175
Asp Trp Asn His Asp His Asp Leu Arg Gly Glu Arg Ile Ala Val Val
                180                 185                 190
Gly Thr Gly Ala Ser Ala Val Gln Ile Ile Pro Arg Leu Gln Pro Leu
            195                 200                 205
Ala Asp Thr Leu Thr Val Phe Gln Arg Thr Pro Thr Trp Ile Leu Pro
    210                 215                 220
His Pro Asp Gln Pro Met Thr Gly Trp Pro Ser Ala Leu Phe Glu Arg
225                 230                 235                 240
Val Pro Leu Thr Gln Arg Leu Ala Arg Lys Gly Leu Asp Leu Leu Gln
                245                 250                 255
Glu Ala Leu Val Pro Gly Phe Val Tyr Lys Pro Ser Leu Leu Lys Gly
                260                 265                 270
Leu Ala Ala Leu Gly Arg Ala His Leu Arg Arg Gln Val Arg Asp Pro
            275                 280                 285
Glu Leu Arg Ala Lys Leu Leu Pro His Tyr Ala Phe Gly Cys Lys Arg
    290                 295                 300
Pro Thr Phe Ser Asn Thr Tyr Tyr Pro Ala Leu Ala Ser Pro Asn Val
305                 310                 315                 320
Glu Val Val Thr Asp Gly Ile Val Glu Val Gln Glu Arg Gly Val Leu
                325                 330                 335
Thr Ala Asp Gly Ala Phe Arg Glu Val Asp Thr Ile Val Met Gly Thr
                340                 345                 350
Gly Phe Arg Met Gly Asp Asn Pro Ser Phe Asp Thr Ile Arg Gly Gln
            355                 360                 365
Asp Gly Arg Ser Leu Ala Gln Thr Trp Asn Gly Ser Ala Glu Ala Phe
    370                 375                 380
Leu Gly Thr Thr Ile Ser Gly Phe Pro Asn Phe Phe Met Ile Leu Gly
385                 390                 395                 400
Pro Asn Ser Val Val Tyr Thr Ser Gln Val Val Thr Ile Glu Ala Gln
                405                 410                 415
Val Glu Tyr Ile Val Ser Cys Ile Leu Gln Met Asp Glu Arg Gly Ile
                420                 425                 430
Gly Ser Ile Asp Val Arg Ala Asp Val Gln Arg Glu Phe Val Arg Ala
            435                 440                 445
Thr Asp Arg Arg Leu Ala Thr Ser Val Trp Asn Ala Gly Gly Cys Ser
    450                 455                 460
Ser Tyr Tyr Leu Val Asp Gly Gly Arg Asn Tyr Thr Phe Tyr Pro Gly
465                 470                 475                 480
Phe Asn Arg Ser Phe Arg Ala Arg Thr Lys Arg Ala Asp Leu Ala His
                485                 490                 495
Tyr Ala Gln Val Gln Pro Val Ser Ser Ala Ala Leu Thr Thr Ala Arg
                500                 505                 510
Glu Thr Val Arg Ser Arg
            515

<210> SEQ ID NO 25
```

<211> LENGTH: 1626
<212> TYPE: DNA
<213> ORGANISM: Rhodococcus erythropolis AN12

<400> SEQUENCE: 25

```
atgaccgatc ctgacttctc caccgcacca ctcgacgtcg tagtcatcgg cgccggcgtc      60
gctggcatgt acgccatgca ccgacttcgc gagcagggc tgcgtgtcca cggcttcgag     120
gcgggctccg gagtgggcgg cacgtggtat ttcaaccgct accccggcgc acgctgcgac    180
gtcgagagtt tcgactactc ctactcgttc tccgaagagc tgcaacagga ttgggactgg    240
agcgagaagt acgccgcgca accggagatc tctcgtacc tcgatcacgt ggctgatcgc     300
ttcgacctac gcactggctt caccttcgac acacgcgttc tgagcgcaca gttcgacgag    360
ggtactgcca cgtggcgagt acagaccgac ggcggtcacg acgtcacctc acgcttcgtc    420
gtgtgcgcca cgggcagcct ctcgaccgca aacgttccga acattgcggg ccgtgagacc    480
ttcggtggcg atgtgttcca caccggtttc tggccgcacg agggcgtcga cttcaccggc    540
aaacgcgtcg gcgtgatcgg caccggatcc tcgggcatcc agtccattcc gctgatcgcc    600
gagcaggcca tcatctcta cgtgttccag cggtccgcga attacagtgt gccggcagga    660
aacacgcctc tcgatgacaa cgccgcgcc gagatcaagg ccggctacgc agagcgtcga    720
gcgctgtcca gcgcagtgg cggtggatcc cgttcgtttc ggatcctcg cagcgccctc      780
gaagtctcgg aggccgagag aaacgcggca tacgaggagc ggtggaagct cggcggtgtc    840
ctgttcgcca agacattcgc agaccagacg agcaacatcg aggccaacgg acagcggca     900
gcgtttgccg aacgcaagat tcgctcggaa gtccaggatc aggcgatcgc cgacctgctc    960
attccgaacg accaccccat cggaaccaag cggatagtca cggacacgaa ctactaccag   1020
agctacaacc gtgacaacgt cagcctggta gatctcaagt ccgcaccgat cgaggcgatc   1080
gacgaggctg gaatcaagac ggccgatgcg cactacgaac tggatgcgct ggtgtttgcc   1140
accgggttcg acgcgatgac gggagcgctc gatcgcatcg agatccgcgg ccgcaatggc   1200
gagacgttgc gcgagaactg gcatgcgggt ccaaggacgt atctaggcct cggagtacac   1260
gggttcccca acctgttcat cgtcaccggg ccgggtagcc cgagtgtgct gtccaacatg   1320
attctcgctg ccgagcagca cgtggactgg atcgcgggcg cgatcaacca cctcgattcg   1380
gcgggcatcg acaccatcga accgagtgcc gaagccgtgg acaactggct cgacgaatgc   1440
tcacgccggg cgtcggcgac gctgtttcca tccgcgaact cctggtacat gggagccaac   1500
attccgggaa agccgaggat attcatgcca ttcatcggag gattcggtgt ctactccgac   1560
atctgtgcag acgtggcagc agcgggatac cgaggcttcg aactgaacag tgcggtgcac   1620
gcatga                                                              1626
```

<210> SEQ ID NO 26
<211> LENGTH: 541
<212> TYPE: PRT
<213> ORGANISM: Rhodococcus erythropolis AN12

<400> SEQUENCE: 26

```
Met Thr Asp Pro Asp Phe Ser Thr Ala Pro Leu Asp Val Val Val Ile
 1               5                  10                  15

Gly Ala Gly Val Ala Gly Met Tyr Ala Met His Arg Leu Arg Glu Gln
            20                  25                  30

Gly Leu Arg Val His Gly Phe Glu Ala Gly Ser Gly Val Gly Gly Thr
        35                  40                  45
```

```
Trp Tyr Phe Asn Arg Tyr Pro Gly Ala Arg Cys Asp Val Glu Ser Phe
 50                  55                  60

Asp Tyr Ser Tyr Ser Phe Ser Glu Glu Leu Gln Gln Asp Trp Asp Trp
 65                  70                  75                  80

Ser Glu Lys Tyr Ala Ala Gln Pro Glu Ile Leu Ser Tyr Leu Asp His
                 85                  90                  95

Val Ala Asp Arg Phe Asp Leu Arg Thr Gly Phe Thr Phe Asp Thr Arg
                100                 105                 110

Val Leu Ser Ala Gln Phe Asp Glu Gly Thr Ala Thr Trp Arg Val Gln
            115                 120                 125

Thr Asp Gly Gly His Asp Val Thr Ser Arg Phe Val Val Cys Ala Thr
    130                 135                 140

Gly Ser Leu Ser Thr Ala Asn Val Pro Asn Ile Ala Gly Arg Glu Thr
145                 150                 155                 160

Phe Gly Gly Asp Val Phe His Thr Gly Phe Trp Pro His Glu Gly Val
                165                 170                 175

Asp Phe Thr Gly Lys Arg Val Gly Val Ile Gly Thr Gly Ser Ser Gly
                180                 185                 190

Ile Gln Ser Ile Pro Leu Ile Ala Glu Gln Ala Asp His Leu Tyr Val
            195                 200                 205

Phe Gln Arg Ser Ala Asn Tyr Ser Val Pro Ala Gly Asn Thr Pro Leu
    210                 215                 220

Asp Asp Lys Arg Arg Ala Glu Ile Lys Ala Gly Tyr Ala Glu Arg Arg
225                 230                 235                 240

Ala Leu Ser Lys Arg Ser Gly Gly Ser Pro Phe Val Ser Asp Pro
                245                 250                 255

Arg Ser Ala Leu Glu Val Ser Glu Ala Glu Arg Asn Ala Ala Tyr Glu
            260                 265                 270

Glu Arg Trp Lys Leu Gly Gly Val Leu Phe Ala Lys Thr Phe Ala Asp
    275                 280                 285

Gln Thr Ser Asn Ile Glu Ala Asn Gly Thr Ala Ala Ala Phe Ala Glu
290                 295                 300

Arg Lys Ile Arg Ser Glu Val Gln Asp Gln Ala Ile Ala Asp Leu Leu
305                 310                 315                 320

Ile Pro Asn Asp His Pro Ile Gly Thr Lys Arg Ile Val Thr Asp Thr
                325                 330                 335

Asn Tyr Tyr Gln Ser Tyr Asn Arg Asp Asn Val Ser Leu Val Asp Leu
                340                 345                 350

Lys Ser Ala Pro Ile Glu Ala Ile Asp Glu Ala Gly Ile Lys Thr Ala
            355                 360                 365

Asp Ala His Tyr Glu Leu Asp Ala Leu Val Phe Ala Thr Gly Phe Asp
    370                 375                 380

Ala Met Thr Gly Ala Leu Asp Arg Ile Glu Ile Arg Gly Arg Asn Gly
385                 390                 395                 400

Glu Thr Leu Arg Glu Asn Trp His Ala Gly Pro Arg Thr Tyr Leu Gly
                405                 410                 415

Leu Gly Val His Gly Phe Pro Asn Leu Phe Ile Val Thr Gly Pro Gly
                420                 425                 430

Ser Pro Ser Val Leu Ser Asn Met Ile Leu Ala Glu Gln His Val
            435                 440                 445

Asp Trp Ile Ala Gly Ala Ile Asn His Leu Asp Ser Ala Gly Ile Asp
    450                 455                 460

Thr Ile Glu Pro Ser Ala Glu Ala Val Asp Asn Trp Leu Asp Glu Cys
```

| | | | |
|---|---|---|---|
| 465 | 470 | 475 | 480 |

Ser Arg Arg Ala Ser Ala Thr Leu Phe Pro Ser Ala Asn Ser Trp Tyr
                   485                   490                 495

Met Gly Ala Asn Ile Pro Gly Lys Pro Arg Ile Phe Met Pro Phe Ile
        500                   505                 510

Gly Gly Phe Gly Val Tyr Ser Asp Ile Cys Ala Asp Val Ala Ala Ala
       515                   520                 525

Gly Tyr Arg Gly Phe Glu Leu Asn Ser Ala Val His Ala
   530                 535                 540

<210> SEQ ID NO 27
<211> LENGTH: 1389
<212> TYPE: DNA
<213> ORGANISM: Rhodococcus erythropolis AN12

<400> SEQUENCE: 27

```
atgagcccct cccccttgcc gagcgtctgc atcatcggcg ccgggcctac cggaatcacc      60
acggccaagc gaatgaagga attcggaata cccttcgact gctacgaagc gtccgacgag     120
gtcggcggaa actggtacta caagaacccc aacggaatgt cggcctgcta ccagagcctg     180
catatcgaca cgtcgaagtg gcgcttggca ttcgaggact cccggtctc tgccgacctt      240
cccgatttcc cccaccattc cgaactcttc cagtacttca aggactacgt cgagcatttc     300
ggcctgcgtg agtcgatcat cttcaacacc agtgttgttg ctgcagagcg tgatgcaaac    360
ggactgtgga ccgtcacgcg ctcggacggc gaagtccgta cctacgacgt cctgatggtc     420
tgcaatggtc accactggga tcccaatatc ccggattacc cgggcgagtt cgacggcgtc     480
ctcatgcaca gccacagcta caacgacccg ttcgatccga tcgacatgcg cggcaagaaa     540
gtagtcgtgg tcggaatggg gaactccggc ttggacattg cttccgaact ggggcagaga     600
tacctcgccg acaagctcat cgtctcggcc gccgcggcg tgtgggtgtt gccgaaatac      660
ctgggcggcg tgccgggaga caaactgatc accccgccct ggatgcctcg ggggctgcgc     720
ctgttcctga gtcgtcgatt cctcggcaag aacctgggaa ccatggaggg ctacggacta     780
cccaagccag atcaccgccc cttcgaggca catccgtcag ccagtggcga gttcttggga     840
cgtgccgggt ccggcgacat caccttcaag ccggcgatca ccaaactcga cggaaagcag     900
gttcatttcg ccgacggcac cgccgaggac gtcgacgtgg tcgtctgcgc caccggctac     960
aacatcagct tccccttctt cgacgacccg aacctgctgc cggacaaaga caaccgattc    1020
ccactcttca aacgcatgat gaagcccgga atcgacaacc tcttcttcat gggactcgct    1080
cagcccatgc cgacgctcgt aaacttcgcc gagcagcaga gcaagctcgt cgcggcctac    1140
ctcaccggta ataccagct gccgtccgcg aacgagatgc aggagatcac caaggccgac    1200
gaggcgtact cctcgcccc ctattacaag tcaccgcgcc acaccattca gctcgagttc     1260
gacccgtacg tccgcaacat gaacaaggaa attgccaagg gcaccaagcg tgccgcggcc    1320
tcggggaaca aactacctgt tgcggcgcgt gcagcagcac acgaactcga gaaggcggat    1380
cgcgcatga                                                            1389
```

<210> SEQ ID NO 28
<211> LENGTH: 462
<212> TYPE: PRT
<213> ORGANISM: Rhodococcus erythropolis AN12

<400> SEQUENCE: 28

Met Ser Pro Ser Pro Leu Pro Ser Val Cys Ile Ile Gly Ala Gly Pro

-continued

```
1               5                   10                  15

Thr Gly Ile Thr Thr Ala Lys Arg Met Lys Glu Phe Gly Ile Pro Phe
                20                  25                  30

Asp Cys Tyr Glu Ala Ser Asp Glu Val Gly Gly Asn Trp Tyr Tyr Lys
                35                  40                  45

Asn Pro Asn Gly Met Ser Ala Cys Tyr Gln Ser Leu His Ile Asp Thr
            50                  55                  60

Ser Lys Trp Arg Leu Ala Phe Glu Asp Phe Pro Val Ser Ala Asp Leu
65                      70                  75                  80

Pro Asp Phe Pro His His Ser Glu Leu Phe Gln Tyr Phe Lys Asp Tyr
                    85                  90                  95

Val Glu His Phe Gly Leu Arg Glu Ser Ile Ile Phe Asn Thr Ser Val
                100                 105                 110

Val Ala Ala Glu Arg Asp Ala Asn Gly Leu Trp Thr Val Thr Arg Ser
                115                 120                 125

Asp Gly Glu Val Arg Thr Tyr Asp Val Leu Met Val Cys Asn Gly His
                130                 135                 140

His Trp Asp Pro Asn Ile Pro Asp Tyr Pro Gly Glu Phe Asp Gly Val
145                     150                 155                 160

Leu Met His Ser His Ser Tyr Asn Asp Pro Phe Asp Pro Ile Asp Met
                    165                 170                 175

Arg Gly Lys Lys Val Val Val Gly Met Gly Asn Ser Gly Leu Asp
                180                 185                 190

Ile Ala Ser Glu Leu Gly Gln Arg Tyr Leu Ala Asp Lys Leu Ile Val
                195                 200                 205

Ser Ala Arg Arg Gly Val Trp Val Leu Pro Lys Tyr Leu Gly Gly Val
                210                 215                 220

Pro Gly Asp Lys Leu Ile Thr Pro Pro Trp Met Pro Arg Gly Leu Arg
225                     230                 235                 240

Leu Phe Leu Ser Arg Arg Phe Leu Gly Lys Asn Leu Gly Thr Met Glu
                    245                 250                 255

Gly Tyr Gly Leu Pro Lys Pro Asp His Arg Pro Phe Glu Ala His Pro
                260                 265                 270

Ser Ala Ser Gly Glu Phe Leu Gly Arg Ala Gly Ser Gly Asp Ile Thr
                275                 280                 285

Phe Lys Pro Ala Ile Thr Lys Leu Asp Gly Lys Gln Val His Phe Ala
                290                 295                 300

Asp Gly Thr Ala Glu Asp Val Asp Val Val Cys Ala Thr Gly Tyr
305                     310                 315                 320

Asn Ile Ser Phe Pro Phe Asp Asp Pro Asn Leu Leu Pro Asp Lys
                    325                 330                 335

Asp Asn Arg Phe Pro Leu Phe Lys Arg Met Met Lys Pro Gly Ile Asp
                340                 345                 350

Asn Leu Phe Phe Met Gly Leu Ala Gln Pro Met Pro Thr Leu Val Asn
                    355                 360                 365

Phe Ala Glu Gln Gln Ser Lys Leu Val Ala Ala Tyr Leu Thr Gly Lys
                370                 375                 380

Tyr Gln Leu Pro Ser Ala Asn Glu Met Gln Glu Ile Thr Lys Ala Asp
385                     390                 395                 400

Glu Ala Tyr Phe Leu Ala Pro Tyr Tyr Lys Ser Pro Arg His Thr Ile
                    405                 410                 415

Gln Leu Glu Phe Asp Pro Tyr Val Arg Asn Met Asn Lys Glu Ile Ala
                420                 425                 430
```

Lys Gly Thr Lys Arg Ala Ala Ala Ser Gly Asn Lys Leu Pro Val Ala
    435                 440                 445

Ala Arg Ala Ala Ala His Glu Leu Glu Lys Ala Asp Arg Ala
    450                 455                 460

<210> SEQ ID NO 29
<211> LENGTH: 1572
<212> TYPE: DNA
<213> ORGANISM: Rhodococcus erythropolis AN12

<400> SEQUENCE: 29

| | |
|---|---:|
| gtgaacaacg aatctgacca cttcgaggtc gtgatcatcg gcggtggaat ttccggaatc | 60 |
| ggcgcggcta tccacctgca gcgtctcgga atcgacaact tcgcactcct cgagaaggcc | 120 |
| gactccctcg gtggaacctg cgcgccaac acctatcccg ggtgcgcctg cgacgttcca | 180 |
| tccggtctgt actcgtactc ctttgccgcc aatccggatt ggacgcgctt gttcgcggag | 240 |
| caaccggaga tccgcgaata catcgagaac acggcgggca cgcacggagt cgacaaacac | 300 |
| gttcgcttcg gggtcgaaat gctctccgcg cgatgggatg cgtcgcaatc actgtggaag | 360 |
| ataacaactt ccagcggcga actgactgct cgcttcgtga tagccgctgc cggcccatgg | 420 |
| aacgaacccc tgacaccggc gatccccgga ctggaagcgt cgagggaga ggtgttcat | 480 |
| tcctcgcagt ggaatcacga ctacgacctg accggaaaac tcgtcgccgt cgtaggaacc | 540 |
| ggagcgtcgg cagtccagtt cgttccgcgc atcgtctccc aggtctcgc ccttcacctc | 600 |
| taccagcgaa ccgctcaatg ggttctcccc aaacccgatc actacgtacc gcggatcgaa | 660 |
| aggtccgtca tgcgattcgt gccgggagca cagaaagcct tgcgcagcat cgaatacgga | 720 |
| atcatggaag cgctcggatt gggattccgt aatccatgga tcctgcgaat cgtgcagaaa | 780 |
| ctcgggtcag cccaattgcg cctacaggta cgcgatccga agctgcgcaa ggcattgact | 840 |
| cccgactaca ccctcggttg caagcgactg ctcatgtcga actcgtacta tccgccctc | 900 |
| ggcaaaccca acgtcagcgt ccatgccaac gccgtcgagc agatccgcgg taacaccgtg | 960 |
| atcgcgccg acgagtgga ggcggaggtg gacgccatca tcttcggaac gggcttccac | 1020 |
| atcctcgaca tgcccatcgc atccaaggta ttcgacggag aaggtcgatc actcgacgat | 1080 |
| cattggcagg gaagcccgca ggcgtacttc ggctccgccg tcagtggatt ccccaacgca | 1140 |
| ttcatcctgc tgggcccgag cctcggcacc gggcacacat cggcgttcat gatcttggaa | 1200 |
| gcccaactga actatgtggc gcaggcaatc ggccacgccc gtcgtcacgg ctggcagacc | 1260 |
| atcgacgtgc gagaggaagt tcaggcagcc ttcaattctc aggttcagga ggcattgggg | 1320 |
| accacggtct acaacgccgg tggttgcgaa agctatttct tcgacgtcaa cggccgcaac | 1380 |
| agtttcaact ggccgtggtc gtccggcgcc atgcgtcgac ggctacggga cttcgatccg | 1440 |
| tatgcctaca accacgtc gaaccctgag tcagacaaca cgccccctga acccacgcca | 1500 |
| tccgaaccca cgccatctga acccacgcca tccgagccca ccaccagtcc ggaaccggag | 1560 |
| tacaccgcat ga | 1572 |

<210> SEQ ID NO 30
<211> LENGTH: 523
<212> TYPE: PRT
<213> ORGANISM: Rhodococcus erythropolis AN12

<400> SEQUENCE: 30

Val Asn Asn Glu Ser Asp His Phe Glu Val Val Ile Ile Gly Gly Gly
1               5                   10                  15

```
Ile Ser Gly Ile Gly Ala Ala Ile His Leu Gln Arg Leu Gly Ile Asp
             20                  25                  30

Asn Phe Ala Leu Leu Glu Lys Ala Asp Ser Leu Gly Gly Thr Trp Arg
             35                  40              45

Ala Asn Thr Tyr Pro Gly Cys Ala Cys Asp Val Pro Ser Gly Leu Tyr
             50                  55                  60

Ser Tyr Ser Phe Ala Ala Asn Pro Asp Trp Thr Arg Leu Phe Ala Glu
 65                  70                  75                  80

Gln Pro Glu Ile Arg Glu Tyr Ile Glu Asn Thr Ala Gly Thr His Gly
                 85                  90                  95

Val Asp Lys His Val Arg Phe Gly Val Glu Met Leu Ser Ala Arg Trp
            100                 105                 110

Asp Ala Ser Gln Ser Leu Trp Lys Ile Thr Thr Ser Ser Gly Glu Leu
            115                 120                 125

Thr Ala Arg Phe Val Ile Ala Ala Gly Pro Trp Asn Glu Pro Leu
            130                 135             140

Thr Pro Ala Ile Pro Gly Leu Glu Ala Phe Glu Gly Glu Val Phe His
145                 150                 155                 160

Ser Ser Gln Trp Asn His Asp Tyr Asp Leu Thr Gly Lys Leu Val Ala
                165                 170                 175

Val Val Gly Thr Gly Ala Ser Ala Val Gln Phe Val Pro Arg Ile Val
            180                 185                 190

Ser Gln Val Ser Ala Leu His Leu Tyr Gln Arg Thr Ala Gln Trp Val
            195                 200                 205

Leu Pro Lys Pro Asp His Tyr Val Pro Arg Ile Glu Arg Ser Val Met
210                 215                 220

Arg Phe Val Pro Gly Ala Gln Lys Ala Leu Arg Ser Ile Glu Tyr Gly
225                 230                 235                 240

Ile Met Glu Ala Leu Gly Leu Gly Phe Arg Asn Pro Trp Ile Leu Arg
                245                 250                 255

Ile Val Gln Lys Leu Gly Ser Ala Gln Leu Arg Leu Gln Val Arg Asp
                260                 265                 270

Pro Lys Leu Arg Lys Ala Leu Thr Pro Asp Tyr Thr Leu Gly Cys Lys
            275                 280                 285

Arg Leu Leu Met Ser Asn Ser Tyr Tyr Pro Ala Leu Gly Lys Pro Asn
            290                 295                 300

Val Ser Val His Ala Asn Ala Val Glu Gln Ile Arg Gly Asn Thr Val
305                 310                 315                 320

Ile Gly Ala Asp Gly Val Glu Ala Glu Val Asp Ala Ile Ile Phe Gly
                325                 330                 335

Thr Gly Phe His Ile Leu Asp Met Pro Ile Ala Ser Lys Val Phe Asp
                340                 345                 350

Gly Glu Gly Arg Ser Leu Asp Asp His Trp Gln Gly Ser Pro Gln Ala
            355                 360                 365

Tyr Phe Gly Ser Ala Val Ser Gly Phe Pro Asn Ala Phe Ile Leu Leu
            370                 375                 380

Gly Pro Ser Leu Gly Thr Gly His Thr Ser Ala Phe Met Ile Leu Glu
385                 390                 395                 400

Ala Gln Leu Asn Tyr Val Ala Gln Ala Ile His Ala Arg Arg His
                405                 410                 415

Gly Trp Gln Thr Ile Asp Val Arg Glu Glu Val Gln Ala Ala Phe Asn
            420                 425                 430
```

-continued

Ser Gln Val Gln Glu Ala Leu Gly Thr Thr Val Tyr Asn Ala Gly Gly
        435                 440                 445

Cys Glu Ser Tyr Phe Phe Asp Val Asn Gly Arg Asn Ser Phe Asn Trp
    450                 455                 460

Pro Trp Ser Ser Gly Ala Met Arg Arg Arg Leu Arg Asp Phe Asp Pro
465                 470                 475                 480

Tyr Ala Tyr Asn His Thr Ser Asn Pro Glu Ser Asp Asn Thr Pro Pro
                485                 490                 495

Glu Pro Thr Pro Ser Glu Pro Thr Pro Ser Glu Pro Thr Pro Ser Glu
            500                 505                 510

Pro Thr Thr Ser Pro Glu Pro Glu Tyr Thr Ala
            515                 520

<210> SEQ ID NO 31
<211> LENGTH: 1482
<212> TYPE: DNA
<213> ORGANISM: Rhodococcus erythropolis AN12

<400> SEQUENCE: 31
atgagcaccg aacacctcga tgtcctgatc gtcggcgccg gcttgtccgg catcggtgct    60
gcttatcgac tccagaccga gctcccagga aagtcgtacg caatcctcga ggcccgagcg   120
aacagcggcg gaacctggga cctcttcaag tatcccggca tccgatcgga ttccgacatg   180
ttcacgctcg gctacccgtt tcgcccgtgg acagatgcca agcaatcgc cgacggtgat   240
tcgatcctgc ggtacgtgcg cgacaccgcg cgagagaacg ggatcgacaa gaagattcgg   300
tacaaccgga aggtgacggc cgcatcatgg tcgtcagcga cctcgacctg acagtcacg    360
gtcacgaccg cgacgaaga cgaaacattg acctgtaact tcctctatct ctgcagcggg    420
tactacagct acgacggcgg atacacccccc gacttccccg acgtgaatc gtttgccggt    480
gaggtagtgc acccccagtt ctggcccgaa gaactcgatt actccgacaa gaaggtcgtt   540
gtgatcggaa gcggcgccac cgcagtcact ttggtcccca cgatgtcacg ggacgcaagc   600
cacgtcacga tgctccagcg atcaccgacg tacattctgg cgcttccgtc cagcgacaaa   660
ttatcggaca ccattcgcgc ggtactgccg aatcaactcg cgcacagcat cgctcgatgg   720
aagagcgtcg tagtgaacct gagtttctac caactgtgcc gacgcagtcc ggcgcgtgca   780
aagaggatgc tgaacctcgc gatcagtcgt caactcccga agacatccc cctcgatcct   840
cacttcacac cctcctacga tccctgggac cagcgcttgt gcgtcgtacc cgacggcgat   900
ttgttcaaag ccctccgatc cggcaaggcc tcgatcgaga ccgatcacat cgacaccttc   960
accgagaccg ggatccttct cgcgtcaggt cgcgaactcg aagctgacat catcgtcact  1020
gcaacaggat tgaagatgga ggcgtgcggc gggatgtcca tcgaagtgga cggcgaactc  1080
gtcaccctcg gtgatcgtta cgcctacaag ggcatgatga tcagcgacgt accgaacttc  1140
gcgatgtgcg tcggctacac caacgcctcg tggactctgc gagcagatct cacgtcgatg  1200
tacgtgtgcc gactgctgac ggagatggac aagcgcgact attcgaagtg cgtgccgcac  1260
gcgaccgaag aaatggacca gcggccgatc ctggatctgg cgtcggggta cgtcatgcgt  1320
gccgtggaac agttcccgaa gcagggatcg aagtcaccgt ggaacatgcg tcagaactac  1380
atccttgacc gtcttcactc cacgttcggg agcatcaacg accacatgac gttctcgaag  1440
gcaccagctc gacattcgac gccggtaccg agcaagagtt ga                     1482

<210> SEQ ID NO 32
<211> LENGTH: 493

```
<212> TYPE: PRT
<213> ORGANISM: Rhodococcus erythropolis AN12

<400> SEQUENCE: 32

Met Ser Thr Glu His Leu Asp Val Leu Ile Val Gly Ala Gly Leu Ser
1               5                   10                  15

Gly Ile Gly Ala Ala Tyr Arg Leu Gln Thr Glu Leu Pro Lys Ser
            20                  25                  30

Tyr Ala Ile Leu Glu Ala Arg Ala Asn Ser Gly Gly Thr Trp Asp Leu
                35                  40                  45

Phe Lys Tyr Pro Gly Ile Arg Ser Asp Ser Asp Met Phe Thr Leu Gly
    50                  55                  60

Tyr Pro Phe Arg Pro Trp Thr Asp Ala Lys Ala Ile Ala Asp Gly Asp
65                  70                  75                  80

Ser Ile Leu Arg Tyr Val Arg Asp Thr Ala Arg Glu Asn Gly Ile Asp
                85                  90                  95

Lys Lys Ile Arg Tyr Asn Arg Lys Val Thr Ala Ala Ser Trp Ser Ser
                100                 105                 110

Ala Thr Ser Thr Trp Thr Val Thr Val Thr Thr Gly Asp Glu Asp Glu
            115                 120                 125

Thr Leu Thr Cys Asn Phe Leu Tyr Leu Cys Ser Gly Tyr Tyr Ser Tyr
    130                 135                 140

Asp Gly Gly Tyr Thr Pro Asp Phe Pro Gly Arg Glu Ser Phe Ala Gly
145                 150                 155                 160

Glu Val Val His Pro Gln Phe Trp Pro Glu Glu Leu Asp Tyr Ser Asp
                165                 170                 175

Lys Lys Val Val Val Ile Gly Ser Gly Ala Thr Ala Val Thr Leu Val
                180                 185                 190

Pro Thr Met Ser Arg Asp Ala Ser His Val Thr Met Leu Gln Arg Ser
            195                 200                 205

Pro Thr Tyr Ile Leu Ala Leu Pro Ser Ser Asp Lys Leu Ser Asp Thr
    210                 215                 220

Ile Arg Ala Val Leu Pro Asn Gln Leu Ala His Ser Ile Ala Arg Trp
225                 230                 235                 240

Lys Ser Val Val Asn Leu Ser Phe Tyr Gln Leu Cys Arg Arg Ser
            245                 250                 255

Pro Ala Arg Ala Lys Arg Met Leu Asn Leu Ala Ile Ser Arg Gln Leu
            260                 265                 270

Pro Lys Asp Ile Pro Leu Asp Pro His Phe Thr Pro Ser Tyr Asp Pro
    275                 280                 285

Trp Asp Gln Arg Leu Cys Val Val Pro Asp Gly Asp Leu Phe Lys Ala
290                 295                 300

Leu Arg Ser Gly Lys Ala Ser Ile Glu Thr Asp His Ile Asp Thr Phe
305                 310                 315                 320

Thr Glu Thr Gly Ile Leu Leu Ala Ser Gly Arg Glu Leu Glu Ala Asp
            325                 330                 335

Ile Ile Val Thr Ala Thr Gly Leu Lys Met Glu Ala Cys Gly Gly Met
                340                 345                 350

Ser Ile Glu Val Asp Gly Glu Leu Val Thr Leu Gly Asp Arg Tyr Ala
            355                 360                 365

Tyr Lys Gly Met Met Ile Ser Asp Val Pro Asn Phe Ala Met Cys Val
    370                 375                 380

Gly Tyr Thr Asn Ala Ser Trp Thr Leu Arg Ala Asp Leu Thr Ser Met
385                 390                 395                 400
```

Tyr Val Cys Arg Leu Leu Thr Glu Met Asp Lys Arg Asp Tyr Ser Lys
            405                 410                 415

Cys Val Pro His Ala Thr Glu Glu Met Asp Gln Arg Pro Ile Leu Asp
            420                 425                 430

Leu Ala Ser Gly Tyr Val Met Arg Ala Val Glu Gln Phe Pro Lys Gln
            435                 440                 445

Gly Ser Lys Ser Pro Trp Asn Met Arg Gln Asn Tyr Ile Leu Asp Arg
        450                 455                 460

Leu His Ser Thr Phe Gly Ser Ile Asn Asp His Met Thr Phe Ser Lys
465                 470                 475                 480

Ala Pro Ala Arg His Ser Thr Pro Val Pro Ser Lys Ser
                485                 490

<210> SEQ ID NO 33
<211> LENGTH: 1620
<212> TYPE: DNA
<213> ORGANISM: Rhodococcus erythropolis AN12

<400> SEQUENCE: 33

| | | | | | |
|---|---|---|---|---|---|
| atgacagacg | aattcgacgt | agtgatcgtg | ggtgcaggtc | tcgcaggtat | gcagatgctg | 60 |
| cacgaggttc | gcatggtcgg | cctcacggcc | aaagttttcg | aggccggcgg | aggtgcaggt | 120 |
| ggcacctggt | attggaaccg | ctacccgggt | gctcggtgtg | acgtggagag | tttggagtac | 180 |
| tcctatcagt | tctccgaggt | gctccaacag | gaatgggaat | ggaccgcccg | gtacgcagat | 240 |
| caggccgaga | tcatgcgcta | catcagccac | gtcgtcgaaa | ccttcgacct | ggcccgcgac | 300 |
| atcaggtttc | ataccgggt | cgaggcgatg | acctacgagg | agaccaccgc | caggtggacg | 360 |
| gttcagacgg | acagtgccgg | cgaggttgtg | gccaaattcg | tgattatggc | caccgggtgt | 420 |
| ctgtcggagc | cgaacgtgcc | gtacataccg | ggtgtggaga | cattcgcggg | cgacgtgctg | 480 |
| cacaccgggc | gctggccgca | ggatcccgtc | gacttcacag | gcaagcgggt | cggcgtgatc | 540 |
| ggaaccggat | catctggcgt | gcaagccatc | ccactcatcg | cgcggcaagc | ggccgagctc | 600 |
| gtagtctttc | agcgcactcc | tgcatacacg | ttgcccgctg | tcgacgagcc | gctcgacccg | 660 |
| gaattgcagg | cggcgatcaa | ggccgattac | aggggggttcc | gtgcgcgaaa | caacgaagtg | 720 |
| cccaccgcgg | gactctcccg | atttccgacg | aatccgaact | cggttttcct | gttctcaacg | 780 |
| aaggagcggg | atgccatcct | gaacacaat | tggaaccgag | gcgggccgtt | gatgctgcgc | 840 |
| gccttcggcg | atctgctggt | ggactcagcc | gctaacgagg | tggtagccga | gttcgtccgc | 900 |
| aacaagatcc | gccagatcgt | taccgacccc | gaggtcgctg | cgaagctcac | accgacacac | 960 |
| gtgatcggat | gcaaacgaat | ctgtctcagc | gacggctatt | acgagaccta | caaccgggtc | 1020 |
| aacgtgcgct | tagtcgacat | caaacgccac | ccaatcgagg | agatcacgcc | tactacagcc | 1080 |
| cggaccggcg | aggactcgca | tgacctggac | atgctcgtgt | cgccactgg | ctacgatgcc | 1140 |
| atcactggcg | cactctcacg | catcgacatc | cgcggccgcg | cagggttgtc | attgcaggaa | 1200 |
| gcatggtcgg | acggaccgcg | cacctatctc | gggctcgggg | tctccggctt | cccaaatctg | 1260 |
| ttcatcatga | ccggccccgg | aagcccatcg | gtattgacca | atgttcttgt | cgccatacac | 1320 |
| caacatgcga | catggatcgg | cgaatgcctg | aagcatatga | ccgacaacga | tattcggaca | 1380 |
| atggaagcca | cgcccgaagc | cgagcagaac | tgggggggacc | acgtgcgcga | cctcgccgag | 1440 |
| cagaccctgc | tctcatcgtg | cgggtcctgg | tacctcggag | caaacatccc | cggtaagaga | 1500 |
| caagtattca | tgccgctggt | cgggtttccg | gactacgcca | agaaatgcgc | ggaaatcgca | 1560 | tccgccggct acccgggctt cgccttccag tacgaccccg tccctgtgaa ccagagctga    1620

<210> SEQ ID NO 34
<211> LENGTH: 539
<212> TYPE: PRT
<213> ORGANISM: Rhodococcus erythropolis AN12

<400> SEQUENCE: 34

```
Met Thr Asp Glu Phe Asp Val Val Ile Val Gly Ala Gly Leu Ala Gly
  1               5                  10                  15
Met Gln Met Leu His Glu Val Arg Met Val Gly Leu Thr Ala Lys Val
             20                  25                  30
Phe Glu Ala Gly Gly Ala Gly Gly Thr Trp Tyr Trp Asn Arg Tyr
         35                  40                  45
Pro Gly Ala Arg Cys Asp Val Glu Ser Leu Tyr Ser Tyr Gln Phe
     50                  55                  60
Ser Glu Val Leu Gln Gln Glu Trp Glu Trp Thr Arg Arg Tyr Ala Asp
 65                  70                  75                  80
Gln Ala Glu Ile Met Arg Tyr Ile Ser His Val Val Glu Thr Phe Asp
                 85                  90                  95
Leu Ala Arg Asp Ile Arg Phe His Thr Arg Val Glu Ala Met Thr Tyr
            100                 105                 110
Glu Glu Thr Thr Ala Arg Trp Thr Val Gln Thr Asp Ser Ala Gly Glu
        115                 120                 125
Val Val Ala Lys Phe Val Ile Met Ala Thr Gly Cys Leu Ser Glu Pro
130                 135                 140
Asn Val Pro Tyr Ile Pro Gly Val Glu Thr Phe Ala Gly Asp Val Leu
145                 150                 155                 160
His Thr Gly Arg Trp Pro Gln Asp Pro Val Asp Phe Thr Gly Lys Arg
                165                 170                 175
Val Gly Val Ile Gly Thr Gly Ser Ser Gly Val Gln Ala Ile Pro Leu
            180                 185                 190
Ile Ala Arg Gln Ala Ala Glu Leu Val Val Phe Gln Arg Thr Pro Ala
        195                 200                 205
Tyr Thr Leu Pro Ala Val Asp Glu Pro Leu Asp Pro Glu Leu Gln Ala
    210                 215                 220
Ala Ile Lys Ala Asp Tyr Arg Gly Phe Arg Ala Arg Asn Asn Glu Val
225                 230                 235                 240
Pro Thr Ala Gly Leu Ser Arg Phe Pro Thr Asn Pro Asn Ser Val Phe
                245                 250                 255
Leu Phe Ser Thr Lys Glu Arg Asp Ala Ile Leu Glu His Asn Trp Asn
            260                 265                 270
Arg Gly Gly Pro Leu Met Leu Arg Ala Phe Gly Asp Leu Leu Val Asp
        275                 280                 285
Ser Ala Ala Asn Glu Val Val Ala Glu Phe Val Arg Asn Lys Ile Arg
    290                 295                 300
Gln Ile Val Thr Asp Pro Glu Val Ala Ala Lys Leu Thr Pro Thr His
305                 310                 315                 320
Val Ile Gly Cys Lys Arg Ile Cys Leu Ser Asp Gly Tyr Tyr Glu Thr
                325                 330                 335
Tyr Asn Arg Val Asn Val Arg Leu Val Asp Ile Lys Arg His Pro Ile
            340                 345                 350
Glu Glu Ile Thr Pro Thr Thr Ala Arg Thr Gly Glu Asp Ser His Asp
        355                 360                 365
Leu Asp Met Leu Val Phe Ala Thr Gly Tyr Asp Ala Ile Thr Gly Ala
```

```
                    370                 375                 380
Leu Ser Arg Ile Asp Ile Arg Gly Arg Ala Gly Leu Ser Leu Gln Glu
385                 390                 395                 400

Ala Trp Ser Asp Gly Pro Arg Thr Tyr Leu Gly Leu Gly Val Ser Gly
                405                 410                 415

Phe Pro Asn Leu Phe Ile Met Thr Gly Pro Gly Ser Pro Ser Val Leu
                420                 425                 430

Thr Asn Val Leu Val Ala Ile His Gln His Ala Thr Trp Ile Gly Glu
                435                 440                 445

Cys Leu Lys His Met Thr Asp Asn Asp Ile Arg Thr Met Glu Ala Thr
450                 455                 460

Pro Glu Ala Glu Gln Asn Trp Gly Asp His Val Arg Asp Leu Ala Glu
465                 470                 475                 480

Gln Thr Leu Leu Ser Ser Cys Gly Ser Trp Tyr Leu Gly Ala Asn Ile
                485                 490                 495

Pro Gly Lys Arg Gln Val Phe Met Pro Leu Val Gly Phe Pro Asp Tyr
                500                 505                 510

Ala Lys Lys Cys Ala Glu Ile Ala Ser Ala Gly Tyr Pro Gly Phe Ala
                515                 520                 525

Phe Gln Tyr Asp Pro Val Pro Val Asn Gln Ser
530                 535

<210> SEQ ID NO 35
<211> LENGTH: 1950
<212> TYPE: DNA
<213> ORGANISM: Rhodococcus erythropolis AN12

<400> SEQUENCE: 35
atgactatcg tcactgacct ggaccgtgac cacctgcgtt cggcggtgtt acggggcaat      60
gttccgacca tgctcgccgt gttgctggag ctgaccgccg atgagcggtg ggtggcaccc     120
cgctatcaac ccacgcgcag tcggggcatg gatgacaatt ccacgggagg acttccggag     180
gaggttcagt ccgaaatccg gagcgcgttg atcgacgcag tggaacgctg gtggacgctg     240
gacgagccgt cccggcggac gctggacagc tcggaagtag agcgaatcct caacttcacc     300
tgcagcgaga ccgtaccgcc ggacttcgcg ccgatgatgg cggagatagt caatggtccg     360
cagatcaagc ctgccaccgc caagtgcgac gagcgactcc acgccatcgt gatcggcgcc     420
ggcatcgcgg ggatgctggc ctccgtcgag ctcagccgcg ctgggatccc tcacgtgatc     480
ctggagaaga cgacgacgt cggcggatca tggtgggaga accgctatcc gggcgccgga     540
gttgatacac cgagccacct ttactcgatc tcgtcgttcc ctcgtaactg gtcgacccac     600
ttcggcaagc gcgacgaggt tcagggatat ctcgaggact ttgcggaggc caacgacatc     660
cggcgcaatg tccgcttccg tcatgaggtg acgcgcgccg agttcgagga gtcgaaacag     720
agttggcgtg tgtccgtcca gcgaccaggt gaggcgtcgg agaccctcga ggctcccatc     780
ctgatcagcg cggtcggtct gctcaatcgt ccgaagatcc gcatctaccg ggaatcgag      840 accttccgtg gtcgcctctt ccactccgcc gagtggccga gcgagctcga cgatcccgag     900
tcgctccgcg gaaagcgagt gggcatcgtc ggtaccggag ccagtgctat gcagatcggc     960
ccggccatcg cggatcgtgt cggatcgctg acgatcttcc agcgctcacc acagtggatc    1020
gcaccgaacg acgactactt cacgaccatc gacgacggcg tccactggct gatggacaac    1080
atccccggct atcgcgagtg gtaccggggcg cgtctgtcgt ggatcttcaa cgacaaggtg    1140
tactcgtccc tccaggtcga ccccgactgg ccagagccga gcgcctcgat caatgcgacc    1200
```

-continued

```
aaccatggtc atcgcaagtt ctacgaacgc tatctccgcg atcagctggg tgatcgaaca   1260
gatctgatcg aggcatctct tccggactat ccgccctttg gtaagcgaat gctgctggac   1320
aatggctggt tcacgatgct tcgtaagccc gacgtcacac tggtgcccca cggagtcgac   1380
gccctgacac cttctggact cgtcgacacg aacggcgtcg agcaccagct ggacgtcatt   1440
gtcatggcga cggtttcca cagtgtgcgc gttctttacc cgatggacat cgtcggtcga   1500
tccggccggt ccaccggaga atctggggc gagcacgacg cgcgcgccta cctggggatc   1560
acagttcctg acttccccaa tttcttcgtc atgaccggac cgaacaccgg cctgggacat   1620 gggggagct tcatcacgat cctggaatgt caggtccgct acatcatgga tgccttgaag   1680
ttgatgcaat cggaaaaacct cggcgcgatg gagtgccggg ccgaggtcaa cgatcgatac   1740
aacgaggccg tcgaccgaca gcacgcacag atggtctgga cccatccggc aatggagaac   1800
tggtaccgaa accccggacgg tcgcgtcgtg tcggtccttc cgtggcggat caacgactac   1860
tgggccatga cctaccgagt cgacccgtca gatttttcgta ccgagccggc acgctccgag   1920
tcggtcccga ctccgaccgc gcgagggtga                                    1950
```

<210> SEQ ID NO 36
<211> LENGTH: 649
<212> TYPE: PRT
<213> ORGANISM: Rhodococcus erythropolis AN12

<400> SEQUENCE: 36

```
Met Thr Ile Val Thr Asp Leu Asp Arg Asp His Leu Arg Ser Ala Val
1               5                   10                  15

Leu Arg Gly Asn Val Pro Thr Met Leu Ala Val Leu Leu Glu Leu Thr
                20                  25                  30

Ala Asp Glu Arg Trp Val Ala Pro Arg Tyr Gln Pro Thr Arg Ser Arg
            35                  40                  45

Gly Met Asp Asp Asn Ser Thr Gly Gly Leu Pro Glu Val Gln Ser
        50                  55                  60

Glu Ile Arg Ser Ala Leu Ile Asp Ala Val Glu Arg Trp Trp Thr Leu
65                  70                  75                  80

Asp Glu Pro Ser Arg Arg Thr Leu Asp Ser Ser Glu Val Glu Arg Ile
                85                  90                  95

Leu Asn Phe Thr Cys Ser Glu Thr Val Pro Pro Asp Phe Ala Pro Met
                100                 105                 110

Met Ala Glu Ile Val Asn Gly Pro Gln Ile Lys Pro Ala Thr Ala Lys
            115                 120                 125

Cys Asp Glu Arg Leu His Ala Ile Val Ile Gly Ala Gly Ile Ala Gly
        130                 135                 140

Met Leu Ala Ser Val Glu Leu Ser Arg Ala Gly Ile Pro His Val Ile
145                 150                 155                 160

Leu Glu Lys Asn Asp Asp Val Gly Gly Ser Trp Trp Glu Asn Arg Tyr
                165                 170                 175

Pro Gly Ala Gly Val Asp Thr Pro Ser His Leu Tyr Ser Ile Ser Ser
            180                 185                 190

Phe Pro Arg Asn Trp Ser Thr His Phe Gly Lys Arg Asp Glu Val Gln
        195                 200                 205

Gly Tyr Leu Glu Asp Phe Ala Glu Ala Asn Asp Ile Arg Arg Asn Val
    210                 215                 220

Arg Phe Arg His Glu Val Thr Ala Glu Phe Glu Glu Ser Lys Gln
225                 230                 235                 240
```

```
Ser Trp Arg Val Ser Val Gln Arg Pro Gly Glu Ala Ser Glu Thr Leu
                245                 250                 255
Glu Ala Pro Ile Leu Ile Ser Ala Val Gly Leu Leu Asn Arg Pro Lys
            260                 265                 270
Ile Pro His Leu Pro Gly Ile Glu Thr Phe Arg Gly Arg Leu Phe His
        275                 280                 285
Ser Ala Glu Trp Pro Ser Glu Leu Asp Asp Pro Glu Ser Leu Arg Gly
    290                 295                 300
Lys Arg Val Gly Ile Val Gly Thr Gly Ala Ser Ala Met Gln Ile Gly
305                 310                 315                 320
Pro Ala Ile Ala Asp Arg Val Gly Ser Leu Thr Ile Phe Gln Arg Ser
                325                 330                 335
Pro Gln Trp Ile Ala Pro Asn Asp Asp Tyr Phe Thr Thr Ile Asp Asp
            340                 345                 350
Gly Val His Trp Leu Met Asp Asn Ile Pro Gly Tyr Arg Glu Trp Tyr
        355                 360                 365
Arg Ala Arg Leu Ser Trp Ile Phe Asn Asp Lys Val Tyr Ser Ser Leu
    370                 375                 380
Gln Val Asp Pro Asp Trp Pro Glu Pro Ser Ala Ser Ile Asn Ala Thr
385                 390                 395                 400
Asn His Gly His Arg Lys Phe Tyr Glu Arg Tyr Leu Arg Asp Gln Leu
                405                 410                 415
Gly Asp Arg Thr Asp Leu Ile Glu Ala Ser Leu Pro Asp Tyr Pro Pro
            420                 425                 430
Phe Gly Lys Arg Met Leu Leu Asp Asn Gly Trp Phe Thr Met Leu Arg
        435                 440                 445
Lys Pro Asp Val Thr Leu Val Pro His Gly Val Asp Ala Leu Thr Pro
    450                 455                 460
Ser Gly Leu Val Asp Thr Asn Gly Val Glu His Gln Leu Asp Val Ile
465                 470                 475                 480
Val Met Ala Thr Gly Phe His Ser Val Arg Val Leu Tyr Pro Met Asp
                485                 490                 495
Ile Val Gly Arg Ser Gly Arg Ser Thr Gly Glu Ile Trp Gly Glu His
            500                 505                 510
Asp Ala Arg Ala Tyr Leu Gly Ile Thr Val Pro Asp Phe Pro Asn Phe
        515                 520                 525
Phe Val Met Thr Gly Pro Asn Thr Gly Leu His Gly Gly Ser Phe
    530                 535                 540
Ile Thr Ile Leu Glu Cys Gln Val Arg Tyr Ile Met Asp Ala Leu Lys
545                 550                 555                 560
Leu Met Gln Ser Glu Asn Leu Gly Ala Met Glu Cys Arg Ala Glu Val
                565                 570                 575
Asn Asp Arg Tyr Asn Glu Ala Val Asp Arg Gln His Ala Gln Met Val
            580                 585                 590
Trp Thr His Pro Ala Met Glu Asn Trp Tyr Arg Asn Pro Asp Gly Arg
        595                 600                 605
Val Val Ser Val Leu Pro Trp Arg Ile Asn Asp Tyr Trp Ala Met Thr
    610                 615                 620
Tyr Arg Val Asp Pro Ser Asp Phe Arg Thr Glu Pro Ala Arg Ser Glu
625                 630                 635                 640
Ser Val Pro Thr Pro Thr Ala Arg Gly
                645
```

<210> SEQ ID NO 37
<211> LENGTH: 1485
<212> TYPE: DNA
<213> ORGANISM: Rhodococcus erythropolis AN12

<400> SEQUENCE: 37

```
gtgaagcttc cgaacatgt cgaaacattg atcgtcggtg ccggattcgc cggtatgggc      60
ttggcggcca gaatgcttcg tgacaaccga acggcggacg tcgtgttgat cgagcgcgga     120
gctgatatcg gtggcacctg gcgagacaac acctacccag ttgtgcctg tgacgtgccg     180
acggcgctgt actcgtattc ttttgcgccg agcgctgatt ggagtcatac ctttgctcgt    240
cagcccgaga tctacgacta tctgaagaaa gtggccgcag acaccggcat cggggatcgc    300
gtaatcctga actgcgaact cgaagccgct gtgtgggacg aggatgcggc gctgtggcgg    360
gtccggacat ccctggggtc gttgacagtc aaagcgctgg tcgctgcgac cggggcgttg    420
tcgacaccca agatcccgga ttttcccggt ctcgaccaat tctccggtac cactttccat    480
tcggcgacgt ggaaccacga acacgaactg cgtggtgagc gcgtagccgt gatcggaacg    540
ggagcgtcgg cggttcagtt cgttcccgaa attgccgacc ctgctgccca tgtcaccgtg    600
ttccagagaa ctccggcctg ggtgattccg cgaatggatc gcaccctgcc tgcggcgcag    660
aaggccgtct actcgcggat tcccgctacg cagaaagttg ttcgcggagc ggtttacggt    720
tttcgcgagt tgctcggtgc cgcgatgtca catgcgacgt gggtcctgcc ggccttcgag    780
gcggccgcgc gcctccatct cgcagacag gtgaaagatc cggagttgcg ccggaaactg    840
actcccgatt tcacgatcgg ttgcaagcgc atgcttctgt ccaacgactg gttgcgcacc    900
ctcgaccgcg cggacgtgag cctggtcgac agcgggctcg tctcggtcac cgagggcggg    960
gtggtcgacg ggcacggagt cgagcacaag gtcgacacca tcatcttcgc cacggggttc   1020
acgccgacgg aaccgcctgt ggcgcatctg atcaccggaa acgtggcga acgctggcc    1080
gcgcattgga acggtagccc caatgcctac aagggcactg cggtcagcgg gttcccgaat   1140
ctgttcctca tgtacggtcc gaacaccaac ctcggacaca gttcgatcgt gtacatgctc   1200
gagtcccagg ccgagtacgt caacgacgcg ttgaacacca tgaaacgtga gcgactggac   1260
gctcttgatg tcaacgagtc ggtacaggtg cactacaaca agggaattca gcacgagttg   1320
cagcacacgg tgtggaacaa gggcggatgc tcgagttggt acatcgatcc ggaggggcgc   1380
aactcggtgc agtggccgac gttcacattc aaattccgtt cgctgctgga gcatttcgat   1440
cgtgagaact actccgctcg caagatcgaa agcgtccagg catga                   1485
```

<210> SEQ ID NO 38
<211> LENGTH: 494
<212> TYPE: PRT
<213> ORGANISM: Rhodococcus erythropolis AN12

<400> SEQUENCE: 38

```
Val Lys Leu Pro Glu His Val Glu Thr Leu Ile Val Gly Ala Gly Phe
1               5                  10                  15

Ala Gly Met Gly Leu Ala Ala Arg Met Leu Arg Asp Asn Arg Thr Ala
            20                  25                  30

Asp Val Val Leu Ile Glu Arg Gly Ala Asp Ile Gly Gly Thr Trp Arg
        35                  40                  45

Asp Asn Thr Tyr Pro Gly Cys Ala Cys Asp Val Pro Thr Ala Leu Tyr
    50                  55                  60

Ser Tyr Ser Phe Ala Pro Ser Ala Asp Trp Ser His Thr Phe Ala Arg
```

```
        65                   70                   75                   80
Gln Pro Glu Ile Tyr Asp Tyr Leu Lys Lys Val Ala Ala Asp Thr Gly
                    85                   90                   95
Ile Gly Asp Arg Val Ile Leu Asn Cys Glu Leu Glu Ala Ala Val Trp
                100                  105                  110
Asp Glu Asp Ala Ala Leu Trp Arg Val Arg Thr Ser Leu Gly Ser Leu
                115                  120                  125
Thr Val Lys Ala Leu Val Ala Ala Thr Gly Ala Leu Ser Thr Pro Lys
        130                  135                  140
Ile Pro Asp Phe Pro Gly Leu Asp Gln Phe Ser Gly Thr Thr Phe His
145                  150                  155                  160
Ser Ala Thr Trp Asn His Glu His Glu Leu Arg Gly Glu Arg Val Ala
                165                  170                  175
Val Ile Gly Thr Gly Ala Ser Ala Val Gln Phe Val Pro Glu Ile Ala
                180                  185                  190
Asp Pro Ala Ala His Val Thr Val Phe Gln Arg Thr Pro Ala Trp Val
                195                  200                  205
Ile Pro Arg Met Asp Arg Thr Leu Pro Ala Ala Gln Lys Ala Val Tyr
        210                  215                  220
Ser Arg Ile Pro Ala Thr Gln Lys Val Val Arg Gly Ala Val Tyr Gly
225                  230                  235                  240
Phe Arg Glu Leu Leu Gly Ala Ala Met Ser His Ala Thr Trp Val Leu
                245                  250                  255
Pro Ala Phe Glu Ala Ala Arg Leu His Leu Arg Arg Gln Val Lys
                260                  265                  270
Asp Pro Glu Leu Arg Arg Lys Leu Thr Pro Asp Phe Thr Ile Gly Cys
                275                  280                  285
Lys Arg Met Leu Leu Ser Asn Asp Trp Leu Arg Thr Leu Asp Arg Ala
        290                  295                  300
Asp Val Ser Leu Val Asp Ser Gly Leu Val Ser Val Thr Glu Gly Gly
305                  310                  315                  320
Val Val Asp Gly His Gly Val Glu His Lys Val Asp Thr Ile Ile Phe
                325                  330                  335
Ala Thr Gly Phe Thr Pro Thr Glu Pro Pro Val Ala His Leu Ile Thr
                340                  345                  350
Gly Lys Arg Gly Glu Thr Leu Ala Ala His Trp Asn Gly Ser Pro Asn
        355                  360                  365
Ala Tyr Lys Gly Thr Ala Val Ser Gly Phe Pro Asn Leu Phe Leu Met
        370                  375                  380
Tyr Gly Pro Asn Thr Asn Leu Gly His Ser Ser Ile Val Tyr Met Leu
385                  390                  395                  400
Glu Ser Gln Ala Glu Tyr Val Asn Asp Ala Leu Asn Thr Met Lys Arg
                405                  410                  415
Glu Arg Leu Asp Ala Leu Asp Val Asn Glu Ser Val Gln Val His Tyr
                420                  425                  430
Asn Lys Gly Ile Gln His Glu Leu Gln His Thr Val Trp Asn Lys Gly
                435                  440                  445
Gly Cys Ser Ser Trp Tyr Ile Asp Pro Glu Gly Arg Asn Ser Val Gln
        450                  455                  460
Trp Pro Thr Phe Thr Phe Lys Phe Arg Ser Leu Leu Glu His Phe Asp
465                  470                  475                  480
Arg Glu Asn Tyr Ser Ala Arg Lys Ile Glu Ser Val Gln Ala
                485                  490
```

<210> SEQ ID NO 39
<211> LENGTH: 1500
<212> TYPE: DNA
<213> ORGANISM: Rhodococcus erythropolis AN12

<400> SEQUENCE: 39

```
atgacacagc atgtcgacgt actgatcatc ggcgctggct tgtccggaat cggcgcggct      60
tgccacctca ttcgtgagca gaccggaagc acttacgcga tcctcgagcg ccgcgagaac     120
atcggtggca cctgggacct gttcaagtac ccgggcatcc gttcggactc cgacatgctc     180
accttcggat tcggtttccg tccttggatc ggcaccaaag tgctcgcaga cggcgccagt     240
atccgtgact acgtcgagga aaccgccaag gaatacggcg tcaccgacca catcaacttc     300
ggccgcaagg tcgtggctat ggacttcgac cgtaccgccg cgcagtggtc cgtgaccgtc     360
ctggtcgagg cgacagggga gaccgagacg tggaccgcga acgtcctcgt cggcgcctgt     420
ggttactaca actacgacaa gggttaccgc cccgccttcc ccggtgagga cgacttccgc     480
ggtcagatcg tgcacccgca gcactggccg gaggatctcg attacaccgg aaagaaggta     540
gtggtcatcg gttccggcgc caccgcgatc acgctgatcc cgtcgatggc ccccaccgcc     600
ggtcacgtca ccatgctgca gcgctcgccc acgtggatcc aggcgcttcc gtccgaggac     660
cctgttgcca agggtctcaa gctcgcacgc gttccgacc agattgctta caagattggt     720
cgagcccgca atatcgcact gcaacgcgcc agctttcagc tttctcgcac caacccgaag     780
ctggccaaga agctgttcct cgcccagatc cgcctgcagc tcggcaagaa cgtggacctg     840
cgtcacttca ctcccagcta caaccgtgg atcagcgcc tgtgcgtggt tcccaacggg     900
gacctgttca aggtgctcaa gagcggcaag gccgacatcg tcaccgaccg tatcgccacg     960
ttcaccgaga agggcatcgt gaccgagtcg ggccgcgaaa tcgaggccga cgtcatcgtc    1020
acggcgaccg gcttgaacgt acagattctg ggcggcgcaa ccatgagcat cgacggcgag    1080
ccggtcaagc tcaacgagac tgtggcctac aagagcgtgc tctactccga catcccgaac    1140
ttcctgatga tcctcggcta caccaacgcg tcgtggacgc tcaaggctga cctggccgcg    1200
tcctatctgt gtcgcgtgct caagatcatg cgcgatcgca gctacacgac tttcgaggtt    1260
cacgccgaac ccgaggactt cgccgaagaa tctctcatgg gcggagccct gacctcgggc    1320
tacatccagc gcggcgacgg agaaatgccg cgtcagggtg cccgcggcgc gtggaaagtg    1380
gtcaacaatt actaccgcga ccgcaagctg atgcacgacg ccgagatcga agacggtgtg    1440
ctgcagttca gcaaggtcga tattgctgtc gtgcctgata gcaaggtcgc cagcgcatag    1500
```

<210> SEQ ID NO 40
<211> LENGTH: 499
<212> TYPE: PRT
<213> ORGANISM: Rhodococcus erythropolis AN12

<400> SEQUENCE: 40

```
Met Thr Gln His Val Asp Val Leu Ile Ile Gly Ala Gly Leu Ser Gly
 1               5                  10                  15

Ile Gly Ala Ala Cys His Leu Ile Arg Glu Gln Thr Gly Ser Thr Tyr
            20                  25                  30

Ala Ile Leu Glu Arg Arg Glu Asn Ile Gly Gly Thr Trp Asp Leu Phe
        35                  40                  45

Lys Tyr Pro Gly Ile Arg Ser Asp Ser Asp Met Leu Thr Phe Gly Phe
    50                  55                  60
```

```
Gly Phe Arg Pro Trp Ile Gly Thr Lys Val Leu Ala Asp Gly Ala Ser
 65                  70                  75                  80

Ile Arg Asp Tyr Val Glu Thr Ala Lys Glu Tyr Gly Val Thr Asp
                 85                  90                  95

His Ile Asn Phe Gly Arg Lys Val Val Ala Met Asp Phe Asp Arg Thr
                100                 105                 110

Ala Ala Gln Trp Ser Val Thr Val Leu Val Glu Ala Thr Gly Glu Thr
            115                 120                 125

Glu Thr Trp Thr Ala Asn Val Leu Val Gly Ala Cys Gly Tyr Tyr Asn
        130                 135                 140

Tyr Asp Lys Gly Tyr Arg Pro Ala Phe Pro Gly Glu Asp Asp Phe Arg
145                 150                 155                 160

Gly Gln Ile Val His Pro Gln His Trp Pro Glu Asp Leu Asp Tyr Thr
                165                 170                 175

Gly Lys Lys Val Val Ile Gly Ser Gly Ala Thr Ala Ile Thr Leu
            180                 185                 190

Ile Pro Ser Met Ala Pro Thr Ala Gly His Val Thr Met Leu Gln Arg
        195                 200                 205

Ser Pro Thr Trp Ile Gln Ala Leu Pro Ser Glu Asp Pro Val Ala Lys
210                 215                 220

Gly Leu Lys Leu Ala Arg Val Pro Asp Gln Ile Ala Tyr Lys Ile Gly
225                 230                 235                 240

Arg Ala Arg Asn Ile Ala Leu Gln Arg Ala Ser Phe Gln Leu Ser Arg
                245                 250                 255

Thr Asn Pro Lys Leu Ala Lys Lys Leu Phe Leu Ala Gln Ile Arg Leu
            260                 265                 270

Gln Leu Gly Lys Asn Val Asp Leu Arg His Phe Thr Pro Ser Tyr Asn
        275                 280                 285

Pro Trp Asp Gln Arg Leu Cys Val Val Pro Asn Gly Asp Leu Phe Lys
    290                 295                 300

Val Leu Lys Ser Gly Lys Ala Asp Ile Val Thr Asp Arg Ile Ala Thr
305                 310                 315                 320

Phe Thr Glu Lys Gly Ile Val Thr Glu Ser Gly Arg Glu Ile Glu Ala
                325                 330                 335

Asp Val Ile Val Thr Ala Thr Gly Leu Asn Val Gln Ile Leu Gly Gly
            340                 345                 350

Ala Thr Met Ser Ile Asp Gly Glu Pro Val Lys Leu Asn Glu Thr Val
        355                 360                 365

Ala Tyr Lys Ser Val Leu Tyr Ser Asp Ile Pro Asn Phe Leu Met Ile
    370                 375                 380

Leu Gly Tyr Thr Asn Ala Ser Trp Thr Leu Lys Ala Asp Leu Ala Ala
385                 390                 395                 400

Ser Tyr Leu Cys Arg Val Leu Lys Ile Met Arg Asp Arg Ser Tyr Thr
                405                 410                 415

Thr Phe Glu Val His Ala Glu Pro Glu Asp Phe Ala Glu Glu Ser Leu
            420                 425                 430

Met Gly Gly Ala Leu Thr Ser Gly Tyr Ile Gln Arg Gly Asp Gly Glu
        435                 440                 445

Met Pro Arg Gln Gly Ala Arg Gly Ala Trp Lys Val Val Asn Asn Tyr
    450                 455                 460

Tyr Arg Asp Arg Lys Leu Met His Asp Ala Glu Ile Glu Asp Gly Val
465                 470                 475                 480

Leu Gln Phe Ser Lys Val Asp Ile Ala Val Val Pro Asp Ser Lys Val
```

Ala Ser Ala

<210> SEQ ID NO 41
<211> LENGTH: 1482
<212> TYPE: DNA
<213> ORGANISM: Rhodococcus erythropolis AN12

<400> SEQUENCE: 41

```
atgtcatcac gggtcaacga cggccacatc gcgatcatcg gaaccgggtt ttccgggctg      60
tgcatggcga tcgaactgaa gaagaagggc atcgacgact tcgtcctgta cgaacgcgcc     120
gacgatgtcg gcggaacctg gcgcgacaac acatacccag gggcagcctg cgatgtgccc     180
agcgtgttgt attcctactc cttcgctcag aacccgaact ggacccgtat cttcccgcca     240
tggtcggaac tgctcgacta tctcagatct gttgctgcgc agtatgattt gctgccgcac     300
atccgcttcg gtgtcgaggt ctccgaaatg cggttcgacg aggaccggct ccggtggaac     360
atccagttcg catccggcga atcagtgacg gcggccgttg tcgtcaacgg ctcaggggc      420
ttgagtaatc cgtacatccc gcagctaccc ggactggaat cattcgaggg tgccgcattc     480
cactccgcca agtggcgaca tgacctcgac atgtcgggaa ggcgtgtcgc ggtgataggt     540
tccggcgcca gtgcgatcca gttcgtcccc gaaatcgccc cgcacaccga gacccttcat     600
gtgtttcagc gatcacccaa ctgggtcatg ccacgtggtg atgccgcgct gtcgcccgcc     660
acccgcgaaa gattctcacg gcgtccttat cgtcaacggt ggctgcgatg gcggacctac     720
tgggcattcg aaaagctcgc cagcgccttc ctcggaaatc gcaaactcgt cgaacagtac     780
cgatcccagg cgctcgccaa tcttcaacag caagtgccgg attcggactt gaggcagaag     840
gtcacccag attacgatcc tggctgtaaa cgtcgcttga tatccgacga ctggtacccc     900
gcgctgcaac gggaaaatgt gcacttgaac acctcggggg tttccgagat ccgcccgcat     960
tcgatcattg actcagaggg agcggaacac gaagtcgaca ccctgatctt cgcgaccgga    1020
ttccaggcaa ccagcttcct ggcaccgatg aaagtattcg gccgcgaagg agtcgaactc    1080
tccgacagtt ggcgcgaggg cgccgcaaca aagctcgggc ttgcatccgc cgcgttcccg    1140
aacctgtggt tcctcaacgg cccgaatacc ggtctcggtc acaactcgat catcttcatg    1200
atcgaagcac aagccagata catcgcttcg gcagtgcagt acatgcgccg aaaaagtatc    1260
actgccctcg aactcgatcg caccgtccaa acaggcagct acgccgccac ccaagaacgc    1320
atgcgccgaa ctgtatgggc atcgggtggc tgcgacagct ggtatcaatc cgctgacggt    1380
cgaatcgaca ccctgtggcc ggccagcaca atcgaatact ggttgcgcac caggctattc    1440
cgcaagtccg acttccatgc actgacgaca ggcaaaggat ga                       1482
```

<210> SEQ ID NO 42
<211> LENGTH: 493
<212> TYPE: PRT
<213> ORGANISM: Rhodococcus erythropolis AN12

<400> SEQUENCE: 42

```
Met Ser Ser Arg Val Asn Asp Gly His Ile Ala Ile Ile Gly Thr Gly
1               5                  10                  15

Phe Ser Gly Leu Cys Met Ala Ile Glu Leu Lys Lys Lys Gly Ile Asp
            20                  25                  30

Asp Phe Val Leu Tyr Glu Arg Ala Asp Asp Val Gly Gly Thr Trp Arg
        35                  40                  45
```

-continued

```
Asp Asn Thr Tyr Pro Gly Ala Ala Cys Asp Val Pro Ser Val Leu Tyr
    50                  55                  60

Ser Tyr Ser Phe Ala Gln Asn Pro Asn Trp Thr Arg Ile Phe Pro Pro
65                  70                  75                  80

Trp Ser Glu Leu Leu Asp Tyr Leu Arg Ser Val Ala Ala Gln Tyr Asp
                85                  90                  95

Leu Leu Pro His Ile Arg Phe Gly Val Glu Val Ser Glu Met Arg Phe
                100                 105                 110

Asp Glu Asp Arg Leu Arg Trp Asn Ile Gln Phe Ala Ser Gly Glu Ser
                115                 120                 125

Val Thr Ala Ala Val Val Asn Gly Ser Gly Leu Ser Asn Pro
    130                 135                 140

Tyr Ile Pro Gln Leu Pro Gly Leu Glu Ser Phe Glu Gly Ala Ala Phe
145                 150                 155                 160

His Ser Ala Lys Trp Arg His Asp Leu Asp Met Ser Gly Arg Arg Val
                165                 170                 175

Ala Val Ile Gly Ser Gly Ala Ser Ala Ile Gln Phe Val Pro Glu Ile
                180                 185                 190

Ala Pro His Thr Glu Thr Leu His Val Phe Gln Arg Ser Pro Asn Trp
                195                 200                 205

Val Met Pro Arg Gly Asp Ala Ala Leu Ser Pro Ala Thr Arg Glu Arg
    210                 215                 220

Phe Ser Arg Arg Pro Tyr Arg Gln Arg Trp Leu Arg Trp Arg Thr Tyr
225                 230                 235                 240

Trp Ala Phe Glu Lys Leu Ala Ser Ala Phe Leu Gly Asn Arg Lys Leu
                245                 250                 255

Val Glu Gln Tyr Arg Ser Gln Ala Leu Ala Asn Leu Gln Gln Gln Val
                260                 265                 270

Pro Asp Ser Asp Leu Arg Gln Lys Val Thr Pro Asp Tyr Asp Pro Gly
                275                 280                 285

Cys Lys Arg Arg Leu Ile Ser Asp Asp Trp Tyr Pro Ala Leu Gln Arg
    290                 295                 300

Glu Asn Val His Leu Asn Thr Ser Gly Val Ser Glu Ile Arg Pro His
305                 310                 315                 320

Ser Ile Ile Asp Ser Glu Gly Ala Glu His Glu Val Asp Thr Leu Ile
                325                 330                 335

Phe Ala Thr Gly Phe Gln Ala Thr Ser Phe Leu Ala Pro Met Lys Val
                340                 345                 350

Phe Gly Arg Glu Gly Val Glu Leu Ser Asp Ser Trp Arg Glu Gly Ala
                355                 360                 365

Ala Thr Lys Leu Gly Leu Ala Ser Ala Phe Pro Asn Leu Trp Phe
    370                 375                 380

Leu Asn Gly Pro Asn Thr Gly Leu Gly His Asn Ser Ile Ile Phe Met
385                 390                 395                 400

Ile Glu Ala Gln Ala Arg Tyr Ile Ala Ser Ala Val Gln Tyr Met Arg
                405                 410                 415

Arg Lys Ser Ile Thr Ala Leu Glu Leu Asp Arg Thr Val Gln Thr Gly
                420                 425                 430

Ser Tyr Ala Ala Thr Gln Glu Arg Met Arg Arg Thr Val Trp Ala Ser
                435                 440                 445

Gly Gly Cys Asp Ser Trp Tyr Gln Ser Ala Asp Gly Arg Ile Asp Thr
    450                 455                 460

Leu Trp Pro Ala Ser Thr Ile Glu Tyr Trp Leu Arg Thr Arg Leu Phe
```

465           470           475           480
Arg Lys Ser Asp Phe His Ala Leu Thr Thr Gly Lys Gly
                485               490

<210> SEQ ID NO 43
<211> LENGTH: 1626
<212> TYPE: DNA
<213> ORGANISM: Rhodococcus erythropolis AN12

<400> SEQUENCE: 43

| | | | | |
|---|---|---|---|---|
| atgactacac | aaaaggccct | gaccactgtc | gatgccatcg | tcatcggcgc cggattcggc | 60 |
| gggatctacg | ccgtccacaa | actggccaac | gagctcggcc | tcacgacggt cggcttcgac | 120 |
| aaggcagacg | cccgggcgg | cacgtggtac | tggaaccgct | acccgggtgc actgtccgac | 180 |
| accgaaagcc | acgtctaccg | gttctcattc | gaccgtgacc | tgcttcagga cggtacctgg | 240 |
| aagcacacct | acaccactca | acccgagatt | ctcgaatacc | ttgaggatgt cgtttcccgg | 300 |
| ttcgacctac | gccggcactt | ccacttcggc | actgccgtcg | aatctgcggt gtatctcgaa | 360 |
| gacgaacaac | tgtgggaagt | caccaccgac | acaggcgaga | tctaccgcgc tacctacgtc | 420 |
| gtcaatgctg | tcgggctcct | ctccgccatc | aatcgaccgg | atctgcccgg tctcgagaca | 480 |
| ttcgaaggcg | agaccatcca | caccgcagcg | tggcccgagg | gcaaggatct caccggccgc | 540 |
| cgcgtcggcg | tgatcggtac | cggatctact | gggcaacagg | tcatcacggc cctggcgcca | 600 |
| acggtcgaac | acctcactgt | attcgtgcga | actccccagt | actcggtgcc ggtcggcaag | 660 |
| cgcgcggtga | ccgacgagca | gatcgacgca | gtcaaagccg | actacgagaa catctggact | 720 |
| caggtcaaaa | gatcctcggt | ggcattcggc | ttcgaggaat | ctactgttcc ggccatgagc | 780 |
| gtgtccgcgg | aagaacgcct | cagggtctac | gaagaggcat | gggagcaggg cggcggtttc | 840 |
| cgattcatgt | tcggaacctt | cggtgacatc | gctaccgacg | aagaagccaa cgaaactgca | 900 |
| gcatcgttca | ttcgctcgaa | gatcaccgcc | atgatcgaag | acccggagac tgcccgcaaa | 960 |
| ctgacgccca | ccggactatt | cgcgagacga | ccgttgtgcg | acgacgggta cttccaggtc | 1020 |
| ttcaaccgcc | cgaacgtcga | ggcggtcgcc | atcaaggaaa | accccattcg tgagatcaca | 1080 |
| gccaagggcg | tggtgaccga | ggacggcgtc | ctgcacaaat | ggacgtcct ggtcctcgcc | 1140 |
| accggcttcg | acgccgtcga | cgggaactac | cgccgcatga | ccatttccgg tcgcggtggc | 1200 |
| ctgaacatca | cgaccattg | ggacggccaa | cccaccagct | acctggggat tgccaccgcg | 1260 |
| aacttcccca | actggttcat | ggtgctcggc | cccaacggac | cgttcacgaa ccttcctcca | 1320 |
| agcatcgaaa | ctcaggtcga | gtggatcagc | gacaccatag | gttacgtcga gcggacaggt | 1380 |
| gtgcgggcga | tcgaacccac | accggaggcg | gaatccgcat | ggaccgcgac ctgcacggac | 1440 |
| atcgcgaaca | tgaccgtctt | caccaaggtt | gattcatgga | tcttcggggc caatgttcca | 1500 |
| ggaaagaagc | ccagcgtgct | gttctacctt | ggcgggctcg | gcaactaccg cgccgtcctg | 1560 |
| gcagacgtca | ccgagggggg | ctatcagggc | tttgctctga | agacggccga caccgtcgac | 1620 |
| gcctga | | | | | 1626 |

<210> SEQ ID NO 44
<211> LENGTH: 541
<212> TYPE: PRT
<213> ORGANISM: Rhodococcus erythropolis AN12

<400> SEQUENCE: 44

Met Thr Thr Gln Lys Ala Leu Thr Thr Val Asp Ala Ile Val Ile Gly
1               5                   10                  15

-continued

```
Ala Gly Phe Gly Gly Ile Tyr Ala Val His Lys Leu Ala Asn Glu Leu
            20                  25                  30

Gly Leu Thr Thr Val Gly Phe Asp Lys Ala Asp Gly Pro Gly Gly Thr
        35                  40                  45

Trp Tyr Trp Asn Arg Tyr Pro Gly Ala Leu Ser Asp Thr Glu Ser His
    50                  55                  60

Val Tyr Arg Phe Ser Phe Asp Arg Asp Leu Leu Gln Asp Gly Thr Trp
65                  70                  75                  80

Lys His Thr Tyr Thr Thr Gln Pro Glu Ile Leu Glu Tyr Leu Glu Asp
                85                  90                  95

Val Val Ser Arg Phe Asp Leu Arg Arg His Phe His Phe Gly Thr Ala
            100                 105                 110

Val Glu Ser Ala Val Tyr Leu Glu Asp Glu Gln Leu Trp Glu Val Thr
        115                 120                 125

Thr Asp Thr Gly Glu Ile Tyr Arg Ala Thr Tyr Val Val Asn Ala Val
130                 135                 140

Gly Leu Leu Ser Ala Ile Asn Arg Pro Asp Leu Pro Gly Leu Glu Thr
145                 150                 155                 160

Phe Glu Gly Glu Thr Ile His Thr Ala Ala Trp Pro Glu Gly Lys Asp
                165                 170                 175

Leu Thr Gly Arg Arg Val Gly Val Ile Gly Thr Gly Ser Thr Gly Gln
            180                 185                 190

Gln Val Ile Thr Ala Leu Ala Pro Thr Val Glu His Leu Thr Val Phe
        195                 200                 205

Val Arg Thr Pro Gln Tyr Ser Val Pro Val Gly Lys Arg Ala Val Thr
    210                 215                 220

Asp Glu Gln Ile Asp Ala Val Lys Ala Asp Tyr Glu Asn Ile Trp Thr
225                 230                 235                 240

Gln Val Lys Arg Ser Ser Val Ala Phe Gly Phe Glu Glu Ser Thr Val
                245                 250                 255

Pro Ala Met Ser Val Ser Ala Glu Glu Arg Leu Arg Val Tyr Glu Glu
            260                 265                 270

Ala Trp Glu Gln Gly Gly Phe Arg Phe Met Phe Gly Thr Phe Gly
        275                 280                 285

Asp Ile Ala Thr Asp Glu Glu Ala Asn Glu Thr Ala Ala Ser Phe Ile
    290                 295                 300

Arg Ser Lys Ile Thr Ala Met Ile Glu Asp Pro Glu Thr Ala Arg Lys
305                 310                 315                 320

Leu Thr Pro Thr Gly Leu Phe Ala Arg Arg Pro Leu Cys Asp Asp Gly
                325                 330                 335

Tyr Phe Gln Val Phe Asn Arg Pro Asn Val Glu Ala Val Ala Ile Lys
            340                 345                 350

Glu Asn Pro Ile Arg Glu Ile Thr Ala Lys Gly Val Val Thr Glu Asp
        355                 360                 365

Gly Val Leu His Lys Leu Asp Val Leu Val Leu Ala Thr Gly Phe Asp
370                 375                 380

Ala Val Asp Gly Asn Tyr Arg Arg Met Thr Ile Ser Gly Arg Gly Gly
385                 390                 395                 400

Leu Asn Ile Asn Asp His Trp Asp Gly Gln Pro Thr Ser Tyr Leu Gly
                405                 410                 415

Ile Ala Thr Ala Asn Phe Pro Asn Trp Phe Met Val Leu Gly Pro Asn
            420                 425                 430
```

```
Gly Pro Phe Thr Asn Leu Pro Pro Ser Ile Glu Thr Gln Val Glu Trp
            435                 440                 445
Ile Ser Asp Thr Ile Gly Tyr Val Glu Arg Thr Gly Val Arg Ala Ile
        450                 455                 460
Glu Pro Thr Pro Glu Ala Glu Ser Ala Trp Thr Ala Thr Cys Thr Asp
465                 470                 475                 480
Ile Ala Asn Met Thr Val Phe Thr Lys Val Asp Ser Trp Ile Phe Gly
                485                 490                 495
Ala Asn Val Pro Gly Lys Lys Pro Ser Val Leu Phe Tyr Leu Gly Gly
                500                 505                 510
Leu Gly Asn Tyr Arg Ala Val Leu Ala Asp Val Thr Glu Gly Gly Tyr
            515                 520                 525
Gln Gly Phe Ala Leu Lys Thr Ala Asp Thr Val Asp Ala
        530                 535                 540
```

<210> SEQ ID NO 45
<211> LENGTH: 1638
<212> TYPE: DNA
<213> ORGANISM: Rhodococcus erythropolis AN12

<400> SEQUENCE: 45

```
atgacaacta ccgaatccag aactcagacc gacaaggctg gggccgtcac gctcgatgcg    60
ttgatcatcg gcgccggagt cgccggtttg tatcagctcc acatgcttcg cgagcaggga   120
ctgaacgtcc gcgcctacga cgctgcggaa gacgtcggcg gtacgtggta ctggaaccgt   180
tacccaggcg cacgattcga ctccgaagcc tacatctacc agtacctgtt ctccgaggac   240
ctgtacaaga actggagctg gagtcaacgc ttcccggccc agcccgaaat tgagcggtgg   300
atgcgctacg tcgccgacac cctggacctg cgtcgcagca ttcagttttc cacaacaatc   360
accagcgccg agttcgacga ggtagctgag cgttggacca ttcgcaccga ccgcggcgag   420
gaaatcagca cccgattctt catcacctgt tgcggaatgc tgtcggcgcc gatgaagat    480
ttgttccccg gacaacagga cttccggggg cagatcttcc acacctcgcg atggccgcac   540
ggagatgtag aactcaccgg taagcgtgtc ggtgtcgtcg cgtcggcgc cactggcatt   600
caggtaatcc agaccatcgc cgacgaggtt gatcaactga aggtgttcgt gcggacaccc   660
cagtacgcct tgccgatgaa aaaccctcag tacgacagcg acgacgtcgc ggcctacaag   720
gaccgattcg aggagcttcg aaccacactg ccgcacacct tcacaggctt cgaatacgat   780
ttcgaatacg tgtgggccga cctagccccc gaacagcgcc gcgaggtgct cgagaacatc   840
tacgagtacg atcactcaa gctgtggctg tcgtcgttcg cggagatgtt cttcgatgag   900
caggtcagtg acgagatctc cgagttcgtt cgcgagaaaa tgcgggcgcg gctcatcgat   960
ccggagctgt gcgacctgct gattcccact gactatggct tcggcacaca ccgtgtgccg  1020
ctcgaaacca actacctcga ggtgtaccac cgcccgaatg tgacggccat cggcgtcaag  1080
aacaacccga tcgcgcgaat cgtccccaa ggcatcgagt tgaccgacgg taccttccac  1140
gaactagacg tgatcatttt ggccactggg ttcgatgcag gcaccggcgc actgactcga  1200
atcgacatcc gcggccgcgg tggtcggtct ctgaaggaag actggggacg cgatattcgc  1260
acgacaatgg gcctgatggt gcacggttac ccgaacatgc tgacgaccgc cgtgcccctg  1320
gcaccctccg cggcactgtg caacatgacc acgtgcttgc agcagcagac cgagtggatc  1380
agcgaagcaa ttcgctacat gcaagagcgc gatctgaccg tcatcgagcc taccaaggag  1440
gccgaggacg cgtgggtggc gcaccacgac gaaacagccg cagtgaatct gatctccaag  1500
```

-continued

```
acggattcct ggtacgtagg ttccaacgtt ccagggaagc cgcgacgggt cctgtcctac    1560 acgggggggag tcggcgcata ccgagaaaag gcgcaggaaa tcgccgacgc cggatacaag    1620
ggcttcaatc tgcgctga                                                   1638
```

<210> SEQ ID NO 46
<211> LENGTH: 545
<212> TYPE: PRT
<213> ORGANISM: Rhodococcus erythropolis AN12

<400> SEQUENCE: 46

```
Met Thr Thr Thr Glu Ser Arg Thr Gln Thr Asp Lys Ala Gly Ala Val
1               5                   10                  15

Thr Leu Asp Ala Leu Ile Ile Gly Ala Gly Val Ala Gly Leu Tyr Gln
            20                  25                  30

Leu His Met Leu Arg Glu Gln Gly Leu Asn Val Arg Ala Tyr Asp Ala
        35                  40                  45

Ala Glu Asp Val Gly Gly Thr Trp Tyr Trp Asn Arg Tyr Pro Gly Ala
    50                  55                  60

Arg Phe Asp Ser Glu Ala Tyr Ile Tyr Gln Tyr Leu Phe Ser Glu Asp
65                  70                  75                  80

Leu Tyr Lys Asn Trp Ser Trp Ser Gln Arg Phe Pro Ala Gln Pro Glu
                85                  90                  95

Ile Glu Arg Trp Met Arg Tyr Val Ala Asp Thr Leu Asp Leu Arg Arg
            100                 105                 110

Ser Ile Gln Phe Ser Thr Thr Ile Thr Ser Ala Glu Phe Asp Glu Val
        115                 120                 125

Ala Glu Arg Trp Thr Ile Arg Thr Asp Arg Gly Glu Glu Ile Ser Thr
    130                 135                 140

Arg Phe Phe Ile Thr Cys Cys Gly Met Leu Ser Ala Pro Met Glu Asp
145                 150                 155                 160

Leu Phe Pro Gly Gln Gln Asp Phe Arg Gly Gln Ile Phe His Thr Ser
                165                 170                 175

Arg Trp Pro His Gly Asp Val Glu Leu Thr Gly Lys Arg Val Gly Val
            180                 185                 190

Val Gly Val Gly Ala Thr Gly Ile Gln Val Ile Gln Thr Ile Ala Asp
        195                 200                 205

Glu Val Asp Gln Leu Lys Val Phe Val Arg Thr Pro Gln Tyr Ala Leu
    210                 215                 220

Pro Met Lys Asn Pro Gln Tyr Asp Ser Asp Val Ala Ala Tyr Lys
225                 230                 235                 240

Asp Arg Phe Glu Glu Leu Arg Thr Thr Leu Pro His Thr Phe Thr Gly
                245                 250                 255

Phe Glu Tyr Asp Phe Glu Tyr Val Trp Ala Asp Leu Ala Pro Glu Gln
            260                 265                 270

Arg Arg Glu Val Leu Glu Asn Ile Tyr Glu Tyr Gly Ser Leu Lys Leu
        275                 280                 285

Trp Leu Ser Ser Phe Ala Glu Met Phe Phe Asp Glu Gln Val Ser Asp
    290                 295                 300

Glu Ile Ser Glu Phe Val Arg Glu Lys Met Arg Ala Arg Leu Ile Asp
305                 310                 315                 320

Pro Glu Leu Cys Asp Leu Leu Ile Pro Thr Asp Tyr Gly Phe Gly Thr
                325                 330                 335

His Arg Val Pro Leu Glu Thr Asn Tyr Leu Glu Val Tyr His Arg Pro
            340                 345                 350
```

-continued

```
Asn Val Thr Ala Ile Gly Val Lys Asn Asn Pro Ile Ala Arg Ile Val
            355                 360                 365

Pro Gln Gly Ile Glu Leu Thr Asp Gly Thr Phe His Glu Leu Asp Val
        370                 375                 380

Ile Ile Leu Ala Thr Gly Phe Asp Ala Gly Thr Gly Ala Leu Thr Arg
385                 390                 395                 400

Ile Asp Ile Arg Gly Arg Gly Arg Ser Leu Lys Glu Asp Trp Gly
                405                 410                 415

Arg Asp Ile Arg Thr Thr Met Gly Leu Met Val His Gly Tyr Pro Asn
            420                 425                 430

Met Leu Thr Thr Ala Val Pro Leu Ala Pro Ser Ala Ala Leu Cys Asn
            435                 440                 445

Met Thr Thr Cys Leu Gln Gln Gln Thr Glu Trp Ile Ser Glu Ala Ile
        450                 455                 460

Arg Tyr Met Gln Glu Arg Asp Leu Thr Val Ile Glu Pro Thr Lys Glu
465                 470                 475                 480

Ala Glu Asp Ala Trp Val Ala His His Asp Glu Thr Ala Ala Val Asn
                485                 490                 495

Leu Ile Ser Lys Thr Asp Ser Trp Tyr Val Gly Ser Asn Val Pro Gly
            500                 505                 510

Lys Pro Arg Arg Val Leu Ser Tyr Thr Gly Val Gly Ala Tyr Arg
            515                 520                 525

Glu Lys Ala Gln Glu Ile Ala Asp Ala Gly Tyr Lys Gly Phe Asn Leu
        530                 535                 540

Arg
545

<210> SEQ ID NO 47
<211> LENGTH: 540
<212> TYPE: PRT
<213> ORGANISM: Artificial Sequence
<220> FEATURE:
<223> OTHER INFORMATION: consensus sequence

<400> SEQUENCE: 47

Met Thr Ala Gln Glu Ser Leu Thr Val Val Asp Ala Val Val Ile Gly
1               5                   10                  15

Ala Gly Phe Gly Gly Ile Tyr Ala Val His Lys Leu Arg Glu Gln Gly
            20                  25                  30

Leu Thr Val Val Gly Phe Asp Ala Ala Asp Gly Pro Gly Gly Thr Trp
        35                  40                  45

Tyr Trp Asn Arg Tyr Pro Gly Ala Leu Ser Asp Thr Glu Ser His Val
50                  55                  60

Tyr Arg Phe Ser Phe Asp Glu Asp Leu Leu Gln Asp Trp Thr Trp Lys
65                  70                  75                  80

Glu Thr Tyr Pro Thr Gln Pro Glu Ile Leu Glu Tyr Leu Glu Asp Val
                85                  90                  95

Val Asp Arg Phe Asp Leu Arg Arg Asp Phe Arg Phe Gly Thr Glu Val
            100                 105                 110

Thr Ser Ala Thr Tyr Leu Glu Asp Glu Asn Leu Trp Glu Val Thr Thr
        115                 120                 125

Asp Gly Gly Glu Val Tyr Arg Ala Arg Phe Val Val Asn Ala Val Gly
    130                 135                 140

Leu Leu Ser Ala Ile Asn Phe Pro Asn Ile Pro Gly Leu Asp Thr Phe
145                 150                 155                 160
```

```
Glu Gly Glu Thr Ile His Thr Ala Ala Trp Pro Glu Gly Val Asp Leu
            165                 170                 175

Thr Gly Lys Arg Val Gly Val Ile Gly Thr Gly Ser Thr Gly Ile Gln
            180                 185                 190

Val Ile Thr Ala Leu Ala Pro Glu Val Glu His Leu Thr Val Phe Val
            195                 200                 205

Arg Thr Pro Gln Tyr Ser Val Pro Val Gly Asn Arg Pro Val Thr Ala
            210                 215                 220

Glu Gln Ile Asp Ala Ile Lys Ala Asp Tyr Asp Glu Ile Trp Ala Gln
225                 230                 235                 240

Val Lys Arg Ser Gly Val Ala Phe Gly Phe Glu Glu Ser Thr Val Pro
                245                 250                 255

Ala Met Ser Val Ser Glu Glu Arg Asn Arg Val Phe Glu Ala
            260                 265                 270

Trp Glu Glu Gly Gly Gly Phe Arg Phe Met Phe Gly Thr Phe Gly Asp
            275                 280                 285

Ile Ala Thr Asp Glu Ala Ala Asn Glu Thr Ala Ala Ser Phe Ile Arg
            290                 295                 300

Ser Lys Ile Arg Glu Ile Val Lys Asp Pro Glu Thr Ala Arg Lys Leu
305                 310                 315                 320

Thr Pro Thr Gly Leu Phe Ala Arg Arg Leu Cys Asp Asp Gly Tyr
                325                 330                 335

Tyr Glu Val Tyr Asn Arg Pro Asn Val Glu Ala Val Asp Ile Lys Glu
            340                 345                 350

Asn Pro Ile Arg Glu Ile Thr Ala Lys Gly Val Val Thr Glu Asp Gly
            355                 360                 365

Val Leu His Glu Leu Asp Val Leu Val Phe Ala Thr Gly Phe Asp Ala
            370                 375                 380

Val Asp Gly Asn Tyr Arg Arg Ile Asp Ile Arg Gly Arg Gly Gly Leu
385                 390                 395                 400

Ser Leu Asn Asp His Trp Asp Gly Gln Pro Thr Ser Tyr Leu Gly Leu
                405                 410                 415

Ser Thr Ala Gly Phe Pro Asn Trp Phe Met Val Leu Gly Pro Asn Gly
            420                 425                 430

Pro Phe Thr Asn Leu Pro Pro Ser Ile Glu Thr Gln Val Glu Trp Ile
            435                 440                 445

Ser Asp Thr Ile Ala Tyr Ala Glu Glu Asn Gly Ile Arg Ala Ile Glu
450                 455                 460

Pro Thr Pro Glu Ala Glu Asp Glu Trp Thr Ala Thr Cys Thr Asp Ile
465                 470                 475                 480

Ala Asn Ala Thr Leu Phe Thr Lys Ala Asp Ser Trp Ile Phe Gly Ala
                485                 490                 495

Asn Val Pro Gly Lys Lys Pro Ser Val Leu Phe Tyr Leu Gly Gly Leu
                500                 505                 510

Gly Asn Tyr Arg Ala Val Leu Ala Asp Val Ala Ala Gly Tyr Arg
            515                 520                 525

Gly Phe Ala Leu Lys Ser Ala Asp Ala Val Thr Ala
            530                 535                 540

<210> SEQ ID NO 48
<211> LENGTH: 497
<212> TYPE: PRT
<213> ORGANISM: Artificial Sequence
<220> FEATURE:
```

```
<223> OTHER INFORMATION: consensus sequence
<220> FEATURE:
<221> NAME/KEY: MISC_FEATURE
<222> LOCATION: (3)..(3)
<223> OTHER INFORMATION: G or A or T or C
<220> FEATURE:
<221> NAME/KEY: MISC_FEATURE
<222> LOCATION: (6)..(6)
<223> OTHER INFORMATION: G or A or T or C
<220> FEATURE:
<221> NAME/KEY: MISC_FEATURE
<222> LOCATION: (9)..(9)
<223> OTHER INFORMATION: G or A or T or C
<220> FEATURE:
<221> NAME/KEY: MISC_FEATURE
<222> LOCATION: (30)..(30)
<223> OTHER INFORMATION: G or A or T or C
<220> FEATURE:
<221> NAME/KEY: MISC_FEATURE
<222> LOCATION: (63)..(63)
<223> OTHER INFORMATION: G or A or T or C
<220> FEATURE:
<221> NAME/KEY: MISC_FEATURE
<222> LOCATION: (81)..(81)
<223> OTHER INFORMATION: G or A or T or C
<220> FEATURE:
<221> NAME/KEY: MISC_FEATURE
<222> LOCATION: (95)..(95)
<223> OTHER INFORMATION: G or A or T or C
<220> FEATURE:
<221> NAME/KEY: MISC_FEATURE
<222> LOCATION: (96)..(96)
<223> OTHER INFORMATION: G or A or T or C
<220> FEATURE:
<221> NAME/KEY: MISC_FEATURE
<222> LOCATION: (99)..(99)
<223> OTHER INFORMATION: G or A or T or C
<220> FEATURE:
<221> NAME/KEY: MISC_FEATURE
<222> LOCATION: (100)..(100)
<223> OTHER INFORMATION: G or A or T or C
<220> FEATURE:
<221> NAME/KEY: MISC_FEATURE
<222> LOCATION: (123)..(123)
<223> OTHER INFORMATION: G or A or T or C
<220> FEATURE:
<221> NAME/KEY: MISC_FEATURE
<222> LOCATION: (132)..(132)
<223> OTHER INFORMATION: G or A or T or C
<220> FEATURE:
<221> NAME/KEY: MISC_FEATURE
<222> LOCATION: (143)..(143)
<223> OTHER INFORMATION: G or A or T or C
<220> FEATURE:
<221> NAME/KEY: MISC_FEATURE
<222> LOCATION: (158)..(158)
<223> OTHER INFORMATION: G or A or T or C
<220> FEATURE:
<221> NAME/KEY: MISC_FEATURE
<222> LOCATION: (159)..(159)
<223> OTHER INFORMATION: G or A or T or C
<220> FEATURE:
<221> NAME/KEY: MISC_FEATURE
<222> LOCATION: (164)..(164)
<223> OTHER INFORMATION: G or A or T or C
<220> FEATURE:
<221> NAME/KEY: MISC_FEATURE
<222> LOCATION: (195)..(195)
<223> OTHER INFORMATION: G or A or T or C
<220> FEATURE:
<221> NAME/KEY: MISC_FEATURE
<222> LOCATION: (197)..(197)
<223> OTHER INFORMATION: G or A or T or C
<220> FEATURE:
<221> NAME/KEY: MISC_FEATURE
<222> LOCATION: (215)..(215)
<223> OTHER INFORMATION: G or A or T or C
<220> FEATURE:
<221> NAME/KEY: MISC_FEATURE
```

```
<222> LOCATION: (219)..(219)
<223> OTHER INFORMATION: G or A or T or C
<220> FEATURE:
<221> NAME/KEY: MISC_FEATURE
<222> LOCATION: (221)..(221)
<223> OTHER INFORMATION: G or A or T or C
<220> FEATURE:
<221> NAME/KEY: MISC_FEATURE
<222> LOCATION: (237)..(237)
<223> OTHER INFORMATION: G or A or T or C
<220> FEATURE:
<221> NAME/KEY: MISC_FEATURE
<222> LOCATION: (252)..(252)
<223> OTHER INFORMATION: G or A or T or C
<220> FEATURE:
<221> NAME/KEY: MISC_FEATURE
<222> LOCATION: (254)..(254)
<223> OTHER INFORMATION: G or A or T or C
<220> FEATURE:
<221> NAME/KEY: MISC_FEATURE
<222> LOCATION: (259)..(259)
<223> OTHER INFORMATION: G or A or T or C
<220> FEATURE:
<221> NAME/KEY: MISC_FEATURE
<222> LOCATION: (260)..(260)
<223> OTHER INFORMATION: G or A or T or C
<220> FEATURE:
<221> NAME/KEY: MISC_FEATURE
<222> LOCATION: (261)..(261)
<223> OTHER INFORMATION: G or A or T or C
<220> FEATURE:
<221> NAME/KEY: MISC_FEATURE
<222> LOCATION: (279)..(279)
<223> OTHER INFORMATION: G or A or T or C
<220> FEATURE:
<221> NAME/KEY: MISC_FEATURE
<222> LOCATION: (303)..(303)
<223> OTHER INFORMATION: G or A or T or C
<220> FEATURE:
<221> NAME/KEY: MISC_FEATURE
<222> LOCATION: (320)..(320)
<223> OTHER INFORMATION: G or A or T or C
<220> FEATURE:
<221> NAME/KEY: MISC_FEATURE
<222> LOCATION: (343)..(343)
<223> OTHER INFORMATION: G or A or T or C
<220> FEATURE:
<221> NAME/KEY: MISC_FEATURE
<222> LOCATION: (346)..(346)
<223> OTHER INFORMATION: G or A or T or C
<220> FEATURE:
<221> NAME/KEY: MISC_FEATURE
<222> LOCATION: (348)..(348)
<223> OTHER INFORMATION: G or A or T or C
<220> FEATURE:
<221> NAME/KEY: MISC_FEATURE
<222> LOCATION: (369)..(369)
<223> OTHER INFORMATION: G or A or T or C
<220> FEATURE:
<221> NAME/KEY: MISC_FEATURE
<222> LOCATION: (384)..(384)
<223> OTHER INFORMATION: G or A or T or C
<220> FEATURE:
<221> NAME/KEY: MISC_FEATURE
<222> LOCATION: (399)..(399)
<223> OTHER INFORMATION: G or A or T or C
<220> FEATURE:
<221> NAME/KEY: MISC_FEATURE
<222> LOCATION: (413)..(413)
<223> OTHER INFORMATION: G or A or T or C
<220> FEATURE:
<221> NAME/KEY: MISC_FEATURE
<222> LOCATION: (414)..(414)
<223> OTHER INFORMATION: G or A or T or C
<220> FEATURE:
<221> NAME/KEY: MISC_FEATURE
<222> LOCATION: (431)..(431)
<223> OTHER INFORMATION: G or A or T or C
<220> FEATURE:
```

```
<221> NAME/KEY: MISC_FEATURE
<222> LOCATION: (432)..(432)
<223> OTHER INFORMATION: G or A or T or C
<220> FEATURE:
<221> NAME/KEY: MISC_FEATURE
<222> LOCATION: (435)..(435)
<223> OTHER INFORMATION: G or A or T or C
<220> FEATURE:
<221> NAME/KEY: MISC_FEATURE
<222> LOCATION: (456)..(456)
<223> OTHER INFORMATION: G or A or T or C
<220> FEATURE:
<221> NAME/KEY: MISC_FEATURE
<222> LOCATION: (465)..(465)
<223> OTHER INFORMATION: G or A or T or C
<220> FEATURE:
<221> NAME/KEY: MISC_FEATURE
<222> LOCATION: (471)..(471)
<223> OTHER INFORMATION: G or A or T or C
<220> FEATURE:
<221> NAME/KEY: MISC_FEATURE
<222> LOCATION: (472)..(472)
<223> OTHER INFORMATION: G or A or T or C
<220> FEATURE:
<221> NAME/KEY: MISC_FEATURE
<222> LOCATION: (486)..(486)
<223> OTHER INFORMATION: G or A or T or C
<220> FEATURE:
<221> NAME/KEY: MISC_FEATURE
<222> LOCATION: (495)..(495)
<223> OTHER INFORMATION: G or A or T or C
<220> FEATURE:
<221> NAME/KEY: MISC_FEATURE
<222> LOCATION: (496)..(496)
<223> OTHER INFORMATION: G or A or T or C

<400> SEQUENCE: 48

Met Val Xaa Ile Pro Xaa Arg His Xaa Glu Val Val Ile Ile Gly Ala
1               5                   10                  15

Gly Phe Ala Gly Ile Gly Ala Ala Val Glu Leu Lys Arg Xaa Gly Ile
            20                  25                  30

Asp Asp Phe Val Leu Leu Glu Arg Ala Asp Val Gly Gly Thr Trp
        35                  40                  45

Arg Asp Asn Thr Tyr Pro Gly Ala Ala Cys Asp Val Pro Ser Xaa Leu
50                  55                  60

Tyr Ser Tyr Ser Phe Ala Pro Asn Pro Asn Trp Thr Arg Leu Phe Ala
65                  70                  75                  80

Xaa Gln Pro Glu Ile Tyr Asp Tyr Leu Glu Asp Val Ala Ala Xaa Xaa
                85                  90                  95

Gly Leu Xaa Xaa His Val Arg Phe Gly Val Glu Val Thr Glu Ala Arg
            100                 105                 110

Trp Asp Glu Ser Ala Gln Leu Trp Arg Val Xaa Thr Ala Ser Gly Glu
        115                 120                 125

Leu Thr Ala Xaa Phe Leu Val Ala Ala Thr Gly Pro Leu Ser Xaa Pro
130                 135                 140

Lys Ile Pro Asp Leu Pro Gly Leu Glu Ser Phe Glu Gly Xaa Xaa Phe
145                 150                 155                 160

His Ser Ala Xaa Trp Asn His Asp Leu Asp Leu Arg Gly Glu Arg Val
            165                 170                 175

Ala Val Val Gly Thr Gly Ala Ser Ala Val Gln Phe Val Pro Glu Ile
        180                 185                 190

Ala Asp Xaa Ala Xaa Thr Leu Thr Val Phe Gln Arg Thr Pro Gln Trp
    195                 200                 205

Val Leu Pro Arg Pro Asp Xaa Thr Leu Pro Xaa Ala Xaa Arg Ala Val
210                 215                 220
```

-continued

```
Phe Ser Arg Val Pro Gly Thr Gln Lys Trp Leu Arg Xaa Arg Leu Tyr
225                 230                 235                 240

Gly Ile Phe Glu Ala Leu Gly Ser Gly Phe Val Xaa Pro Xaa Trp Leu
            245                 250                 255

Leu Pro Xaa Xaa Xaa Ala Leu Ala Arg Ala His Leu Arg Arg Gln Val
        260                 265                 270

Arg Asp Pro Glu Leu Arg Xaa Lys Leu Thr Pro Asp Tyr Thr Pro Gly
    275                 280                 285

Cys Lys Arg Met Leu Leu Ser Asn Asp Trp Tyr Pro Ala Leu Xaa Lys
290                 295                 300

Pro Asn Val Ser Leu Val Thr Ser Gly Val Val Glu Val Thr Glu Xaa
305                 310                 315                 320

Gly Val Val Asp Ala Asp Gly Val Glu His Glu Val Asp Thr Ile Ile
                325                 330                 335

Phe Ala Thr Gly Phe His Xaa Thr Asp Xaa Pro Xaa Ala Met Lys Ile
            340                 345                 350

Phe Gly Arg Glu Gly Arg Ser Leu Ala Asp His Trp Asn Gly Ser Ala
        355                 360                 365

Xaa Ala Tyr Leu Gly Thr Ala Val Ser Gly Phe Pro Asn Leu Phe Xaa
    370                 375                 380

Leu Leu Gly Pro Asn Thr Gly Leu Gly His Thr Ser Ile Val Xaa Ile
385                 390                 395                 400

Leu Glu Ala Gln Ala Glu Tyr Ile Ala Ser Ala Leu Xaa Xaa Met Arg
                405                 410                 415

Arg Glu Gly Leu Gly Ala Leu Asp Val Arg Ala Glu Val Gln Xaa Xaa
            420                 425                 430

Phe Asn Xaa Ala Val Gln Glu Arg Leu Ala Thr Thr Val Trp Asn Ala
        435                 440                 445

Gly Gly Cys Ser Ser Trp Tyr Xaa Asp Pro Asp Gly Arg Asn Ser Thr
    450                 455                 460

Xaa Trp Pro Trp Ser Thr Xaa Xaa Phe Arg Ala Arg Thr Arg Arg Phe
465                 470                 475                 480

Asp Pro Ser Asp Tyr Xaa Pro Ser Ser Pro Thr Pro Glu Thr Xaa Xaa
                485                 490                 495

Gly
```

<210> SEQ ID NO 49
<211> LENGTH: 471
<212> TYPE: PRT
<213> ORGANISM: Artificial Sequence
<220> FEATURE:
<223> OTHER INFORMATION: consensus sequence
<220> FEATURE:
<221> NAME/KEY: MISC_FEATURE
<222> LOCATION: (22)..(22)
<223> OTHER INFORMATION: G or A or T or C
<220> FEATURE:
<221> NAME/KEY: MISC_FEATURE
<222> LOCATION: (25)..(25)
<223> OTHER INFORMATION: G or A or T or C
<220> FEATURE:
<221> NAME/KEY: MISC_FEATURE
<222> LOCATION: (28)..(28)
<223> OTHER INFORMATION: G or A or T or C
<220> FEATURE:
<221> NAME/KEY: MISC_FEATURE
<222> LOCATION: (31)..(31)
<223> OTHER INFORMATION: G or A or T or C
<220> FEATURE:
<221> NAME/KEY: MISC_FEATURE

```
<222> LOCATION: (62)..(62)
<223> OTHER INFORMATION: G or A or T or C
<220> FEATURE:
<221> NAME/KEY: MISC_FEATURE
<222> LOCATION: (72)..(72)
<223> OTHER INFORMATION: G or A or T or C
<220> FEATURE:
<221> NAME/KEY: MISC_FEATURE
<222> LOCATION: (75)..(75)
<223> OTHER INFORMATION: G or A or T or C
<220> FEATURE:
<221> NAME/KEY: MISC_FEATURE
<222> LOCATION: (85)..(85)
<223> OTHER INFORMATION: G or A or T or C
<220> FEATURE:
<221> NAME/KEY: MISC_FEATURE
<222> LOCATION: (86)..(86)
<223> OTHER INFORMATION: G or A or T or C
<220> FEATURE:
<221> NAME/KEY: MISC_FEATURE
<222> LOCATION: (93)..(93)
<223> OTHER INFORMATION: G or A or T or C
<220> FEATURE:
<221> NAME/KEY: MISC_FEATURE
<222> LOCATION: (95)..(95)
<223> OTHER INFORMATION: G or A or T or C
<220> FEATURE:
<221> NAME/KEY: MISC_FEATURE
<222> LOCATION: (99)..(99)
<223> OTHER INFORMATION: G or A or T or C
<220> FEATURE:
<221> NAME/KEY: MISC_FEATURE
<222> LOCATION: (102)..(102)
<223> OTHER INFORMATION: G or A or T or C
<220> FEATURE:
<221> NAME/KEY: MISC_FEATURE
<222> LOCATION: (111)..(111)
<223> OTHER INFORMATION: G or A or T or C
<220> FEATURE:
<221> NAME/KEY: MISC_FEATURE
<222> LOCATION: (112)..(112)
<223> OTHER INFORMATION: G or A or T or C
<220> FEATURE:
<221> NAME/KEY: MISC_FEATURE
<222> LOCATION: (113)..(113)
<223> OTHER INFORMATION: G or A or T or C
<220> FEATURE:
<221> NAME/KEY: MISC_FEATURE
<222> LOCATION: (115)..(115)
<223> OTHER INFORMATION: G or A or T or C
<220> FEATURE:
<221> NAME/KEY: MISC_FEATURE
<222> LOCATION: (123)..(123)
<223> OTHER INFORMATION: G or A or T or C
<220> FEATURE:
<221> NAME/KEY: MISC_FEATURE
<222> LOCATION: (124)..(124)
<223> OTHER INFORMATION: G or A or T or C
<220> FEATURE:
<221> NAME/KEY: MISC_FEATURE
<222> LOCATION: (125)..(125)
<223> OTHER INFORMATION: G or A or T or C
<220> FEATURE:
<221> NAME/KEY: MISC_FEATURE
<222> LOCATION: (131)..(131)
<223> OTHER INFORMATION: G or A or T or C
<220> FEATURE:
<221> NAME/KEY: MISC_FEATURE
<222> LOCATION: (137)..(137)
<223> OTHER INFORMATION: G or A or T or C
<220> FEATURE:
<221> NAME/KEY: MISC_FEATURE
<222> LOCATION: (138)..(138)
<223> OTHER INFORMATION: G or A or T or C
<220> FEATURE:
<221> NAME/KEY: MISC_FEATURE
<222> LOCATION: (158)..(158)
<223> OTHER INFORMATION: G or A or T or C
<220> FEATURE:
```

-continued

```
<221> NAME/KEY: MISC_FEATURE
<222> LOCATION: (160)..(160)
<223> OTHER INFORMATION: G or A or T or C
<220> FEATURE:
<221> NAME/KEY: MISC_FEATURE
<222> LOCATION: (166)..(166)
<223> OTHER INFORMATION: G or A or T or C
<220> FEATURE:
<221> NAME/KEY: MISC_FEATURE
<222> LOCATION: (170)..(170)
<223> OTHER INFORMATION: G or A or T or C
<220> FEATURE:
<221> NAME/KEY: MISC_FEATURE
<222> LOCATION: (188)..(188)
<223> OTHER INFORMATION: G or A or T or C
<220> FEATURE:
<221> NAME/KEY: MISC_FEATURE
<222> LOCATION: (193)..(193)
<223> OTHER INFORMATION: G or A or T or C
<220> FEATURE:
<221> NAME/KEY: MISC_FEATURE
<222> LOCATION: (195)..(195)
<223> OTHER INFORMATION: G or A or T or C
<220> FEATURE:
<221> NAME/KEY: MISC_FEATURE
<222> LOCATION: (196)..(196)
<223> OTHER INFORMATION: G or A or T or C
<220> FEATURE:
<221> NAME/KEY: MISC_FEATURE
<222> LOCATION: (197)..(197)
<223> OTHER INFORMATION: G or A or T or C
<220> FEATURE:
<221> NAME/KEY: MISC_FEATURE
<222> LOCATION: (199)..(199)
<223> OTHER INFORMATION: G or A or T or C
<220> FEATURE:
<221> NAME/KEY: MISC_FEATURE
<222> LOCATION: (221)..(221)
<223> OTHER INFORMATION: G or A or T or C
<220> FEATURE:
<221> NAME/KEY: MISC_FEATURE
<222> LOCATION: (226)..(226)
<223> OTHER INFORMATION: G or A or T or C
<220> FEATURE:
<221> NAME/KEY: MISC_FEATURE
<222> LOCATION: (228)..(228)
<223> OTHER INFORMATION: G or A or T or C
<220> FEATURE:
<221> NAME/KEY: MISC_FEATURE
<222> LOCATION: (229)..(229)
<223> OTHER INFORMATION: G or A or T or C
<220> FEATURE:
<221> NAME/KEY: MISC_FEATURE
<222> LOCATION: (230)..(230)
<223> OTHER INFORMATION: G or A or T or C
<220> FEATURE:
<221> NAME/KEY: MISC_FEATURE
<222> LOCATION: (231)..(231)
<223> OTHER INFORMATION: G or A or T or C
<220> FEATURE:
<221> NAME/KEY: MISC_FEATURE
<222> LOCATION: (232)..(232)
<223> OTHER INFORMATION: G or A or T or C
<220> FEATURE:
<221> NAME/KEY: MISC_FEATURE
<222> LOCATION: (235)..(235)
<223> OTHER INFORMATION: G or A or T or C
<220> FEATURE:
<221> NAME/KEY: MISC_FEATURE
<222> LOCATION: (236)..(236)
<223> OTHER INFORMATION: G or A or T or C
<220> FEATURE:
<221> NAME/KEY: MISC_FEATURE
<222> LOCATION: (240)..(240)
<223> OTHER INFORMATION: G or A or T or C
<220> FEATURE:
<221> NAME/KEY: MISC_FEATURE
<222> LOCATION: (244)..(244)
<223> OTHER INFORMATION: G or A or T or C
```

-continued

```
<220> FEATURE:
<221> NAME/KEY: MISC_FEATURE
<222> LOCATION: (249)..(249)
<223> OTHER INFORMATION: G or A or T or C
<220> FEATURE:
<221> NAME/KEY: MISC_FEATURE
<222> LOCATION: (262)..(262)
<223> OTHER INFORMATION: G or A or T or C
<220> FEATURE:
<221> NAME/KEY: MISC_FEATURE
<222> LOCATION: (264)..(264)
<223> OTHER INFORMATION: G or A or T or C
<220> FEATURE:
<221> NAME/KEY: MISC_FEATURE
<222> LOCATION: (272)..(272)
<223> OTHER INFORMATION: G or A or T or C
<220> FEATURE:
<221> NAME/KEY: MISC_FEATURE
<222> LOCATION: (289)..(289)
<223> OTHER INFORMATION: G or A or T or C
<220> FEATURE:
<221> NAME/KEY: MISC_FEATURE
<222> LOCATION: (296)..(296)
<223> OTHER INFORMATION: G or A or T or C
<220> FEATURE:
<221> NAME/KEY: MISC_FEATURE
<222> LOCATION: (298)..(298)
<223> OTHER INFORMATION: G or A or T or C
<220> FEATURE:
<221> NAME/KEY: MISC_FEATURE
<222> LOCATION: (310)..(310)
<223> OTHER INFORMATION: G or A or T or C
<220> FEATURE:
<221> NAME/KEY: MISC_FEATURE
<222> LOCATION: (317)..(317)
<223> OTHER INFORMATION: G or A or T or C
<220> FEATURE:
<221> NAME/KEY: MISC_FEATURE
<222> LOCATION: (330)..(330)
<223> OTHER INFORMATION: G or A or T or C
<220> FEATURE:
<221> NAME/KEY: MISC_FEATURE
<222> LOCATION: (331)..(331)
<223> OTHER INFORMATION: G or A or T or C
<220> FEATURE:
<221> NAME/KEY: MISC_FEATURE
<222> LOCATION: (332)..(332)
<223> OTHER INFORMATION: G or A or T or C
<220> FEATURE:
<221> NAME/KEY: MISC_FEATURE
<222> LOCATION: (338)..(338)
<223> OTHER INFORMATION: G or A or T or C
<220> FEATURE:
<221> NAME/KEY: MISC_FEATURE
<222> LOCATION: (339)..(339)
<223> OTHER INFORMATION: G or A or T or C
<220> FEATURE:
<221> NAME/KEY: MISC_FEATURE
<222> LOCATION: (347)..(347)
<223> OTHER INFORMATION: G or A or T or C
<220> FEATURE:
<221> NAME/KEY: MISC_FEATURE
<222> LOCATION: (348)..(348)
<223> OTHER INFORMATION: G or A or T or C
<220> FEATURE:
<221> NAME/KEY: MISC_FEATURE
<222> LOCATION: (350)..(350)
<223> OTHER INFORMATION: G or A or T or C
<220> FEATURE:
<221> NAME/KEY: MISC_FEATURE
<222> LOCATION: (356)..(356)
<223> OTHER INFORMATION: G or A or T or C
<220> FEATURE:
<221> NAME/KEY: MISC_FEATURE
<222> LOCATION: (357)..(357)
<223> OTHER INFORMATION: G or A or T or C
<220> FEATURE:
<221> NAME/KEY: MISC_FEATURE
<222> LOCATION: (358)..(358)
```

```
<223> OTHER INFORMATION: G or A or T or C
<220> FEATURE:
<221> NAME/KEY: MISC_FEATURE
<222> LOCATION: (359)..(359)
<223> OTHER INFORMATION: G or A or T or C
<220> FEATURE:
<221> NAME/KEY: MISC_FEATURE
<222> LOCATION: (368)..(368)
<223> OTHER INFORMATION: G or A or T or C
<220> FEATURE:
<221> NAME/KEY: MISC_FEATURE
<222> LOCATION: (384)..(384)
<223> OTHER INFORMATION: G or A or T or C
<220> FEATURE:
<221> NAME/KEY: MISC_FEATURE
<222> LOCATION: (392)..(392)
<223> OTHER INFORMATION: G or A or T or C
<220> FEATURE:
<221> NAME/KEY: MISC_FEATURE
<222> LOCATION: (393)..(393)
<223> OTHER INFORMATION: G or A or T or C
<220> FEATURE:
<221> NAME/KEY: MISC_FEATURE
<222> LOCATION: (395)..(395)
<223> OTHER INFORMATION: G or A or T or C
<220> FEATURE:
<221> NAME/KEY: MISC_FEATURE
<222> LOCATION: (396)..(396)
<223> OTHER INFORMATION: G or A or T or C
<220> FEATURE:
<221> NAME/KEY: MISC_FEATURE
<222> LOCATION: (400)..(400)
<223> OTHER INFORMATION: G or A or T or C
<220> FEATURE:
<221> NAME/KEY: MISC_FEATURE
<222> LOCATION: (401)..(401)
<223> OTHER INFORMATION: G or A or T or C
<220> FEATURE:
<221> NAME/KEY: MISC_FEATURE
<222> LOCATION: (402)..(402)
<223> OTHER INFORMATION: G or A or T or C
<220> FEATURE:
<221> NAME/KEY: MISC_FEATURE
<222> LOCATION: (403)..(403)
<223> OTHER INFORMATION: G or A or T or C
<220> FEATURE:
<221> NAME/KEY: MISC_FEATURE
<222> LOCATION: (404)..(404)
<223> OTHER INFORMATION: G or A or T or C
<220> FEATURE:
<221> NAME/KEY: MISC_FEATURE
<222> LOCATION: (407)..(407)
<223> OTHER INFORMATION: G or A or T or C
<220> FEATURE:
<221> NAME/KEY: MISC_FEATURE
<222> LOCATION: (410)..(410)
<223> OTHER INFORMATION: G or A or T or C
<220> FEATURE:
<221> NAME/KEY: MISC_FEATURE
<222> LOCATION: (411)..(411)
<223> OTHER INFORMATION: G or A or T or C
<220> FEATURE:
<221> NAME/KEY: MISC_FEATURE
<222> LOCATION: (412)..(412)
<223> OTHER INFORMATION: G or A or T or C
<220> FEATURE:
<221> NAME/KEY: MISC_FEATURE
<222> LOCATION: (413)..(413)
<223> OTHER INFORMATION: G or A or T or C
<220> FEATURE:
<221> NAME/KEY: MISC_FEATURE
<222> LOCATION: (421)..(421)
<223> OTHER INFORMATION: G or A or T or C
<220> FEATURE:
<221> NAME/KEY: MISC_FEATURE
<222> LOCATION: (423)..(423)
<223> OTHER INFORMATION: G or A or T or C
<220> FEATURE:
<221> NAME/KEY: MISC_FEATURE
```

-continued

```
<222> LOCATION: (424)..(424)
<223> OTHER INFORMATION: G or A or T or C
<220> FEATURE:
<221> NAME/KEY: MISC_FEATURE
<222> LOCATION: (426)..(426)
<223> OTHER INFORMATION: G or A or T or C
<220> FEATURE:
<221> NAME/KEY: MISC_FEATURE
<222> LOCATION: (429)..(429)
<223> OTHER INFORMATION: G or A or T or C
<220> FEATURE:
<221> NAME/KEY: MISC_FEATURE
<222> LOCATION: (432)..(432)
<223> OTHER INFORMATION: G or A or T or C
<220> FEATURE:
<221> NAME/KEY: MISC_FEATURE
<222> LOCATION: (434)..(434)
<223> OTHER INFORMATION: G or A or T or C
<220> FEATURE:
<221> NAME/KEY: MISC_FEATURE
<222> LOCATION: (435)..(435)
<223> OTHER INFORMATION: G or A or T or C
<220> FEATURE:
<221> NAME/KEY: MISC_FEATURE
<222> LOCATION: (437)..(437)
<223> OTHER INFORMATION: G or A or T or C
<220> FEATURE:
<221> NAME/KEY: MISC_FEATURE
<222> LOCATION: (438)..(438)
<223> OTHER INFORMATION: G or A or T or C
<220> FEATURE:
<221> NAME/KEY: MISC_FEATURE
<222> LOCATION: (439)..(439)
<223> OTHER INFORMATION: G or A or T or C
<220> FEATURE:
<221> NAME/KEY: MISC_FEATURE
<222> LOCATION: (440)..(440)
<223> OTHER INFORMATION: G or A or T or C
<220> FEATURE:
<221> NAME/KEY: MISC_FEATURE
<222> LOCATION: (443)..(443)
<223> OTHER INFORMATION: G or A or T or C
<220> FEATURE:
<221> NAME/KEY: MISC_FEATURE
<222> LOCATION: (444)..(444)
<223> OTHER INFORMATION: G or A or T or C
<220> FEATURE:
<221> NAME/KEY: MISC_FEATURE
<222> LOCATION: (447)..(447)
<223> OTHER INFORMATION: G or A or T or C
<220> FEATURE:
<221> NAME/KEY: MISC_FEATURE
<222> LOCATION: (449)..(449)
<223> OTHER INFORMATION: G or A or T or C
<220> FEATURE:
<221> NAME/KEY: MISC_FEATURE
<222> LOCATION: (450)..(450)
<223> OTHER INFORMATION: G or A or T or C
<220> FEATURE:
<221> NAME/KEY: MISC_FEATURE
<222> LOCATION: (451)..(451)
<223> OTHER INFORMATION: G or A or T or C
<220> FEATURE:
<221> NAME/KEY: MISC_FEATURE
<222> LOCATION: (452)..(452)
<223> OTHER INFORMATION: G or A or T or C
<220> FEATURE:
<221> NAME/KEY: MISC_FEATURE
<222> LOCATION: (453)..(453)
<223> OTHER INFORMATION: G or A or T or C
<220> FEATURE:
<221> NAME/KEY: MISC_FEATURE
<222> LOCATION: (454)..(454)
<223> OTHER INFORMATION: G or A or T or C
<220> FEATURE:
<221> NAME/KEY: MISC_FEATURE
<222> LOCATION: (455)..(455)
<223> OTHER INFORMATION: G or A or T or C
<220> FEATURE:
```

```
<221> NAME/KEY: MISC_FEATURE
<222> LOCATION: (456)..(456)
<223> OTHER INFORMATION: G or A or T or C
<220> FEATURE:
<221> NAME/KEY: MISC_FEATURE
<222> LOCATION: (457)..(457)
<223> OTHER INFORMATION: G or A or T or C
<220> FEATURE:
<221> NAME/KEY: MISC_FEATURE
<222> LOCATION: (458)..(458)
<223> OTHER INFORMATION: G or A or T or C
<220> FEATURE:
<221> NAME/KEY: MISC_FEATURE
<222> LOCATION: (459)..(459)
<223> OTHER INFORMATION: G or A or T or C
<220> FEATURE:
<221> NAME/KEY: MISC_FEATURE
<222> LOCATION: (460)..(460)
<223> OTHER INFORMATION: G or A or T or C
<220> FEATURE:
<221> NAME/KEY: MISC_FEATURE
<222> LOCATION: (464)..(464)
<223> OTHER INFORMATION: G or A or T or C
<220> FEATURE:
<221> NAME/KEY: MISC_FEATURE
<222> LOCATION: (465)..(465)
<223> OTHER INFORMATION: G or A or T or C
<220> FEATURE:
<221> NAME/KEY: MISC_FEATURE
<222> LOCATION: (466)..(466)
<223> OTHER INFORMATION: G or A or T or C
<220> FEATURE:
<221> NAME/KEY: MISC_FEATURE
<222> LOCATION: (468)..(468)
<223> OTHER INFORMATION: G or A or T or C
<220> FEATURE:
<221> NAME/KEY: MISC_FEATURE
<222> LOCATION: (469)..(469)
<223> OTHER INFORMATION: G or A or T or C
<220> FEATURE:
<221> NAME/KEY: MISC_FEATURE
<222> LOCATION: (470)..(470)
<223> OTHER INFORMATION: G or A or T or C
<220> FEATURE:
<221> NAME/KEY: MISC_FEATURE
<222> LOCATION: (471)..(471)
<223> OTHER INFORMATION: G or A or T or C

<400> SEQUENCE: 49

Met Ser Thr Glu His Leu Asp Val Leu Ile Ile Gly Ala Gly Leu Ser
1               5                   10                  15

Gly Ile Gly Ala Ala Xaa Arg Leu Xaa Arg Glu Xaa Gly Ile Xaa Phe
            20                  25                  30

Ala Ile Leu Glu Ala Arg Asp Asn Val Gly Gly Thr Trp Asp Leu Phe
        35                  40                  45

Asn Tyr Pro Gly Ile Arg Ser Asp Ser Asp His Leu Thr Xaa Gly Lys
50                  55                  60

Gly Ala Phe Arg Pro Phe Pro Xaa Ala Lys Xaa Leu Ala Asp Gly Pro
65                  70                  75                  80

Ser His Glu Leu Xaa Xaa Tyr Val Arg Asp Thr Ala Xaa Glu Xaa Gly
                85                  90                  95

Leu Arg Xaa His Ile Xaa Phe Gly Thr Lys Val Val Ala Ala Xaa Xaa
            100                 105                 110

Xaa Ala Xaa Ser Leu Trp Thr Val Thr Val Xaa Xaa Xaa Gly Glu Thr
        115                 120                 125

Glu Val Xaa Thr Tyr Asn Val Leu Xaa Xaa Ala Asn Gly Tyr Tyr Ser
130                 135                 140

Tyr Asp Lys Gly Asn Ile Pro Asp Phe Pro Gly Glu Phe Xaa Gly Xaa
145                 150                 155                 160
```

-continued

```
Leu Val His Pro Gln Xaa Tyr Pro Glu Xaa Leu Asp Tyr Arg Gly Lys
            165                 170                 175
Lys Val Val Ile Gly Ser Gly Ala Ser Gly Xaa Thr Leu Ala Pro
        180                 185                 190
Xaa Met Xaa Xaa Xaa Ala Xaa His Val Thr Met Leu Gln Arg Ser Gly
        195                 200                 205
Thr Tyr Ile Ala Leu Pro Ser Asp Ala Val Val Pro Xaa Gln Leu Ala
    210                 215                 220
Gly Xaa Arg Xaa Xaa Xaa Xaa Leu Gln Xaa Xaa Gln Leu Arg Xaa
225                 230                 235                 240
Pro Pro Trp Xaa Ala Lys Arg Leu Xaa Leu Leu Ile Arg Arg Gln
            245                 250                 255
Leu Gly Lys Asn Val Xaa Leu Xaa Gly Phe Pro Thr Pro Ser Tyr Xaa
            260                 265                 270
Pro Trp Asp Gln His Leu Cys Val Val Pro Asn Gly Asp Leu Leu Lys
        275                 280                 285
Xaa Leu Gly Ser Gly Asp Ala Xaa Ile Xaa Thr Asp Ile Asp Thr Phe
290                 295                 300
Thr Gly Lys Gly Val Xaa Phe Ala Ser Gly Arg Glu Xaa Asp Ala Asp
305                 310                 315                 320
Val Val Val Thr Ala Thr Gly Leu Asn Xaa Xaa Xaa Gly Gly Pro Phe
                325                 330                 335
Ile Xaa Xaa Asp Gly Leu Leu Val Asp Leu Xaa Xaa Arg Xaa Ala Leu
            340                 345                 350
Phe Tyr Lys Xaa Xaa Xaa Xaa Ser Asp Asn Leu Asn Phe Leu Gly Xaa
            355                 360                 365
Val Gly Tyr Thr Asn Ala Ser Trp Thr Leu Arg Ala Asp Leu Ala Xaa
        370                 375                 380
Leu Val Ala Cys Arg Leu Leu Xaa Xaa Met Xaa Xaa Arg Ser Ala Xaa
385                 390                 395                 400
Xaa Xaa Xaa Xaa His Ala Xaa Ala Glu Xaa Xaa Xaa Xaa Leu Leu Ala
                405                 410                 415
Ser Gly Tyr Lys Xaa Arg Xaa Xaa Gly Xaa Met Pro Xaa Gln Gly Xaa
            420                 425                 430
Lys Xaa Xaa Trp Xaa Xaa Xaa Xaa Asn Tyr Xaa Xaa Asp Arg Xaa Leu
        435                 440                 445
Xaa Xaa Xaa Xaa Xaa Xaa Xaa Xaa Xaa Xaa Xaa Phe Ser Lys Xaa
450                 455                 460
Xaa Xaa Ala Xaa Xaa Xaa Xaa
465                 470

<210> SEQ ID NO 50
<211> LENGTH: 19
<212> TYPE: DNA
<213> ORGANISM: Artificial Sequence
<220> FEATURE:
<223> OTHER INFORMATION: Primer HK12

<400> SEQUENCE: 50
gagtttgatc ctggctcag                                                19

<210> SEQ ID NO 51
<211> LENGTH: 18
<212> TYPE: DNA
<213> ORGANISM: Artificial Sequence
<220> FEATURE:
```

```
<223> OTHER INFORMATION: Primer

<400> SEQUENCE: 51
caggmgccgc ggtaatwc                                              18

<210> SEQ ID NO 52
<211> LENGTH: 18
<212> TYPE: DNA
<213> ORGANISM: Artificial Sequence
<220> FEATURE:
<223> OTHER INFORMATION: Primer HK21

<400> SEQUENCE: 52
gctgcctccc gtaggagt                                              18

<210> SEQ ID NO 53
<211> LENGTH: 19
<212> TYPE: DNA
<213> ORGANISM: Artificial Sequence
<220> FEATURE:
<223> OTHER INFORMATION: Primer

<400> SEQUENCE: 53
ctaccagggt aactaatcc                                             19

<210> SEQ ID NO 54
<211> LENGTH: 15
<212> TYPE: DNA
<213> ORGANISM: Artificial Sequence
<220> FEATURE:
<223> OTHER INFORMATION: Primer

<400> SEQUENCE: 54
acgggcggtg tgtac                                                 15

<210> SEQ ID NO 55
<211> LENGTH: 20
<212> TYPE: DNA
<213> ORGANISM: Artificial Sequence
<220> FEATURE:
<223> OTHER INFORMATION: Primer

<400> SEQUENCE: 55
cacgagctga cgacagccat                                            20

<210> SEQ ID NO 56
<211> LENGTH: 16
<212> TYPE: DNA
<213> ORGANISM: Artificial Sequence
<220> FEATURE:
<223> OTHER INFORMATION: Primer HK13

<400> SEQUENCE: 56
taccttgtta cgactt                                                16

<210> SEQ ID NO 57
<211> LENGTH: 18
<212> TYPE: DNA
<213> ORGANISM: Artificial Sequence
<220> FEATURE:
<223> OTHER INFORMATION: Primer

<400> SEQUENCE: 57
gwattaccgc ggckgctg                                              18
```

<210> SEQ ID NO 58
<211> LENGTH: 19
<212> TYPE: DNA
<213> ORGANISM: Artificial Sequence
<220> FEATURE:
<223> OTHER INFORMATION: Primer

<400> SEQUENCE: 58
ggattagata ccctggtag					19

<210> SEQ ID NO 59
<211> LENGTH: 20
<212> TYPE: DNA
<213> ORGANISM: Artificial Sequence
<220> FEATURE:
<223> OTHER INFORMATION: Primer

<400> SEQUENCE: 59
atggctgtcg tcagctcgtg					20

<210> SEQ ID NO 60
<211> LENGTH: 16
<212> TYPE: DNA
<213> ORGANISM: Artificial Sequence
<220> FEATURE:
<223> OTHER INFORMATION: Primer HK15

<400> SEQUENCE: 60
gcccccgyca attcct					16

<210> SEQ ID NO 61
<211> LENGTH: 17
<212> TYPE: DNA
<213> ORGANISM: Artificial Sequence
<220> FEATURE:
<223> OTHER INFORMATION: Primer HK14

<400> SEQUENCE: 61
gtgccagcag ymgcggt					17

<210> SEQ ID NO 62
<211> LENGTH: 16
<212> TYPE: DNA
<213> ORGANISM: Artificial Sequence
<220> FEATURE:
<223> OTHER INFORMATION: Primer JCR15

<400> SEQUENCE: 62
gccagcagcc gcggta					16

<210> SEQ ID NO 63
<211> LENGTH: 17
<212> TYPE: DNA
<213> ORGANISM: Artificial Sequence
<220> FEATURE:
<223> OTHER INFORMATION: Primer

<400> SEQUENCE: 63
cggagcagat cgavvvv					17

<210> SEQ ID NO 64
<211> LENGTH: 17
<212> TYPE: DNA
<213> ORGANISM: Artificial Sequence
<220> FEATURE:
<223> OTHER INFORMATION: M13 Reverse Primer

```
<400> SEQUENCE: 64
caggaaacag ctatgac                                                  17

<210> SEQ ID NO 65
<211> LENGTH: 16
<212> TYPE: DNA
<213> ORGANISM: Artificial Sequence
<220> FEATURE:
<223> OTHER INFORMATION: M13 (-20) Forward Primer

<400> SEQUENCE: 65
ctggccgtcg ttttac                                                   16

<210> SEQ ID NO 66
<211> LENGTH: 34
<212> TYPE: DNA
<213> ORGANISM: Acinetobacter sp. NCIB 9871

<400> SEQUENCE: 66
gagtctgagc atatgtcaca aaaaatggat tttg                               34

<210> SEQ ID NO 67
<211> LENGTH: 39
<212> TYPE: DNA
<213> ORGANISM: Acinetobacter sp. NCIB 9871

<400> SEQUENCE: 67
gagtctgagg gatccttagg cattggcagg ttgcttgat                          39

<210> SEQ ID NO 68
<211> LENGTH: 25
<212> TYPE: DNA
<213> ORGANISM: Brevibacterium sp. HCU

<400> SEQUENCE: 68
atgccaatta cacaacaact tgacc                                         25

<210> SEQ ID NO 69
<211> LENGTH: 23
<212> TYPE: DNA
<213> ORGANISM: Brevibacterium sp. HCU

<400> SEQUENCE: 69
ctatttcata cccgccgatt cac                                           23

<210> SEQ ID NO 70
<211> LENGTH: 22
<212> TYPE: DNA
<213> ORGANISM: Brevibacterium sp. HCU

<400> SEQUENCE: 70
atgacgtcaa ccatgcctgc ac                                            22

<210> SEQ ID NO 71
<211> LENGTH: 21
<212> TYPE: DNA
<213> ORGANISM: Brevibacterium sp. HCU

<400> SEQUENCE: 71
cacttaagtc gcattcagcc c                                             21

<210> SEQ ID NO 72
<211> LENGTH: 21
```

-continued

```
<212> TYPE: DNA
<213> ORGANISM: Acinetobacter sp. SE19

<400> SEQUENCE: 72
atggattttg atgctatcgt g                                          21

<210> SEQ ID NO 73
<211> LENGTH: 19
<212> TYPE: DNA
<213> ORGANISM: Acinetobacter sp. SE19

<400> SEQUENCE: 73
ggcattggca ggttgcttg                                             19

<210> SEQ ID NO 74
<211> LENGTH: 22
<212> TYPE: DNA
<213> ORGANISM: Arthrobacter sp. BP2

<400> SEQUENCE: 74
atgactgcac agaacacttt cc                                         22

<210> SEQ ID NO 75
<211> LENGTH: 18
<212> TYPE: DNA
<213> ORGANISM: Arthrobacter sp. BP2

<400> SEQUENCE: 75
tcaaagccgc ggtatccg                                              18

<210> SEQ ID NO 76
<211> LENGTH: 23
<212> TYPE: DNA
<213> ORGANISM: Rhodococcus sp. phi1

<400> SEQUENCE: 76
atgactgcac agatctcacc cac                                        23

<210> SEQ ID NO 77
<211> LENGTH: 22
<212> TYPE: DNA
<213> ORGANISM: Rhodococcus sp. phi1

<400> SEQUENCE: 77
tcaggcggtc accgggacag cg                                         22

<210> SEQ ID NO 78
<211> LENGTH: 23
<212> TYPE: DNA
<213> ORGANISM: Rhodococcus sp. phi2

<400> SEQUENCE: 78
atgaccgcac agaccatcca cac                                        23

<210> SEQ ID NO 79
<211> LENGTH: 20
<212> TYPE: DNA
<213> ORGANISM: Rhodococcus sp. phi2

<400> SEQUENCE: 79
tcagaccgtg accatctcgg                                            20

<210> SEQ ID NO 80
```

```
<211> LENGTH: 21
<212> TYPE: DNA
<213> ORGANISM: Brachymonas sp. CHX

<400> SEQUENCE: 80
atgtcttcct cgccaagcag c                                              21

<210> SEQ ID NO 81
<211> LENGTH: 21
<212> TYPE: DNA
<213> ORGANISM: Brachymonas sp. CHX

<400> SEQUENCE: 81
cagtggttgg aacgcaaagc c                                              21

<210> SEQ ID NO 82
<211> LENGTH: 23
<212> TYPE: DNA
<213> ORGANISM: Rhodococcus erythropolis AN12

<400> SEQUENCE: 82
atgagcacag agggcaagta cgc                                            23

<210> SEQ ID NO 83
<211> LENGTH: 25
<212> TYPE: DNA
<213> ORGANISM: Rhodococcus erythropolis AN12

<400> SEQUENCE: 83
tcagtccttg ttcacgtagt aggcc                                          25

<210> SEQ ID NO 84
<211> LENGTH: 23
<212> TYPE: DNA
<213> ORGANISM: Rhodococcus erythropolis AN12

<400> SEQUENCE: 84
atggtcgaca tcgacccaac ctc                                            23

<210> SEQ ID NO 85
<211> LENGTH: 24
<212> TYPE: DNA
<213> ORGANISM: Rhodococcus erythropolis AN12

<400> SEQUENCE: 85
ttatcggctc ctcacggttt ctcg                                           24

<210> SEQ ID NO 86
<211> LENGTH: 24
<212> TYPE: DNA
<213> ORGANISM: Rhodococcus erythropolis AN12

<400> SEQUENCE: 86
atgaccgatc ctgacttctc cacc                                           24

<210> SEQ ID NO 87
<211> LENGTH: 24
<212> TYPE: DNA
<213> ORGANISM: Rhodococcus erythropolis AN12

<400> SEQUENCE: 87
tcatgcgtgc accgcactgt tcag                                           24
```

```
<210> SEQ ID NO 88
<211> LENGTH: 23
<212> TYPE: DNA
<213> ORGANISM: Rhodococcus erythropolis AN12

<400> SEQUENCE: 88
atgagcccct ccccttgcc gag                                          23

<210> SEQ ID NO 89
<211> LENGTH: 24
<212> TYPE: DNA
<213> ORGANISM: Rhodococcus erythropolis AN12

<400> SEQUENCE: 89
tcatgcgcga tccgccttct cgag                                        24

<210> SEQ ID NO 90
<211> LENGTH: 24
<212> TYPE: DNA
<213> ORGANISM: Rhodococcus erythropolis AN12

<400> SEQUENCE: 90
gtgaacaacg aatctgacca cttc                                        24

<210> SEQ ID NO 91
<211> LENGTH: 23
<212> TYPE: DNA
<213> ORGANISM: Rhodococcus erythropolis AN12

<400> SEQUENCE: 91
tcatgcggtg tactccggtt ccg                                         23

<210> SEQ ID NO 92
<211> LENGTH: 22
<212> TYPE: DNA
<213> ORGANISM: Rhodococcus erythropolis AN12

<400> SEQUENCE: 92
atgagcaccg aacacctcga tg                                          22

<210> SEQ ID NO 93
<211> LENGTH: 23
<212> TYPE: DNA
<213> ORGANISM: Rhodococcus erythropolis AN12

<400> SEQUENCE: 93
tcaactcttg ctcggtaccg gcg                                         23

<210> SEQ ID NO 94
<211> LENGTH: 26
<212> TYPE: DNA
<213> ORGANISM: Rhodococcus erythropolis AN12

<400> SEQUENCE: 94
atgacagacg aattcgacgt agtgat                                      26

<210> SEQ ID NO 95
<211> LENGTH: 23
<212> TYPE: DNA
<213> ORGANISM: Rhodococcus erythropolis AN12

<400> SEQUENCE: 95
tcagctctgg ttcacaggga cgg                                         23
```

```
<210> SEQ ID NO 96
<211> LENGTH: 23
<212> TYPE: DNA
<213> ORGANISM: Rhodococcus erythropolis AN12

<400> SEQUENCE: 96
atggcggaga tagtcaatgg tcc                                           23

<210> SEQ ID NO 97
<211> LENGTH: 22
<212> TYPE: DNA
<213> ORGANISM: Rhodococcus erythropolis AN12

<400> SEQUENCE: 97
tcaccctcgc gcggtcggag tc                                            22

<210> SEQ ID NO 98
<211> LENGTH: 26
<212> TYPE: DNA
<213> ORGANISM: Rhodococcus erythropolis AN12

<400> SEQUENCE: 98
gtgaagcttc ccgaacatgt cgaaac                                        26

<210> SEQ ID NO 99
<211> LENGTH: 25
<212> TYPE: DNA
<213> ORGANISM: Rhodococcus erythropolis AN12

<400> SEQUENCE: 99
tcatgcctgg acgctttcga tcttg                                         25

<210> SEQ ID NO 100
<211> LENGTH: 25
<212> TYPE: DNA
<213> ORGANISM: Rhodococcus erythropolis AN12

<400> SEQUENCE: 100
atgacacagc atgtcgacgt actga                                         25

<210> SEQ ID NO 101
<211> LENGTH: 24
<212> TYPE: DNA
<213> ORGANISM: Rhodococcus erythropolis AN12

<400> SEQUENCE: 101
ctatgcgctg gcgaccttgc tatc                                          24

<210> SEQ ID NO 102
<211> LENGTH: 25
<212> TYPE: DNA
<213> ORGANISM: Rhodococcus erythropolis AN12

<400> SEQUENCE: 102
atgtcatcac gggtcaacga cggcc                                         25

<210> SEQ ID NO 103
<211> LENGTH: 24
<212> TYPE: DNA
<213> ORGANISM: Rhodococcus erythropolis AN12

<400> SEQUENCE: 103
tcatcctttg cctgtcgtca gtgc                                          24
```

```
<210> SEQ ID NO 104
<211> LENGTH: 24
<212> TYPE: DNA
<213> ORGANISM: Rhodococcus erythropolis AN12

<400> SEQUENCE: 104
atgactacac aaaaggccct gacc                                    24

<210> SEQ ID NO 105
<211> LENGTH: 22
<212> TYPE: DNA
<213> ORGANISM: Rhodococcus erythropolis AN12

<400> SEQUENCE: 105
tcaggcgtcg acggtgtcgg cc                                      22

<210> SEQ ID NO 106
<211> LENGTH: 25
<212> TYPE: DNA
<213> ORGANISM: Rhodococcus erythropolis AN12

<400> SEQUENCE: 106
atgacaacta ccgaatccag aactc                                   25

<210> SEQ ID NO 107
<211> LENGTH: 26
<212> TYPE: DNA
<213> ORGANISM: Rhodococcus erythropolis AN12

<400> SEQUENCE: 107
tcagcgcaga ttgaagccct tgtatc                                  26

<210> SEQ ID NO 108
<211> LENGTH: 20
<212> TYPE: DNA
<213> ORGANISM: Artificial Sequence
<220> FEATURE:
<223> OTHER INFORMATION: Primer A102FI for screening Arthrobacter sp.
      BP2 library

<400> SEQUENCE: 108
gcacacctac atcacccagc                                         20

<210> SEQ ID NO 109
<211> LENGTH: 17
<212> TYPE: DNA
<213> ORGANISM: Artificial Sequence
<220> FEATURE:
<223> OTHER INFORMATION: Primer CONR for screening Arthrobacter sp.
      BP2 library

<400> SEQUENCE: 109
ccgcccaggt agaacag                                            17

<210> SEQ ID NO 110
<211> LENGTH: 24
<212> TYPE: DNA
<213> ORGANISM: Artificial Sequence
<220> FEATURE:
<223> OTHER INFORMATION: Primer A228FI for screening Rhodococcus sp.
      phi2 library

<400> SEQUENCE: 110
ggatctcgat ccggcggtag ttgc                                    24
```

<210> SEQ ID NO 111
<211> LENGTH: 23
<212> TYPE: DNA
<213> ORGANISM: Artificial Sequence
<220> FEATURE:
<223> OTHER INFORMATION: Primer A228RI for screening Rhodococcus sp. phi2 library

<400> SEQUENCE: 111
gctgatgccg accggtctgt acg                                    23

<210> SEQ ID NO 112
<211> LENGTH: 23
<212> TYPE: DNA
<213> ORGANISM: Artificial Sequence
<220> FEATURE:
<223> OTHER INFORMATION: Primer A2FI for screening Rhodococcus sp. phi1 library

<400> SEQUENCE: 112
ccacagttgt cgacgccgtt gtc                                    23

<210> SEQ ID NO 113
<211> LENGTH: 22
<212> TYPE: DNA
<213> ORGANISM: Artificial Sequence
<220> FEATURE:
<223> OTHER INFORMATION: Primer A34RI for screening Rhodococcus sp. phi1 library

<400> SEQUENCE: 113
tcgaaacctc ggtagctgtc gg                                     22